US011739303B2

(12) United States Patent
Kawaoka et al.

(10) Patent No.: US 11,739,303 B2
(45) Date of Patent: Aug. 29, 2023

(54) RECOMBINANT INFLUENZA VIRUSES WITH STABILIZED NA

(71) Applicants: Wisconsin Alumni Research Foundation (WARF), Madison, WI (US); The University of Tokyo, Tokyo (JP)

(72) Inventors: Yoshihiro Kawaoka, Middleton, WI (US); Yuri Furusawa, Tokyo (JP); Seiya Yamayoshi, Kanagawa (JP)

(73) Assignees: Wisconsin Alumni Research Foundation (WARF), Madison, WI (US); The University of Tokyo, Tokyo (JP)

( * ) Notice: Subject to any disclaimer, the term of this patent is extended or adjusted under 35 U.S.C. 154(b) by 0 days.

(21) Appl. No.: 17/155,625

(22) Filed: Jan. 22, 2021

(65) Prior Publication Data

US 2021/0246432 A1 Aug. 12, 2021

Related U.S. Application Data

(60) Provisional application No. 62/965,225, filed on Jan. 24, 2020.

(51) Int. Cl.
*A61K 39/145* (2006.01)
*C12N 7/00* (2006.01)
*A61K 39/00* (2006.01)

(52) U.S. Cl.
CPC .............. *C12N 7/00* (2013.01); *A61K 39/145* (2013.01); *A61K 2039/5252* (2013.01); *A61K 2039/552* (2013.01); *C12N 2760/16121* (2013.01); *C12N 2760/16134* (2013.01); *C12N 2760/16151* (2013.01); *C12N 2760/16163* (2013.01)

(58) Field of Classification Search
CPC ...... A61K 2039/5252; A61K 2039/552; A61K 39/12; A61K 39/145; A61K 33/00; A61K 39/00; A61K 2039/6075; A61K 2039/5254; A61K 2039/5256; C07K 16/1018; G01N 2333/11; G01N 33/68; C12N 15/86; C12N 2720/12134; C12N 2720/12143; C12N 2720/12171; C12N 2770/36134; C12N 7/00; C12N 2710/24171; C12N 2710/24143; C12N 2710/24134
See application file for complete search history.

(56) References Cited

FOREIGN PATENT DOCUMENTS

| WO | 02074795 | 9/2002 |
|----|----------|--------|
| WO | 2011126370 | 10/2011 |
| WO | 2020264141 | 12/2020 |

OTHER PUBLICATIONS

Kim et al. Molecular Therapy 2014, vol. 22, Issue 7, pp. 1364-1374.*
Friers et al. Phil. Trans. R. Soc. Lond. B (2001). vol. 356, pp. 1961-1963.*
Tetsutani et al. Vaccine 2021, vol. 30, pp. 7658-7661.*
Zanin et al. Journal of Virology, 2017, Vo. 91, No. 2, pp. 1-12.*
"International Application Serial No. PCT US2021 014586, Written Opinion dated May 20, 2021", 8 pgs.
Broecker, Felix, "Extending the Stalk Enhances Inmunogenicity of the Influenza Virus Neuraminidase", Journal of Virology, 93,(18), e00840-19, (Sep. 1, 2019), 1-12.
Da Silva, Diogo V, "Assembly of Subtype 1 Influenza Neuraminidase is Driven by Both the Transmembrane and Head Domains", Journal of Biological Chemistry, 288(1), (Jan. 1, 2013), 644-653.
Kon, Theone C, "Influenza Vaccine Manufacturing: Effect of Inactivation, Splitting and Site of Manufacturing. Comparison of Influenza Vaccine Production Processes", PLoS One, 11(3), e0150700, (Mar. 9, 2016), 19 pgs.
"International Application Serial No. PCT/US2021/014586, International Preliminary Report on Patentability dated Aug. 4, 2022", 10 pgs.
"U.S. Appl. No. 17/004,583, Supplemental Amendment filed Mar. 28, 2023", 6 pgs.
"", Result 1, NCBI Blast nucleotide search of SEQ ID No. 3, database "nr"; Result 4, NCBI Blast nucleotide search of SEQ ID No. 4, database "nr", (Jul. 22, 2006), 11 pgs.
"", Result 2, NCBI Blast nucleotide search of SEQ ID No. 5, database "nr"; Result 4, NCBI Blast nucleotide search of SEQ ID No. 6, database "nr", (Jul. 22, 2006), 6 pgs.
"", Results 1, NCBI Blast nucleotide search of SEQ ID No. 7, database "nr"; Result 1, NCBI Blast nucleotide search of SEQ ID No. 8, database "nr", (Jul. 23, 2006), 8 pgs.
"", Result 17, NCBI Blast nucleotide search of SEQ ID No. 2, database "nr", (Jul. 18, 2006), 3 pgs.
"", Result 7, NCBI Blast nucleotide search of SEQ ID: 1, database "nr", (Jul. 18, 2006), 3 pgs.
"1.A.32 The Type B Influenza Virus NB Channel (NB-C) Family", Transport Protein Database, (University of California, San Diego, The Sailer Laboratory Bioinformatics Group) [online}. http://www.web.archive.org/web/200301311055254/http://tcdb.ucsd.edu/tcdb/tcfamilybrowse.php?tcname=1.A.32, (Archived Jan. 31, 2003), 1 pg.
"U.S. Appl. No. 10/855,975 Response filed Aug. 28, 2007 to Final Office Action dated Jun. 28, 2007", 16 pgs.
"Final O.A Jun. 28, 2007", 5 pgs.

(Continued)

*Primary Examiner* — Bao Q Li

(74) *Attorney, Agent, or Firm* — Schwegman Lundberg & Woessner, P.A.

(57) ABSTRACT

Modified influenza virus neuraminidases are described herein that have stabilized NA tetramers which may improve vaccine production efficiency, thus improving the yield of vaccine viruses.

12 Claims, 22 Drawing Sheets

Specification includes a Sequence Listing.

(56) References Cited

OTHER PUBLICATIONS

"Application Serial No. 04809419.7, Office Action dated Sep. 9, 2009", 3 pgs.
"U.S. Appl. No. 09/834,095, Advisory Action dated Jan. 8, 2004", 3 pgs.
"U.S. Appl. No. 09/834,095, Final Office Action dated Aug. 26, 2003", 12 pgs.
"U.S. Appl. No. 09/834,095, Non-Final Office Action dated Nov. 4, 2002", 12 pgs.
"U.S. Appl. No. 09/834,095, Notice of Allowance dated Sep. 27, 2004", 13 pgs.
"U.S. Appl. No. 09/834,095, Office Action dated Apr. 20, 2004", 11 pgs.
"U.S. Appl. No. 09/834,095, Response filed Feb. 4, 2003 to Office Action dated Nov. 4, 2002", 14 pgs.
"U.S. Appl. No. 09/834,095, Response filed Jun. 12, 2003 to Restriction Requirement dated Apr. 22, 2003", 2 pgs.
"U.S. Appl. No. 09/834,095, Response filed Jun. 18, 2004 to Office Action dated Apr. 20, 2004", 11 pgs.
"U.S. Appl. No. 09/834,095, Response filed Aug. 1, 2002 to Restriction Requirement dated Jul. 1, 2002", 3 pgs.
"U.S. Appl. No. 09/834,095, Response filed Nov. 26, 2003 to Final Office Action dated Aug. 26, 2003", 10 pgs.
"U.S. Appl. No. 09/834,095, Restriction Requirement dated Apr. 22, 2003", 5 pgs.
"U.S. Appl. No. 09/834,095, Restriction Requirement dated Jul. 1, 2002", 9 pgs.
"U.S. Appl. No. 09/834,095, Supplemental Amendment filed Aug. 4, 2004", 7 pgs.
"U.S. Appl. No. 10/081,170, Advisory Action dated Sep. 27, 2004", 3 pgs.
"U.S. Appl. No. 10/081,170, Final Office Action dated Apr. 12, 2006", 7 pgs.
"U.S. Appl. No. 10/081,170, Final Office Action dated Jul. 13, 2004", 8 pgs.
"U.S. Appl. No. 10/081,170, Non Final Office Action dated Jan. 15, 2004", 9 pgs.
"U.S. Appl. No. 10/081,170, Non Final Office Action dated Feb. 8, 2005", 9 pgs.
"U.S. Appl. No. 10/081,170, Non Final Office Action dated Aug. 24, 2005", 9 pgs.
"U.S. Appl. No. 10/081,170, Notice of Allowance dated Sep. 18, 2006", 8 pgs.
"U.S. Appl. No. 10/081,170, Preliminary Amendment filed May 20, 2003", 2 pgs.
"U.S. Appl. No. 10/081,170, Preliminary Amendment filed Jun. 6, 2002", 1 pg.
"U.S. Appl. No. 10/081,170, Response filed Jan. 24, 2006 to Non Final Office Action dated Aug. 24, 2005", 11 pgs.
"U.S. Appl. No. 10/081,170, Response filed Apr. 12, 2004 to Non Final Office Action dated Jan. 15, 2004", 12 pgs.
"U.S. Appl. No. 10/081,170, Response filed Jun. 8, 2005 to Non Final Office Action dated Feb. 8, 2005", 11 pgs.
"U.S. Appl. No. 10/081,170, Response filed Aug. 17, 2006 to Final Office Action dated Apr. 12, 2006", 9 pgs.
"U.S. Appl. No. 10/081,170, Response filed Sep. 13, 2004 to Final Office Action dated Jul. 13, 2004", 10 pgs.
"U.S. Appl. No. 10/081,170, Response filed Oct. 10, 2003 to Restriction Requirement dated Sep. 10, 2003", 3 pgs.
"U.S. Appl. No. 10/081,170, Restriction Requirement dated Sep. 10, 2003", 4 pgs.
"U.S. Appl. No. 10/353,856, Final Office Action dated Jun. 1, 2006", 10 pgs.
"U.S. Appl. No. 10/353,856, Non-Final Office Action dated Sep. 30, 2005", 9 pgs.
"U.S. Appl. No. 10/353,856, Non-Final Office Action dated Dec. 16, 2004", 11 pgs.
"U.S. Appl. No. 10/353,856, Notice of Allowance dated Oct. 18, 2006", 9 pgs.
"U.S. Appl. No. 10/353,856, Preliminary Amendment filed May 20, 2003", 2 pgs.
"U.S. Appl. No. 10/353,856, PTO Response to 312 Amendment dated Mar. 8, 2007", 2 pgs.
"U.S. Appl. No. 10/353,856, Response filed Feb. 28, 2006 to Non-Final Office Action dated Sep. 30, 2005", 10 pgs.
"U.S. Appl. No. 10/353,856, Response filed Apr. 7, 2005 to Non-Final Office Action dated Dec. 16, 2004", 10 pgs.
"U.S. Appl. No. 10/353,856, Response filed Aug. 17, 2006 to Final Office Action dated Jun. 1, 2006", 11 pgs.
"U.S. Appl. No. 10/353,856, Response filed Oct. 8, 2004 to Restriction Requirement mailed Sep. 10, 2004", 2 pgs.
"U.S. Appl. No. 10/353,856, Restriction Requirement dated Sep. 10, 2004", 5 pgs.
"U.S. Appl. No. 10/353,856, Supplemental Amendment filed Jan. 9, 2007", 4 pgs.
"U.S. Appl. No. 10/353,856, Supplemental Preliminary Amendment filed Jun. 23, 2003", 4 pgs.
"U.S. Appl. No. 10/827,995, Final Office Action dated Nov. 15, 2006", 10 pgs.
"U.S. Appl. No. 10/827,995, Non-Final Office Action dated Jun. 2, 2006", 15 pgs.
"U.S. Appl. No. 10/827,995, Non-Final Office Action dated Oct. 25, 2007", 7 pgs.
"U.S. Appl. No. 10/827,995, Notice of Allowance dated Feb. 17, 2009", 9 pgs.
"U.S. Appl. No. 10/827,995, Notice of Allowance dated Jul. 2, 2008", 9 pgs.
"U.S. Appl. No. 10/827,995, Notice of Allowance dated Oct. 17, 2008", 7 pgs.
"U.S. Appl. No. 10/827,995, Notice of Non-Compliant Amendment dated Jul. 25, 2007", 4 pgs.
"U.S. Appl. No. 10/827,995, Proposed Examiner's Amendment dated Jun. 5, 2008", 6 pgs.
"U.S. Appl. No. 10/827,995, Response filed Mar. 3, 2008 to Office Action dated Oct. 25, 2007", 10 pgs.
"U.S. Appl. No. 10/827,995, Response filed May 14, 2007 Final Office Action dated Nov. 15, 2006", 16 pgs.
"U.S. Appl. No. 10/827,995, Response filed Aug. 13, 2007 to Notice of Non-Compliant Amendment Jul. 25, 2007", 16 pgs.
"U.S. Appl. No. 10/827,995, Response filed Aug. 17, 2006 Non-Final Office Action dated Jun. 2, 2006", 15 pgs.
"U.S. Appl. No. 10/855,875 , Response filed May 17, 2012 to Non Final Office Action dated Mar. 15, 2012", 15 pgs.
"U.S. Appl. No. 10/855,875, Final Office Action dated Mar. 11, 2008", FOAR, 20 Pgs.
"U.S. Appl. No. 10/855,875, Final Office Action dated Aug. 2, 2006", 34 pgs.
"U.S. Appl. No. 10/855,875, Final Office Action dated Dec. 10, 2010", 15 pgs.
"U.S. Appl. No. 10/855,875, Non Final Office Action dated Mar. 15, 2012", 15 pgs.
"U.S. Appl. No. 10/855,875, Non-Final Office Action dated Feb. 19, 2010", 7 pgs.
"U.S. Appl. No. 10/855,875, Non-Final Office Action dated May 3, 2007", 13 pgs.
"U.S. Appl. No. 10/855,875, Non-Final Office Action dated Aug. 7, 2009", 32 pgs.
"U.S. Appl. No. 10/855,875, Non-Final Office Action dated Nov. 6, 2008", 12 pgs.
"U.S. Appl. No. 10/855,875, Non-Final Office Action dated Nov. 30, 2005", 13 pgs.
"U.S. Appl. No. 10/855,875, Preliminary Amendment filed Feb. 2, 2007", 14 pgs.
"U.S. Appl. No. 10/855,875, Response filed Jan. 29, 2007 to Final Office Action dated Aug. 2, 2007", 14 pgs.
"U.S. Appl. No. 10/855,875, Response filed Mar. 18, 2011 to Final Office Action dated Dec. 10, 2010", 15 pgs.
"U.S. Appl. No. 10/855,875, Response filed Aug. 17, 2010 to Non Final Office Action dated Feb. 19, 2010", 20 pgs.
"U.S. Appl. No. 10/855,875, Response filed Dec. 7, 2009 to Non Final Office Action dated Aug. 7, 2009", 15 pgs.

(56) References Cited

OTHER PUBLICATIONS

"U.S. Appl. No. 10/855,875, Response filed Mar. 31, 2009 to Non Final Office Action dated Nov. 6, 2008", 14 pgs.
"U.S. Appl. No. 10/855,875, Response filed May 1, 2006 Non-Final Office Action dated Nov. 30, 2005", 13 pgs.
"U.S. Appl. No. 10/855,875, Response filed Aug. 18, 2008 to final Office Action dated Mar. 11, 2008", 15 pgs.
"U.S. Appl. No. 10/855,875, Response filed Sep. 20, 2005 to Restriction Requirement dated Jul. 26, 2005", 4 pgs.
"U.S. Appl. No. 10/855,875, Restriction Requirement dated Dec. 23, 2011", 9 pgs.
"U.S. Appl. No. 10/855,875, Restriction Requirement dated Jul. 26, 2005", 9 pgs.
"U.S. Appl. No. 10/855,975, Advisory Action dated Sep. 6, 2006", 3 pgs.
"U.S. Appl. No. 10/855,975, Advisory Action dated Sep. 13, 2007", 3 pgs.
"U.S. Appl. No. 10/855,975, Advisory Action dated Dec. 24, 2008", 4 pgs.
"U.S. Appl. No. 10/855,975, Final Office Action dated May 17, 2006", 7 pgs.
"U.S. Appl. No. 10/855,975, Final Office Action dated Jun. 28, 2007", 7 pgs.
"U.S. Appl. No. 10/855,975, Final Office Action dated Aug. 7, 2008", 5 pgs.
"U.S. Appl. No. 10/855,975, Non-Final Office Action dated Jan. 4, 2008", 10 pgs.
"U.S. Appl. No. 10/855,975, Non-Final Office Action dated Jan. 19, 2007", 7 pgs.
"U.S. Appl. No. 10/855,975, Non-Final Office Action dated May 29, 2009", 5 pgs.
"U.S. Appl. No. 10/855,975, Non-Final Office Action dated Nov. 30, 2005", 11 pgs.
"U.S. Appl. No. 10/855,975, Notice of Allowance dated Dec. 16, 2009", 19 pgs.
"U.S. Appl. No. 10/855,975, Response filed Jan. 29, 2009 to Advisory Action dated Dec. 24, 2008", 15 pgs.
"U.S. Appl. No. 10/855,975, Response filed Feb. 28, 2006 to Non-Final Office Action dated Nov. 30, 2005", 15 pgs.
"U.S. Appl. No. 10/855,975, Response filed Apr. 3, 2008 to Non Final Office Action dated Jan. 4, 2008", 16 pgs.
"U.S. Appl. No. 10/855,975, Response filed Apr. 19, 2007 to Non-Final Office Action dated Jan. 19, 2007", 16 pgs.
"U.S. Appl. No. 10/855,975, Response filed Aug. 13, 2009 to Non Final Office Action dated May 29, 2009", 19 pgs.
"U.S. Appl. No. 10/855,975, Response filed Aug. 17, 2006 to Final Office Action dated May 17, 2006", 13 pgs.
"U.S. Appl. No. 10/855,975, Response filed Aug. 28, 2007 to Final Office Action dated Jun. 28, 2007", 15 pgs.
"U.S. Appl. No. 10/855,975, Response filed Sep. 28, 2005 to Restriction Requirement dated Jul. 12, 2005", 3 pgs.
"U.S. Appl. No. 10/855,975, Response filed Dec. 11, 2008 to Final Office Action dated Aug. 7, 2008", 14 pgs.
"U.S. Appl. No. 10/855,975, Restriction Requirement dated Jul. 12, 2005", 8 pgs.
"U.S. Appl. No. 10/8558/5, Response filed Nov. 2, 2007 to Office Action dated May 3, 2007", 16 pgs.
"U.S. Appl. No. 11/043,768 Non-Final Office Action dated Sep. 27, 2010", 8 pgs.
"U.S. Appl. No. 11/043,768, Final Office Action dated Jun. 27, 2008", 8 pgs.
"U.S. Appl. No. 11/043,768, Non-Final Office Action dated Feb. 23, 2010", 6 pgs.
"U.S. Appl. No. 11/043,768, Non-Final Office Action dated Feb. 23, 2009", 7 pgs.
"U.S. Appl. No. 11/043,768, Non-Final Office Action dated Nov. 28, 2007", 9 pgs.
"U.S. Appl. No. 11/043,768, Notice of Allowance dated Jun. 29, 2011", 12 pgs.
"U.S. Appl. No. 11/043,768, Response filed May 2, 2011 to Final Office Action dated Feb. 3, 2011", 11 pgs.
"U.S. Appl. No. 11/043,768, Response filed Jun. 15, 2010 to Non Final Office Action dated Feb. 23, 2010", 9 pgs.
"U.S. Appl. No. 11/043,768, Response filed Jun. 23, 2009 to Non-Final Office Action dated Feb. 23, 2009", 9 pgs.
"U.S. Appl. No. 11/043,768, Response filed Sep. 13, 2007 to Restriction Requirement dated Mar. 13, 2007", 10 pgs.
"U.S. Appl. No. 11/043,768, Response filed Oct. 26, 2010 to Non Final Office Action dated Sep. 27, 2010", 11 pgs.
"U.S. Appl. No. 11/043,768, Response filed Dec. 12, 2008 to Final Office Action dated Jun. 27, 2008", 9 pgs.
"U.S. Appl. No. 11/043,768, Response filed Mar. 10, 2008 to Office Action dated Nov. 28, 2007", 12 pgs.
"U.S. Appl. No. 11/043,768, Restriction Requirement dated Mar. 13, 2007", 9 pgs.
"U.S. Appl. No. 11/043,786, Final Office Action dated Feb. 3, 2011", 10 pgs.
"U.S. Appl. No. 11/283,498, Non Final Office Action dated Sep. 3, 2009", 5 pgs.
"U.S. Appl. No. 11/283,498, Non Final Office Action dated Jul. 9, 2007", 7 pgs.
"U.S. Appl. No. 11/283,498, Non-Final Office Action dated Jan. 23, 2008", 20 pgs.
"U.S. Appl. No. 11/283,498, Non-Final Office Action dated Apr. 29, 2010", 10 pgs.
"U.S. Appl. No. 11/283,498, Notice of Allowance dated Feb. 23, 2011", 9 pgs.
"U.S. Appl. No. 11/283,498, Response filed Jan. 4, 2010 to Non Final Office Action dated Sep. 3, 2009", 12 pgs.
"U.S. Appl. No. 11/283,498, Response filed Oct. 28, 2010 to Non Final Office Action dated Apr. 29, 2010", 13 pgs.
"U.S. Appl. No. 11/283,498, Response filed Nov. 7, 2007 to Office Action dated Jul. 9, 2007", 17 pgs.
"U.S. Appl. No. 11/283,498, Response filed Apr. 16, 2007 to Restriction Requirement dated Oct. 16, 2006", 17 pgs.
"U.S. Appl. No. 11/283,498, Response filed Jul. 22, 2008 to Non Final Office Action dated Jan. 23, 2008", 12 pgs.
"U.S. Appl. No. 11/283,498, Restriction Requirement dated Oct. 16, 2006", 6 pgs.
"U.S. Appl. No. 11/283,498, Supplemental Amendment Response to Non Final Office Action dated Oct. 28, 10", 11 pgs.
"U.S. Appl. No. 11/509,249, Final Office Action dated Jun. 12, 2008", 5 pgs.
"U.S. Appl. No. 11/509,249, Non Final Office Action with Restriction Requirement dated Aug. 24, 2007", 8 pgs.
"U.S. Appl. No. 11/509,249, Notice of Allowance dated Apr. 9, 2009", 7 pgs.
"U.S. Appl. No. 11/509,249, Notice of Allowance dated Nov. 17, 2008", 4 pgs.
"U.S. Appl. No. 11/509,249, Response filed Feb. 20, 2008 to Non Final Office Action dated Aug. 24, 2007", 11 pgs.
"U.S. Appl. No. 11/509,249, Response filed Oct. 6, 2008 to Office Action dated Jun. 12, 2008", 11 pgs.
"U.S. Appl. No. 11/644,179, Final Office Action dated Jul. 2, 2010", 8 pgs.
"U.S. Appl. No. 11/644,179, Non Final Office Action dated Nov. 29, 2012", 19 pgs.
"U.S. Appl. No. 11/644,179, Non Final Office Action dated Dec. 8, 2009", 7 pgs.
"U.S. Appl. No. 11/644,179, Preliminary Amendment filed Dec. 22, 2006", 5 pgs.
"U.S. Appl. No. 11/644,179, Response filed Jan. 30, 2008 to Restriction Requirement dated Oct. 30, 2007", 5 pgs.
"U.S. Appl. No. 11/644,179, Response filed Apr. 8, 2010 to Non Final Office Action dated Dec. 8, 2009", 8 pgs.
"U.S. Appl. No. 11/644,179, Response filed Aug. 17, 2010 to Final Office Action dated Jul. 2, 2010", 8 pgs.
"U.S. Appl. No. 11/644,179, Restriction Requirement dated Oct. 30, 2007", 7 pgs.
"U.S. Appl. No. 11/644,179, Supplemental Preliminary Amendment filed Feb. 6, 2008", 6 pgs.

(56) References Cited

OTHER PUBLICATIONS

"U.S. Appl. No. 11/654,863 Restriction Requirement dated Sep. 3, 2010", 5 pgs.
"U.S. Appl. No. 11/654,863, Final Office Action dated Oct. 25, 2011", 9 pgs.
"U.S. Appl. No. 11/654,863, Non Final Office Action dated Jun. 27, 2011", 9 pgs.
"U.S. Appl. No. 11/654,863, Non Final Office Action dated Dec. 2, 2010", 8 pgs.
"U.S. Appl. No. 11/654,863, Preliminary Amendment filed May 7, 2007", 15 pgs.
"U.S. Appl. No. 11/654,863, Response filed Apr. 18, 2012 to Final Office Action dated Oct. 25, 2011", 8 pgs.
"U.S. Appl. No. 11/654,863, Response filed Jun. 2, 2011 to Non Final Office Action dated Dec. 2, 2010", 6 pgs.
"U.S. Appl. No. 11/654,863, Response filed Sep. 28, 2010 to Restriction Requirement dated Sep. 3, 2010", 6 pgs.
"U.S. Appl. No. 11/654,863, Response filed Oct. 6, 2011 to Non Final Office Action dated Jun. 27, 2011", 9 pgs.
"U.S. Appl. No. 11/729,557, Advisory Action dated May 9, 2011", 3 pgs.
"U.S. Appl. No. 11/729,557, Final Office Action dated Feb. 2, 2011", 14 pgs.
"U.S. Appl. No. 11/729,557, Final Office Action dated Aug. 20, 2009", 13 Pgs.
"U.S. Appl. No. 11/729,557, Non-Final Office Action dated Jan. 30, 2009", 20 pgs.
"U.S. Appl. No. 11/729,557, Non-Final Office Action dated Feb. 22, 2010", 16 pgs.
"U.S. Appl. No. 11/729,557, Non-Final Office Action dated Aug. 23, 2010", 15 pgs.
"U.S. Appl. No. 11/729,557, Respons filed Jun. 22, 2010 to Non Final Office Action dated Feb. 22, 2010", 33 pgs.
"U.S. Appl. No. 11/729,557, Response filed Apr. 27, 2011 to Final Office Action dated Feb. 2, 2011", 14 pgs.
"U.S. Appl. No. 11/729,557, Response filed Apr. 30, 2009 to Non Final Office Action dated Jan. 30, 2009", 18 pgs.
"U.S. Appl. No. 11/729,557, Response filed May 28, 2008 to Restriction Requirement dated Nov. 28, 2007", 13 pgs.
"U.S. Appl. No. 11/729,557, Response filed Jun. 22, 2010 to Non Final Office Action dated Feb. 22, 2010", 16 pgs.
"U.S. Appl. No. 11/729,557, Response filed Oct. 28, 2010 to Non Final Office Action dated Aug. 23, 2010", 13 pgs.
"U.S. Appl. No. 11/729,557, Response filed Dec. 1, 2009 to Final Office Action dated Aug. 26, 2009", 16 pgs.
"U.S. Appl. No. 11/729,557, Restriction Requirement dated Nov. 28, 2007", 9 pgs.
"U.S. Appl. No. 11/810,956, Final Office Action dated Mar. 22, 2010", 8 pgs.
"U.S. Appl. No. 11/810,956, Non-Final Office Action dated Aug. 11, 2009", 9 pgs.
"U.S. Appl. No. 11/810,956, Response filed Jan. 11, 2010 to Non Final Office Action dated Aug. 11, 2009", 8 pgs.
"U.S. Appl. No. 11/810,956, Response filed Apr. 23, 2009 to Restriction Requirement dated Mar. 23, 2009", 6 pgs.
"U.S. Appl. No. 11/810,956, Restriction Requirement dated Mar. 23, 2009", 6 pgs.
"U.S. Appl. No. 12/058,389, Final Office Action dated Jan. 22, 2010", 8 pgs.
"U.S. Appl. No. 12/058,389, Final Office Action dated Nov. 14, 2012", 7 pgs.
"U.S. Appl. No. 12/058,389, Non Final Office Action dated Aug. 10, 2012", 5 pgs.
"U.S. Appl. No. 12/058,389, Non Final Office Action dated Dec. 8, 2011", 8 pgs.
"U.S. Appl. No. 12/058,389, Non-Final Office Action dated Apr. 13, 2009", 12 pgs.
"U.S. Appl. No. 12/058,389, Preliminary Amendment filed Jun. 23, 2008", 7 pgs.
"U.S. Appl. No. 12/058,389, Respnse filed Nov. 6, 2012 to Non Final Office Action dated Aug. 10, 2012", 7 pgs.
"U.S. Appl. No. 12/058,389, Response filed Feb. 6, 2009 to Restriction Requirement dated Dec. 3, 2008", 7 pgs.
"U.S. Appl. No. 12/058,389, Response filed Apr. 10, 2012 to Non Final Office Action dated Dec. 8, 2011", 7 pgs.
"U.S. Appl. No. 12/058,389, Response filed Jun. 16, 2010 to Final Office Action dated Jan. 22, 2010", 6 pgs.
"U.S. Appl. No. 12/058,389, Response filed Oct. 13, 2009 to Non Final Office Action dated Apr. 13, 2009", 9 pgs.
"U.S. Appl. No. 12/113,690, Final Office Action dated Apr. 15, 2011", 10 pgs.
"U.S. Appl. No. 12/113,690, Non-Final Office Action dated Nov. 10, 2010", 11 pgs.
"U.S. Appl. No. 12/113,690, Preliminary Amendment filed Jul. 31, 2008", 14 pgs.
"U.S. Appl. No. 12/113,690, Response filed Jun. 23, 2011 to Final Office Action dated Apr. 15, 2011", 17 pgs.
"U.S. Appl. No. 12/113,690, Response filed Aug. 5, 2010 to Restriction Requirement dated Apr. 6, 2010", 14 pgs.
"U.S. Appl. No. 12/113,690, Response filed Dec. 22, 2010 dated Nov. 10, 2010", 19 pgs.
"U.S. Appl. No. 12/113,690, Restriction Requirement dated Apr. 6, 2010", 10 pgs.
"U.S. Appl. No. 12/139,183, Non Final Office Action dated Jan. 6, 2011", 12 pgs.
"U.S. Appl. No. 12/139,183, Non-Final Office Action dated Jan. 4, 2010", 6 pgs.
"U.S. Appl. No. 12/139,183, Non-Final Office Action dated Jul. 13, 2010", 15 pgs.
"U.S. Appl. No. 12/139,183, Notice of Allowance dated Jun. 27, 2011", 11 pgs.
"U.S. Appl. No. 12/139,183, Preliminary Amendment filed Sep. 11, 2008", 17 pgs.
"U.S. Appl. No. 12/139,183, Response filed Mar. 22, 2011 to Non Final Office Action dated Jan. 6, 2011", 21 pgs.
"U.S. Appl. No. 12/139,183, Response filed Apr. 12, 2010 to Non Final Office Action dated Jan. 4, 2010", 17 pgs.
"U.S. Appl. No. 12/139,183, Response filed Aug. 18, 2009 to Restriction Requirement dated Jul. 24, 2009", 16 pgs.
"U.S. Appl. No. 12/139,183, Response filed Sep. 21, 2010 to Non Final Office Action dated Jul. 13, 2010", 21 pgs.
"U.S. Appl. No. 12/139,183, Restriction Requirement dated Jul. 24, 2009", 12 pgs.
"U.S. Appl. No. 12/214,414, Advisory Action dated Oct. 21, 2011", 5 pgs.
"U.S. Appl. No. 12/214,414, Final Office Action dated Aug. 2, 2011", 7 pgs.
"U.S. Appl. No. 12/214,414, Non Final Office Action dated Dec. 10, 2010", 6 pgs.
"U.S. Appl. No. 12/214,414, Non-Final Office Action dated Mar. 2, 2010", 9 pgs.
"U.S. Appl. No. 12/214,414, Response filed May 3, 2017 to Non Final Office Action dated Dec. 10, 2010", 12 pgs.
"U.S. Appl. No. 12/214,414, Response filed Aug. 31, 2010 to Non Final Office Action dated Mar. 2, 2010", 11 pgs.
"U.S. Appl. No. 12/214,414, Response filed Oct. 3, 2011 to Non Final Office Action dated Aug. 2, 2011", 9 pgs.
"U.S. Appl. No. 12/214,414, Response filed Dec. 21, 2011 to Advisory Action dated Oct. 21, 2011", 10 pgs.
"U.S. Appl. No. 12/245,296, Final Office Action dated Dec. 17, 2010", 16 pgs.
"U.S. Appl. No. 12/245,296, Non-Final Office Action dated Jun. 1, 2010", 13 pgs.
"U.S. Appl. No. 12/245,296, Preliminary Amendment dated Jan. 28, 2009", 14 pgs.
"U.S. Appl. No. 12/245,296, Response filed Apr. 8, 2010 to Restriction Requirement dated Mar. 9, 2010", 6 pgs.
"U.S. Appl. No. 12/245,296, Response filed May 17, 2011 to Final Office Action dated Dec. 17, 2010", 10 pgs.
"U.S. Appl. No. 12/245,296, Response filed Oct. 1, 2010 to Non Final Office Action dated Jun. 1, 2010", 12 pgs.

(56) References Cited

OTHER PUBLICATIONS

"U.S. Appl. No. 12/245,296, Restriction Requirement dated Mar. 9, 2010", 6 pgs.
"U.S. Appl. No. 12/470,287, Restriction Requirement dated Nov. 22, 2010", 6 pgs.
"U.S. Appl. No. 12/470,287 , Response filed Jan. 23, 2012 to Non Final Office Action dated Jul. 22, 2011", 13 pgs.
"U.S. Appl. No. 12/470,287 , Response filed May 31, 2012 to Final Office Action dated Apr. 3, 2012", 14 pgs.
"U.S. Appl. No. 12/470,287, Corrected Notice of Allowability dated Sep. 11, 2012", 2 pgs.
"U.S. Appl. No. 12/470,287, Final Office Action dated Apr. 3, 2012", 7 pgs.
"U.S. Appl. No. 12/470,287, Non Final Office Action dated Jul. 22, 2011", 9 pgs.
"U.S. Appl. No. 12/470,287, Notice of Allowance dated Jun. 19, 2012", 5 pgs.
"U.S. Appl. No. 12/470,287, Response filed Apr. 28, 2011 to Restriction Requirement dated Dec. 29, 2010", 8 pgs.
"U.S. Appl. No. 12/470,287, Restriction Requirement dated Dec. 29, 2010", 6 pgs.
"U.S. Appl. No. 12/854,578 , Response filed Oct. 1, 2012 to Non Final Office Action dated Jun. 29, 2012", 10 pgs.
"U.S. Appl. No. 12/854,578, Final Office Action dated Nov. 29, 2012", 8 pgs.
"U.S. Appl. No. 12/854,578, Non Final Office Action dated Jun. 29, 2012", 8 pgs.
"U.S. Appl. No. 12/854,578, Restriction Requirement dated Apr. 6, 2012", 6 pgs.
"U.S. Appl. No. 12/912,411, Restriction Requirement dated Oct. 17, 2012", 9 pgs.
"U.S. Appl. No. 13/113,244, Non Final Office Action dated Oct. 1, 2012", 7 pgs.
"U.S. Appl. No. 13/113,244, Restriction Requirement dated Oct. 31, 2011", 8 pgs.
"Australian Application Serial No. 2001255336, Examiner's First Report dated Feb. 16, 2005", 2 pgs.
"Australian Application Serial No. 2001255336, Response filed Aug. 23, 2005 to Examiner's First Report dated Feb. 16, 2005", 10 pgs.
"Australian Application Serial No. 2003219745, Examiner's First Report dated Feb. 14, 2007", 2 pgs.
"Australian Application Serial No. 2003219745, Response filed Mar. 14, 2008 to Examiner's First Report dated Feb. 14, 2007", 24 pgs.
"Australian Application Serial No. 2004249133, First Examiner's Report dated May 5, 2008", 4 pgs.
"Australian Application Serial No. 2004249133, Response filed Mar. 30, 2009 to First Examiner's Report dated May 5, 2008", 30 pgs.
"Australian Application Serial No. 2004274860, Office Action dated May 21, 2008", 2 pgs.
"Australian Application Serial No. 2007245192, Office Action dated Aug. 25, 2011", 2 pgs.
"Australian Application Serial No. 2007245192, Response filed Feb. 28, 2012 to Office Action dated Aug. 25, 2011", 22 pgs.
"Australian Application Serial No. 2008203186, First Examiner Report dated Jan. 28, 2011", 2 pgs.
"Australian Application Serial No. 2008203186, Office Action Received dated Sep. 16, 2010", 1 page.
"Australian Application Serial No. 2008203186, Response filed Aug. 29, 2011 to Official Action dated Apr. 13, 2011", 20 pgs.
"Australian Application Serial No. 2008203186, Subsequent Examiner Report dated Apr. 13, 2011", 2 pgs.
"Avian Inluenza", Queensland Government—Department of Primary Industries, (Observed Feb. 22, 2003), 2 pgs.
"Avian Inluenza", http://www.iah.bbsrc.ac.uk/reports/1997/ainf.html, (Observed Feb. 22, 2003), 2 pgs.
"Brazilian Application Serial No. PI 0307679-2, Office Action published in Patent Gazette No. 1871 dated Nov. 14, 2006", 2 pgs.
"Brazilian Application Serial No. PI 0307679-2, Petition filed Jan. 10, 2007 in response to publication dated Nov. 14, 2006", 6 pgs.
"Brazilian Application Serial No. PI0410702-0, Office Action dated Feb. 23, 2012", w/ English Translation, 4 pgs.
"Brazilian Application Serial No. 0410702-0, Response filed May 7, 2012 to Office Action dated Feb. 23, 2012", w/ English Claims, 11 pgs.
"Canadian Application Serial No. 11/509,249, Response filed May 16, 2011 to Office Acttion dated Nov. 18, 2010", 15 pgs.
"Canadian Application Serial No. 2,406,180, Office Action dated Sep. 9, 2008", 5 pgs.
"Canadian Application Serial No. 2,406,180, Office Action dated Nov. 10, 2011", 3 pgs.
"Canadian Application Serial No. 2,406,180, Office Action dated Nov. 23, 2009", 3 pgs.
"Canadian Application Serial No. 2,406,180, Office Action dated Dec. 10, 2010", 2 Pgs.
"Canadian Application Serial No. 2,406,180, Response filed Jan. 26, 2009 to Official Action dated Sep. 9, 2008", 22 pgs.
"Canadian Application Serial No. 2,406,180, Response filed May 21, 2010 to Office action dated Nov. 23, 2009", 13 pgs.
"Canadian Application Serial No. 2,406,180, Response filed Jun. 14, 2011 to Office Action dated Dec. 10, 2010", 10 pgs.
"Canadian Application Serial No. 2,492,097, Office Action dated Jan. 10, 2012", 4 pgs.
"Canadian Application Serial No. 2,492,097, Office Action dated Apr. 24, 2008", 3 pgs.
"Canadian Application Serial No. 2,492,097, Office Action dated Jul. 31, 2009", 3 pgs.
"Canadian Application Serial No. 2,492,097, Response filed Jan. 29, 2010 to Office Action dated Jul. 31, 2009", 13 pgs.
"Canadian Application Serial No. 2,492,097, Response filed May 2, 2012 to Office Action dated Jan. 10, 2012", 12 pgs.
"Canadian Application Serial No. 2,492,097, Response filed Oct. 23, 2008 to Office Action dated Apr. 24, 2008", 14 pgs.
"Canadian Application Serial No. 2,522,081, Office Action filed Nov. 18, 2011", 11 pgs.
"Canadian Application Serial No. 2,522,081, Office Action dated Jun. 6, 2011", 2 pgs.
"Canadian Application Serial No. 2,522,081, Office Action dated Aug. 30, 2010", 2 pgs.
"Canadian Application Serial No. 2,522,081, Office Action dated Oct. 8, 2009", 6 pgs.
"Canadian Application Serial No. 2,522,081, Response filed Feb. 28, 2011 to Office Action dated Aug. 30, 2010", 10 pgs.
"Canadian Application Serial No. 2,522,081, Response filed Apr. 8, 2010 to Office Action dated Oct. 8, 2009", 30 pgs.
"Canadian Application Serial No. 2,525,953, Office Action dated Jul. 31, 2012", 4 pgs.
"Canadian Application Serial No. 2,525,953, Office Action dated Jun. 22, 2011", 4 pgs.
"Canadian Application Serial No. 2,525,953, Office Action received Jun, 22, 2011", 4 pgs.
"Canadian Application Serial No. 2,525,953, Response filed Dec. 22, 2011 to Office Action dated Jun. 22, 2011", 17 pgs.
"Canadian Application Serial No. 2406180, Response filed May 7, 2012 to Office Action dated Nov. 10, 2011", 11 pgs.
"Canadian Application Serial No. 2492097, Office Action dated Nov. 18, 2010", 4 pgs.
"Chinese Application Serial No. 03808356.6, Office Action dated Sep. 5, 2008", (English Translation), 6 pgs.
"Chinese Application Serial No. 03808356.6, Office Action received Jul. 1, 2011", (w/ English Translation of Office Action), 8 pgs.
"Chinese Application Serial No. 03808356.6, Response filed Mar. 16, 2009 to Office Action dated Sep. 5, 2008", (w/ English Translation of Claims), 8 pgs.
"Chinese Application Serial No. 03808356.6, Response filed Oct. 14, 2011 to Office Action dated Jul. 1, 2011", (w/ English Translation of Amended Claims), 25 pgs.
"Chinese Application Serial No. 200480017037, First Office Action dated May 25, 2007", (w/ English Translation), 10 pgs.

(56) References Cited

OTHER PUBLICATIONS

"Chinese Application Serial No. 200480017037, Response filed Oct. 30, 2007 to First Office Action dated May 25, 2007", (w/ English Translation of Claims), 26 pgs.
"Chinese Application Serial No. 200480017037.X, Response filed May 14, 2010 to Third Office Action dated Mar. 1, 2010", (w/ English Translation of Claims), 16 pgs.
"Chinese Application Serial No. 200480017037.X, Response filed Aug. 4, 2009 to Second Office Action dated Mar. 20, 2009", (w/ English Translation of Amended Claims), 15 pgs.
"Chinese Application Serial No. 200480017037.X, Second Office Action dated Mar. 20, 2009", (English Translation), 7 pgs.
"Chinese Application Serial No. 200480017037.X, Third Office Action dated Mar. 1, 2010", (w/ English Translation), 9 pgs.
"Chinese Application Serial No. 200480021259.9 Office Action Sep. 11, 2009", (English Translation), 7 pgs.
"Chinese Application Serial No. 200480021259.9 Response filed Aug. 20, 2010 to Office Acton dated May 6, 2010", (w/ English Translation of Claims), 26 pgs.
"Chinese Application Serial No. 200480021259.9, First Offiice Action dated Aug. 24, 2007", (w/ English Translation), 9 pgs.
"Chinese Application Serial No. 200480021259.9, Notice of Reexamination dated Jul. 3, 2012", (w/ English Translation), 10 pgs.
"Chinese Application Serial No. 200480021259.9, Office Action dated Jan. 11, 2011", (w/ English Translation), 15 pgs.
"Chinese Application Serial No. 200480021259.9, Office Action dated May 6, 2010", (w/English Translation), 12 pgs.
"Chinese Application Serial No. 200480021259.9, Office Action dated Jul. 3, 2012", (w/ English Translation), 10 pgs.
"Chinese Application Serial No. 200480021259.9, Request for Reexamination filed Apr. 26, 2011", (w/ English Translation of Amended Claims), 23 pgs.
"Chinese Application Serial No. 200480021259.9, Response filed Mar. 7, 2008 to Offiice Action dated Aug. 24, 2007", (w/ English Translation of Claims), 13 pgs.
"Chinese Application Serial No. 200480021259.9, Response filed Oct. 16, 2012 t Office Action dated Jul. 3, 2012", (w/ English Translation of Claims), 13 pgs.
"Chinese Application Serial No. 200480022014, First Office Action dated Aug. 24, 2007", w/English Translation, 6 pgs.
"Chinese Application Serial No. 200580046922.5, Office Action dated Jul. 24, 2009", 12 pgs.
"Chinese Application Serial No. 200780020095.1, First Office Action dated Jun. 24, 2011", (w/ English Translation), 13 pgs.
"Chinese Application Serial No. 200780020095.1, Office Action dated May 3, 2012", (w/ English Translation), 10 pgs.
"Chinese Application Serial No. 200780020095.1, Response filed Sep. 17, 2012 to Office Action dated May 3, 2012", (w/ English Translation of Claims), 17 pgs.
"Chinese Application Serial No. 200780020095.1, Response filed Nov. 8, 2011 to Office Action dated Jun. 24, 2011", (w/ English Translation of Amended Claims), 20 pgs.
"Chinese Application Serial No. 200480021259.9, Office Action dated May 8, 2009", (w/English Translation), 6 pgs.
"Confirmed Cases of Avian Influenza A(H5N1)", World Health Organization, (Jan. 28, 2004), 1 pg.
"Eurasian Application No. 200501890, Notice of Allowance dated Jun. 23, 2009", 1 pg.
"Eurasian Application Serial No. 200501890, Office Action dated Mar. 23, 2007", (w/ English Translation), 2 pgs.
"Eurasian Application Serial No. 200501890, Office Action dated Sep. 4, 2008", (English Translation), 1 pg.
"Eurasian Application Serial No. 200501890, Office Action dated Dec. 17, 2007", (w/ English Translation), 6 pgs.
"Eurasian Application Serial No. 200501890, Response filed Mar. 26, 2008 to Office Action dated Dec. 17, 2007", (w/ English Translation of Claims), 15 pgs.
"Eurasian Application Serial No. 200501890, Response filed Jun. 14, 2007 to Office Action dated Mar. 23, 2007", (w/ English Translation of Claims), 11 pgs.
"Eurasian Application Serial No. 200501890, Response filed Dec. 17, 2008 to Office Action dated Sep. 4, 2008", (w/ English Translation of Claims), 14 pgs.
"Eurasian Application Serial No. 200701097,Office Action dated Sep. 4, 2008", OAR-MISC, 2 pgs.
"Eurasion Application Serial No. 200701097, Office Action dated Jun. 16, 2009", 3 pgs.
"European Application 04750333.9, Communication dated Oct. 12, 2006", 6 pgs.
"European Application 04750333.9, Communication dated Dec. 8, 2006", 4 pgs.
"European Application 04750333.9, Communication dated Apr. 11, 2008", 6 pgs.
"European Application 04750333.9, Response filed Oct. 4, 2007 to Communication dated Dec. 8, 2006", 42 pgs.
"European Application 04750333.9, Response filed Nov. 21, 2006 to Communication Oct. 12, 2006", 4 pgs.
"European Application Serial No. 03716017.3, Office Action dated Aug. 23, 2012", 4 pgs.
"European Application Serial No. 01928486.8 Office Action dated Oct. 1, 2009", 2 pgs.
"European Application Serial No. 01928486.8, Communication dated Aug. 10, 2007", 3 pgs.
"European Application Serial No. 01928486.8, Communication dated Sep. 20, 2005", 4 pgs.
"European Application Serial No. 01928486.8, Office Action dated Feb. 19, 2009", 3 pgs.
"European Application Serial No. 01928486.8, Response filed Jan. 30, 2006 to Communication dated Sep. 20, 2005", 9 pgs.
"European Application Serial No. 01928486.8, Response filed Aug. 28, 2009 to Communication dated Feb. 19, 2009", 5 pgs.
"European Application Serial No. 01928486.8, Response filed Jan. 21, 2008 to Communication dated Aug. 10, 2007", 11 pgs.
"European Application Serial No. 01928486.8, Response filed Dec. 9, 2009 to Office Action dated Oct. 1, 2009", 11 pgs.
"European Application Serial No. 02724994.5, Office Action dated Mar. 27, 2009", 2 pgs.
"European Application Serial No. 03716017.3, Communication and Supplementary European Search Report, dated Jan. 2, 2008", 8 pgs.
"European Application Serial No. 03716017.3, Communication dated May 23, 2006", 3 pgs.
"European Application Serial No. 03716017.3, Communication dated Jul. 26, 2006", 2 pgs.
"European Application Serial No. 03716017.3, Communication dated Oct. 20, 2008", 7 pgs.
"European Application Serial No. 03716017.3, Office Action dated Jul. 27, 2010", 4 pgs.
"European Application Serial No. 03716017.3, Response filed Feb. 4, 2011 to Office Action dated Jul. 27, 2010", 12 pgs.
"European Application Serial No. 03716017.3, Response filed Jul. 28, 2006 to Communication dated May 23, 2006", 5 pgs.
"European Application Serial No. 03716017.3, Response filed Aug. 19, 2009 to Communication dated Oct. 20, 2008", 17 pgs.
"European Application Serial No. 04750333.9, Office Action dated Jan. 22, 2009", 5 pgs.
"European Application Serial No. 04750333.9, Response filed Oct. 21, 2008 to Communication dated Apr. 11, 2008", 15 pgs.
"European Application Serial No. 04750333.9, Response filed Nov. 17, 2009 to Communication dated Jan. 22, 2009", 17 pgs.
"European Application Serial No. 04750333.9, Summons To Attend Oral Proceedings dated Aug. 3, 2011", 13 pgs.
"European Application Serial No. 04776133.3, Communication dated Mar. 30, 2006", 3 pgs.
"European Application Serial No. 04776133.3, Office Action dated Jan. 5, 2010", 4 pgs.
"European Application Serial No. 04776133.3, Response filed Jan. 25, 2007 to Communication dated Mar. 30, 2006", 20 pgs.
"European Application Serial No. 04776133.3, Response filed Jul. 15, 2010 to Office Action dated Jan. 5, 2010", 9 pgs.
"European Application Serial No. 04809419.7, Communication dated Apr. 3, 2007", 3 pgs.
"European Application Serial No. 04809419.7, Response filed Oct. 19, 2007 to Communication dated Apr. 3, 2007", 20 pgs.

(56) References Cited

OTHER PUBLICATIONS

"European Application Serial No. 07754132.4, Office Action dated Apr. 28, 2009", 4 pgs.
"European Application Serial No. 07754132.4, Office Action dated Sep. 5, 2011", 5 pgs.
"European Application Serial No. 07754132.4, Response filed Feb. 5, 2010 to Office Action dated Apr. 28, 2009", 15 pgs.
"European Application Serial No. 07754132.4, Response filed Mar. 15, 2012 to Office Action dated Sep. 5, 2011", 21 pgs.
"Evaluation of Medicines for human Use", EMEA/CPMP/BWP/2289/01, London The European Agency for the Evaluation of Medicinal Products, Committee for Proprietary Medicinal Products (CPMP), (Feb. 20, 2003), 14.
"Genbank Accession #AAA43733, Neuraminidase Protein of Influenza B/Beijing/1/87 virus,", (1993), 4 pg.
"Genbank Accession # AAU94753, Neuraminidase Protein of Influenza B/Aichi/5/88 virus,", (2004), 7 pgs.
"Genbank Accession # ABA02233, Neuraminidase Protein of Influenza B/Perth/211/2001 virus", (2006), 3 pgs.
"Genbank Accession #,", neuraminidase influenza virus B/memphis/20/96,, (1999), 3 pgs.
"GFP antibody (ab6556) datasheet", (r) abcam, [online], [retrieved on Dec. 5, 2004], Retrieved from the Internet: <URL: http://www.abcam.com/index.html?datasheet=6556>, (2004), 5 pgs.
"Indian Application Serial No. 02082/KOLNP/2005, Examination Report dated Mar. 17, 2008", 1 pg.
"Indian Application Serial No. 02082/KOLNP/2005, Examination Report dated Dec. 28, 2007", 1 pg.
"Indian Application Serial No. 02082/KOLNP/2005, First Examination Report dated Jan. 25, 2007", 9 pgs.
"Indian Application Serial No. 02082/KOLNP/2005, Response filed Jan. 22, 2008 to Examination Report dated Dec. 28, 2007", 13 pgs.
"Indian Application Serial No. 0282/KOLNP/2005, Response filed Jun. 10, 2008 to Examination Report dated Mar. 17, 2008", 3 pgs.
"Indian Application Serial No. 02082/KOLNP/2005, Response filed Nov. 19, 2007 to First Examination Report dated Jan. 25, 2007", 26 pgs.
"Indian Application Serial No. 2272/KOLNP/2005, First Examination Report dated Mar. 17, 2008", 10 pgs.
"Indian Application Serial No. 2272/KOLNP/2005, Response filed Mar. 16, 2009 to Subsequent Examination Report dated Mar. 6, 2009", 12 pgs.
"Indian Application Serial No. 2272/KOLNP/2005, Response filed Oct. 11, 2008 to First Examination Report dated Mar. 17, 2008", 27 pgs.
"Indian Application Serial No. 2272/KOLNP/2005, Subsequent Examination Report dated Mar. 6, 2009", 1 pg.
"Indian Application Serial No. 2388/KOLNP/2005, First Examination Report dated Mar. 28, 2007", 10 pgs.
"Influenza B/lee/40, neuraminidase & nb (seg 6) rna", Database EM_VI E.B.I. Hinxton U.K., (Jun. 13, 1985), 10 pgs.
"International Application No. PCT/US2004/016680, International Search Report", (dated Feb. 2, 2005), 7 pgs.
"International Application Serial No. PCT/US01/11963, Amendment filed Sep. 9, 2002 to Written Opinion dated Aug. 7, 2002", 12 pgs.
"International Application Serial No. PCT/US01/11963, International Preliminary Examination Report dated Oct. 15, 2002", 13 pgs.
"International Application Serial No. PCT/US01/11963, International Search Report dated May 7, 2002", 5 pgs.
"International Application Serial No. PCT/US01/11963, Response filed Sep. 9, 2002 to Written Opinion dated Aug. 7, 2002", 12 pgs.
"International Application Serial No. PCT/US01/11963, Written Opinion dated Jun. 14, 2002", 2 pgs.
"International Application Serial No. PCT/US01/11963, Written Opinion dated Aug. 7, 2002", lpgs.
"International Application Serial No. PCT/US2004/012050, International Search Report dated Feb. 2, 2005", 8 pgs.
"International Application Serial No. PCT/US2004/012050, Written Opinion dated Feb. 2, 2005", 12 pgs.
"International Application Serial No. PCT/US2004/016649, International Preliminary Report on Patentability dated Dec. 15, 2005", 7 pgs.
"International Application Serial No. PCT/US2004/016649, International Search Report dated Apr. 18, 2005", 6 pgs.
"International Application Serial No. PCT/US2004/016680, International Preliminary Report on Patentability dated Dec. 15, 2005", 11 pgs.
"International Application Serial No. PCT/US2005/041991, International Search Report dated Jun. 4,2007", 5 pgs.
"International Application Serial No. PCT/US2005/041991, Written Opinion dated Jun. 4, 2007", 6 pgs.
"International Application Serial No. PCT/US2007/007562, International Search Report dated Jan. 14, 2008", 8 pgs.
"International Application Serial No. PCT/US2007/007562, Written Opinion dated Jan. 14, 2008", 9 pgs.
"International Application Serial No. PCT/US2007/013407, International Search Report dated Oct. 24, 2008", 10 pgs.
"International Application Serial No. PCT/US2007/013407, Written Opinion dated Oct. 24, 2008", 14 pgs.
"International Application Serial No. PCT/US2008/004125, International Search Report dated Feb. 20, 2009", 6 pgs.
"International Application Serial No. PCT/US2008/004125, Written Opinion dated Feb. 20, 2009", 8 pgs.
"International Application Serial No. PCT/US2008/005641, International Search Report dated Feb. 4, 2009", 6 pgs.
"International Application Serial No. PCT/US2008/005641, Written Opinion dated Feb. 4, 2009", 8 pgs.
"International Application Serial No. PCT/US2008/007417, International Search Report dated Jan. 30, 2009", 20 pgs.
"International Application Serial No. PCT/US2008/007417, Written Opinion dated Jan. 30, 2009", 10 pgs.
"International Application Serial No. PCT/US2008/007582, International Search Report and Written Opinion dated Feb. 18, 2009", 16 pgs.
"International Application Serial No. PCT/US2009/000056, International Search Report dated Feb. 9, 2010", 3 pgs.
"International Application Serial No. PCT/US2009/000056, Written Opinion dated Feb. 9, 2010", 5 pgs.
"International Application Serial No. PCT/US2009/006019, International Preliminary Report on Patentability dated May 19, 2011", 8 pgs.
"International Application Serial No. PCT/US2009/006019, Invitation to Pay Additional Fee dated Apr. 6, 2010", 8 pgs.
"International Application Serial No. PCT/US2009/006019, Search Report dated Jun. 10, 2010", 7 Pgs.
"International Application Serial No. PCT/US2009/006019, Written Opinion dated Jun. 10, 2010", 6 pgs.
"International Application Serial No. PCT/US2010/054128, Preliminary Report on Patentability dated May 10, 2012", 10 pgs.
"International Application Serial No. PCT/US2010/054128, Search Report dated Feb. 23, 2011", 6 pgs.
"International Application Serial No. PCT/US2010/054128, Written Opinion dated Feb. 23, 2011", 8 pgs.
"Israel Application Serial No. 163,546, Office Action dated Nov. 12, 2009", w/English Translation, 1 pg.
"Israel Application Serial No. 163,546, Response filed Oct. 20, 2010 to Office Action dated Jun. 8, 2010", w/English Claims, 8 pgs.
"Israel Application Serial No. 163,546, Response filed Nov. 27, 2008 to First Examination Report dated Jul. 28, 2008", w/English Claims, 13 pgs.
"Israel Application Serial No. 163546, Office Action dated Jun. 8, 2010", w/English Translation, 2 pgs.
"Israel Application Serial No. 183026, Office Action dated Feb. 9, 2009", w/English Translation, 2 pgs.
"Israeli Application Serial No. 171831, Notification of Defects dated Nov. 10, 2008", w/English Translation, 10 pgs.
"Israeli Application Serial No. 163,546, First Examination Report dated Jul. 28, 2008", (English Translation), 2 pgs.
"Israeli Application Serial No. 163,546, Substantive Examination Report dated Feb. 23, 2009", w/English Translation, 3 pgs.

(56) References Cited

OTHER PUBLICATIONS

"Israeli Application Serial No. 171372, Office Action dated Feb. 21, 2010", w/English Translation, 2 pgs.
"Israeli Application Serial No. 171372, Office Action dated Nov. 6, 2008", (Translation), 12 pgs.
"Israeli Application Serial No. 171372, Response filed Nov. 18, 2010 to Office Action dated Feb. 21, 2010", w/English Translation, 19 pgs.
"Israeli Application Serial No. 171831, Office Action dated Feb. 21, 2010", Translation, 2 pgs.
"Israeli Application Serial No. 171831, Office Action dated Apr. 18, 2012", (English Translation), 2 pgs.
"Israeli Application Serial No. 171831, Response filed Nov. 6, 2012 to Office Action dated Apr. 18, 2012", w/English Claims, 54 pgs.
"Israeli Application Serial No. 171372,Office Action dated Feb. 20, 2011", (Translation), 2 pgs.
"Japanese Application No. 2001-576868, Office Action dated May 31, 2011", (w/ English Translation), 5 pgs.
"Japanese Application No. 2001-5768687 Response filed Apr. 26, 2011 to Office Action dated Nov. 2, 2010", (w/ Translation of Amended Claims), 14 pgs.
"Japanese Application Serial No. 2001-576868, Office Action dated Nov. 2, 2010", w/ English Translation), 10 pgs.
"Japanese Application Serial No. 2001-576868, Response filed Dec. 1, 2011 to Office Action dated May 3, 2011", (w/ English Translation of Amended Claims), 37 pgs.
"Japanese Application Serial No. 2003-315106, Amended Claims filed Oct. 15, 2009 in Response to Office Action dated Jun. 24, 2009", (English Translation), 6 pgs.
"Japanese Application Serial No. 2003-315106, Notice of Allowance dated Jan. 5, 2010", (w/ English Translation), 5 pgs.
"Japanese Application Serial No. 2003-315106, Office Action dated Jun. 24, 2009", (w/ English Translation), 10 pgs.
"Japanese Application Serial No. 2003-568038, Amendment filed Aug. 19, 2005", (English Translation), 8 pgs.
"Japanese Application Serial No. 2003-568038, Notice of Allowance dated Nov. 30, 2009", w/out English Translation, 3 pgs.
"Japanese Application Serial No. 2003-568038, Office Action dated May 15, 2009", (w/ English Translation), 7 pgs.
"Japanese Application Serial No. 2003-568038, Office Action dated Jul. 10, 2008", (w/ English Translation), 11 pgs.
"Japanese Application Serial No. 2003-568038, Office Action dated Jul. 21, 2005", w/out English Translation, 3 pgs.
"Japanese Application Serial No. 2003-568038, Request for Examination filed Aug. 19, 2005 in Response to Official Action dated Jul. 21, 2005", (w/ Partial English Translation of Specification), 8 pgs.
"Japanese Application Serial No. 2003-568038, Response filed Sep. 14, 2009 to Office Action dated May 15, 2009", (w/ English Translation of Amended Claims), 10 pgs.
"Japanese Application Serial No. 2003-568038, Response filed Dec. 10, 2008 to Office Action dated Jul. 10, 2008", (w/ English Translation of Amended Claims), 15 pgs.
"Japanese Application Serial No. 2006-513125, Office Action dated Mar. 9, 2010", (English Translation), 11 pgs.
"Japanese Application Serial No. 2006-513125, Response filed Aug. 30, 2010 to Office Action dated Mar. 9, 2010", (w/ English Translation of Amended Claims), 60 pgs.
"Japanese Application Serial No. 2006-533439, Decision of Final Rejection dated Aug. 14, 2012", (w/ English Translation), 5 pgs.
"Japanese Application Serial No. 2006-533439, Office Action dated Mar. 9, 2010", (w/ English Translations), 20 pgs.
"Japanese Application Serial No. 2006-533439, Office Action dated Mar. 27, 2012", w/ English Translation, 8 pgs.
"Japanese Application Serial No. 2006-533439, Response filed May 21, 2012 to Office Action dated Mar. 27, 2012", (w/ English Translation of Amended Claims), 19 pgs.
"Japanese Application Serial No. 2006-533439, Response filed Aug. 3, 2011 to Office Action dated Feb. 15, 2011", (w/ English Translation of Amended Claims), 18 pgs.
"Japanese Application Serial No. 2006-533439,Office Action dated Feb. 15, 2011", (w/ English Translation), 13 pgs.
"Japanese Application Serial No. 2006-533439; Office Action Response filed Jul. 9, 2010", (w/English Translation of Claims), 25 pgs.
"Japanese Application Serial No. 2008-315106, Office Action dated Jun. 24, 2009", (w/ English Translation), 10 pgs.
"Japanese Application Serial No. 2008-315106, Response filed Oct. 15, 2009 to Office Action dated Jun. 24, 2009", w/English Translation, 103 pgs.
"Japanese Application Serial No. 2008-315106, Response filed Oct. 15, 2009 to Office Action dated Jun. 24, 2009", (w/ English Translation of Amended Claims), 103 pgs.
"Japanese Application Serial No. 2008-315106, Response filed Dec. 3, 2009 to Office Action dated Jun. 24, 2009", (w/ English Translation of Claims), 9 pgs.
"Japanese Application Serial No. 2009-238781, Office Action dated Oct. 11, 2011", (w/ English Translation), 3 pgs.
"Japanese Application Serial No. 2009-502945, Office Action dated Oct. 23, 2012", (w/English Translation), 16 pgs.
"Japanese Application Serial No. 2011-111048, Office Action dated Sep. 18, 2012", (w/ English Translation), 10 pga.
"Japanese Application Serial No. 2012-536963, Voluntary Amendment filed Jun. 27, 2012", (w/ English Translation of Amended Claims), 17 pgs.
"Japanese Application Serial No. 2006-513125,Final Office Action dated Jan. 18, 2011", (English Translation), 4 pgs.
"Korean Application Serial No. 10-2005-7020077, Response filed Apr. 28, 2008 to Examination Report dated Dec. 28, 2007", (w/ English Translation of Revised Claims), 41 pgs.
"Korean Application Serial No. 10-2004-7012647, Office Action dated Feb. 26, 2010", (w/English Translation), 7 pgs.
"Korean Application Serial No. 10-2004-7012647, Response filed Jun. 10, 2010 to Office Action dated Feb. 26, 2010", (w/ English Translation of Claims), 17 pgs.
"Korean Application Serial No. 10-2005-7020077, Examination Report dated Dec. 28, 2007", (w/ English Translation), 8 pgs.
"Korean Application Serial No. 10-2005-7020077, Notice of Preliminary Rejection dated Jun. 28, 2007", (w/ English Translation), 9 pgs.
"Korean Application Serial No. 10-2005-7020077, Response filed Aug. 28, 2007 to Notice of Preliminary Rejection dated Jun. 28, 2007", (w/ EnglishTranslation), 40 pgs.
"Korean Application Serial No. 10-2005-7022564, Notice of Preliminary Rejection dated Jul. 25, 2007", W/ English Translation, 5 pgs.
"Korean Application Serial No. 10-2005-7022564, Office Action dated Aug. 6, 2008", W/ English Translation, 4 pgs.
"Korean Application Serial No. 10-2005-7022564, Response and Amendment filed Dec. 29, 2008 to Office Action dated Aug. 6, 2008", W/ English Translation, 16 pgs.
"Korean Application Serial No. 10-2005-7022564, Response filed Mar. 25, 2008 to Notice of Preliminary Rejection dated Jul. 25, 2007", (w/ English Translation of Claims), 35 pgs.
"Korean Application Serial No. 10-2005-7022564, Response filed Dec. 29, 2008 to Office Action dated Aug. 6, 2008", (w/ English Translation of Claims), 16 pgs.
"Korean Application Serial No. 10-2010-7011520, Office Action dated Jul. 20, 2010", (w/English Translation), 6 pgs.
"Korean Application Serial No. 10-2010-7011520, Response filed Oct. 20, 2010 to Office Actiion dated Jul. 20, 2010", (w/ English Translation of Amended Claims), 30 pgs.
"Korean Application Serial No. 10-2010-7011520, Amended Claims filed May 24, 2011 in Response to Office Action dated Feb. 24, 2011", (English Translation of Amended Claims), 22 pgs.
"Korean Application Serial No. 10-2010-7011520, Office Action dated Feb. 24, 2011", (w/English Translation), 5 pgs.
"Mexican Application No. PA/a/2005/012712 Office Action dated Jul. 21, 2009", (w/ English Translation), 9 pgs.
"Mexican Application Serial No. MX/a/2009/006341, Office Action dated Mar. 29, 2012", (English Translation), 1 pg.
"Mexican Application Serial No. MX/a/2009/006341, Response filed Jun. 4, 2012 to Mar. 29, 2012", (w/ English Translation of Amended Claims), 16 pgs.

(56) References Cited

OTHER PUBLICATIONS

"Mexican Application Serial No. PA/a/2004/007914, Office Action dated Feb. 14, 2008", (w/English Translation), 3 pgs.
"Mexican Application Serial No. PA/a/2004/007914, Office Action dated Feb. 22, 2008", (English Translation), 3 pgs.
"Mexican Application Serial No. PA/a/2004/007914, Response filed Jun. 11, 2008 to Office Action dated Feb. 22, 2008", (w/ English Translation of Claims), 68 pgs.
"Mexican Application Serial No. PA/a/2005/011250, Office Action dated Aug. 23, 2010", W/ English Translation, 4 pgs.
"Mexican Application Serial No. PA/a/2005/011250, Response Filed Dec. 20, 2010 to Office Action dated Aug. 23, 2010", (w/ English Translation of Claims), 14 pgs.
"Mexican Application Serial No. PA/a/2005/012712 , Office Action dated Aug. 11, 2009", (English Translation), 5 pgs.
"Mexican Application Serial No. PA/a/2005/012712, Office Action dated May 12, 2010", (w/ English Translation), 19 pgs.
"Mexican Application Serial No. PA/a/2005/012712, Office Action dated Jun. 9, 2010", (w/ English Translation), 11 pgs.
"Mexican Application Serial No. PA/a/2005/012712, Office Action dated Nov. 30, 2009", (w/ English Translation), 14 pgs.
"Mexican Application Serial No. PA/a/2005/012712, Official Action dated Mar. 5, 2009", (English Translation), 2 pgs.
"Mexican Application Serial No. PA/a/2005/012712, Response filed Sep. 27, 2010 to Office Action dated May 12, 2010", (w/ English Translation of Claims), 19 pgs.
"Neuraminidase [Influenza A virus (A/Aichi/2/1968 (H3N2))]", GenBank: BAD16642.1, NCBI, [online]. Retrieved from the Internet: <URL: http://www.ncbi.nlm.nih.gov/protein/46401580>, (2008), 3 pgs.
"Neuraminidase [Influenza B virus]", GenBank: CAB71147.1, NCBI, [online]. Retrieved from the Internet: <URL: http://www.ncbi.nlm.nih.gov/protein/6851026>, (2005), 3 pgs.
"New Zealand Application Serial No. 542935, Examination Report, dated Feb. 25, 2008", 2 pgs.
"New Zealand Application Serial No. 542935, Examination Report dated Jun. 14, 2006", 2 pgs.
"New Zealand Application Serial No. 542935, Response filed Jun. 30, 2008 to Examination Report dated Feb. 25, 2008", 32 pgs.
"New Zealand Application Serial No. 542935, Response filed Aug. 7, 2007 to Examination Report dated Jun. 14, 2006", 18 pgs.
"New Zealand Application Serial No. 542935, Voluntary Amendments filed Sep. 12, 2007", 10 pgs.
"New Zealand Application Serial No. 543446, Examination Report, dated Feb. 29, 2008", 2 pgs.
"New Zealand Application Serial No. 543446, Examination Report, dated May 12, 2008", 1 pg.
"New Zealand Application Serial No. 543446, Response mailed Mar. 20, 2008 to Examination Report dated Feb. 29, 2008", 2 pgs.
"New Zealand Application Serial No. 543587, Examination Report dated Mar. 1, 2007", 1 pg.
"New Zealand Application Serial No. 543587, Examination Report dated Jul. 7, 2006", 2 pgs.
"New Zealand Application Serial No. 543587, Response filed Aug. 7, 2007 to Examination Reports dated Jul. 7, 2006 and Mar. 1, 2007", 24 pgs.
"New Zealand Application Serial No. 543587, Second Examination Report dated Feb. 25, 2008", 2 pgs.
"New Zealand Application Serial No. 555245, First Examination Report dated Aug. 26, 2008", 2 pgs.
"New Zealand Application Serial No. 555245, Subsequent Examiner Report dated Jul. 3, 2009", 1 pg.
"Nucleotide sequences of influenza virus segments 1 and 3 reveal mosaic structure of a small viral RNA segment", Database Uniprot, (Nov. 14, 2001), 2 pgs.
"PCT Application Serial No. PCT/US2005/041991, International Preliminary Report on Patentability / Written Opinion dated Jul. 19, 2007", 8 pgs.
"RNA World", http://faculty.uca.edu/~benw/biol4415/lecture10a/tsld003.htm, (Observed Feb. 25, 2003), 1 pg.

"Russian Federation Application No. 2005136233, Office Action dated Dec. 25, 2007", 2 pgs.
"Russian Federation Application No. 2005136233, Response filed May 29, 2008 to Office Action dated Dec. 25, 2007", (w/ Partial English Translation), 7 pgs.
"Russian Federation Application Serial No. 2005136233, First Office Action dated Feb. 27, 2007", (w/ English Translation), 5 pgs.
"Russian Federation Application Serial No. 2005136233, Response filed Nov. 20, 2007 to Office Action", (w/ English Translation of Amended Claims), 18 pgs.
"Singapore Application Serial No. 200507467-9, Invitation to Respond to Written Opinion dated Jun. 19, 2007", 5 pgs.
"Singaporean Application Serial No. 200506858-0, Examination Report dated Feb. 9, 2007", 4 pgs.
"Singaporean Application Serial No. 200506858-0, Response filed Dec. 22, 2006 to Written Opinion dated Jul. 26, 2006", 18 pgs.
"Singaporean Application Serial No. 200506858-0, Written Opinion dated Jul. 26, 2006", 8 pgs.
"Singaporean Application Serial No. 200507468-7, Examination Report dated Mar. 19, 2008", 5 pgs.
"Singaporean Application Serial No. 200507468-7, Invitation to Respond to Written Opinion dated Jun. 12, 2007", 6 pgs.
"Singaporean Application Serial No. 200507468-7, Response filed Nov. 7, 2007 to Invitation to Respond to Written Opinion dated Jun. 12, 2007", 9 pgs.
"The Integral Membrane Proteins of Influenza A, B, and C Viruses", The Influenza Sequence Database, http://www.flu.lanl.gov/review/fluc.review2.html, (Observed Feb. 26, 2003), 1 pg.
"Ukrainian Application Serial No. 200512619, Office Action dated Feb. 27, 2009", (w/ English Translation), 21 pgs.
"Ukrainian Application Serial No. 200512619, Office Action dated Jun. 17, 2009", (w/ English Translation), 4 pgs.
"Ukrainian Application Serial No. 200512619, Response filed Apr. 8, 2009 to Office Action dated Feb. 27, 2009", (w/ English Translation of Claims), 9 pgs.
Akarsu, H., et al., "Crystal structure of the M1 protein-binding domain of the influenza A virus nuclear export protein (NEP/NS2).", EMBO J., 22(18), (Sep. 15, 2003), 4646-55.
Albo, C., et al., "The 5' Ends of Thogoto Virus (Orthomyxoviridae) mRNAS Are Homogeneous in both Length and Sequence", Journal of Virology, 70(12), (1996), 9013-9017.
Alonso-Caplen, et al., "Efficient Transcription, Not Translation, is Dependent on Adenovirus Tripartite Leader Sequences at Late Times of Infection", Journal of Virology, vol. 62, No. 5, 1606-1616, (1988), 11 pgs.
Bancroft, C. T, et al., "Evidence for segment-nonspecific packaging of the influenza a virus genome", J Virol., 76(14), (Jul. 2002), 7133-9.
Banerjee, A. K., et al., "Gene Expression of Vesicular Stomatitis Virus Genome RNA.", Virology, 188(2), (1992), 417-428.
Baron, M. D., et al., "Rescue of Rinderpest Virus From Cloned cDNA", Journal of Virology, 71(2), (1997), 1265-1271.
Basler, C. F, et al., "Mutation of Neuraminidase Cysteine Residues Yields Temprature-Sensitive Influenza Viruses", Journal of Virology, 73(10), (Jun. 30, 1999), 8095-8103.
Beare, A. S., "Trials in Man With Live Recombinants Made From A/PR/8/34 (H0 N1) and Wild H3 N2 Influenza Viruses", The Lancet, 2(7938), (1975), 729-732.
Betakova, T., et al., "The NB protein is an Integral component of the membrane of influenza B virus.", J Gen Virol., 77 ( Pt 11), (Nov. 1996), 2689-94.
Bilsel, P., et al., "Mutations in the Cytoplasmic Tail of Influenza A Virus Neuraminidase Affect Incorporation into Virions", Journal of Virology, 67(11), (Nov. 30, 1993), 6762-6767.
Blount, K. F., et al., "The Hammerhead Ribozyme", Biochemical Society Transactions, 30(6), (2002), 1119-1122.
Bourmakina, S. V, et al., "Reverse genetics studies on the Filamentous morphology of influenza A Virus", Journal of General Virology (2003) 84,, (2003), 517-527.
Bowie, et al., "Deciphering the Message In Protein Sequences: Tolerance to Amino Acid I Substitutions", Science, 247, (Mar. 1990), 1306-1310.

(56) References Cited

OTHER PUBLICATIONS

Bowie, J. U., et al., "Deciphering the Message in Protein Sequences: Tolerance to Amino Acid Substitutions", Science, 247(4948) 1306-1310, (1990), 5 pgs.

Boyer, J. C., et al., "Infectious transcripts and cDNA clones of RNA viruses", Virology, 198(2), (Feb. 1994), 415-426.

Bradsher, K., "Cases of New Bird Flue in Hong Kong Prompt Worldwide Alerts", The New York Times web site, (Observed Feb. 22, 2003), 3 pgs.

Bradsher, K., "Man's Death of 'Bird Flu' in Hong Kong Raises Fears", The New York Times web site, (Observed Feb. 22, 2003), 3 pgs.

Brandli, A. W, et al., "A Polarized Epithelial Cell Mutant Deficient in Translocation of UDP-galactose into the Golgi Complex", Journal of Biological Chemistry, 263(31), (Nov. 5, 1988), 16283-16290.

Brands, R., et al., "Influvac: A Safe Madin Darby Canine Kidney (MDCK) Cell Culture-Based Influenza Vaccine", Dev. Biol. Stand., 98, (1999), 93-100.

Brassard, D.L., et al.. "Influenza B virus NB glycoprotein is a component of the virion", Virol., 220(2), No Document, (1996), 350-360.

Bridgen, A., et al., "Rescue of a Segmented Negative-Strand RNA Virus Entirely From Cloned Complementary DNAs", Proc. Natl. Acad. Sci. USA, 93, (1996), 15400-15404.

Bruhl, P., et al., "Humoral and Cell-Mediated Immunity to Vero Cell-Derived Influenza Vaccine", Vaccine, 19, (2001), 1149-1158.

Buchholz, U. J., et al., "Generation of Bovine Respiratory Syncytial (BRSV) From cDNA: BRSV NS2 is Not Essentiial for Virus Replication in Tissue Culture, and the Human RSV Leader Region Acts as a Functional BRSV Genome Promoter", Journal of Virology, 73(1), (1999), 251-259.

Bukreyev, A., et al., "Chimeric human parainfluenza virus bearing the Ebola virus glycoprotein as the sole surface protein is immunogenic and highly protective against Ebola virus challenge", Virology, 383(2), (Abstract Only), (2009), 1 pg.

Bukreyev, A., et al., "Recovery of infectious respiratory syncytial virus expressing an additional, foreign gene", Journal of Virology, 70(10), (Oct. 1996), 6634-6641.

Bullido, R., et al., "Influenza A Virus NEP (NS2 protein) Downregulates RNA Synthesis of Model Template RNAs", Journal of Virology, 75(10), (May 2001), 4912-4917

Bullido, R., et al., "Influenza A virus NEP(NS2 protein) downregulates RNA synthesis of model template RNAs", Journal of Virology, vol. 75 4912-4917, (May 2001), 6 pgs.

Burmeister, W. P., et al., "The 2.2 A resolution crystal structure of influenza B neuraminidase and its complex with sialic acid", The EMBO Journal, 11(1), (1992), 49-56.

Cardona, C. J., "Avian Influenza", http://www.vetmed.ucdavis.edu/vetex/INF-PO_AvianInfluenzaFS.html, ((Observed Feb. 22, 2003), 3 pgs.

Castrucci, M. R, et al., "Attenuation of Influenza A Virus by Insertion of a Foreign Epitope into the Neuraminidase", Journal of Virology, 66(8), (1992), 4647-4653.

Castrucci, M. R., et al., "Biologic Importance of Neuraminidase Stalk Length in Influenza A Virus", Journal of Virology, 67(2), (1993), 759-764.

Castrucci, M. R, et al., "Protection against Lethal Lymphocytic Choriomeningitis Virus (LCMV) Infection by Immunization of Mice with an Influenza Virus Containing an LCMV Epitope Recognized by Cytotoxic T Lymphocytes", Journal of Virology, 68(6), (1994), 3486-3490.

Castrucci, Maria R., et al., "Reverse genetics system for generation of an influenza A virus mutant containing a deletion of the carboxyl-terminal residue of M2 protein.", J Virol., 69(5), (May 1995), 2725-8.

Chang, M. W., et al., "Analysis of HIV Wild-Type and Mutant Structures via in Silico Docking against Diverse Ligand Libraries", J. Chem. Inf. Model., 47(3), (2007), 1258-1262.

Chen, H, et al., "Generation and evaluation of a high-growth reassortant H9N2 influenza A virus as a pandemic vaccine candidate", Vaccine, 21(17-18), (May 16, 2003), 1974-9.

Chen, Z., et al., "Influenza A Virus NS1 Protein Targets Poly(A)-Binding Protein II of the Cellular'-End Processing Machinery", The EMBO Journal, 18(8), (1999), 2273-2283.

Chowrira, B M., et al., "In Vitro and in Vivo Comparision of Hammerhead, Hairpin, and Hepatitis Delta Virus Self-Processing Ribozyme Cassettes", The Journal of Biological Chemistry, 269(41), (1994), 25856-25864.

Claas, E C. J., et al., "Human Influenza A H5N1 Virus Related to a Highly Pathogenic Avian Influenza Virus", The Lancet, 351, (1998), 472-477.

Clarke, D. K., et al., "Rescue of Mumps Virus From cDNA", Journal of Virology, 74(10), (2000), 4831-4838.

Coleman, P. M., et al., "Sequence and Structure Alignment, of Paramyxovirus Hemagglutinin-Neuraminidase with Influenza Virus Neuraminidase", Journal of Virology, 67(6), (1993), 2972-2980.

Collins, P. L., et al., "Chapter 41—Parainfluenza Viruses", In: Fields Virology, edited by Fields, B. N., et al. (3rd Edition, 1996, Lippincott—Raven Publishers, Philadelphia, PA, 1205-1241.

Collins, P. L., et al., "Production of Infectious Human Respiratory Syncytial Virus From Cloned cDNA Confirms an Essential Role for the Transcription Elongation Factor From the 5' Proximal Open Reading Frame of the M2 mRNA in Gene Expression and Provides a Capability for Vaccine D", Proc. Natl. Acad. Sci. USA, 92, (1995), 11563-11567.

Collins, P. L., "Rescue of Synthetic Analogs of Respiratory Syncytial Virus Genomic RNA and Effect of Truncations and Mutations on the Expression of a Foreign Reporter Gene", Proc. Natl. Acad. Sci. USA, 88, (1991), 9663-9667.

Conzelmann, K.-K., "Genetic Engineering of Animal RNA Viruses", Trends in Microbiology, 4(10), (1996), 386-393.

Conzelmann, K.-K., "Genetic manipulation of non-segmented negative-strand RNA viruses", Journal of General Virology, 77(Pt. 3), (Mar. 1996), 381-389.

Conzelmann, K.-K., "Nonsegmented Negative-Strand RNA Viruses: Genetics and Manipulation of Viral Genomes", Annu. Rev. Genet., 32, (1998), 123-162.

Conzelmann, K.-K., "Rescue of Synthetic Genomic RNA Analogs of Rabies Virus by Plasmid-Encoded Proteins", Journal of Virology, 68(2), (1994), 713-719.

Craven, R. C., et al., "Late Domain Function Identified in the Vesicular Stomatitis Virus M Protein by Use of Rhabdovirus-Retrovirus Chimeras", Journal of Virology, 73(4), (1999), 3359-3365.

Crescenzo-Chaigne, B., et al., "Comparative Analysis of the Ability of the Polymerase Complexes of Influenza Viruses Type A, B and C to Assemble into Functional RNPs that Allow Expression and Replication of Heterotypic Model RNA Templates In Vivo", Virology, 265(2), (1999), 342-353.

De, B. P., et al., "Requirements and Functions of Vesicular Stomatitis Virus L and NS Proteins in the Transcription Process in Vitro", Biochemical and Biophysical Research Communications, 126(1), (1985), 40-49.

De, B. P., et al., "Rescue of synthetic analogs of genome RNA of human parainfluenza virus type 3", Virology, 196(1), (Sep. 1993), 344-348.

De, B. P., et al., "Reverse Genetics of Negative Strand RNA Viruses", Indian Journal of Biochemistry & Biophysics, 31, (1994), 367-375.

De La Luna, S., et al., "Influenza virus naked RNA can be expressed upon transfection into cells co-expressing the three subunits of the polymerase and the nucleoprotein from simian virus 40 recombinant viruses", Journal of General Virology, 74(pt. 3), (Mar. 1993), 535-539.

De La Luna, S., et al., "Influenza Virus NS1 Protein Enhances the Rate of Translation Initiation of Viral mRNAs", Journal of Virology, 69(4), (1995), 2427-2435.

Desselberger, Ulrich, et al., "The 3' and 5'-terminal sequences of influenza A, B and I C virus RNA segments are highly conserved and show partial inverted complementarity", Gene, 8 (3), (Feb. 1980), 315-328.

(56) References Cited

OTHER PUBLICATIONS

Dimmock, Nigel J, et al., "In vivo antiviral activity: defective interfering virus protects better against virulent Influenza A virus than avirulent virus", Journal of General Virology 87, (Jan. 8, 2006), 1259-1265.
Dimock, K., et al., "Rescue of Synthetic Analogs of Genomic RNA and Replicative-Intermediate RNA of Human Parainfluenza Virus Type 3", Journal of Virology, 67(5), (1993), 2772-2778.
Dollenmaier, G., et al., "Membrane-Associated Respiratory Syncytial Virus F Protein Expressed From a Human Rhinovirus Type 14 Vector is Immunogenic", Virology, 281(2), (Mar. 15, 2001), 216-230.
Dreher, T. W., et al., "Mutational Analysis of the Sequence and Structural Requirements in Brome Mosaic Virus RNA for Minus Strand Promoter Activity", Journal of Molecular Biology, 201(1), (1988), 31-40.
Du, Q., "Ribozyme Enzymology", http://academic.brooklyn.cuny.edu/chem/zhuang/QD/toppage1.htm, (Observed Feb. 25, 2003), 8 pgs.
Duff, K. C., et al., "The secondary structure of influenza A M2 transmembrane domain", FEBS Letters, 311 (3), (Oct. 1992), pp. 256-258.
Duff, K. C., et al., "The Transmembrane Domain of Influenza A M2 Protein Forms Amantadine-Sensitive Proton Channels in Planar Lipid Bilayers", Vilology, 190(1), (Sep. 1992), pp. 485-489.
Duhaut, S., et al., "Approximately 150 Nucleotides from the 5' End of an Influenza a segment 1 Defective Virion RNA Are needed for Genome Stability during passage of Defective Virus in Infected Cells", Virology, 275(2) 278-285 Academic Press, Orlando, US, (Sep. 30, 2000), 8 pgs.
Duhaut, S. D, et al., "Defective segment 1 RNAs that interfere with production of infectious influenza A virus require at least 150 nucleotides of 5' sequence: evidence from a plasmid-driven system", Journal of General Virology 83, (2002), 403-411.
Duhaut, S. D, et al., "Heterologous Protection of Misce from a lethal human HlNI Influenza A Virus Infection by H3NB Equine Defective Interfering Virus: Comparison of Defective RNA Sequences Isolated from the DI Inoculum and Mouse Lung", Virology, 248(2), Academic Press, Orlando, Us, (Sep. 1, 1998), 241-253.
Duhaut, Susan, et al., "Approximately 150 Nucleotides from the 5' End of an Influenza A Segment 1 defective virion RNA are Needed for Genome Stability During Passage of Defective Virus in Infected Cells.", Virology, 275(2), (2000), 278-285.
Dunham, Eleca J., et al., "Different Evolutionary Trajectories of European Avian-Like and Classical Swine H1N1 Influenza A Viruses", Journal of Virology, 83(11), (Jun. 2009), 5485-5494.
Dunn, E. F., et al., "Transcription of a recombinant bunyavirus RNA template by transiently expressed bunyavirus proteins", Virology, 211(1), (1995), 133-143.
Durbin, A. P, et al., "Human Parainfluenza Virus Type 3 (PIV) Expressing The Hemagglutinin Protein of Measles Virus Provides A Potential Method For Immunization Against Measles Virus and PIV3 in Early Infancy", Journal of Virology, 74(15), (Aug. 2000), 6821-6831.
Durbin, A. P., et al., "Recovery of infectious human parainfluenza virus type 3 from cDNA", Virology, 235(2), (Sep. 1, 1997), 323-332.
Dyall, J., et al., ""Identification of inhibitors of Ebola virus with a subgenomic replication system"", Antiviral Research,70(1), 19th International Conference on Antiviral Research, San Juan, PR (May 7-11, 20006), (May 2006), p. A39.
Elliott, R. M., "Emerging Viruses: The Bunyaviridae", Molecular Medicine, 3(9), (1997), 572-577.
Elliott, R. M., et al., "Rescue of Infectious Bunyavirus Entirely From Cloned cDNA", 10th International Conference on Negative Strand Virus, (Abstract No. 96), (1997), 1 pg.
Elliott, R. M., et al., "Some Highlights of Virus Research in 1990", Journal of General Virology, 72(Part8), (1991), 1761-1779.

Emerson, S. U., et al., "Both NS and L Proteins are Required for In Vitro RNA Synthesis by Vesicular Stomatitis Virus", Journal of Virology, 15(6), (1975), 1348-1356.
Enami, K., et al., "Influenza virus NS1 protein stimulates translation of the M1 protein", Journal of Virology, 68 1432-1437, (1994), 6 pgs.
Enami, M., "An influenza Virus Containing Nine Different RNA Segments", Virology, 185(1), (1991), 291-298.
Enami, M., et al., "High-Efficiency Formation of Influenza Virus Transfectants", Journal of Virology, 65(5), (1991), 2711-2713.
Enami, M., et al., "Introduction of Site-Specific Mutations into the Genome of influenza Virus", Proc. Natl. Acad. Sci. USA, 87, (1990), 3802-3805.
Enterlein, S., et al., "Antiviral Strategies Against: Exploring Gene Silencing Mechanisms to Identify Potential Antiviral Targets", Antiviral Research, 70(1), (Abstract 33), 19th International Conference on Antiviral Research, San Juan, PR (May 7-11, 2006), (May 2006), p. A38.
Enterlein, S., et al., "Untersuchungen zur Replikation und Transkription von Marburgund Ebolavirus", [Online]. 2005, Philipps-Universitat Marburg , XP002563470, Retrieved from the Internet: <URL:http://deposit.ddb.de/cgi-bin/dokserv?>idn=977005607&dok_var=d1&dok_ext=pdf&filename=977005607 .pdf> [retrieved on Jan. 15, 2010], (2005), p. 70-p. 84.
Fahey, J. L., et al., "Status of Immune-Based Therapies in HIV Infection and Aids", Clinincal and Experimental Immunology, 88(1), (1992), 1-5.
Feng, L., et al., "The mouse Pol I terminator is more efficient than the hepatitis delta virus ribozyme in generating influenza-virus-like RNAs with precise 3' ends in a plasmid-only-based virus rescue system", Arch Virol., 154(7), (2009), 1151-6.
Fischer, W, B, et al., "Viral ion channels: structure and function.", Biochim Biophys Acta., 1561(1), (Mar. 19, 2002), 27-45.
Flandorfer, A., et al., "Chimeric Influenza A Viruses with a Functional Influenza B Virus Neuraminidase or Hemagglutinin", Journal of Virology, 77(17), (2003), 9116-9123.
Fodor, E., et al., "Rescue of Influenza A Virus from Recombinant DNA", Journal of Virology, 73(11), XP002151487; ISSN:0022-538X, (Nov. 1999), 9679-9682.
Fortes, P., et al., "Influenza Virus NS1 Protein Inhibits Pre-mRNA Splicing and Blocks mRNA Nucleocytoplasmic Transport", The EMBO Journal, 13(3), (1994), 704-712.
Fouchier, R. A. M., et al., "Avian Influenze A Virus (H7N7) Associated With Human Conjunctivitis and a Fatal Case of Acute Respiratory Distress Syndrome", Proc. Natl. Acad. Sci. USA, 101(5) 1356-1361, (2004), 6 pgs.
Fuji, Y., et al., "Selective Incorporation of influenza virus RNA segments into virions", Proc. Natl. Acad. Sci. USA, 100(4) 2002-2007, (2003), 6 pgs.
Fujii, Y, et al., "The packaging of influenza viral genome", Virus, 52 (1), Uirusu (Japanese Journal Name), (Jun. 2002), 203-206.
Garay, R. P, et al., "Cancer relapse under chemotherapy: why TLR2/4 receptor agonists can help", Eur J Pharmacol., 563(1-3), (Jun. 1, 2007), 1-17.
Garcia-Sastre, A., et al., "Genetic Manipulation of Negative-Strand RNA Virus Genomes", Annu. Rev. Microbiol., 47, (1993), 765-790.
Garcia-Sastre, A., et al., "Introduction of Foreign Sequences into the Genome of influenza A Virus", Dev. Biol. Stand. vol. 82, (1994), 237-246.
Garcia-Sastre, A., et al., "Introduction of Foreign Sequences into the Genome of Influenza A Virus", In: Recombinant Vectors In Vaccine Development. Dev. Biol. Stand., 82, Fred Brown, Editor, (1994), 237-246.
Garcia-Sastre, A., et al., "Introduction of foreign sequences into the genome of influenza A virus.", Dev Biol Stand., 82, (1994), 237-246.
Garcia-Sastre, A., et al., "The cytoplasmic tail of the neuraminidase protein of influenza A virus does not play an important role in the packaging of this protein into viral envelopes", Virus Research, 37(1), (1995), 37-47.
Garcia-Sastre, A., et al., "Use of a mammalian internal ribosomal entry site element for expression of a foreign protein by a transfectant influenza virus.", Journal of Virology, 68(10), (1994), 6254-6261.

(56) References Cited

OTHER PUBLICATIONS

Garcia-Sastre, Adolfo, et al., "Use of a Mammalian Internal Ribosomal Entry Site Element for Expression of a Foreign Protein by a Transfectant Influenza Virus", Journal of Virology, 68(10) 6254-6261, (Jun. 30, 1994), 8 pgs.
Garcin, D., et al., "A Highly Recombinogenic System for the Recovery of Infectious Sendai Paramyxovirus From cDNA: Generation of a Novel Copy-Back Nondefective Interfering Virus", The EMBO Journal, 14(24), (1995), 6087-6094.
Garrett, L., "Deadly Ebola, Avian Influenza Re-Emerging", (Feb. 20, 2003), 3 pgs.
Genbank, "", ABD36884.1, (2007).
Genbank, "", CY002484.1, (2005).
Gerdil, C., "The Annual Production Cycle for Influenza Vaccine", Vaccine, 21 1776-1779, (2003), 4 pgs.
Ghate, Anita A, et al., "Influenza Type B Neuraminidase Can Replace the Function of Type A Neuraminidase", Virology, 264 (2), (Nov. 1999), 265-277.
Giddings, A M, et al., "The matrix prolein of HIV-is not sufficient for assembly and release of virus-like particles", Virology, 248(1), (1998), 108-16.
Gilleland, H. E, et al., "Chimeric Influenza Virus Incorporating Epitopes of Outer Membrane Protein F as a Vaccine Against Pulmonary Infection with Pseudomonas Aeruginosa", Behring Inst. Mitt. 98, (Feb. 28, 1997), 291-301.
Gomez-Puertas, P., et al., "Influenza Virus Matrix Protein is The Major Driving Force in Virus Budding", Journal of Virology, 74 11538-11547, (Dec. 1, 2000), 10 pgs.
Goto, H., "Mutations Affecting the Sensitivity of the Influenza Virus Neuraminidase to 4-Guanidino-2, 4-dideoxy 2, 3-dehydro-N-acetylneuraminic Acid", Virology, 238, (1997), 265-272.
Grambas, S., et al., "Influence of amantadine resistance mutations on the pH regulatory function of the M2 protein of Influenza A viruses", Virology, 191(2), (Dec. 1992), 541-549.
Green, R. F., et al., "Glycosylation Does Not Determine Segregation of Viral Envelope T Proteins in the Plasma Membrane of Epithelial Cells", J. Cell Biol., 89(2), (1981), 230-239.
Groseth, A., et al., "RNA Polymerase I-Driven Minigenome System for Ebola Viruses", Journal of Virology, 79(7), (2005), 4425-4433.
Grosfeld, H., et al., "RNA Replication by Respiratory Syncytial Virus (RSV) is Directed by the N, P, and L Proteins; Transcription Also Occurs Under These Conditions but Requires RSV Superinfection for Efficient Synthesis of Full-Length mRNA", Journal of Virology, 69(9), (1995), 5677-5686.
Gubareva, "Molecular mechanisms of influenza virus resistance to neuraminidase inhibitors", Virus Research, vol. 103, (2004), pp. 199-203.
Gunther, S, et al., "Application of real-time PCR for testing antiviral compounds against Lassa virus, SARS coronavirus and Ebola virus in vitro", Antiviral Research, Elsevier BV, NL, vol. 63, No. 3, XP004580000 ISSN: 0166-3542, (Sep. 1, 2004), 209-215.
Hagen, M., et al., "Recombinant Influenza Virus Polymerase: Requirement of both 5' and 3' Viral Ends for Endonuclease Activity", Journal of Virology, 68(3), (1994), 1509-1515.
Halfmann, P., et al., "Generation of biologically contained Ebola viruses", Proceedings of the National Academy of Sciences of the United States of America 1129-1133, vol. 105, No. 4, XP002563467 ISSN: 1091-6490 the whole document, (Jan. 29, 2008), 6 pgs.
Halfmann, P., et al., "Replication-Deficient Ebolavirus as a Vaccine Candidate", Journal of Virology, vol. 83, No. 8 3810-3815, XP002563468; ISSN: 1098-5514; the whole document, (Apr. 2009), 6 pgs.
Halperin, S. A., et al., "Safety and Immunogenicity of a Trivalent, Inactivated, Mammalian Cell Culture-Derived Influenza Vaccine in Healthy Adults, Seniors, and Children", Vaccine, 20 1240-1247, (2002), 8 pgs.
Harty, R. N, et al., "A PPxY Motif within the VP40 Protein of Ebola Virus Interacts Physically and Functionally with a Ubiquitin Ligase: Implications for Filovirus Budding", Proc. Natl. Acad. Sci, 97 (25), (Dec. 5, 2000), 13871-13876.
Harty, Ronald N, "A Proline-Rich Motif within the Matrix Protein of Vesicular Stomatitis Virus and Rabies Virus Interacts with WW Domains of Cellular Proteins: Implications for Viral Budding", Journal of Virology, 73 (4), (1999), 2921-2929.
Hatada, E., et al., "Binding of Influenza A Virus NS1 Protein to dsRNA in vitro", Journal of General Virology, 73, (1992), 3325-3329.
Hatakeyama, S., et al., "Emergence of Influenza B Viruses With Reduced Sensitivity to Neuraminidase Inhibitors", Journal of the American Medical Association, 297(13) 1435-1442, (Apr. 4, 2007), 8 pgs.
Hatakeyma, S., et al., "The molecular basis of resistance to anti-influenza drugs", Japanese Journal of Clinical Medicine—Nippon Rinsho, 64(10) 1845-1852, (Oct. 1, 2006), 8 pgs.
Hatta, M., et al., "The NB protein of influenza B virus is not necessary for virus replication in vitro", Journal of Virology, 77(10), (May 2003), 6050-6054.
Hay, A. J., et al., "The role of the M2 protein in influenza A virus infection", Proceedings of the International Conference on Options for the Control of Influenza, Courchevel, (1992), 281-288.
He. B., et al., "Recovery of infectious SV5 from cloned DNA and expression of a foreign gene", Virology, 237(2), (1997), 249-260.
Helenius, A., "Unpacking the Incoming Influenza Virus", Cell, 69, (May 1992), pp. 577-578.
Hevey, Michael, et al., "Marburg virus vaccines based upon alphavirus replicons protect guinea pigs and nonhuman primates", Virology, 251(1), (Nov. 10, 1998), 28-37.
Hiromoto, Y., et al., "Phylogenetic Analysis of the Three Polymerase Genes (PB1, PB2 and PA) of Influenza B Virus", Journal of General Virology, 81, (Apr. 2000), 929-937.
Hiti, A. L., et al., "P03470—Neuraminidase", Entrez Protein Database, http://www.ncbi.nlm.nih.gov/entrez/viewer.fcgi?db=protein&val=84028231, (1982), 730-734.
Hiti, A. L., et al., "P03470—Neuraminidase", Entrez Protein Database, [online]. [retrieved on Aug. 30, 2006]. Retrieved from the Internet: <URL: http://www.ncbi.nlm.nih.gov/entrez/viewer.fcgi?db=protein&val=84028231>, (1982), 730-734 (8 pgs.).
Hoffman, E., et al., "Ambisense Approach for the Generation of Influenza A Virus: vRNA and mRNA Synthesis from One Template", Virology 267(2) 310-317, (Feb. 15, 2006), 8 pgs.
Hoffman, M. A., et al., "An Infectious Clone of Human Parainfluenza Virus Type 3", Journal of Virology, 71(6), (1997), 4272-4277.
Hoffmann, E., et al., "A DNA transfection system for generation of influenza A virus from eight plasmids", Proc Natl Acad Sci U S A., 97(11), (May 23, 2000), 6108-13.
Hoffmann, E., et al., "Ambisense Approach for the Generation of Influenza A Virus: vRNA and mRNA Synthesis from One Template", Virology, 267, (2000), 310-317.
Hoffmann, E., et al., "Eight-plasmid System for Rapid Generation of Influenza Virus Vaccines", Vaccine, Butterworth Scientific Guildford, 20(25-56), (Aug. 19, 2002), 3165-3170.
Hoffmann, E., et al., "Rescue of Influenza B Virus from Eight Plasmids", Proceedings of the National Academy of Sciences of USA, National Academy of Science, 99(17), (Aug. 20, 2002), 11411-11416.
Holmes, E. C, et al., "Whole-Genome Analysis of Human Influenza A Virus Reveals Multiple Persistent Lineages and Reassortment Among Recent H3N2 Viruses", PLoS Biology, 3(9) 1579-1589, (2005), 11 pgs.
Holsinger, L. J., et al., "Influenza A Virus M2 Ion Channel Protein: a Structure-Function Analysis", Journal of Virology, 68 (3), (1994), pp. 1551-1563.
Honda, A., et al., "RNA Polymerase of Influenza Virus: Role of NP in RNA Chain Elongation", The Journal of Biochemistry, 104(6), (1988), 1021-1026.
Horimoto, T., et al., "Enhanced growth of seed viruses for H5N1 influenza vaccines", Virology, 366(1), (Sep. 15, 2007), 23-27.
Horimoto, T., et al., "Generation of Influenza A Viruses with Chimeric (Type A/B) Hemagglutinins", Journal of Virology, 77(14) 8031-8038, (2003), 11 pgs.

(56) References Cited

OTHER PUBLICATIONS

Horimoto, T., et al., "Reverse Genetics Provides Direct Evidence for a Correction of Hemagglutinin Cleavability and Virulence of an Avian Influenza A Virus", Journal of Virology, 68(5), (1994), 3120-3128.
Horimoto, T., et al., "The Development and Characterization of H5 Influenza Virus Vaccines Derived from a 2003 Human Isolate", Vaccine, 24(17) 3669-3676, (2006), 8 pgs.
Huang, T. S, et al., "Determinaton of Influenza Virus Proteins Required for Genome Replication", Jounal of Virology, vol. 64 5669-5673, (1990), 5 pgs.
Huang, T.-S., et al., "Determination of Influenza Virus Proteins Required for Genome Replication", Journal of Virology, 64(11), (1990), 5669-5673.
Huddleston, J. A., et al., "The Sequence of the Nucleoprotein Gene of Human Influenza A Virus, Strain A/NT/60/68", Nucleic Acids Research, 10(3), (1982), 1029-1038.
Huggins, J., et al., "Antiviral drug therapy of filovirus infections: S-adenosyihomocysteine hydrolase inhibitors inhibit Ebola virus in vitro and in a lethal mouse model.", Journal of Infectious Diseases, vol. 179, NR .(Suppl 1). XP002574255 ISSN: 0022-1899 abstract, (Feb. 1999), 240-247.
Hughes, M. T., et al., "Adaptation of Influenza A Viruses to Cells Expressing Low Levels of Sialic Acid Leads to Loss of Neuraminidase Activity", Journal of Virology, 75(8), (2001), 3766-3770.
Hughes, M. T., et al., "Influenza A Viruses Lacking Sialidase Activity Can Undergo Multiple Cycles of Replication in Cell Culture, Eggs, or Mice", Journal of Virology, 74 (11), (2000), 5206-5212.
Hughes, M. T, et al., "Influenza A Viruses Lacking Sialidase Activity Can Undergo Multiple Cycles of Replication in Cell Culture, Eggs, or Mice", Journal of Virology, 74(11) 5206-212, (2000), 7 pgs.
Hunt, R., "Virology—Chapter Eight—Vaccines: Past Successes and Future Prospects", Microbiology and Immunology On-Line, http://www.med.sc.edu:85/lecture/vaccines.htm, (Observed Feb. 26, 2003), 15 pgs.
Hurt, A. C, et al., "Identification of a human influenza type B strain with reduced sensitivity to neuraminidase inhibitor drugs", Virus Research, vol. 103, (2004), 205-211.
Ito, T, et al., "Differences in Sialic Acid-Galactose Linkages in the Chicken Egg Amnion and Allantois Influence Human Influenza Virus Receptor Specificity and Variant Selection", Journal of Virology, 71 (4), (Apr. 1997), 3357-3362.
Iwatsuki-Horimoto, K., et al., "The cytoplasmic tail of the influenza A virus M2 protein plays a role in viral assembly.", J Virol., 80(11), (Jun. 2006), 5233-40.
Jackson, et al., "Characterization of recombinant influenza B viruses with key neuraminidase inhibitor resistance mutations,", Journal of Antimicrobial Chemotherapy, vol. 55, (2005), 162-169.
Jackson, D., et al., "A reverse genetics approach for recovery of recombinant influenza B viruses entirely from cDNA.", J Virol., 76(22), (Nov. 2002), 11744-7.
Jasenosky, Luke D, et al., "Ebola Virus VP40-Induced Particle Formation and Association with the Lipid Bilayer", Journal of Virology, 75 (110, (Jun. 2001), 5205-5214.
Jin, H., et al., "Imparting temperature sensitivity and attenuation in ferrets to A/Puerto Rico/8/34 influenza virus by transferring the genetic signature for temperature sensitivity from cold-adapted A/Ann Arbor/6/60", Journal of Virology, 78(2), (2004), 995-998.
Jin, H., et al., "Influenza virus hemagglutinin and neuraminidase cytoplasmic tails control particle shape", The EMBO Journal, 16(6), (1997), 1236-1247.
Jin, H., et al., "The influenza virus hemagglutinin cytoplasmic tail is not essential for virus assembly or infectivity", The EMBOL Journal, 13(22), (1994), 5504-5515.
Johnson, David A, et al., "TLR4 Agonists as Vaccine Adjuvants", Vaccine Adjuvants and Delivery Systems, (2007), 131-156.

Johnson, R. F., et al., "Ebola Virus VP35-VP40 Interaction is Sufficient for Packaging 3E-5E Minigenome RNA into Virus-Like Particles", Journal of Virology, 80(11), (Jun. 2006), 5135-5144.
Justice, P, A., et al., "Membrane Vesiculation Function and Exocytosis of Wild-Type and Mutant Matrix Proteins of Vesicular Stomatitis Virus", Journal of Virology, 69(5), (1995), 3156-3160.
Kaplan, G., et al., "In vitro Synthesis of Infectious Poliovirus RNA", Proc. Natl. Acad. Sci. USA, 82, (1985), 8824-8428.
Katinger, D., et al., "Attenuated Influenza Viruses as a Vector for Mucosal Immunization T Against HIV-1", Vaccines, 97, Cold Spring Harbor, (1997), 315-319.
Kato, A., et al., "Initiation of Sendai Virus Multiplication From Transfected CDNA or RNA With Negative or Positive Sense", Genes to Cells, 1, (1996), 569-579.
Kawaoka, Y., "Identification by siRNA of host proteins involved in Ebolavirus replication", Great Lakes Regional Center of Excellence for Biodefense and Emerging Infectious Diseases Research, [Online]; Retrieved from the Internet: URL:http://www.rcebiodefense.org/glrce/docs/2007/Kawaoka.pdf> [retrieved on Jan. 13, 2010] p. 10, under item C, -& ANONYMOUS: "Index of GLRCE: documents from 2007" Great Lakes Regional Center of Excellence Index, [Online] 2007, XP002563469 Retrieved from the Internet: URL: http://www.rcebiodefense.org/glrce/docs/2007/> [retrieved on Jan. 14, 2010]-& Kawaoka Y.:, (2007), pp. 1-19.
Kawaoka, Y., "Mutant Cells With Altered Sialic Acid", U.S. Appl. No. 11/644,179, filed Dec. 22, 2006, 51 pgs.
Kawaoka, Y., "Prevention and Control of Ebola Virus Infection (Ongoing Research)", Great Lakes Regional Center of Excellence (GLRCE) Annual Meeting Schedule, (Abstract), [online] [retrieved on Jan. 14, 2010]. Retrieved from the Internet: <URL:http://www.rcebiodefense.org/glrce/annualmeeting/2007Agenda.pdf>, (Nov. 29, 2007), 4 pgs.
Keitel, W. A., et al., "Chapter 28—Live Cold-Adapted, Reassortant Influenza Vaccines (USA)", In: Textbook of Influenza, Nicoholson, K. G., et al., Editors, Blackwell Science Ltd., (1998), 373-390.
Kijima, H., et al., "Therapeutic Application of Ribozymes", Pharmac. Ther., 68(2), (1995), 247-267.
Kilbourne, E. D, et al., "Related studies of a recombinant influenzavirus vaccine. I. Derivation and characterization of virus and vaccine", J Infect Dis., 124(5), (Nov. 1971), 449-62.
Kimura, N., et al., "An In Vivo Study of the Replication Origin in the Influenza Virus Complementary RNA", The Journal of Biochemistry, 113(1), (1993), 88-92.
Kimura, N., et al., "Transcription of a Recombinant Influenza Virus RNA in Cells That Can Express the Influenza Virus RNA Polymerase and Nucleoprotein Genes", Journal of General Virology, 73, (1992), 1321-1328.
Kiseleva. I., et al., "Role of individual genesol the A-Leningrad/134/17/57 (H2N2) cold-adapted donor strain in manifestation of the temperature-sensitive phenotype of reassortant influenza A viruses", International Congress Series, vol. 1263, (2004), 547-550.
Kistner, O., et al., "A Novel Mammalian Cell (Vero) Derived Influenza Virus Vaccine: Development, Characterization and Industrial Scale Production", Wiener Klinische Wochenschrift, 111/5, (1999), 207-214.
Kistner, O., et al., "Development of a mammalian cell (Vero) derived candidate influenza virus vaccine", Vaccine, 16(9-10), (May-Jun. 1998), 960-8.
Kistner, O., et al., "Development of a Vero Cell-Derived Influenza Whole Virus Vaccine", T Dev. Biol. Stand., 98, (1999), 101-110.
Kobayashi, M., et al., "Reconstitution of Influenza Virus RNA Polymerase From Three Subunits Expressed Using Recombinant Baculovirus System", Virus Research, 22, (1992), 235-245.
Kochendoerfer, G. G, et al., "Total Chemical Synthesis of the Integral Membrane Protein Influenza A Virus M2: Role of its C-Terminal Domain in Tetramer Assembly", Biochemistry 38, (1999), 11905-11913.
Konarska, M. M., et al., "Structure of RNAs Replicated by the DNA-Dependent T7 RNA Polymerase", Cell, 63(2), (1990), 609-618.
Koopmans, M., et al., "Transmission of H7N7 Avian Influenza Virus to Human Beings During a Large Outbreak in Commercial Poultry Farms in the Netherlands", The Lancet, 363 587-593, (2004), 7 pgs.

(56) References Cited

OTHER PUBLICATIONS

Kovacova, A., et al., "Sequence similarities and evolutionary relationships of influenza virus A hemagglutinins.", Virus Genes, 24(1), (2002), 57-63.
Kovesdi, et al., "Adenoviral vectors for gene transfer", Current Opinion in Biotechnology, vol. 8, (1997), 583-589.
Kovesdi, I., et al., "Adenoviral Vectors for Gene Transfer", Current Opinion in Biotechnology, 8(5), (Oct. 1997), 583-589.
Krystal, M., et al., "Expression of the Three Influenza Virus Polymerase Proteins in a T Single Cell Allows Growth Complementation of Viral Mutants", Proc. Natl. Acad. Sci. USA, 83, (1986), 2709-2713.
Krystal, M., "Influenza B/Lee/40, hemagglutinin (seg 4), complete segment.", Database EM_VI E.B.I. Hinxton U.K., (Apr. 25, 1990), 9 pgs.
Kumar, P. K. R., et al., "Artificial Evolution and Natural Ribozymes", The FASEB Journal, 9, (1995), 1183-1195.
Kunkel, T. A., "Rapid and Efficient Site-Specific Mutagenesis Without Phenotypic T Selection", Proc. Natl. Acad. Sci. USA, 82, (1985), 488-492.
Lamb, Robert A., et al., "Chapter 20—Paramyxoviridae: The Viruses and Their Replication", In: Fundamental Virology, Fields, B. N., et al., editors, Lippincott-Raven (2nd Edition), (1996), 577-647.
Latham, T, et al., "Formation of Wild-Type and Chimeric Influenza Virus-Like Particles following Simultaneous Expression of Only Four Structural Proteins", Journal of Virology 75 (13), (2001), 6154-6165.
Lawson, N. D., "Recombinant Vesicular Stomatitis Viruses From DNA", Proc. Natl. Acad. Sci. USA, 92(10), (1995), 4477-4481.
Laxman, B., "Noninvasive Real-Time Imaging of Apoptosis", PNAS, 99(26), (2002), 16551-16555.
Lazarovits, Janette, et al., "Endocytosis of Chimeric Influenza Virus Hemaggulutinin Proteins That Lack a Cytoplasmic Recognition Feature for Coated Pits", The Journal of Cell Biology, vol. 134, No. 2, (1996), 339-348.
Leahy, M. B., et al., "An Endonuclease Switching Mechanism in the Virion RNA and CRNA Promoters of Thogoto Orthomyxovirus", Journal of Virology, 72(3), (1998), 2305-2309.
Leahy, M. B., et al., "In Vitro Polymerase Activity of Thogoto Virus: Evidence for a Unique Cap-Snatching Mechanism in a Tick-Borne Orthomyxovirus", Journal of Virology, 71(11), (1997), 8347-8351.
Leahy, M. B., et al., "Striking Conformational Similarities between the Transcription Promoters of Thogoto and Influenza A Viruses: Evidence for Intrastrand Base Pairing in the 5' Promoter Arm", Journal of Virology, 71(11), (1997), 8352-8356.
Lee, C. W, et al., "Generation of reassortant influenza vaccines by reverse genetics that allows utilization of a DIVA (Differentiating Infected from Vaccinated Animals) strategy for the control of avian influenza", Vaccine, vol. 22, (2004), 3175-3181.
Lee, M. S, et al., "Genetic and pathogenic characterization of H6NI avian influenza viruses isolated in Taiwan between 1972 and 2005", Avian Diseases, 50(4), (Dec. 2006), 561-571.
Lembo, A, et al., "Administration of a synthetic TLR4 agonist protects mice from pneumonic tularemia.", J Immunol., 180(11), 7574-81.
Levis, R., et al., "Deletion Mapping of Sindbis Virus DI RNAs Derived From cDNAs Defines the Sequences Essential for Replication and Packaging", Cell, 44, (1986), 137-145.
Li, K. S, et al., "Genesis of a highly pathogenic and potentially pandemic H5NI influenza virus in eastern Asia", Nature, 430(6996), (Jul. 8, 2004), 209-213.
Li, S., et al., "Electroporation of Influenza Virus Ribonucleoprotein Complexes for Rescue of the Nucleoprotein and Matrix Genes", Virus Research, 37(2), (1995), 153-161.
Li, S., et al., "Influenza A Virus Transfectants with Chimeric Hemagglutinins Containing Epitopes from Different Subtypes", Journal of Virology, 66(1), (1992), 399-404.
Li, S., et al., "Recombinant Influenza A Virus Vaccines for the Pathogenic Human A/Hong Kong/97 (H5N1) Viruses", J Infect Dis., 179(5), (1999), 1132-1138.
Li, Shengqiang, et al., "Influenza A Virus Transfectants with Chimeric Hemagglutinins containing Epitopes from different subtypes", Journal of Virology 399-404, (1992), 6 pgs.
Li, Y, et al., "Viral liposomes released from insect cells infected with recombinant baculovirus expressing the matrix protein of vesicular stomatitis virus", Journal of Virology, 67 (7), (1993), 4415-4420.
Liu, C., et al., "Influenza type A virus neuraminidase does not play a role in viral entry, replication, assembly, or budding.", Journal of Virology, 69(2), (1995), 1099-1106.
Liu, C., et al., "Selection and Characterization of a Neuraminidase-Minus Mutant, of Influenza Virus and its Rescue by Cloned Neuraminidase Genes", Virology, 194(1), (1993), 403-407.
Lott, W. B., et al., "A Two-Metal Ion Mechanism Operates in the Hammerhead Ribozyme-Mediated Cleavage of an RNA Substrate", Proc. Natl. Acad. Sci. USA, 95, (1998), 542-547.
Luo, M., "Inhibitors of Influenza Virus Neuraminidase", Abstract No. WO296, from a paper presented at the Annual Meeting of the American Crystallographic Association, http://www.hwi.buffalo.edu/ACA/ACA98/abstracts/text/WO296.html, (Observed Feb. 27, 2003), 1 pg.
Luytjes, W., "Amplification, Expression, and Packaging of a Foreign Gene by Influenza Virus", Cell, 59(6), (1989), 1107-1113.
Martin, J., et al., "Studies of the Binding Properties of Influenza Hemagglutinin Receptor-Site Mutants", Virology, 241(1), (Feb. 1, 1998), 101-111.
Masuda, H., et al., "Substitution of Amino Acid Residue in Influenza A Virus Hemagglutinin Affects Recognition of Sialyl-Oligosaccharides Containing N-Glycolylneuraminic Acid", FEBS Letters, 464, (1999), 71-74.
Matsuoka, et al., "Neuraminidase Stalk Length and Additional Glycosylation of the Hemagglutinin Influence the Virulence of Influenza H5N1 Viruses for Mice", Journal of Virology, vol. 83, No. 9,, (2009), pp. 4704-4708.
Matta, M, et al., "Cell-surface sialoglycoconjugate structures in wild-type and mutant Crithidia fasciculata", Parasitol. Res., 85(4), (1999), 293-299.
McCown, M F, et al., "The influenza A virus M2 cytoplasmic tail is required for infectious virus production and efficient genome packaging.", J Virol., 79(6), (Mar. 2005), 3595-605.
McCown, M. F, et al., "Distinct domains of the influenza a virus M2 protein cytoplasmic tail mediate binding to the M1 protein and facilitate infectious virus production.", J Virol., 80(16), (Aug. 2006), 8178-89.
McCullers, et al., "Multiple Genotypes of Influenza B Virus Circulated between 1979 and 2003,", Journal of Virology, vol. 78, No. (23) 12817-12828, (2004), 13 pgs.
McKimm, J. L., et al., "Mutations in a Conserved Residue in the Influenza Virus Neuraminidase Active Site Decreases Sensitivity to Neu5Ac2en-Derived Inhibitors", Journal of Virology, 72(3), (1998), 2456-2462.
McSharry, J. J, et al., "Phenotypic Drug Susceptibility Assay for Influenza Virus Neuraminidase Inhibitors", Cinical and Diagnostic Laboratory Immunology vol. 11, No. 2,, (2004), 10 pgs.
Mebatsion, Teshome, et al., "Budding of Rabies Virus Particles in the Absence of the Spike Glycoprotein", Cell, 84(6), (1996), 941-951.
Mebatsion, Teshome, et al., "Matrix Protein of Rabies Virus is Responsible for the Assembly and Budding of Bullet-Shaped Particles and Interacts with the Transmembrane Spike Glycoprotein G", Journal of Virology, 73 (1), (Jan. 1999), 242/250.
Mena, I., "Rescue of a Synthetic Choramphenicol Acetyltransferase RNA into influenza Virus-Like Particles obtained from recombinant plasmids", Journal of Virology, 70(8), (1996), 5016-5024.
Mena, I., et al., "Synthesis of biologically active influenza virus core proteins using a vaccinia virus- T7 RNA polymerase expression system", Journal of General Virology, 75 2109-2114, (1994), 6 pgs.
Mena, I., et al., "Synthesis of Biologically Active Influenza Virus Core Proteins Using a Vaccinia Virus-T7 RNA Polymerase Expression System", Journal of General Virology, 75, (1994), 2109-2114.
Mishin, V. P, et al., "Protection afforded by intranasal immunization with the neuraminidase-lacking mutant of influenza A virus in a ferret model", Vaccine, 23(22), (Apr. 22. 2005), 2922-7.

(56) References Cited

OTHER PUBLICATIONS

Mitnaul, et al., "The Cytoplasmic Tail of Influenza a Virus Neuraminidase (NA) Affects NA Incorporation into Virons, Viron Morphology, and Virulence in Mice but is not essential for Virus Replication", Journal of Virology, 70 (2), (1996), 873-879.

Mitnaul, L. J., et al., "Balanced Hemagglutinin and Neuraminidase Activities are Critical for Efficient Replication of Influenza A Virus", Journal of Virology, 74 (13), (2000), 6015-6020.

Miyoshi, H., et al., "Development of Self-Inactivating Lentivirus Vector", Journal of Virology, 72(10), (1998), 8150-8157.

Monto, A. S, et al., "Detection of influenza viruses resistant to neuraminidase inhibitors in global surveillance during the first 3 years of their use", Antimicrobal Agents and Chemotherapy, 50(7) 2395-2402, (2006), 8 pgs.

Monto, Arnold S, et al., "Comparative efficacy of inactivated and live attenuated influenza vaccines.", N Engl J Med., 361(13) 1260-7, (Sep. 24, 2009), 8 pgs.

Morita, S., et al., "Plat-E: an efficient and stable system for trsansient packaging of retroviruses", Gene Therapy, 7(12), (2000), 1063-1066.

Moss, B., et al., "New Mammalian Expression Vectors", Nature, 348, (1990), 91-92.

Moyer, S. A., et al., "Assembly and Transcription of Synthetic Vesicular Stomatitis Virus Nucleocapsids", Journal of Virology, 65(5), (1991), 2170-2178.

Muhlberger, E., et al., "Comparision orf the Transcription and Replication Strategies of Marburg Virus and Ebola Virus by Using Artificial Replication Systems", Journal of Virology, 73(3) 2333-2342, (1999), 10 pgs.

Muhlberger, E., et al., "Three of the four nucleocapsld proteins of Marburg virus,NP, VP35, and L, are sufficient to mediate replication and transcription of Marburg virus-specific monocistronic minigenomes", Journal of Virology, 72(11) 8756-8764, (1998), 11 pgs.

Murphy, B. R, et al., "An influenza A live attenuated reassortant virus possessing three T temperature-sensitive mutations in the PB2 polymerase gene rapidly loses temperature sensitivity following replication in hamsters", Vaccine,15(12-13) 1372-8, (1997), 7 pgs.

Murphy, Brian R, et al., "Virulence of Avian Influenza A Viruses for Squirrel Monkeys", Infection and Immunity 37 (3), (Sep. 1982), 1119-1126.

Muster, T., et al., "An Influenza A Virus Containing Influenza B Virus 5' and 3' Noncoding Regions on the Neuraminidase Gene is Attenuated in Mice", Proc. Natl. Acad. Sci. USA, 88, (1991), 5177-5181.

Naim, H. Y., et al., "Basis for Selective Incorporation of Glycoproteins into the Influenza Virus Envelope", Journal of Virology, 67(8), (1993), 4831-4841.

Naito, S., et al., "Function and Structure of RNA Polymerase From Vesicular Stomatitis Virus", The Journal of Biological Chemistry, 251(14), (1976), 4307-4314.

Nara, P. L., et al., "Simple, Rapid, Quantitative, Syncytium-Forming Microassay for the Detection of Human Immunodeficiency Virus Neutralizing Antibody", Aids Research and Human Retroviruses, 3(3), (1987), 283-302.

Neirynck, S., "A universal influenza A vaccine based on the extracellular domain of the M2 protein", Nature Medicine, 5 (10), (Oct. 1999), pp. 1157-1163.

Nemeroff, M. E., et al., "Influenza Virus NS1 Protein Interacts With the Cellular 30 kDa Subunit of CPSF and Inhibits 3' End Formation of Cellular Pre-mRNAs", Molecular Cell, 1(7), (1998), 991-1000.

Neumann, G., et al., "A Decade After the Generation of a Negative-Sense RNA Virus From Cloned CDNA—What Have We Learned?", Journal of General Virology, 83(11), (Nov. 2002), 2635-2662.

Neumann, G., et al., "An Improved Reverse Genetics System for Influenza A Virus Generation and Its Implications for Vaccine Production", Proc. Natl. Acad. Sci. USA, 102(46) 16825-16829, (2005), 5 pgs.

Neumann, G., et al., "Emergence and pandemic potential of swine-origin H1N1 influenza virus", Nature (LONDON), 459(7249), (Jun. 2009), 931-939.

Neumann, G., et al., "Generation of influenza A virus from cloned cDNAs-historical perspective and outlook for the new millenium.", Rev Med Virol., 12(1), XP002314285, (Jan.-Feb. 2002), 13-30.

Neumann, G., et al., "Generation of influenza A viruses entirely from cloned cDNAs", Proc. Natl. Acad. Sci. USA., 96(16), (1999), 9345-9350.

Neumann, G., et al., "Genetic Engineering of Influenza and Other Negative-Strand RNA Viruses Containing Segmented Genomes", Advances in Virus Research, 53, (1999), 265-300.

Neumann, G., et al., "Influenza A virus NS2 protein mediates vRNP nuclear export through NES-independent interaction with hCRM1", The EMBO Journal, 19 (24), (2000), 6751-6758.

Neumann, G., et al., "Mutational analysis of influenza virus promoter elements in vivo", Journal of General Virology, 76 1709-1717, (1995), 9 pgs.

Neumann, G., et al., "Nuclear Import and Export of Influenza Virus Nucleoprotein", Journal of Virology, 71(12), (1997), 9690-9700.

Neumann, G., et al., "Plasmid-driven formation of influenza virus-like particles", J Virol., 74(1), [Online] Retrieved From Internet: <http://www.ncbi.nlm.nih.gov/pmc/articles/PMC111569/>, (Jan. 2000), 547-551.

Neumann, G., et al., "Reverse genetics of influenza virus.", Virology, 287(2), (Sep. 1, 2001), 243-50.

Neumann, G., et al., "Reverse Genetics of Influenza Viruses—Applications in Research and Vaccine Design", Monographs in Virology, 27, (2008), 118-133.

Neumann, G., et al., "RNA Polymerase I-Mediated Expression of Influenza Viral RNA Molecules", Virology, 202(1), (1994), 477-479.

Neumann, G., et al., "Synthesis of Influenza Virus: New impetus from an old enzyme, RNA polymerase I", Virus Research 82(1-2), (Jan. 30, 2002), 153-158.

Neumann, Gabriele, et al., "Reverse Genetics Demonstrates that Proteolytic Processing of the Ebola Virus Glycoprotein is Not Essential for Replication in Cell Culture", Journal of Virology, 76 (1), (Jan. 2002), 406-410.

Nicolson, C., et al., "Generation of Influenza Vaccine Viruses on Vero Cells by Reverse Genetics: an H5N1 Candidate Vaccine Strain Produced Under a Quality System", Vaccine, 23 2943-2952, (2005), 10 pgs.

Niwa, H., et al., "Efficient Selection for High-Expression Transfectants With a Novel Eukaryotic Factor", Gene, 108(2), (1991), 193-199.

Odagiri, T., et al., "Nucleotide Sequence of the PA Gene of Influenza A/WSN/33 (H1N1)", Nucleic Acids Research, 18 (3), Department of Virology, (Jan. 9, 1990), 1 pg.

Olivo, P. D, et al., "Detection and quantitation of human respiratory syncytial virus (RSV) using minigenome cDNA and a Sindbis virus replicon: a prototype assay for negative-strand RNA viruses.", Virology, 251(1), (Nov. 10, 1998), 198-205.

Onishi, M., et al., "Applications of retrovirus-mediated expression cloning", Experimental Hematology, 24(2), (1996), 324-329.

Orkin, S. H, et al., "Report and Recommendations of the Panel to Assess the NIH Investment in Research on Gene Therapy", http://www.nih.gov/news/panelrep.html, (Dec. 7, 1995), 37 pgs.

Ozaki, H., et al., "Generation of High-Yielding Influenza A Viruses in African Green Money Kidney (Vero) Cells by Reverse Genetiics", Journal of Virology, 78(4) 1851-1857, (2004), 6 pgs.

Ozawa, M., et al., "An adenovirus vector-mediated reverse genetics system for influenza A virus generation", Journal of Virology, The American society For Microbiology, US vol. 81 (17), XP002471230, ISSN: 0022-538X, (Jun. 27, 2007), 9556-9559.

Palache, A. M., et al., "Safety, Reactogenicity and Immunogenicity of Madin Darby Canine Kidney Cell-Derived Inactivated Influenza Subunit Vaccine. A Meta-Analysis of Clinical Studies", Dev. Biol. Stand., 98 133-134 abstract, (1999), 1 pg.

Palese, P., "Negative-Strand RNA Viruses: Genetic Engineering and Applications", Proc. Natl. Acad. Sci. USA, 93(21), (1996), 11354-11358.

(56) References Cited

OTHER PUBLICATIONS

Park, Eun K., et al., "The M2 Ectodomain is important for its incorporation into influenza A virions", J. of Virology, vol. 72, No. 3, XP002196797, (Mar. 1998), 2449-2455.

Park, K. H., et al., "Rescue of a Foreign Gene by Sendai Virus", Proc. Natl. Acad. Sci. USA, 88, (1991), 5537-5541.

Pattnaik, A. K., et al., "Cells That Express All Five Proteins of Vesicular Stomatitis Virus From Cloned cDNAs Support Replication, Assembly, and Budding of Defective Interfering Particles", Proc. Natl. Acad. Sci. USA, 88(4), (1991), 1379-1383.

Pattnaik, A. K., et al., "The Termini of VSV DI Particle RNAs are Sufficient to Signal RNA Encapsidation, Replication, and Budding to Generate Infectious Particles", Virology, 206, (1995), 760-764.

Peeters, B. P. H., et al., "Rescue of Newcastle Disease Virus From Cloned cDNA: Evidence That Cleavability of the Fusion Protein Is a Major Determinant for Virulence", Journal of Virology, 73(6), (1999), 5001-5009.

Peiris, J. S. M., et al., "Re-Emergence of Fatal Human Influenza A Subtype H5N1 Disease", The Lancet, 363 617-619, (2004), 3 pgs.

Pekosz, A., "Commentary—Reverse Genetics of Negative-Strand RNA Viruses: Closing the Circle", Proc. Natl. Acad. Sci. USA, 96, (1999), 8804-8806.

Pekosz, A., et al., "Influenza C virus CM2 integral membrane glycoprotein is produced from a polypeptide precursor by cleavage of an internal signal sequence", PNAS, vol. 95, XP002196653, (Oct. 1998), 13233-13238.

Pelet, T., et al., "High throughput screening assay for negative single stranded RNA virus polymerase inhibitors", Journal of Virological Methods, 128 29-36, (2005), 8 pgs.

Percy, N., et al., "Expression of a Foreign Protein by Influenza A Virus", Journal of Virology, 68(7), (1994), 4486-4492.

Perdue, M., et al., "Virulence and the Avian Influenza Virus Hemagglutinin Gene", United States Department of Agriculture—Agriculture Research Service, http://www.nps.ars.usda.gov/publications/publications.htm?SEQ_NO_155=106036, (Observed Feb. 22, 2003), 1 pg.

Perez, D. R., et al., "The Matrix 1 Protein of Influenza A Virus Inhibits the Transcriptase Activity of a Model Influenza Reporter Genome in Vivo", Virology, 249(1), (1998), 52-61.

Piatti, G., "Identification of immunodominant epitopes In the filamentous Hemagglutinin of Bordetella pertusis", FEMS Immunology and Medical Microbiology, 23(3), (1999), 235-241.

Piller, S C., et al., "Vpr protein of human immunodeficiency virus type 1 forms cation-selective channels in planar lipid bilayers", PNAS, 93, (1996), 111-1115.

Pinto, L. H., et al., "Influenza Virus M2 Protein Has Ion Channel Activity", Cell, 69, (May 1992), pp. 517-528.

Pleschka, S., et al.. "A Plasmid-Based Reverse Genetics System for Influenza A Virus", Journal of Virology, 70(6), (1996), 4188-4192.

Pley, H. W., et al., "Three-Dimensional Structure of a Hammerhead Ribozyme", Nature, 372, (1994), 68-74.

Portela, A., et al., "Replication of orthomyxoviruses", Advances in Virus Research, 54, (1999), 319-348.

Potter, C. W., "Chapter 1—Chronicle of Influenza Pandemics", In: Textbook of Influenza, Nicoholson, K. G., et al., Editors, (Blackwell Scientific Publication), (1998), 3-18.

Pushko, P., et al., "Replicon-Helper Systems from Attenuated Venezuelan Equine Encephalitis Virus: Expression of Heterologous Genes in Vitro and Immunization against Heterologous Pathogens in Vivo", Virology, 239(2), (Abstract Only), (1997), 1 page.

Puzelli, S., et al., "Changes in the Hemagglutinins and Neuraminidase of Human Influenza B Viruses Isolated in Italy During the 2001-02, 2002-03, and 2003-04 Seasons", Journal of Medical Virology, 74(4) 629-640, (2004), 12 pgs.

Qiu, Y., et al., "The Influenza Virus NS1 Protein Binds to a Specific Region in Human U6 snRNA and Inhibits U6-U2 and U6-U4 snRNA Interactions During Splicing", RNA, 1, (1995), 304-316.

Qiu, Y., et al., "The Influenza Virus NS1 Protein is a Poly(A)-Protein That Inhibits Nuclear Export of mRNAs Containing Poly(A)", Journal of Virology, 68(4), (1994), 2425-2432.

Racaniello, V. R., et al., "Cloned Poliovirus Complimentary DNA is Infectious in Mammalian Cells", Science, 214, (1981), 4 pgs.

Radecke, F., et al., "Rescue of Measles Viruses From Cloned DNA", The EMBO Journal, 14(23), (1995), 5773-5784.

Radecke, F., et al., "Reverse Genetics Meets the Nonsegmented Negative-Strand RNA Viruses", Reviews in Medical Virology, 7, (1997), 49-63.

Ray, M. K., et al., "A Novel Glycosylation Phenotype Expressed by Lec23, a Chinese Hamster Ovary Mutant Deficient in alpha-Glucosidase I", Journal of Biological Chemistry, 266(34), (1991), 22818-22825.

Rayner, J., et al., "Alphavirus vectors and vaccination", Reviews in Medical Virology, 12, (2002), 279-296.

Restifo, N. P., et al., "Transfectant Influenza A Viruses are Effective Recombinant Immunogens in the Treatment of Experimental Cancer", Virology, 249(1), (1998), 89-97.

Roberts, A., et al., "Minireview—Recovery of Negative-Strand RNA Viruses From Plasmid DNAs: A Positive Approach Revitalizes a Negative Field", Virology, 247(1), (1998), 1-6.

Robison, C. S, et al., "The Membrane-Proximal Stem Region of Vesicular Stomatitis Virus G Protein Confers Efficient Virus Assembly", Journal of Virology, 74 (5), (Mar. 2000), 2239-2246.

Rodrigues, M., et al., "Influenza and Vaccinia Viruses Expressing Malaria CD8+ T and B Cell Epitopes. Comparison of Their Immunogenicity and Capacity to Induce Protective Immunity", J. Immunol., 153(10), (1994), 4636-4648.

Rose, J. K., "Positive Strands to the Rescue Again: A Segmented Negative-Strand RNA Virus Derived From Cloned cDNAs", Proc. Natl. Acad. Sci. USA, 94, (1996), 14998-15000.

Ruigrok, R W, et al., "Structural Characterization and Membrane Binding Properties of the Matrix Protein VP40 of Ebola Virus", Journal of Molecular Biology, 300(1), (2000), 103-112.

Ruiz-Arguello, M. B, et al., "Phosphatidylinositol-Dependent Membrane Fusion Induced by a Putative Fusogenic Sequence of Ebola Virus", Journal of Virology, 72(3), (Mar. 1998), 1775-1781.

Sansom, M. S., et al., "Influenza virus M2 Protein: a molecular modelling study of the ion channel", Protein Engineering, 6 (1), (1993), pp. 65-74.

Satterlee, B., "Production of H5N1 avian influenza virus vaccine by plasmid-based reverse genetics technology", Basic Biotechnology eJournal, vol. 4, pp. 93-98, (2008), 93-98 Pgs.

Schickli, J. H, et al., "Plasmid-only Rescue of Influenza A Virus Vaccine Candidates", Philosophical Transactions of the Royal Society of London. Series B, Biological Sciences, 356(1416), (Dec. 29, 2001), 1965-1973.

Schlesinger, S., "RNA Viruses as Vectors for the Expression of Heterologous Proteins", Molecular Biotechnology, 3(2), (1995), 155-165.

Schnell, M. J., "Infectious Rabies Viruses From Cloned cDNA", The EMBO Journal, 13(18), (1994), 4195-4203.

Schnell, Matthias J, et al., "Requirement for a non-specific glycoprotein cytoplasmic domain sequence to drive efficient budding of vesicular stomatitis virus", EMBO Journal, 17 (5), (1998), 1289-1296.

Schultz-Cherry, S., et al., "Influenza Virus NS1 Protein Induces Apoptosis in Cultured Cells", Journal of Virology, 75(17), (2001), 7875-7881.

Seong, B. L., et al., "A New Method for Reconstituting Influenza Polymerase and RNA in Vitro: A Study of the Promoter Elements for cRNA and vRNA Synthesis in Vitro and Viral Rescue in Vivo", Virology, 186(1), (1992), 247-260.

Shinya, Kyoko, et al., "Characterization of a Neuraminidase-Deficient Influenza A Virus as a Potential Gene Delivery Vector and a Live Vaccine", Journal of Virology, 78(6), (2004), 3083-3088.

Shortridge, K. F., et al., "Characterization of Avian H5N1 Influenza Viruses From Poultry in Hong Kong", Virology, 252 331-342, (1998), 12 pgs.

Sidhu, M. S., et al., "Rescue of Synthetic Measles Virus Minireplicons: Measles Genomic Termini Direct Efficient Expression and Propagation of a Reporter Gene", Virology, 208, (1995), 800-807.

Skehel, J. J., et al., "On the Mechanism of Inhibition of Influenza Virus Replication by Amantadine Hydrochloride", The Journal of General Virology, 38 (1), (1977), pp. 97-110.

(56) References Cited

OTHER PUBLICATIONS

Smeenk, et al., "Mutations in the Hemagglutinin and Matrix Genes of a Virulent Influenza Virus Variant, A/FM/1/47-MA, Control Different Stages in Pathogenesis", Virus Research 44, (1996), 79-95.
Stray, S. J., et al., "Influenza virus infection of desialylated cells", Glycobiology, 10(7), (2000), 649-658.
Strobel, I., et al., "Efficient Expression of the Tumor-Associated Antigen MAGE-3 in Human Dendritic Cells, Using an Avian Influenza Virus Vector", Human Gene Therapy, 11(16), (2000), 2207-2218.
Subbarao, E. K., et al., "Rescue of an InfluenzaA Virus Wild-Type PB2 Gene and a Mutant Derivative Bearing a Site-Specific Temperature-Sensitive and Attenuating Mutation", Journal of Virology, 67(12), (1993), 7223-7228.
Subbarao, E. K., et al., "Sequential Addition of Temperature-Sensitive Missense Mutations into the PB2 Gene of Influenza A Transfectant Viruses Can Effect an Increase in Temperature Sensitivity and Attenuation and Permits the Rational Design of a Genetically Engineered Live Influen", Journal of Virology, 69(10), (1995), 5969-5977.
Subbarao, K., et al., "Characterization of an Avian Influenza A (H5N1) Virus Isolated From a Child With a Fatal Respiratory Illness", Science, 279, (1998), 393-396.
Subbarao, K., et al., "Evaluation of a Genetically Modified Reassortant H5N1 Influenza A Virus Vaccine Candidate Generated by Plasmid-based Reverse Genetics", Virology, vol. 305(1), (Jan. 5, 2003), 192-200.
Sugawara, K., et al., "Development of Vero Cell-Derived Inactivated Japanese Encephalities Vaccine", Biologicals, 30 303-314, (2002), 12 pgs.
Sugrue, R. J., et al., "Specific structural alteration of the influenza haemagglutinin by amantadine", The EMBO Journal, 9 (11), (1990), pp. 3469-3476.
Sugrue, R. J., et al., "Structural Characteristics of the M2 Protein of Influenza A Viruses: Evidence That It Forms a Tetrameric Channel", Virology, 180, (1991), pp. 617-624.
Sunstrom, N. A., et al., "Ion Channels formed by NB, an influenza B virus Protein", J. of Membrane Biology, vol. 150, XP002196654, (Dec. 1996), 127-132.
Sweet, T. M., et al., "Creation of amantadine resistant clones of influenza type A virus using a new transfection procedure.", J Virol Methods., 69(1-2), (Dec. 1997), 103-11.
Szewczyk, B., "Purification, Thioredoxin Renaturation, and Reconstituted Activity of the Three Subunits of the Influenza A Virus RNA Polymerase", Proc. Natl. Acad. Sci. USA, 85, (1988), 7907-7911.
Taira, K., et al., "Construction of a novel RNA-transcript-trimming plasmid which can be used both in vitro in place of run-off and (G)-free transcriptions and in vivo as multi-sequences transcription vectors", Nucleic Acids Research, 19(19), (1991), 5125-5130.
Takeda, M., et al., "Influenza a virus M2 ion channel activity is essential for efficient replication in tissue culture.", J Virol., 76(3), (Feb. 2002), 1391-9.
Takeda, T., et al., "Expression of Podocalyxin Inhibits Cell-Cell Adhesion and Modifies Junctional Properties in Madin-Darby Canine Kidney Cells", Molecular Biology of the Cell, 11, (2000), 3219-3232.
Takeuchi, K., et al., "Influenza Virus M2 Protein Ion Channel Activity Stabilizes the Native Form of Fowl Plague Virus Hemagglutinin during Intracellular Transport", Journal of Virology, 68 (2), (Feb. 1994), pp. 911-919.
Tang, et al., "Recombinant adenovirus encoding the HA gene from swine H3N2 influenza virus partially protects mice from challenge with heterologous virus: AIHK/1/68 (H3N2)", Archives of Virology, vol. 147 2125-2141, (2002), 17 pgs.
Tannock, G. A, et al., "Relative immunogenicity of the cold-adapted influenza virus A/Ann Arbor/6/60 (A/AA/6/60-ca), recombinants of A/AA/6/60-ca, and parental strains with similar surface antigens.", Infect Immun., 43(2), (Feb. 1984), 457-62.
Taylor, J., et al., "Newcastle Disease Virus Fusion Protein Expressed in a Fowlpox Virus Recombinant Confers Protection in Chickens", Journal of Virology, 64(4), (1990), 1441-1450.
Terry, G., et al., "The Contruction of Defective Interfering Rubella Virus Particles", Archives of Virology, 145(3), (2000), 625-633.
Thompson, W. W., et al., "Mortality Associated With Influenza and Respiratory Syncytial Virus in the United States", JAMA, 289(2) 179-186, (2003), 8 pgs.
Towner, J S, et al., "Generation of eGFP express ing recombinant Zaire ebolavirus for analysis of early pathogenesis events and high-throughput antiviral drug screening", Virology, Academic Press ,Orlando, US , vol. 332, No. 1 20-27, XP004715289 ISSN: 0042-6822 the whole document, (Feb. 5, 2005), 8 pgs.
Treanor, J. J, et al., "The B allele of the NS gene of avian influenza viruses, but not the A allele, attenuates a human influenza a virus for squirrel monkeys", Virology, 171(1), (1989), 1-9.
Verma, I. M, et al., "Gene Therapy—Promises, Problems and Prospects", Nature, 389, (1997), 239-242.
Victor, Sylvia T., et al., "A Replication-Incompetent PB2-Knockout Influenza A Virus Vaccine Vector", Journal of Virology, 2012, 86(8):4123; DOL: 10.1128/JVI.06232-11. Journals.ASM.org;, Downloaded from http://jvi.asm.org/ on Aug. 20, 2012 by Univ. of Wisonsin—Mad, (Feb. 1, 2012), 7.
Voeten, J. T, et al., "Characterization of high-growth reassortant influenza A viruses generated in MDCK cells cultured in serum-free medium", Vaccine, vol. 17, (1999), 1942-1950.
Volchkov, Viktor E, et al., "Recovery of Infectious Ebola Virus from Complementary DNA: RNA Editing of the GP Gene and Viral Cytotoxicity", Science Magazine, 291. (Mar. 2001), 1965-1969.
Wagner, R., et al., "Interdependence of hemagglutinin glycosylation and neuraminidase as regulators of influenza virus growth: a study by reverse genetics", Journal of Virology, 74 (14), (Jul. 2000), 6316-6323.
Walker, W. S, et al., "HEL-Flu: an influenza virus containing the hen egg lysozyme epitope recognized by CD4+ T cells from mice transgenic for an alphabeta TCR", J. Immunol., 159(6), (Sep. 1997), 2563-2566.
Wang, C., et al., "Ion Channel Activity of Influenza A Virus M2 Protein: Characterization of the Amantadine Block", Journal of Virology, 67 (9), (Sep. 1993), pp. 5585-5594.
Ward, C. D., et al., "Direct Measurement of the Poliovirus RNA Polymerase Error Frequency In Vitro", Journal of Virology, 62(2), (1988), 558-562.
Wareing, M. D, et al., "Immunogenic and isotype-specific responses to Russian and US cold-adapted influenza a vaccine donor strains A/Leningrad/134/17/57, A/Leningrad/134/47/57, and A/Ann Arbor/6/60 (H2N2) in mice.", J Med Virol., 65(1), (Sep. 2001), 171-7.
Warfield, et al., "", PNAS, vol. 100(26), (2003), pp. 5889-15894.
Watanabe, S., et al., "Ebola virus (EBOV) VP24 inhibits transcription and replication of the | EBOV genome", J Infect Dis., 196(Suppl 2), (Nov. 15, 2007), S284-90.
Watanabe, S., et al., "Influenza A Virus Lacking M2 Protein as a Live Attenuated Vaccine", Journal of Virology, 83(11), (2009), 5947-5950.
Watanabe, S., et al., "Production of Novel Ebola Virus-Like Particles from cDNAs: an Alternative to Ebola Virus Generation by Reverse Genetics", Journal of Virology, 78(2), (Jan. 2004), 999-1005.
Watanabe, T., et al., "Influenza A virus can undergo multiple cycles of replication without M2 ion channel activity", J Virol., 75(12), (Jun. 2001), 5656-62.
Watanabe, T., et al., "Influenza A Virus with Defective M2 Ion Channel Activity as a Live Vaccine", Virology, 299(2), (Aug. 1, 2002), 266-270.
Weber, F., et al., "Conserved vRNA end sequences of Thogoto-orthomyxovirus suggest a new panhandle structure", Archives of Virology, 142(5), (1997), 1029-1033.
Weber, F., et al., "Nucleoprotein Viral RNA and mRNA of Thogoto Virus: a Novel "Cap-Stealing" Mechanism in Tick-Borne Othomyxoviruses?", Journal of Virology, 70(12), (1996), 8361-8367.

(56) References Cited

OTHER PUBLICATIONS

Whelan, S. P. J., et al., "Efficient Recovery of Infectious Vesicular Stomatitis Virus Entirely from cDNA Clones", Proc. Natl. Acad. Sci. USA, 92, (1995), 8388-8392.

Wills, J, W., et al., "An Assembly Domain of the Rous Sarcoma Virus Gag Protein Required Late in Budding", Journal of Virology, 68(10), (1994), 6605-6618.

Wilson, et al., "Vaccine Potential of Ebola Virus VP24, VP30, VP35 and VP40 Proteins", Virology 286, (2001), 384-90.

Wilson, Julie A, et al., "Epitopes Involved in Antibody-Mediated Protection from Ebola Virus", Science, 287(5458), (Mar. 2000), 1664-1666.

Wood, J. M., et al., "From Lethal Virus to Life-Saving Vaccine: Developing Inactivated Vaccines for Pandemic Influenza", Nature Reviews Microbiology, 2(10), (2004), 842-847.

Wu, Rui, et al., "A live bivalent influenza vaccine based on a H9N2 virus strain", Vaccine, 28, (2010), 673-680.

Yagi, Y., et al., "In silico panning for a non-competitive peptide inhibitor", BMC Bioinformatics, 8(11), (2007), 11 pgs.

Yamanaka, K., et al., "In vivo Analysis of the Promoter Structure of the Influenza Virus RNA Genome Using a Transfection System With an Engineered RNA", Proc. Natl. Acad. Sci. USA, 88, (1991), 5369-5373.

Yang, P., et al., "Hemagglutinin Specificity and Neuraminidase Coding Capacity of Meuraminidase-Deficient Influenza Viruses", Virology, 229(1), (1997), 155-165.

Yasuda, J., "Growth Control of Influenza A Virus by M1 Protein: Analysis of Transfectant Viruses Carrying the Chimeric M Gene", Journal of Virology, 68(12), (1994), 8141-8146.

Yonezawa, A., et al., "Studies of Eboa Virus Glycoprotein-Mediated Entry and Fusion by Using Pseudotyped Human Immunodeficiency Virus Type 1 Virions: Involvement of Cytoskeletal Proteins and Enhancement by Tumor Necrosis Factor Alpha", Journal of Virology, 79(2), (2005), 918-926.

Yu, Q., et al., "Functional cDNA Clones of the Human Respiratory Syncytial (RS) Virus N, P, and L Proteins Support Replication of RS Virus Genomic RNA Analogs and Define Minimal trans-Acting Requirements for RNA Replication", Journal of Virology, 69(4), (1995), 2412-2419.

Yusoff, K., et al., "Nucleotide Sequence Analysis of the L Gene of Newcastle Disease Virus: Homologies With Sendai and Vesicular Stomatitis Viruses", Nucleic Acids Research, 15(10), (1987), 3961-3976.

Zaghouani, H, et al., "Induction of Antibodies to the Envelope Protein of the Human Immunodeficiency Virus by Immunization With Monoclonal Anti-Idiotypes", Proc. Natl. Acad. Sci. USA, 88, (1991), 5645-5649.

Zaghouani, H., et al., "Cells Expressing an H Chain 1g Gene Carrying a Viral T Cell Epitope are Lysed by Specific Cytolytic T Cells", The Journal of Immunology, 148(11), (1992), 3604-3609.

Zebedee, S. L, et al., "Characterization of the Influenza Virus M2 Integral Membrane Protein and Expression at the Infected-Cell Surface from Cloned cDNA", Journal of Virology, 56(2), (Nov. 1985), 502-511.

Zhang, H., et al., "Expression of Functional Influenza Virus A Polymerase Proteins and Template From Cloned cDNAs in Recombinant Vaccinia Virus Infected Cells", Biochemical and Biophysical Research Communications, 200(1), (1994), 95-101.

Zhang, Xuming, et al., "Expression of Interferon-y by a Coronavirus Defective-Interfering RNA Vector and its Effect on Viral Replication, Spread, and Pathogenicity", Medical Institute, University of Southern California School of Medicine, (May 1997), 327-338.

Zobel, A., et al., "RNA Polymerase Catalysed Transcription of Insert Viral cDNA", Nucleic Acids Research, 21(16), (1993), 3607-3614.

"U.S. Appl. No. 17/266,049, Non Final Office Action dated Mar. 14, 2023", 12 pgs.

"U.S. Appl. No. 17/004,583, 312 Amendment filed Mar. 16, 2023", 7 pgs.

"Japanese Application Serial No. 2020-182549, Preliminary Examination Report dated Jan. 17, 2023", w English Translation, 3 pgs.

"U.S. Appl. No. 16/785,449, Final Office Action dated Mar. 22, 2023", 16 pgs.

Marzi, "An Ebola whole-virus vaccine is protective in nonhuman primates", Science 348(6233) 439-442, (Apr. 2015), 4 pgs.

Wang, "Glycoengineering of CHO Cells to Improve Product Quality", Methods in Molecular Biology book series (MIMB, vol. 1603) 25-44, (May 11, 2017), 256 pgs.

Wolff, "Downstream porcessing of cell culture-derived virus particles", Expert Rev. Vaccines 10(10) 1451-1475, (2011), 25 pgs.

"U.S. Appl. No. 13/113,244, Preliminary Amendment filed Aug. 11, 2011", 4 pgs.

Broecker, Felix, et al., "Immunodominance of Antigenic Site B in the Hemagglutinin of the Current H3N2 In?uenza Virus in Humans and Mice", Journal of Virology, 92(20) e01100-18, (Oct. 2018), 1-13.

Brooke, C B, "Biological activities of 'noninfectious' influenza A virus particles", Future Virol 9(1) 41-51, (Jan. 2014), 16 pgs.

Brown, E. G., et al., "Genetic analysis of mouse-adapted influenza A virus identifies roles for the NA, PB1, and PB2 genes in virulence", Virus Research, 61(1), (May 1999), 63-76.

Brown, TA, "Studying DNA", Genomes—NCBI Bookshelf, Brown TA. Genomes. 2nd edition. Oxford: Wiley-Liss; 2002, (2002), 26 pgs.

Cannon, Joseph G., "Chapter Nineteen—Analog Design", In: Burger's Medicinal Chemistry and Drug Discovery, Fifth Edition, vol. I: Principles and Practice, Wiley-Interscience, (1995), 783-802.

Cao, S., et al., "Characterization of the Nucleocytoplasmic Shuttle of the Matrix Protein of Influenza B Virus", Journal of Virology., 88(13), (Jul. 2014), 7464-7473.

Catchpole, A P, et al., "Alternative base pains attenuate influenza A virus when introduced into the duplex region of the conserved viral RNA promoter of either the NS or the PA gene", Journal of General Virology, 84, (2003), 507-515.

Chan, Winnie, et al., "The cold adapted and temperature sensitive influenza A/Ann Arbor/6/60 virus, the master donor virus for live attenuated influenza vaccines, has multiple defects in replication at the restrictive temperature", Virology, 380(2), (2008), 304-311.

Chevalie, Christophe, et al., "PB1-F2 Influenza A Virus Protein Adopts a B-Sheet Conformation and Forms Amyloid Fibers in Membrane Environments", The of Biological Chemistry, 285(17), (2010), 13233-13243.

Chiba, Shiho, et al., "Multivalent nanoparticle-based vaccines protect hamsters against SARS-CoV-2 after a single immunization", Communications Biology, 4: 597, (2021), 1-9.

Cho, Alice, et al., "Implications of Broadly Neutralizing Antibodies in the Development of a Universal Influenza Vaccine", Current Opinion in Virology, vol. 17 110-115, (Apr. 1, 2016), 6 pgs.

Chothia, Cyrus, et al., "Canonical Structures for the Hypervariable Regions of Immunoglobulins.", J Mol Biol., 196(4), (1987), 901-917.

Cohen, Alexander A., et al., "Mosaic nanoparticles elicit cross-reactive immune responses to zoonotic coronaviruses in mice", Science, 371(6530), and Supplementary Materials, (2021), 735-741 (30 pgs).

Cunningham, Brian C, et al., "High-Resolution Epitope Mapping of hGH-Receptor Interactions by Alanine-Scanning Mutagenesis", Science 244:4908, (1989), 6 pgs.

Daddario-Dicaprio, K. M, et al., "Cross-protection against Marburg virus strains by using a live, attenuated recombinant vaccine", J Virol., 80(19), (Oct. 2006), 9659-66.

De Filette, Marina, et al., "An influenza A vaccine based on tetrameric ectodomain of matrix protein 2", J Biol Chem. 2008 ; 283 (17):, (Feb. 5, 2008), 11382-7.

Del Guidice, G., et al., "What are the limits of adjuvanticity?", (Abstract), Vaccine, 20(Suppl 1), S38-S41, (2001), 1 pg.

Desheva, J. A, et al., "Characterization of an influenza A H5N2 reassortant as a candidate for live-attenuated and inactivated vaccines against highly pathogenic H5N1 viruses with pandemic potential", Vaccine, 24, (2006), 6859-6866.

Dos Santos Afonso, Emmanuel, et al., "The generation of recombinant influenza A viruses expressing a PB2 fusion protein requires

(56) References Cited

OTHER PUBLICATIONS the conservation of a packaging signal overlapping the coding and noncoding regions at the 5V end of the PB2 segment", Virology, 341,(2005), 34-46.

Dumoulin, Mireille, et al., "Single-domain antibody fragments with high conformational stability", Protein Science, 11, (2002), 500-515.

Elhefnawi, M, et al., "Identification of novel conserved functional motifs across most Influenza A viral strains", Virology Journal, 8:44, (2011), 10 pages.

Essere, Boris, et al., "Critical role of segment-specific packaging signals in genetic reassortment of influenza A viruses", Proc. Natl. Acad. Sci. USA, 110(40), (2013), E3840-E3848.

Fan, J, et al., "Preclinical study of influenza virus A M2 peptide conjugate vaccines in mice, ferrets, and rhesus monkeys", Vaccine, 22, (2004), 2993-3003.

Fields, S., et al., "Nucleotides Sequences of Influenza Virus Segments 1 and 3 Reveal Mosaic Structrure of Small Viral RNA Segment", Cell, 28, (1982), 303-313.

Fleming, D. M, et al., "Comparison of the efficacy and safety of live attenuated cold-adapted influenza vaccine, trivalent, with trivalent inactivated influenza virus vaccine in children and adolescents with asthma", Pediatr Infect Dis J., 25(10), (2006), 860-869.

Forbes, Nicole E, et al., "Multifunctional Adaptive NS1 Mutations Are Selected upon Human Influenza Virus Evolution in the Mouse", Plos One, vol. 7, No. 2, (Feb. 21, 2012), 20 pgs.

Fujii, Ken, et al., "Importance of both the Coding and the Segment-Speci?c Noncoding Regions of the In?uenza A Virus NS Segment for Its Ef?cient", Journal of Virology, 79(6), (Mar. 2005), 3766-3774.

Gao, Qinshan, et al., "A Nine-Segment In?uenza A Virus Carrying Subtype H1 and H3 Hemagglutinins", Journal of Virology, 84(16), (Aug. 2010), 8062-8071.

Gao, Qinshan, et al., "A Seven-Segmented Influenza A Virus Expressing the Influenza C Virus Glycoprotein HEF", Journal of Virology, 82(13), (Jul. 2008), 6419-6426.

Gao, Qinshan, et al., "The In?uenza A Virus PB2, PA, NP, and M Segments Play a Pivotal Role during Genome Packaging", Journal of Virology, 86(13), Chou, (Jul. 2011), 043-7051.

Giles, Brendan Michael, "Development of Broadly Reactive Vaccine for Highly Pathogenic H5N1 Influenza", Retrieved from the Internet: URL<http//search.proquest.com/docview/928138363>, (Jan. 1, 2011), 283 pgs.

Gorman, O T, et al., "Evolution of influenza A virus PB2 genes: implications for evolution of the ribonucleoprotein complex and origin of human influenza A virus", J. Virol., 64(10), (Oct. 1990), 4893-4902.

Gotea, V, et al., "The functional relevance of somatic synonymous mutations in melanoma and other cancers", Pigment Cell & Melanoma Research, 28 issue 6, (Nov. 1, 2015), 673-686.

Goto, Hideo, et al., "The Genome-Packaging Signal of the Influenza A Virus Genome Comprises a Genome Incorporation Signal and a Genome-Bundling Signal", Journal of Virology; vol. 87 No. 21, (Nov. 2013), 11316-11322.

Govorkova, E A, et al., "Replication of Influenza A Viruses in a Green Monkey Kidney Continuous Cell Line (Vero)", J. Infect. Dis. 172(1), (1995), 250-253.

Groseth, A., "13. Generation of Recombinant Ebola Viruses Using Reverse Genetics", In: Hoenen T., et al. (eds), Ebolaviruses: Methods and Protocols, Methods in Molecular Biology, vol. 162, (2017), 177-187.

Hai, Rong, et al., "Influenza B Virus NS1-Truncated Mutants: Live-Attenuated Vaccine Approach", Journal of Virology, 82(21), (2008), 10580-10590.

Halfmann, Peter J., et al., "Potent neutralization of SARS-CoV-2 including variants of concern by vaccines presenting the receptor-binding domain multivalently from nanoscaffolds", Bioengineering & Translational Medicine, 6(3): e10253, (2021), 8 pgs.

Halstead, Scott B,, et al., "Dengue Antibody-Dependent Enhancement: Knowns and Unknowns", Microbiology Spectrum, 2(6), (2014), 1-18.

Harding, Alfred T, et al., "Rationally Designed Influenza Virus Vaccines That Are Antigenically Stable during Growth in Egg", MBIO, vol. 8, No. 3, eO0669-17, (Jul. 5, 2017), 1-16.

Harmsen, M. M., et al., "Properties, production, and applications of camelid single-domain antibody fragments", Appl Microbiol Biotechnol,77, (2007), 13-22.

Harvey, K. F, et al., "All three WW domains of murine Nedd4 are involved in the regulation of epithelial sodium channels by intracellular Na+.", J Biol Chem., 274(18), (Apr. 30, 1999), 12525-30.

Hatakeyama, S., et al., "Dissection and identification of regions required to form pseudoparticles by the interaction between the nucleocapsid (N) and membrane (M) proteins of SARS coronavirus", Virology, 380(1), (2008), 99-108.

Hatakeyama, S., et al., "Enhanced Expression of an a2,6-Linked Sialic Acid on MDCK Cells Improves Isolation of Human Influenza Viruses and Evaluation of Their Sensitivity to a Neuraminidase Inhibitor", J Clin Microbiol, 43(8). (2005), 4139-4146.

He, X., et al., "Generation of SARS-CoV-2 reporter replicon for high-throughput antiviral screening and testing", Proc. Natl. Acad. Sci. USA, 118(15): e2025866118, (2021), 8 pgs.

Hickman, Danielle, et al., "An avian live attenuated master backbone for potential use in epidemic and pandemic influenza vaccines", Journal of General Virology, 89(Part 11), (2008), 2682-2690.

Ho, Y., et al., "Assembly of human severe acute respiratory syndrome coronavirus-like particles", Biochem Biophys Res Commun, 318(4), (2004), 833-838.

Hoenen, T., et al., "11. Reverse Genetics Systems for Filoviruses", In: Perez, Daniel (Ed.), Reverse Genetics of RNA Viruses: Methods and Protocols. Methods in Molecular Biology, vol. 1602, (2017), 159-170.

Hoenen, Thomas, et al., "Minigenomes, Transcription and Replication Competent Virus-Like Particles and Beyong: Reverse Genetics Systgems for Filoviruses and other Negative Stranded Hemorrhagic Fever Viruses", Antiviral Res., 91:195, (2011), 30.

Hoffman, Lucas R, et al., "Structure-Based Identification of an Inducer of the Low-pH Conformational Change in the Influenza Virus Hemagglutinin: Irreversible Inhibition of Infectivity", Journal of Virology , vol. 71, No. 11, (Nov. 1997), 8808-8820.

Hoffmann, Erich, et al., "A DNA transfection system for generation of influenza A virus from eight plasmids", Proceedings of the National Academy of Sciences, vol. 97, No. 11, (2000), 6108-6113.

Honda, Ayae, et al., "Differential Roles of Viral RNA and cRNA in Functional Modulation of the Influenza Virus RNA Polymerase", The Journal of Biological Chemistry, 276(33), (2001), 31179-31185.

Horimoto, "Designing Vaccines for Pandemic Influenza", Current Topics Microbiol Immunol 333, (2009), 165-176.

Hossain, M. J., et al., "Establishment and Characterization of a Madin-Darby Canine Kidney Reporter Cell Line for Influenza A Virus Assays", J Clin Microbiol, 48(7), (2010), 2515-2523.

Hsieh, P.-K., et al., "Assembly of Severe Acute Respiratory Syndrome Coronavirus RNA Packaging Signal into Virus-Like Particles is Nucleocapsid Dependent", J Virol., 79(22), (2005), 13848-13855.

Huang, Y., et al., "Generation of Synthetic Severe Acute Respiratory Syndrome Coronavirus Pseudoparticles: Implications for Assembly and Vaccine Production", J. Virol,, 78(22), (Nov. 2004), 12557-12565.

Huisman, W., et al., "Vaccine-induced enhancement of viral infections", Vaccine, 27(4), (2009) 505-512.

Hutchinson, Edward C., et al., "Genome packaging in influenza A virus", Journal of General Virology, 91 (Pt 2), (2010), 313-328.

Hwang, Jung-Shan, et al., "Expression of Functional Influenza Virus RNA Polymerase in the Methylotrophic Yeast *Pichia pastoris*", Journal of Virology, 74(9), (2000), 4074-4084.

Isakova-Sivak, Irina, et al., "Characterization of Reverse Genetics-Derived Cold-Adapted Master Donor Virus A/Leningrad/134/17/57 (H2N2) and Reassortants with H5N1 Surface Genes in a Mouse Model", Clinical and Vaccine Immunology, 21(5), (May 2014), 722-731.

(56) References Cited

OTHER PUBLICATIONS

Ives, J. A., et al., "The H274Y mutation in the influenza A/H1N1 neuraminidase active site following oseltamivir phosphate treatment leave virus severely compromised both in vitro and in vivo.", Antiviral Research, 55(2), (2002), 307-317.
Jahrling, P. B., et al., "Ebola Hemorrhagic Fever: Evaluation of Passive Immunotherapy in Nonhuman Primates", J. Infect. Dis. 196, (2007), 4 pgs.
Jang, S.-W., et al., "Deoxygedunin, a Natural Product with Potent Neurotrophic Activity in Mice", PLoS One 5(7): e11528, (2010), 1-15.
Jennings, Philip A., et al., "Does the Higher Order Structure of the Influenza Virus Ribonucleoprotein Guide Sequence Rearrangements in Influenza Viral RNA?", Cell, 34, (Sep. 1983), 619-627.
Jiang, H, et al., "Influenza virus genome C4 promoter/origin attenuates its transcription and replication activity by the low polymerase recognition activity", Virology, 408(2), (2010), 190-196.
Jiang, Y., et al., "Genome wide analysis of protein protein interactions and involvement of viral proteins in SARS CoV 2 replication", Cell Biosci, 11:140, 2021, 16 pgs., (2021), 16 pgs.
Ju, X., et al., "A novel cell culture system modeling the SARS-CoV-2 life cycle", PloS Pathogens, 17(3): e1009439, (2021), 23 pgs.
Kang, Byoung-Hoon, et al., "Ultrafast and Real-Time Nanoplasmonic On-Chip Polymerase Chain Reaction for Rapid and Quantitative Molecular Diagnostics", ACS Nano, 15(6), (2021), 10194-10202.
Kawaoka, Y, et al., "Sequence requirements for cleavage activation of influenza virus hemagglutinin expressed in mammalian cells", Proc Natl Acad Sci., 85(2), (1988), 324-328.
Kim, H., et al., "Cold adaptation generates mutations associated with the growth of influenza B vaccine viruses". Vaccine, 33(43), (2015), 5786-5793.
Kiseleva, Irina V, et al., "PB2 and PA genes control the expression of the temperature-sensitive phenotype of cold-adapted B/USSR/60/69 influenza master donor virus", Journal of General Virology, 91(4), (2010), 931-937.
Kistner, Otfried, et al., "Cell culture (Vero) derived whole virus (H5N1) vaccine based on wild-type virus strain induces cross-protective immune responses", Vaccine, 25(32), (2007), 6028-6036.
Kittel, Christian, et al., "Generation of an Influenza A Virus Vector Expressing Biologically Active Human Interleukin-2 from the NS Gene Segment", Journal of Virology, 79(16), (Aug. 2005), 10672-10677.
Kobayashi, H., et al., "A replication-incompetent influenza virus bearing the HN glycoprotein of human parainfluenza virus as a bivalent vaccine", Vaccine, 31(52), (2013), 6239-6246.
Konduru, K., et al., "Ebola virus glycoprotein Fc fusion protein confers protection against lethal challenge in vaccinated mice", Vaccine, 29(16), (Apr. 5, 2011), 2968-77.
Kopecky, S. A, et al., "Matrix protein and another viral component contribute to induction of apoptosis in cells infected with vesicular stomatitis virus", J Virol., 75(24), (Dec. 2001), Abstract Only.
Kovacova, Andrea, et al., "Sequence Similarities and Evolutionary Relationships of Influenza Vrus A Hemagglutinins", Virus Genes, 24(1), (2002), 57-63.
Kugelman, J. R., et al., "Emergence of Ebola Virus Escape Variants in Infected Nonhuman Primates Treated with the MB-003 Antibody Cocktail", Cell Reports 12, (Sep. 2015), 2111-2120.
Kunik, Vered, et al., "Paratome: an online tool for systematic identification of antigenbinding regions in antibodies based on sequence or structure", Nucleic Acids Research, vol. 40, Issue W1, (2012), W521-W524.
Kuwahara, Tomoko, et al., "Characterization of cell-derived and egg-passaged influenza A/Saitama/2014 (H3N2) strain", The 65th Annual Meeting of the Japanese Society of Virology, (2017), 1 pg.
Kuwahara, Tomoko, et al., "Isolation of an Egg-Adapted Influenza A(H3N2) Virus without Amino Acid Substitutions at the Antigenic Sites of Its Hemagglutinin", Japanese Journal of Infectious Diseases, 71 (3), (2018), 234-238.

Le, T., "CaSpeR5, a family of *Drosophila* transgenesis and shuttle vectors with improved multiple cloning sites", Biotechniques, 42(2), (Feb. 2007), 164-166.
Leal, et al., "New challenges in therapeutic vaccines against HIV infection", Expert Review of Vaccines, vol. 16, No. 6, (2017), 587-600.
Lee, D.-H., et al., "H9N2 avian influenza virus-like particle vaccine provides protective immunity and a strategy for the differentiation of infected from vaccinated animals", Vaccine, vol. 29,(2011), 4003-4007.
Lee, Dong-Hun, et al., "Progress and hurdles in development of influenza virus-like particle vaccines for veterinary use", Korean Vaccine Society, (2014), 133-139.
Lee, Jeffrey E., et al., "Complex of a Protective Antibody with Its Ebola Virus GP Peptide Epitope: Unusual Features of a V?x Light Chain", J. Mol. Biol., 375, (2007), 202-216.
Lee, Jong-Soo, et al., "The Highly Conserved HA2 Protein of the Influenza A Virus Induces a Cross Protective Immune Response", Journal of Virological Methods, 194(1-2), (2013), 280-288.
Lefranc, Marie-Paule, et al., "IMGT unique numbering for immunoglobulin and T cell receptor variable domains and Ig superfamily V-like domains", Developmental & Comparative Immunology, 27, (2003), 55-77.
Li, et al., "Selection of antigenically advanced variants of seasonal influenza viruses", Nature Microbiology, 1 (6), (2016), 1-10.
Li, Feng, et al., "Generation of Replication-Competent Recombinant Influenza A Viruses Carrying a Reporter Gene Harbored in the Neuraminidase Segment", Journal of Virology, 84(22), (Nov. 2010), 12075-12081.
Li, Junwei et al., "Engineering Influenza Viral Vectors", Bioengineered, vol. 4, No. 1, (Jan. 1, 2013), 9-14.
Li, K. S., et al., "Genesis of a highly pathogenic and potentially pandemic H5N1 influenza virus in eastern Asia", Nature, vol. 430, (2004), 209-213 pgs.
Li, Qi, et al., "Screening of the high yield influenza B virus on MDCK cell and cloning of its whole genome", (English Abstract), Chinese Journal of Virology, 3, (Sep. 30, 2004), 1 pg.
Li, Qi, et al., "Screening of the high yield influenza B virus on MDCK cell and cloning of its whole genome", International Congress Series 1263, (2004), 610-614.
Li, Y, et al., "The I binding specificity of human VH4-34 (VH4-21) encoded antibodies is determined by both VH framework region 1 and complementarity determining region 3", J. Mol. Biol. 256 577-589, (1996), 13 pgs.
Lin, Y P, et al., "Adaptation of egg-grown and transfectant influenza viruses for growth in mammalian cells: selection of hemagglutinin mutants with elevated pH of membrane fusion", Virology, 233(2), (1997), 402-410.
Lin, Yi Pu, et al., "Adaptation of Egg-Grown and Transfectant Influenza Viruses for Growth in Mammalian Cells: Selection of Hemagglutinin Mutants with Elevated pH of Membrane Fusion", Virology, vol. 233, Issue 2, (1997), 402-410.
Liu, Bo, et al., "Comparison of three methods in construction fusion gene of influenza A virus Nucleoprotein", (English Abstract), Zhonghua Shi Yan He Lin Chuang Bing Du Xue Za Zhi, 26(1), 70-74, (Feb. 2012), 1 pg.
Liu, Z, et al., "Fine mapping of the antigen-antibody interaction of scFv215 A recombinant antibody inhibiting RNA polymerase II from *Drosophila melanogaster*", J. Mol. Recog. 12:103-111, (1999), 9 pgs.
Longnecker, R., et al., "WW- and SH3-domain interactions with Epstein-Barr virus LMP2A", Exp Cell Res., 257(2), (Jun. 15, 2000), Abstract Only.
Lu, Xiuhua, et al., "Cross-protective immunity in mice induced by live-attenuated or inactivated vaccines against highly pathogenic influenza A (H5N1) viruses", Vaccine, 24(44-46), (2006), 6588-6593.
Lugovtsev, V. Y., et al., "Genetic Composition and Mutational Pattern of Influenza B Viruses Adapted to Replication in Embryonated Eggs", GenBank: AAT69446.1, (2005), 1 pg.
Ma, Y.-J., et al., "Cellular micro RNA let-7c inhibits M1 protein expression of the H1N1 influenza A virus in infected human lung epithelial cells", J. Cell. Mol. Med., 16(10), (2012), 2539-2546.

(56) References Cited

OTHER PUBLICATIONS

Manicassamy, Balaji, et al., "Analysis of in vivo dynamics of influenza virus infection in mice using a GFP reporter virus". Proc Natl Acad Sci. USA, 107(25), (2010), 11531-11536.
Mansky, L. M, "Retrovirus mutation rates and their role in genetic variation", J Gen Virol., 79 (Pt 6), (Jun. 1998), 1337-45.
Manz, Benjamin, et al., "Disruption of the Viral Polymerase Complex Assembly as a Novel Approach to Attenuate Influenza A Virus", The Journal of Biological Chemistry, 286(10), (2011), 8414-8424.
Mark, A, et al., "Effect of Mutations and Deletions in a Bicistronic mRNA on the Synthesis of Influenza B Virus NB and NA Glycoproteins", Journal of Virology, vol. 77, No. 10, (May 2003), 6050-6054.
Marsh, Glenn A., et al., "Specific Residues of the Influenza A Virus Hemagglutinin Viral RNA Are Important for Efficient Packaging into Budding Virions", Journal of Virology, 81(18), (Sep. 2007), 9727-9736.
Martinez-Sobrido, L., et al., "Hemagglutinin-Pseudotyped Green Fluorescent Protein-Expressing Influenza Viruses for the Detection of Influenza Virus Neutralizing Antibodies", J Virol., 84(4), (2010), 2157-2163.
Martorelli Di, Genova B., et al., "Intestinal deita-6-desaturase activity determines host range for Toxoplasma sexual reproduction", PLoS Biology, vol. 17, No. 8, E3000364, (Aug. 20, 2019), XP055619380, (Aug. 20, 2019), 1-19.
Matrosovich, M, et al., "Overexpression of the [alpha]-2,6-sialyltransferase in MDCK cells increases influenza virus sensitivity to neuraminidase inhibitors", Journal of Virology, The American Society for Microbiology, US, vol. 77, No. 15, (Aug. 1, 2003), 8418-8425.
Matsuzaki, Y., et al., "Epitope Mapping of the Hemagglutinin Molecule of A/(H1N1)pdm09 Influenza Virus by Using Monoclonal Antibody Escape Mutants", Journal of Virology, 88(21) 12364-12373, (2014), 10 pgs.
McCullers, Jonathan A., et al., "A single amino acid change in the C-terminal domain of the matrix protein M1 of influenza B virus confers mouse adaption and virulence", Virology, 336(2) 318-326, (Jun. 5, 2005), 9 pgs.
McKee, Dwight L, et al., "Candidate drugs against SARS-CoV-2 and COVID-19", Pharmacological Research, Academic Press, London, GB, vol. 157, (Apr. 29, 2020), 9 pgs.
Mittler, E., et al., "Role of the transmembrane domain of marburg virus surface protein GP in assembly of the viral envelope.", J Virol., 81(8), (Apr. 2007), 3942-8.
Muhlberger, Elke, "Filovirus replication and transcription", Future Virol., 2:205, (2007), 16 pgs.
Murakami, Shin, et al., "Enhanced Growth of Influenza Vaccine Seed Viruses in Vero Cells Mediated by Broadening the Optimal pH Range for Virus Membrane Fusion", J Virol 86(3), (2012), 1405-1410.
Murakami, Shin, et al., "Growth Determinants for H5N1 Influenza Vaccine Seed Viruses in MDCK Cells", Journal of Virology, vol. 82, No. 21, (Nov. 2008), 10502-10509.
Muramoto, Y., et al., "Hierarchy among Viral RNA (vRNA) Segments in Their Role in vRNA Incorporation into Influenza A Virions", J. Virol., 80(5), (2006), 2318-2325.
Muramoto, Yukiko, "Hierarchy among Viral RNA (vRNA) Segments in Their Role in vRNA Incorporation into Influenza A Virions", Journal of Virology , 80(5), (2006), 2318-2325.
Muyldermans, S, "Nanobodies: Natural single-domain antibodies", Ann. Rev. Biochem. 82, (2013), 1 pg.
Nara, et al., "How Can Vaccines Against Influenza and Other Viral Diseases Be Made More Effective?", PLoS Biology, 8 (12), (2010), e1000571.
Neumann, G., et al., "An improved reverse genetics system for influenza A virus generation and its implications for vaccine production", Proc. Natl. Acad. Sci. USA. 102(46), (2005), 16825-16829.

Neumann, Gabriele, "MiniReview Reverse Genetics of Influenza Virus", Virology, vol. 287, (2001), 243-250.
Noda, Takeshi, et al., "Three-dimensional analysis of ribonucleoprotein complexes in influenza A virus", Nature Communications, 3, (2012), 1-6.
Odagiri, Takato, et al., "Segment-Specific Noncoding Sequences of the In?uenza Virus Genome RNA Are Involved in the Speci?c Competition between Defective Interfering RNA and Its Progenitor RNA Segment at the Virion Assembly Step", Journal of Virology, 71(3), (1997), 2138-2145.
Ozaki, "Generation of High-Yielding Influenza A Viruses in African Green Monkey Kidney (Vero) Cells by Reverse Genetics", J Virol 78(4), (2004), 1851-1857.
Ozawa, M., et al., "Replication-incompetent influenza A viruses that stably express a foreign gene", Journal of General Virology, 92(Part 12)., (2011), 2879-2888.
Palese, P., et al., "47. Orthomyxoviridae: The Viruses and Their Replication", In: Fields Virology (5th Edition), (2007), 90 pgs.
Perez, Jasmine T., et al., "Unit 15G.4—Insertion of a GFP Reporter Gene in Influenza Virus", Curr Protoc Microbiol., (2013), 20 pgs.
Peterson, B. C., et al., "Homologous sequences other than insertion elements can serve as recombination sites in plasmid drug resistance gene amplification", Journal of Bacteriology,Oct. 1983 156(1) 177-185, (1983), 5 pgs.
Ping, J., et al., "Development of high-yield influenza B virus vaccine viruses", Proc. Natl. Acad. Sci. USA, 113(51), (Dec. 5, 2016), E8296-E8305.
Pittman, Kelly J., et al., "Z-DNA Binding Protein Mediates Host Control of Toxoplasma gondii Infection", Infection and Immunity, 84(10), (Oct. 2016), 3063-3070.
Plant, E P, et al., "Mutations to A/PuertoRico/8/34 PB1 gene improves seasonal reassortant influenza A virus growth kinetics", Vaccine, 31(1), (Dec. 1, 2012), 207-212.
Popova, Lyubov, et al., "Immunodominance of Antigenic Site B over Site of Hemagglutinin of Recent H3N2 Influenza Viruses", PLoS One, vol. 7 No. 7, (Jul. 25, 2012), e41895.
Powell, Robin H., et al., "WRN conditioned media is sufficient for in vitro propagation of intestinal organoids from large farm and small companion animals", Biology Open, vol. 6, No. 5, (Mar. 27, 2017), XP055620505, (Mar. 27, 2017), 698-705.
Preston, Andrew, "Choosing a Cloning Vector", Methods in Molecular Biology, vol. 235, E. coli Plasmid Vectors 19-27, Edited by: N. Casali and A. Preston, (2003), 9 pgs.
Ramanunninair, Manojkumar, et al., "Molecular Signature of High Yield (Growth) Influenza A Virus Reassortants Prepared as Candidate Vaccine Seeds", PLoS One, 8(6): e65955, (2013), 1-16.
Reed, M. L, et al., "Amino Acid Residues in the Fusion peptide Pocket Regulate the pH of Activation of the H5N1 Influenza Virus Hemagglutinin Protein", . J. Virol., 83(8), (2009), 3568-3580.
Ricardo-Lax, I., et al., "Replication and single-cycle delivery of SARS-CoV-2 replicons", Science, 374(6571), (2021), 1099-1106 (9 pgs).
Rimmelzwaan, G. F., et al., "Use of GFP-expressing influenza viruses for the detection of influenza virus A/H5N1 neutralizing antibodies", Vaccine, 29(18), (2011), 3424-3430.
Romanova, J., et al., "Live cold-adapted influenza A vaccine produced in Vero cell line", Virus Research, 103, (2004), 187-193.
Ruigrok, R W, et al., "Characterization of three highly purified influenza virus strains by electron microscopy", J Gen Virol 65 (Pt 4) 799-802, (Apr. 1984), 4 pgs.
Saphire, E. O., et al., "Feverish Quest for Ebola Immunotherapy: Straight or Cocktail", Trends Microbial, 24(9), (Sep. 2016), 684-686.
Saunders, Kevin O., et al., "Neutralizing antibody vaccine for pandemic and pre-emergent coronaviruses", Nature, 594, (2021), 553-559 (27 pgs.).
Schares, G., et al., "Oocysts of Neospora caninum, Hammondia heydorni, Toxoplasma gondii and Hammondia hammondi in faeces collected from dogs in Germany", International Journal of Parasitology, vol. 35, No. 14, (Dec. 1, 2005), XP027737007, (Dec. 1, 2005), 1525-1537.

(56) References Cited

OTHER PUBLICATIONS

Schmidt, Kristina Maria, et al., "Marburg Virus Reverse Genetics Systems", Viruses 2016, 8, 178; doi: 10.3390 / v8060178, www.mdpi.com/journal/viruses, (2016), 17 pgs.
Schotsaert, M, et al., "Universal M2 ectodomain-based influenza A vaccines: preclinical and clinical developments", Expert Rev Vaccines. Apr. 2009;8(4):, 499-508.
Sheridan. Cormac, et al., "Innovators target vaccines for variants and shortages in global South", Nature Biotechnology, 39(4), (Apr. 2021), 393-396.
Shi, Pei-Yong, "Infectious cDNA Clone of the Epidemic West Nile Virus from New York City", Journal of Virology 5847-5856, (Jun. 2002), 10 pgs.
Shimojima, M., et al., "Tyro3 family-mediated cell entry of Ebola and Marburg viruses", J Virol., 80(20), (Oct. 2006), 10109-16.
Silvas, J. A., et al.. "Contribution of SARS-CoV-2 Accessory Proteins to Viral Pathogenicity in K18 Human ACE2 Transgenic Mice", J Virol, 95(17): e00402-21, (Sep. 2021), 1-14.
Siu, Y. L., et al., "The M, E, and N Structural Proteins of the Severe Acute Respiratory Syndrome Coronavirus Are Required for Efficient Assembly, Trafficking, and Release of Virus-Like Particles", J Virol., 82(22), (2008), 11318-11330.
Smatti, Maria K., et al., "Viral-Induced Enhanced Disease Illness", Front Microbiol, vol. 9: Article 2991, (Dec. 2018), 1-19.
Smura, T, "Surface glycoprotein [Severe acute respiratory syndrome coronavirus 2]", Gen Bank Accessions QH062107, (Feb. 11, 2020), 2 pgs.
Stroud, Chad K., et al., "Disruption of FADS2 gene in mice impairs male reproduction and causes dermal and intestinal ulceration", Journal of Lipid Research, vol. 50, (2009), 1870-1880.
Suguitan, A. L, et al., "Live, Attenuated Influenza A H5N1 Candidate Vaccines Provide Broad Cross-Protection in Mice and Ferrets", PLoS Med., 3(9), (2006), 1541-1555.
Sun, Weina, et al., "Development of Influenza B Universal Vaccine Candidates Usingthe "Mosaic" Hemagglutinin Approach", American Society For Microbiology, Journal of Virology, Vaccines and Antiviral Agents, vol. 93, Issue 12, (Jun. 2019), 17 pgs.
Takada, A., et al., "Downregulation of betal integrins by Ebola virus glycoprotein: implication for virus entry", Virology, 278(1), (Dec. 2000), Abstract Only.
Takada, Ayato, et al., "A system for functional analysis of Ebola?virus?glycoprotein", Proc. Natl. Acad. Sci. USA, 94(26), (1997), 14764-14769.
Takada, Ayato, et al., "Antibody-dependent enhancement of viral infection: molecular mechanisms and in vivo implications", Rev Med Virol, 13(6), (2003), 387-398.
Takada, Ayato, et al., "Epitopes Required for Antibody-Dependent Enhancement of Ebola Virus Infection", J Infect Dis, 196 (Suppl 2), (2007), S347-S356.
Takada, Ayato, et al., "Identification of Protective Epitopes on Ebola Virus Glycoprotein at the Single Amino Acid Level by Using Recombinant Vesicular Stomatitis Viruses", Journal of Virology, 77(2), (2003), 1069-1074.
Takada, Ayato, et al., "Infectivity-Enhancing Antibodies to Ebola Virus Glycoprotein", Journal of Virology, 75(5), (2001), 2324-2330.
Takada, Ayato, et al., "Protective efficacy of neutralizing antibodies against Ebola virus infection", Vaccine, 25(6), (2007), 993-999.
Takada, Ayato, et al., "The pathogenesis of Ebola hemorrhagic fever", Trends in Microbiology, 9(10), (2001), 506-511.
Takada, Kosuke, et al., "A Humanized MDCK Cell Line for the Efficient Isolation and Propagation of Human Influenza Viruses", Nature Microbiology, Nature Publishing Group UK, London, vol. 4, No. 8, (Apr. 29, 2019), 1268-1273.
Tan, Tiong Kit, et al., "A COVID-19 vaccine candidate using SpyCatcher multimerization of the SARS-CoV-2 spike protein receptor-binding domain induces potent neutralising antibody responses", Nature Communications, 12: 542, (2021), 1-16.
Thao, Tran Thi Nhu, et al., "Rapid reconstruction of SARS-CoV-2 using a synthetic genomics platform", Nature, vol. 582 561-565, (2020), 24 pgs.
Theriault, S., "The role of reverse genetics systems in determining filovirus pathogenicity", Archives of Virology, Supplementum. 157-177, (2005), 22 pgs.
Thompson, Christine M, et al., "Critical assessment of influenza VLP production in Sf9 and HEK293 expression systems", BMC Biotechnology, 15(1), (May 16, 2015), 12 pgs.
Tobler, K, et al., "Effect of cytoplasmic tail truncations on the activity of the M(2) ion channel of influenza A virus", J Virol., 73(12), (Dec. 1999), 9695-9701.
Uraki, R., et al., "A Bivalent Vacine Based on a PB2-Knockout Influenza Virus Protects Mice From Secondary Pneumoccal Pneumonia", The Journal of Infectious Diseases, 212(12), (2015), 1939-1948.
Uraki, R., et al., "A Novel Bivalent Vaccine Based on a PB2-Knockout Influenza Virus Protects Mice from Pandemic H1N1 and Highly Pathogenic H5N1 Virus Challenges", Journal of Virology, 87(14), (2013), 7874-7881.
Vaishnava, Shipra, et al., "The Antibacterial Lectin Regllly Promotes the Spatial Segregation of Microbiota and Host in the Intestine", Science, 334 255-258, (2011), 4 pgs.
Varner, Chad, "Developing Synthetic Multivalent Cellular Effectors", Thesis, School of Chemical and Biomolecular Engineering, Georgia Institute of Technology, (Aug. 2017), 88 pgs.
Via, L. E, et al., "Isolation of restriction fragments from large plasmids recovered from bacteria with multiple plasmids", Biotechniques, 11(4), (Oct. 1991), Abstract Only.
Victor, Sylvia, et al., "A Replication-Incompetent PB2-Knockout Influenza A Virus Vaccine Vector", Journal of Virology, vol. 86, No. 8, (Apr. 2012), 4123-4128.
Vincke, C, et al., "Introduction to heavy chain antibodies and derived nanobodies", Meth. Mol. Biol. 911, (2012), 13 pgs.
Von Wielink, R., et al., "Mutations in the M-Gene Segment can Substantially Increase Replication Efficiency of NS1 Deletion Influenza A Virus in MCK Cells", Journal of Virology. vol. 86, (2012), 12341-12350.
Waap, Helga, et al., "In vitro isolation and seroprevalence ofin stray cats and pigeons in Lisbon, Portugal", Veterinary Parasitology, vol. 187, No. 3 XP028492469 542-547, (Jan. 17, 2012), 6 pgs.
Wan, Yushun, et al., "Molecular mechanism for Antibody-Dependent Enhancement of Coronavirus EntrM", Journal of Virology, 94(5): e02015-19, (2019), 1-15.
Wang, B., et al., "Construction of Non-infectious SARS-CoV-2 Replicons and Their Application in Drug Evaluation", Virologica Sinica. 36, (2021), 890-900.
Wang, Sheng-Fan, et al., "Antibody-dependent SARS coronavirus infection is mediated by antibodies against spike proteins", Biochem Biophys Res Commun, 451 208-214, (2014), 8 pgs.
Wang, Weijia, et al., "Identification of Critical Residues in the Hemagglutinin and Neuraminidase of Influenza Virus H1N1pdm for Vaccine Virus Replication in Embryonated Chicken Eggs", Journal of Virology, 87(8), (2013), 4642-4649.
Wang, Wenlig, et al., "Robust Immunity and Heterologous Protection against Influenza in Mice Elicited by a Novel Recombinant NP-M2e Fusion Protein Expressed in E. coli", PLoS ONE 7(12): 52488, (Dec. 2012), 1-13.
Wanitchang, Asawin, et al., "Characterization of influenza A virus pseudotyped with the spike protein of porcine epidemic diarrhea virus", Archives of Virology, 163(12), (2018), 3255-3264.
Watanabe, T., et al., "Novel Approach to the Development of Effective H5N1 In?uenza A Virus Vaccines: Use of M2 Cytoplasmic Tail Mutants", Journal of Virology, 82(5), (2008), 2486-2492.
Watanabe, Tokiko, et al., "Exploitation of Nucleic Acid Packaging Signals To Generate a Novel In?uenza Virus-Based Vector Stably Expressing Two Foreign Genes", Journal of Virology, 77(19), (Oct. 2003), 10575-10583.
Watanabe, Tokiko, et al., "Exploitation of Nucleic Acid Packaging Signals to Generate a Novel Influenza Virus-Based Vector Stably Expressing Two Foreign Genes", Journal of Virology, 77(19), (Oct. 2003), 10575-10583.
Watanabe, Tokiko, et al., "Influenza A Virus Can Undergo Multiple Cycles of Replication without M2 Ion Channel Activity", Journal of Virology 75(12), (2001), 5656-5662.

(56) References Cited

OTHER PUBLICATIONS

Webster, R G, et al., "Evolution and molecular epidemiology of H9N2 influenza A viruses from quail in southern China", XP002744257, retrieved from EBI accession No. UNIPR0T:A3R6C9 Database accession No. A3R6C9 the whole document, (Apr. 3, 2007), 1 pg.
Wei, Hung-Ju, et al., "Fabrication of influenza virus-like particles using M2 fusion proteins for imaging single viruses and designing vaccines", Vaccine, 29, (2011), 7163-7172.
Wei, Kai, et al., "Influenza A Virus Acquires Enhanced Pathogenicity and Transmissibility after Serial Passages in Swine", Journal of Virology, 88(20), (Oct. 2014), 11981-11994.
Wentworth, D E, et al., "The NIAID Influenza Genome Sequencing Project", XP002744258, retrieved from EBI accession No. UNIPROT:U3S198 Database accession No. U3S198 the whole document, (Dec. 11, 2013), 1 pg.
Wiedmer, T., et al., "Identification of three new members of the phospholipid scramblase gene family", Biochim Biophys Acta, 1467(1), (Jul. 31, 2000), Abstract Only.
Williams, Mark A., et al., "Effect of Mutations and Deletions in a Bicistronic mRNA on the Synthesis of Influenza B Virus NB and NA Glycoproteins", Journal of Virology, 63(1), (1989), 28-35.
Winkler, K, et al., "Changing the antigen binding specificity by single point mutations of an anti-p24 (HIV-1) antibody", J. Immunol. 165 4505-4514, (2000), 11 pgs.
Winter, G., et al., "The use of synthetic oligodeoxynucleotide primers in cloning and sequencing segment 8 of influenza virus (A/PR/8/34)", Nucleic Acids Res., 9(2), (1981), 237-245.
Wu, Tai Te, et al., "An Analysis of the Sequences of the Variable Regions of Bence Jones Proteins and Myeloma Light Chains and Their Implications for Anti-body complementarity", J. Exp. Med., 132(2), (1970), 211-250.
Xiang, J, et al., "Modification in framework region I results in a decreased affinity of chimeric anti-Tag72 antibody", Mol. Immunol. 28(1/2), (1991), 141-148.
Xu, Ruodan, et al., "Construction of SARS-CoV-2 Virus-Like Particles by Mammalian Expression System", Frontiers in Bioengineering and Technology, 8:862, (2020), 1-6.
Xu, X., et al., "Reassortment and evolution of current human influenza A and B viruses", Virus Research, 103, (2004), 55-60.
Yamamoto, K., et al., "Orientation Dependence in Homologous Recombination", Genetics May 1996; 143(1): 27-36, (1996), 27-36.
Yang, Z. Y, et al., "Identification of the Ebola virus glycoprotein as the main viral determinant of vascular cell cytotoxicity and injury", Nat Med., 6(8), (Aug. 2000), Abstract Only.
Yannarell, Dean A., et al., "Factors affecting the yield of cold-adapted influenza virus vaccine", Journal of Virological Methods, vol. 64, 161-169, (1997), 1 pg.
Yen, H L, et al., "Neuraminidase Inhibitor-Resistant Recombinant A/Vietnam/1203/04 (K5N1) Influenza Viruses Retain Their Replication Efficiency and Pathogenicity In Vitro and In Vivo", Journal of Virology., vol. 81, No. 22, (Nov. 15, 2007), 12418-12426.
Yi, Pu Lin, et al., "Adaptation of Egg-Grown and Transfectant Influenza Viruses for Growth in Mammalian Cells: Selection of Hemagglutinin Mutants with Elevated pH of Membrane Fusion", Virology, 233(2), (Jul. 7, 1997), 402-410.
Yip, Ming S., et al., "Antibody-dependent infection of human macrophages by severe acute respiratory syndrome coronavirus", Virology Journal, 11: 82, (2014), 11 pgs.
Zeitlin, L., et al., "Antibody Therapeutics for Ebola Virus Disease", Curr. Opin. Viral. 17:, (2016), 11 pgs.
Zhang, Baoshan, et al., "A platform incorporating trimeric antigens into self-assembling nanoparticles reveals SARS-CoV-2-spike nanoparticles to elicit substantially higher neutralizing responses than spike alone", Scientific Reports 10, Article No. 18149, (2020), 13 pgs.
Zhang, Q.-Y., et al., "SARS-CoV-2 replicon for high-throughput antiviral screening". J Gen Virol,. 102(5), (2021), 1-4.
Zhang, V. Q, et al., "Easy two-step method for randomizing and cloning gene fragments", Methods Mol Biol., 634, (2010), Abstract Only.
Zhang, Y., et al., "A bacterial artificial chromosome (BAC)-vectored noninfectious replicon of SARS-CoV-2", Antiviral Research, vol. 185, 104974, (Jan. 2021), 1-9.
Zhao, Lili, et al., "New Insights into the Nonconserved Noncoding Region of the Subtype-Determinant Hemagglutinin and Neuraminidase Segments of Influenza A Viruses", Journal of Virology, 88(19) 11493-11503, (Oct. 2014), 11 pgs.
Zhou, Yan, "Membrane-Anchored Incorporation of a Foreign Protein in Recombinant Influenza Virions", Virology 246(1), (1998), 83-94.
"Australian Application Serial No. 2021204721, First Examination Report dated Mar. 16, 2023", 6 pgs.
"U.S. Appl. No. 17/004,583, PTO Response to Rule 312 Communication dated Apr. 6, 2023", 3 pgs.
"European Application Serial No. 21705801.5, Response to Communication pursuant to Rules 161 and 162 filed Mar. 28, 2023", 13 pgs.

\* cited by examiner

Figure 2

SEQ ID NO:1

MNPNQKIITIGSVSLTISTICFFMQIAILITTVTLHFKQYEFNSPPNN
QVMLCEPTIIERNITEIVYLTNTTIEKEICPKLAEYRNWSKPQCNIT
GFAPFSKDNSIRLSAGGDIWVTREPYVSCDPDKCYQFALGQGTTL
NNVHSNDIVHDRTPYRTLLMNELGVPFHLGTKQVCIAWSSSSCHD
GKAWLHVCVTGDDENATASFIYNGRLADSIVSWSKKILRTQESEC
VCINGTCTVVMTDGSASGKADTKILFIEEGKIVHTSTLSGSAQHVE
ECSCYPRYPGVRCVCRDNWKGSNRPIVDINIKDYSIVSSYVCSGLV
GDTPRKNDSSSSSHCLDPNNEEGGHGVKGWAFDDGNDVWMGRT
ISEKLRSGYETFKVIEGWSNPNSKLQINRQVIVDRGNRSGYSGIFSV
EGKSCINRCFYVELIRGRKQETEVLWTSNSIVVFCGTSGTYGTGSW
PDGADINLMPI

A/Yokohama/2017/03

Figure 3

MNPNQKIITIGSVSLTISTICFFMQIAILITTVTLHFKQYEFNSPPNNQVMLCEPTIIERNVTEIVYLTNTTIEKEI
CPKPAEYRNWSKPQCGITGFAPFSKDNSIRLSAGGDIWVTREPYVSCDPDKCYQFALGQGTTLNNVHSNNTVRDRTP
YRTLLMNELGVPFHLGTKQVCIAWSSSSCHDGKAWLHVCITGDDKNATASFIYNGRLVDSVVSWSKDILRTQESECV
CINGTCTVVMTDGSASGKADTKILFIEEGKIVHTSKLSGSAQHVEECSCYPRYPGVRCVCRDNWKGSNRPIVDINIK
DHSIVSSYVCSGLVGDTPRKNDSSSSHCLDPNNEEGGHGVKGWAFDDGNDVWMGRTINETSRLGYETFKVVEGWSN
PKSKLQINRQVIVDRGDRSGYSGIFSVEGKSCINRCFYVELIRGRKEETEVLWTSNSIVVFCGTSGTYGTGSWPDGA
DLNLMPI   (SEQ ID NO:2)

Figure 4

Y2017M3L4-NA(32A, 147N, 329D, 347Q, del46-50aa)
(SEQ ID NO:3)

```
MNPNQKIITIGSVSLTISTICFFMQIAILITAVTLHFKQ
YEFNSPMLCEPTIIERNITEIVYLTNTTIEKEICPKLAE
YRNWSKPQCNITGFAPFSKDNSIRLSAGGDIWVTREP
YVSCDPDKCYQFALGQGTTLNNVHSNNIVHDRTPYR
TLLMNELGVPFHLGTKQVCIAWSSSSCHDGKAWLHV
CVTGDDENATASFIYNGRLADSIVSWSKKILRTQESE
CVCINGTCTVVMTDGSASGKADTKILFIEEGKIVHTS
TLSGSAQHVEECSCYPRYPGVRCVCRDNWKGSNRPI
VDINIKDYSIVSSYVCSGLVGDTPRKDDSSSSHCLD
PNNEEGGQGVKGWAFDDGNDVWMGRTISEKLRSGY
ETFKVIEGWSNPNSKLQINRQVIVDRGNRSGYSGIFS
VEGKSCINRCFYVELIRGRKQETEVLWTSNSIVVFCG
TSGTYGTGSWPDGADINLMPI
```

Figure 5

N3 (Accession No. AAO62039.1)

```
  1 mnpnqkiiti gvvnttlsti alligvgnli fntvihekig dhqtvihptt ttpaipncsd
 61 tiitynntvi nnittiitea erlfkpplpl cpfrgffpfh kdnairlgen kdvivtrepy
121 vscdndncws falaqgallg tkhsngtikd rtpyrsliqf pigtapvlgn ykeiciawss
181 sscfdgkewm hvcmtgndnd asaqiiyagr mtdsikswkr dilrtqesec qcidgtcvva
241 vtdqpaansa dhrvywireg rivkyenvpk tkiqhleecs cyvdidvyci crdnwkgsnr
301 pwmrinneti letgyvcskf hsdtprpadp stvscdspsn vnggpgvkgf qfkvgndvwl
361 grtmstsgrs gfeiikvaeg winspnhaks vtqtlvsnnd wsgysgsfiv ktkacfqpcf
421 yvelirgrpn knddvswtsn sivtfcgldn epgsgnwpdg snigfmpk (SEQ ID NO:4)
```

N4 (Accession No. AAO62043.1)

```
  1 mnpnqkiiti gsvsiiltti gllqitslc siwfshynqv tqtheqpcsn nttnyynetf
 61 vnvtnvqnny ttviepsapd vvhyssgrdl cpirgwapls kdngirigsr gevfvirepf
121 iscsisecrt ffltqgalln dkhsngtvkd rspfrtlmsc pigvapspsn srfesvawsa
181 tacsdgpgwi tlgitgpdat avavikyngi itdtlkswkg nimrtqesec vcqdefcytl
241 itdgpsdaqa fykilkirkg kivsmkdvda tgfhfeecsc ypsqtdiecv crdnwrgsnr
301 pwirfnsdld yqigyvcsgi fgdnprpvdg tgscnspvnn gkgrygvkgf sfrygdgvwi
361 grtkslesrs gfemvwdang wvstdkdsng vqdiidndnw sgysgsfsir gettgrnctv
421 pcfwvemirg qpkektiwts gssiafcgvn sdttgwswpd gallpfdidk (SEQ ID NO:5)
```

N6 (Accession No. AAO62070.1)

```
  1 mnpnqkiici satgmtlsvv slligianlg lniglhykmg dtpdvnipnm netnstttii
 61 nnhtqnnftn itniivnkne egtflnltkp lcevnswhil skdnairige dahilvtrep
121 ylscdpqgcr mfalsqgttl rgrhangtih drspfralis wemgqapspy nvrvecigws
181 stschdgisr msicmsqann nasavvwygg rpvteipswa gnilrtqese cvchkgicpv
241 vmtdqpannr aatkiiyfke gkiqkieela gntqhieecs cygavgvikc icrdnwkgan
301 rpvitidpem mthtskylcs kiltdtsrpn dptngncdap itggspdpgv kqfafldren
361 swlgrtiskd srsgyemlkv pnaetdtqsg pishqvivnn qnwsgysgaf idywankecf
421 npcfyvelir grpkessvlw tsnsivalcg skerlgswsw hdgaeiiyfk (SEQ ID NO:6)
```

N7 (Accession No. AIK26357.1)

```
  1 mnpnqklfal sgvaialsil nlligisnvg lnvslhlkgs sdqdknwtct svtqnnttli
 61 entyvnnttv idketgtakp nylmlnkslc kvegwvvvak dnairfgese qiivtrepyv
121 scdplgckmy alhqgttirn khsngtihdr tafrglistp lqsppvvsns dflcvgwsst
181 schdgigrmt icvqgnndna tatvyydrrl tttiktwagn ilrtqesecv chngtcvvim
241 tdgsassqay tkvlyfhkgl vikeealkgs arhieecscy ghnskvtcvc rdnwqganrp
301 vieidmname htsqylctgv ltdtsrpsdk smgdcnnpit gspgapgvkg fgfldssntw
361 lgrtisprsr sgfemlkipn aetdpnskit erqeivdnnn wsgysgsfid ywdessecyn
```

Figure 5 cont.

```
421 pcfyvelirg rpeeakyvgw tsnslialcg spisvgsgsf pdgaqiqyfs (SEQ ID NO:7)
```

N8 (Accession No. AIK26315.1)

```
  1 mnpnqkiitv qsvslglvvl nillhivsit vtvlvlpgng nnkncnetvi reynetvrie
 61 kvtqwhntnv ieyiekpesg hfmnnteaic dakqfapfsk dngirigsrg hvfvirepfv
121 scsptecrtf fltqgsllnd khsngtvkdr spyrtlmsve igqspnvyqa rfeavawsat
181 achdgkkwmt igvtgpdaka vavvhyggip tdvinswagd ilrtqessct ciqgecywvm
241 tdgpanrqaq yrafkakqgk ivgqteisfn gshieecscy pneqkvecvc rdnwtgtnrp
301 vlvispdlsy ragylcaglp sdtprgedsq ftgsctspvg nqgygvkqfg frqgndvwmg
361 rtisrtsrsg feilkvrngw vqnskeqikr qvvvdnlkws gysgsftlpv eltkrnclvp
421 cfwvemirgk peektiwtss ssivmcgvdh eiadwswhdg ailpfdidkm (SEQ ID NO:8)
```

N9 (Accession No. ALH21371)

```
  1 mnpnqkilct sataiiigai avligianlg lniglhlkpg cncshsqpet tntsqtiinn
 61 yynetnitni qmeertsrnf nnltkglcti nswhiygkdn avrigessdv lvtrepyvsc
121 dpdecrfyal sqgttirgkh sngtihdrsq yraliswpls spptvynsrv ecigwsstsc
181 hdgksrmsic isgpnnnasa vvwynrrpvt eintwarnil rtqesecvch ngvcpvvftd
241 gsatgpadtr iyyfkegkil kwesltgtak hieecscyge rtgitctcrd nwqgsnrpvi
301 qidpvamtht sqyicspvlt dnprpndpni gkcndpypgn nnnqvkqfsy ldgantwlgr
361 tistasrsgy emlkvpnalt ddrskpiqgq tivlnadwsg ysgsfmdywa egdcyracfy
421 velirgrpke dkvwwtsnsi vsmcsstefl gqwnwpdgak ieyfl (SEQ ID NO:9)
```

Figure 6

SEQ ID NO:10

MERIKELRNLMSQSRTREILTKTTVDHMAIIKKY
TSGRQEKNPALRMKWMMAMKYPITADKRITEM
IPERNEQGQTLWSKMNDAGSDRVMVSPLAVTW
WNRNGPMTNTVHYPKIYKTYFERVERLKHGTF
GPVHFRNQVKIRRRVDINPGHADLSAKEAQDVI
MEVVFPNEVGARILTSESQLTITKEKKEELQDCK
ISPLMVAYMLERELVRKTRFLPVAGGTSSVYIE
VLHLTQGTCWEQMYTPGGEVKNDDVDQSLIIA
ARNIVRRAAVSADPLASLLEMCHSTQIGGIRMV
DILKQNPTEEQAVDICKAAMGLRISSSFSFGGFT
FKRTSGSSVKREEEVLTGNLQTLKIRVHEGSEEF
TMVGRRATAILRKATRRLIQLIVSGRDEQSIAEA
IIVAMVFSQEDCMIKAVRGDLNFVNRANQRLNP
MHQLLRHFQKDAKVLFQNWGVEPIDNVMGMIG
ILPDMTPSIEMSMRGVRISKMGVDEYSSTERVV
VSIDRFLRVRDQRGNVLLSPEEVSETQGTEKLTI
TYSSSMMWEINGPESVLVNTYQWIIRNWETVKI
QWSQNPTMLYNKMEFEPFQSLVPKAIRGQYSGF
VRTLFQQMRDVLGTFDTAQIIKLLPFAAAPPKQ
SRMQFSSFTVNVRGSGMRILVRGNSPVFNYNKA
TKRLTVLGKDAGTLTEDPDEGTAGVESAVLRGF
LILGKEDRRYGPALSINELSNLAKGEKANVLIGQ
GDVVLVMKRKRDSSILTDSQTATKRIRMAIN

SEQ ID NO:11

MDVNPTLLFLKVPAQNAISTTFPYTGDPPYSHG
TGTGYTMDTVNRTHQYSEKGRWTTNTETGAPQ
LNPIDGPLPEDNEPSGYAQTDCVLEAMAFLEES
HPGIFENSCIETMEVVQQTRVDKLTQGRQTYDW
TLNRNQPAATALANTIEVFRSNGLTANESGRLID
FLKDVMESMKKEEMGITTHFQRKRRVRDNMTK
KMITQRTIGKRKQRLNKRGYLIRALTLNTMTKD
AERGKLKRRAIATPGMQIRGFVYFVETLARSICE
KLEQSGLPVGGNEKKAKLANVVRKMMTNSQDT
ELSFTITGDNTKWNENQNPRMFLAMITYMTRNQ
PEWFRNVLSIAPIMFSNKMARLGKGYMFESKSM

Figure 6 cont.

KLRTQIPAEMLASIDLKYFNDSTRKKIEKIRPLLI
EGTASLSPGMMMGMFNMLSTVLGVSILNLGQK
RYTKTTYWWDGLQSSDDFALIVNAPNHEGIQAG
VDRFYRTCKLLGINMSKKKSYINRTGTFEFTSFF
YRYGFVANFSMELPSFGVSGINESADMSIGVTVI
KNNMINNDLGPATAQMALQLFIKDYRYTYRCH
RGDTQIQTRRSFEIKKLWEQTRSKAGLLVSDGG
PNLYNIRNLHIPEVCLKWELMDEDYQGRLCNPL
NPFVSHKEIESMNNAVMMPAHGPAKNMEYDAV
ATTHSWIPKRNRSILNTSQRGVLEDEQMYQRCC
NLFEKFFPSSSYRRPVGISSMVEAMVSRARIDAR
IDFESGRIKKEEFTEIMKICSTIEELRRQK

SEQ ID NO:12

MEDFVRQCFNPMIVELAEKTMKEYGEDLKIETN
KFAAICTHLEVCFMYSDFHFINEQGESIIVELGD
PNALLKHRFEIIEGRDRTMAWTVVNSICNTTGA
EKPKFLPDLYDYKENRFIEIGVTRREVHIYYLEK
ANKIKSEKTHIHIFSFTGEEMATRADYTLDEESR
ARIKTRLFTIRQEMASRGLWDSFRQSERGEETIE
ERFEITGTMRKLADQSLPPNFSSLENFRAYVDGF
EPNGYIEGKLSQMSKEVNARIEPFLKTTPRPLRL
PNGPPCSQRSKFLLMDALKLSIEDPSHEGEGIPL
YDAIKCMRTFFGWKEPNVVKPHEKGINPNYLLS
WKQVLAELQDIENEEKIPKTKNMKKTSQLKWA
LGENMAPEKVDFDDCKDVGDLKQYDSDEPELR
SLASWIQNEFNKACELTDSSWIELDEIGEDVAPI
EHIASMRRNYFTSEVSHCRATEYIMKGVYINTA
LLNASCAAMDDFQLIPMISKCRTKEGRRKTNLY
GFIIKGRSHLRNDTDVVNFVSMEFSLTDPRLEPH
KWEKYCVLEIGDMLLRSAIGQVSRPMFLYVRTN
GTSKIKMKWGMEMRRCLLQSLQQIESMIEAESS
VKEKDMTKEFFENKSETWPIGESPKGVEESSIGK
VCRTLLAKSVFNSLYASPQLEGFSAESRKLLLIV
QALRDNLEPGTFDLGGLYEAIEECLINDPWVLL
NASWFNSFLTHALS

SEQ ID NO:13

Figure 6 cont.

MASQGTKRSYEQMETDGERQNATEIRASVGKMI
GGIGRFYIQMCTELKLSDYEGRLIQNSLTIERMV
LSAFDERRNKYLEEHPSAGKDPKKTGGPIYRRV
NGKWMRELILYDKEEIRRIWRQANNGDDATAG
LTHMMIWHSNLNDATYQRTRALVRTGMDPRMC
SLMQGSTLPRRSGAAGAAVKGVGTMVMELVRM
IKRGINDRNFWRGENGRKTRIAYERMCNILKGK
FQTAAQKAMMDQVRESRNPGNAEFEDLTFLAR
SALILRGSVAHKSCLPACVYGPAVASGYDFERE
GYSLVGIDPFRLLQNSQVYSLIRPNENPAHKSQL
VWMACHSAAFEDLRVLSFIKGTKVVPRGKLSTR
GVQIASNENMETMESSTLELRSRYWAIRTRSGG
NTNQQRASAGQISIQPTFSVQRNLPFDRTTVMA
AFTGNTEGRTSDMRTEIIRMMESARPEDVSFQG
RGVFELSDEKAASPIVPSFDMSNEGSYFFGDNA
EEYDN

SEQ ID NO:14

MSLLTEVETYVLSIIPSGPLKAEIAQRLEDVFAG
KNTDLEVLMEWLKTRPILSPLTKGILGFVFTLTV
PSERGLQRRRFVQNALNGNGDPNNMDKAVKLY
RKLKREITFHGAKEISLSYSAGALASCMGLIYNR
MGAVTTEVAFGLVCATCEQIADSQHRSHRQMV
TTTNPLIRHENRMVLASTTAKAMEQMAGSSEQA
AEAMEVASQARQMVQAMRTIGTHPSSSAGLKN
DLLENLQAYQKRMGVQMQRFK

```
  1 mnpnqkiiti gsvcmtigma nlilqignii siwishsiql gnqnqieton qsvityennt
 61 wvnqtyvnis ntnfaagqsv vsvklagnss lcpvsgwaiy skdnsvrigs kgdvfvirep
121 fiscsplecr tffltqgall ndkhsngtik drspyrtlms cpigevpspy nsrfesvaws
181 asachdginw ltigisqpdn gavavlkyng iitdtikswr nnilrtqese cacvngscft
241 vmtdgpsngq asykifriek gkivksvemn apnyhyeecs cypdsseitc vcrdnwhgsn
301 rpwvsfnqnl eyqigyicsg ifgdnprpnd ktqscgpvss ngangvkqfs fkygngvwig
361 rtksissrng femiwdpnqw tgtdnnfsik qdivginews gysgsfvqhp eltgldcirp
421 cfwvelirgr pkentiwtsg ssisfcgvns dtvgwswpdg aelpftidk (SEQ ID
    NO:15)
```

N7

```
  1 mnpnqklfal sgvaiaisil nlligisnvg invslhlkgs sdqdknwtct svtqnnttli
 61 entyvnnttv idketgtakp nylmlnkslc kvegwvvvak dnairfgese qiivtrepyv
121 scdplgckmy alhqgttirn khsngtihdr tafrglistp lgsppvvsns dflcvgwsst
181 schdgigrmt icvqgnndna tatvyydrrl tttiktwagn ilrtqesecv chngtcvvim
241 tdgsassqay tkvlyfhkgl vikeealkgs arhieecscy ghnskvtcvc rdnwqganrp
301 vieidmname htsqylctgv ltdtsrpsdk smqdcnnpit gspgapgvkq fqfldssntw
361 lgrtisprsr sgfemlkipn aetdpnskit erqeivdnnn wsgysgsfid ywdessecyn 421 pcfyvelirg rpeeakyvgw tsnslialcg spisvgsgsf pdgaqiqyfs (SEQ ID
    NO:16)
```

N9

```
  1 mnpnqkilct sataiiigai avligianlg iniglhlkpg cncshsqpet tntsqtiinn
 61 yynetnitni qmeertsrnf nnltkglcti nswhiygkdn avrigessdv lvtrepyvsc
121 dpdecrfyal sqgttirgkh sngtihdrsq yraliswpls spptvynsrv ecigwsstsc
181 hdgksrmsic isgpnnnasa vvwynrrpva eintwarnil rtqesecvch ngvcpvvftd
241 gsatgpadtr iyyfkegkii kwesltgtak hieecscyge rtgitctcrd nwqgsnrpvi
301 qidpvamtht sqyicspvlt dnprpndpni gkcndpypgn nnngvkgfsy ldgantwlgr
361 tistasrsgy emlkvpnalt ddrskpiqgq tivlnadwsg ysgsfmdywa egdcyracfy
  421 velirgrpke dkvwwtsnsi vsmcsstefl gqwnwpdgak ieyfl (SEQ ID
    NO:17)
```

N2

```
  1 mnpnqkiiti gsvsltisti cffmqiaili ttvtlhfkqy efnsppnnqv mlceptiier
 61 niteivyltn ttiekeicpk laeyrnwskp qcnitgfapf skdnsirlsa ggdiwvtrep
```

Figure 7 cont.

```
121 yvscdpdkcy qfalgqgttl nnvhsndivh drtpyrtllm nelgvpfhlg tkqvciawss
181 sschdgkawl hvcvtgdden atasfiyngr ladsivswsk kilrtqesec vcingtctvv
241 mtdgsasgka dtkilfieeg kivhtstlsg saqhveecsc yprypgvrcv crdnwkgsnr
301 pivdinikdy sivssyvcsg lvgdtprknd sssshcldp nneegghgvk gwafddgndv
361 wmgrtisekl rsgyetfkvi eqwsnpnskl qinrqvivdr gnrsgysgif svegkscinr
421 cfyvelirgr kqetevlwts nsivvfcgts gtygtgswpd gadinlmpi (SEQ ID
NO:18)
```

Figure 8

>A/Hong Kong/4801/2014NA(T148K)
ATGAATCCAAATCAAAAGATAATAACGATTGGCTCTGTTTCTCTCACCATTTCCACAATATGCTTTTTCATGC
AAATTGCCATTTTGATAACTACTGTAACATTGCATTTCAAGCAATATGAATTCAACTCCCCCCCAAACAACC
AAGTGATGCTGTGTGAACCAACAATAATAGAAAGAAACATAACAGAGATAGTGTATTTAACCAACACCACC
ATAGAGAAGGAAATATGCCCCAAACCAGCAGAATACAGAAATTGGTCAAAACCGCAATGTGGCATTACAG
GATTTGCACCTTTCTCTAAGGACAATTCGATCAGGCTTTCCGCTGGTGGGGACATCTGGGTGACAAGAGA
ACCTTATGTGTCATGCGATCCTGACAAGTGTTATCAATTTGCCCTTGGACAGGGAACAACACTAAACAACG
TGCATTCAAATAACAAAGTACGTGATAGGACCCCTTATCGGACTCTATTGATGAATGAGTTGGGTGTTCCTT
TCCATCTGGGGACCAAGCAAGTGTGCATAGCATGGTCCAGCTCAAGTTGTCACGATGGAAAAGCATGGCT
GCATGTTTGTATAACGGGGGATGATAAAAATGCAACTGCTAGCTTCATTTACAATGGGAGGCTTGTAGATA
GTGTTGTTTCATGGTCCAAAGATATTCTCAGGACCCAGGAGTCAGAATGCATTTGTATCAATGGAACTTGT
ACAGTAGTAATGACTGATGGAAGTGCTTCAGGAAAAGCTGATACTAAAATACTATTCATTGAGGAGGGA
AAATCGTTCATACTAGCACATTGTCAGGAAGTGCTCAGCATGTCGAAGAGTGCTCTTGCTATCCTCGATATC
CTGGTGTCAGATGTGTCTGCAGAGACAACTGGAAGGGCTCCAATCGGCCCATCGTAGATATAAACATAAA
GGATCATAGCATTGTTTCCAGTTATGTGTGTTCAGGACTTGTTGGAGACACACCCAGAAAAAACGACAGC
TCCAGCAGTAGCCATTGTTTGGATCCTAACAATGAAGAAGGTGGTCATGGAGTGAAAGGCTGGGCCTTT
GATGATGGAAATGACGTGTGGATGGGAAGAACAATCAACGAGACGTCACGCTTAGGGTATGAAACCTTC
AAAGTCATTGAAGGCTGGTCCAACCCTAAGTCCAAATTGCAGACAAATAGGCAAGTCATAGTTGACAGAG
GTGATAGGTCCGGTTATTCTGGTATTTTCTCTGTTGAAGGCAAAAGCTGCATAAATCGGTGCTTTTATGTG
GAGTTGATTAGGGGAAGAAAAGAGGAAACTGAAGTCTTGTGGACCTCAAACAGTATTGTTGTGTTTTGT
GGCACCTCAGGTACATATGGAACAGGCTCATGGCCTGATGGGGCGGACCTCAATCTCATGCCTATATAAGC
TTTCGCAATTTTAGAAAAAACT (SEQ ID NO:19)

> A/Hong Kong/4801/2014NA(T148K, D151E, H347G, T369K)
ATGAATCCAAATCAAAAGATAATAACGATTGGCTCTGTTTCTCTCACCATTTCCACAATATGCTTTTTCATGC
AAATTGCCATTTTGATAACTACTGTAACATTGCATTTCAAGCAATATGAATTCAACTCCCCCCCAAACAACC
AAGTGATGCTGTGTGAACCAACAATAATAGAAAGAAACATAACAGAGATAGTGTATTTAACCAACACCACC
ATAGAGAAGGAAATATGCCCCAAACCAGCAGAATACAGAAATTGGTCAAAACCGCAATGTGGCATTACAG
GATTTGCACCTTTCTCTAAGGACAATTCGATCAGGCTTTCCGCTGGTGGGGACATCTGGGTGACAAGAGA
ACCTTATGTGTCATGCGATCCTGACAAGTGTTATCAATTTGCCCTTGGACAGGGAACAACACTAAACAACG
TGCATTCAAATAACAAAGTACGTGAAAGGACCCCTTATCGGACTCTATTGATGAATGAGTTGGGTGTTCCT
TTCCATCTGGGGACCAAGCAAGTGTGCATAGCATGGTCCAGCTCAAGTTGTCACGATGGAAAAGCATGGC
TGCATGTTTGTATAACGGGGGATGATAAAAATGCAACTGCTAGCTTCATTTACAATGGGAGGCTTGTAGAT
AGTGTTGTTTCATGGTCCAAAGATATTCTCAGGACCCAGGAGTCAGAATGCATTTGTATCAATGGAACTTG
TACAGTAGTAATGACTGATGGAAGTGCTTCAGGAAAAGCTGATACTAAAATACTATTCATTGAGGAGGGG

Figure 8 cont.

AAAATCGTTCATACTAGCACATTGTCAGGAAGTGCTCAGCATGTCGAAGAGTGCTCTTGCTATCCTCGATAT
CCTGGTGTCAGATGTGTCTGCAGAGACAACTGGAAGGGCTCCAATCGGCCCATCGTAGATATAAACATAA
AGGATCATAGCATTGTTTCCAGTTATGTGTGTTCAGGACTTGTTGGAGACACACCCAGAAAAAACGACAG
CTCCAGCAGTAGCCATTGTTTGGATCCTAACAATGAAGAAGGTGGTGGCGGAGTGAAAGGCTGGGCCTT
TGATGATGGAAATGACGTGTGGATGGGAAGAACAATCAACGAGAAGTCACGCTTAGGGTATGAAACCTT
CAAAGTCATTGAAGGCTGGTCCAACCCTAAGTCCAAATTGCAGACAAATAGGCAAGTCATAGTTGACAGA
GGTGATAGGTCCGGTTATTCTGGTATTTTCTCTGTTGAAGGCAAAAGCTGCATAAATCGGTGCTTTTATGT
GGAGTTGATTAGGGGAAGAAAAGAGGAAACTGAAGTCTTGTGGACCTCAAACAGTATTGTTGTGTTTTG
TGGCACCTCAGGTACATATGGAACAGGCTCATGGCCTGATGGGGCGGACCTCAATCTCATGCCTATATAAG
CTTTCGCAATTTTAGAAAAAACT (SEQ ID NO:20)

> A/Alaska/232/2015NA
ATGAATCCAAATCAAAAGATAATAACGATTGGCTCTGTTTCTCTCACCATTTCCACAATATGCTTCTTCATGC
AAATTGCCATCCTGATAACTACTGTAACATTGCATTTCAAGCAATATGAATTCAACTCCCCCCCAAACAACC
AAGTGATGCTGTGTGAACCAACAATAATAGAAAGAAACATAACAGAGATAGTGTATTTGACCAACACCAC
CATAGAGAAGGAAATATGCCCCAAACCAGCAGAATACAGAAATTGGTCAAAACCGCAATGTGGCATTACA
GGATTTGCACCTTTCTCTAAGGACAATTCGATTAGGCTTTCCGCTGGTGGGGACATCTGGGTGACAAGAG
AACCTTATGTGTCATGCGATCCTGACAAGTGTTATCAATTTGCCCTTGGACAGGGAACAACACTAAACAAC
GTGCATTCAAATAACACAGTACGTGATAGGACCCCTTATCGGACTCTATTGATGAATGAGTTGGGTGTTCC
TTTCCATCTGGGGACCAAGCAAGTGTGCATAGCATGGTCCAGCTCAAGTTGTCACGATGGAAAAGCATGG
CTGCATGTTTGTATAACGGGGATGATAAAAATGCAACTGCTAGCTTCATTTACAATGGGAGGCTTGTAGA
TAGTGTTGTTTCATGGTCCAAAGATATTCTCAGGACCCAGGAGTCAGAATGCGTTTGTATCAATGGAACTT
GTACAGTAGTAATGACTGATGGAAATGCTACAGGAAAAGCTGATACTAAAATACTATTCATTGAGGAGGG
GAAAATCGTTCATACTAGCAAATTGTCAGGAAGTGCTCAGCATGTCGAAGAGTGCTCTTGCTATCCTCGAT
ATCCTGGTGTCAGATGTGTCTGCAGAGACAACTGGAAAGGATCCAACCGGCCCATCGTAGATATAAACATA
AAGGATCATAGCATTGTTTCCAGTTATGTGTGTTCAGGACTTGTTGGAGACACACCCAGAAAAAACGACA
GCTCCAGCAGTAGCCATTGTTTGAATCCTAACAATGAAGAAGGTGGTCATGGAGTGAAAGGCTGGGCCT
TTGATGATGGAAATGACGTGTGGATGGGGAGAACAATCAACGAGACGTCACGCTTAGGGTATGAAACCT
TCAAAGTCGTTGAAGGCTGGTCCAACCCTAAGTCCAAATTGCAGATAAATAGGCAAGTCATAGTTGACAG
AGGTGATAGGTCCGGTTATTCTGGTATTTTCTCTGTTGAAGGCAAAAGCTGCATCAATCGGTGCTTTTATGT
GGAGTTGATTAGGGGAAGAAAAGAGGAAACTGAAGTCTTGTGGACCTCAAACAGTATTGTTGTGTTTTG
TGGCACCTCAGGTACATATGGAACAGGCTCATGGCCTGATGGGGCGGACCTCAATCTCATGCATATATAA
(SEQ ID NO:21)

>A/Alaska/232/2015NA(T148K, D151E, N245S, G346V, T369K)
ATGAATCCAAATCAAAAGATAATAACGATTGGCTCTGTTTCTCTCACCATTTCCACAATATGCTTCTTCATGC

Figure 8 cont.

AAATTGCCATCCTGATAACTACTGTAACATTGCATTTCAAGCAATATGAATTCAACTCCCCCCCAAACAACC
AAGTGATGCTGTGTGAACCAACAATAATAGAAAGAAACATAACAGAGATAGTGTATTTGACCAACACCAC
CATAGAGAAGGAAATATGCCCCAAACCAGCAGAATACAGAAATTGGTCAAAACCGCAATGTGGCATTACA
GGATTTGCACCTTTCTCTAAGGACAATTCGATTAGGCTTTCCGCTGGTGGGGACATCTGGGTGACAAGAG
AACCTTATGTGTCATGCGATCCTGACAAGTGTTATCAATTTGCCCTTGGACAGGGAACAACACTAAACAAC
GTGCATTCAAATAACAAAGTACGTGAGAGGACCCCTTATCGGACTCTATTGATGAATGAGTTGGGTGTTCC
TTTCCATCTGGGGACCAAGCAAGTGTGCATAGCATGGTCCAGCTCAAGTTGTCACGATGGAAAAGCATGG
CTGCATGTTTGTATAACGGGGGATGATAAAAATGCAACTGCTAGCTTCATTTACAATGGGAGGCTTGTAGA
TAGTGTTGTTTCATGGTCCAAAGATATTCTCAGGACCCAGGAGTCAGAATGCGTTTGTATCAATGGAACTT
GTACAGTAGTAATGACTGATGGAAGTGCTACAGGAAAAGCTGATACTAAAATACTATTCATTGAGGAGGG
GAAAATCGTTCATACTAGCAAATTGTCAGGAAGTGCTCAGCATGTCGAAGAGTGCTCTTGCTATCCTCGAT
ATCCTGGTGTCAGATGTGTCTGCAGAGACAACTGGAAAGGATCCAACCGGCCCATCGTAGATATAAACATA
AAGGATCATAGCATTGTTTCCAGTTATGTGTGTTCAGGACTTGTTGGAGACACACCCAGAAAAAACGACA
GCTCCAGCAGTAGCCATTGTTTGAATCCTAACAATGAAGAAGGTGTTCATGGAGTGAAAGGCTGGGCCTT
TGATGATGGAAATGACGTGTGGATGGGGAGAACAATCAACGAGAAGTCACGCTTAGGGTATGAAACCTT
CAAAGTCGTTGAAGGCTGGTCCAACCCTAAGTCCAAATTGCAGATAAATAGGCAAGTCATAGTTGACAGA
GGTGATAGGTCCGGTTATTCTGGTATTTTCTCTGTTGAAGGCAAAAGCTGCATCAATCGGTGCTTTTATGT
GGAGTTGATTAGGGGAAGAAAAGAGGAAACTGAAGTCTTGTGGACCTCAAACAGTATTGTTGTGTTTTG
TGGCACCTCAGGTACATATGGAACAGGCTCATGGCCTGATGGGGCGGACCTCAATCTCATGCATATATAA
(SEQ ID NO:22)

A/Yokohama/147/2017NA
ATGAATCCAAATCAAAAGATAATAACGATTGGCTCTGTTTCTCTCACAATTTCCACAATATGCTTCTTCATGC
AAATTGCCATCCTGATAACTACTGTAACATTGCATTTCAAGCAATATGAATTCAACTCCCCCCCAAATAACCA
AGTGATGCTGTGTGAACCAACAATAATAGAAAGAAACATAACAGAGATAGTGTATTTGACCAACACCACC
ATAGAGAAGGAAATATGCCCCAAACCAGCAGAATACAGAAATTGGTCAAAACCGCAATGTGGCATTACAG
GATTTGCACCTTTCTCTAAAGACAATTCGATTAGGCTTTCCGCTGGTGGGACATCTGGGTGACAAGAGA
ACCTTATGTGTCATGCGATCTTGACAAGTGTTATCAATTTGCCCTTGGACAGGGAACAACACTAAACAACG
TGCATTCAAATAACACAGTACGTGATAGGACCCCTTATCGGACTCTATTGATGAATGAGTTGGGTGTTCCTT
TCCATCTGGGGACCAAGCAAGTGTGCATAGCATGGTCCAGCTCAAGTTGTCACGATGGAAAAGCATGGCT
GCATGTTTGTATAACGGGGGATGATAAAAATGCAACTGCTAGCTTCATTTACAwATGGGAGGCTTGTAGAT
AGTGTTGTTTCATGGTCCAACGATATTCTCAGGACCCAGGAGTCAGAATGCGTTTGTATCAATGGAACTTG
TACAGTAGTAATGACTGATGGAAATGCTACAGGAAAAGCTGATACTAAAATACTATTCATTGAGGAGGGG
AAAATCGTTCATACTAGCAAATTGTCAGGAAGTGCTCAGCATGTCGAAGAGTGCTCTTGCTATCCTCGATAT
CCTGGTGTCAGATGTGTCTGCAGAGACAACTGGAAAGGATCCAACCGGCCCATCATAGATATAAACATAA
AGGATCATAGCATTGTTTCCAGTTATGTGTGTTCAGGACTTGTTGGAGACACACCCAGAAAAAGCGACAG

Figure 8 cont.

CTCCAGCAGTAGCCATTGTTTGAATCCTAACAATGAAGAAGGTGGTCATGGAGTGAAAGGCTGGGCCTTT
GATGATGGAAATGACGTGTGGATGGGGAGAACAATCAACGAGACGTCACGCTTAGGGTATGAAACCTTC
AAAGTCGTTGAAGGCTGGTCCAACCCTAAGTCCAAATTGCAGATAAATAGGCAAGTCATAGTTGACAGAG
GTGATAGGTCCGGTTATTCTGGTATTTTCTCTGTTGAAGGCAAAAGCTGCATCAATCGGTGCTTTTATGTG
GAGTTGATCAGGGGAAGAAAAGAGGAAACTGAAGTCTTGTGGACCTCAAACAGTATTGTTGTGTTTTGT
GGCACCTCAGGTACATATGGAACAGGCTCATGGCCTGATGGGGCGGACCTCAATCTCATGCATATATAA
(SEQ ID NO:23)

>A/Yokohama/48/2018NA
ATGAATCCAAATCAAAAGATAATAACGATTGGCTCTGTTTCTCTCACCATTTCCACAATATGCTTCTTCATGC
AAATTGCCATCCTGATAACTACTGTAACATTGCATTTCAAGCAATATGAATTCAACTCCCCCCCAAATAACCA
AGTGATGCTGTGTGAACCAACAATAATAGAAAGAAACATAACAGAGATAGTGTATTTGACCAACACCACC
ATAGAGAAGGAAATATGCCCCAAACCAGCAGAATACAGAAATTGGTCAAAACCGCAATGTGGCATTACAG
GATTTGCACCTTTCTCTAAGGACAATTCGATTAGGCTTTCCGCTGGTGGGGACATCTGGGTGACAAGAGA
ACCTTATGTGTCATGCGATCCTGACAAGTGTTATCAATTTGCCCTTGGACAGGGAACAACACTAAACAACG
TGCATTCAAATAACACAGTACGTGATAGGACCCCTTATCGGACTCTATTGATGAATGAGTTGGGTGTTCCTT
TCCATCTGGGGACCAAGCAAGTGTGCATGGCATGGTCCAGCTCAAGTTGTCACGATGGAAAAGCATGGC
TGCATGTTTGTATAACTGGGGATGATAAAAATGCAACTGCTAGCTTCATTTACAATGGGAGGCTTGTAGAT
AGTGTTGTTTCATGGTCCAAAGATATTCTCAGGACCCAGGAGTCAGAATGCGTTTGCATCAATGGAACTTG
TACAGTAGTAATGACTGATGGAAATGCTACAGGAAAAGCTGATACTAAAATACTATTCATTGAGGAGGGG
AAAATCGTTCATACTAGCAAATTGTCAGGAAGTGCTCAGCATGTCGAAGAGTGCTCCTGCTATCCTCGATA
TCCTGGTGTCAGATGTGTCTGCAGAGACAACTGGAAAGGATCCAACCGGCCCATTGTAGATATAAACATA
AAGGATCATAGCATTGTTTCCAGTTATGTGTGTTCAGGACTTGTTGGAGACACACCCAGAAAAAGCGACA
GCTCCAGCAGTAGCCATTGTTTGAATCCTAACAATGAAGAAGGTGGTCATGGAGTGAAAGGCTGGGCCT
TTGATGATGGAAATGACGTGTGGATGGGGAGAACAATCAACGAGACGTCACGCTTAGGGTATGAAACCT
TCAAAGTCGTTGAAGGCTGGTCCAACTCTAAGTCCAAATTGCAGATAAATAGGCAAGTCATAGTTGACAG
AGGTGATAGGTCCGGTTATTCTGGTATTTTCTCTGTTGAAGGCAAAAGCTGCATCAATCGGTGCTTTTATGT
GGAGTTGATTAGGGGAAGAAAAGAGGAAACTGAAGTCTTGTGGACCTCAAACAGTATTGTTGTGTTTTG
TGGCACCTCAGGTACATATGGAACAGGCTCATGGCCTGATGGGGCGGACCTCAATCTCATGCATATATAA
(SEQ ID NO:24)

>A/Delaware/33/2018NA
ATGAATCCAAATCAAAAGATAATAACGATTGGCTCTGTTTCTCTCACAATTTCCACAATATGCTTCTTCATGC
AAATTGCCATCCTGATAACTACTGTAACATTGCATTTCAAGCAATATGAATTCAACTCCCCCCCAAATAACCA
AGTGATGCTGTGTGAACCAACAATAATAGAAAGAAACATAACAGAGATAGTGTATTTGACCAACACCACC
ATAGAGAAGGAAATATGCCCCAAACCAGCAGAATACAGAAATTGGTCAAAACCGCAATGTGGCATTACAG

Figure 8 cont.

GATTTGCACCTTTCTCTAAGGACAATTCGATTAGGCTTTCCGCTGGTGGGGACATCTGGGTGACAAGAGA
ACCTTATGTGTCATGCGATCTTGACAAGTGTTATCAATTTGCCCTTGGACAGGGAACAACACTAAACAACG
TGCATTCAAATAACACAGTACGTGATAGGACCCCTTATCGGACTCTATTGATGAATGAGTTGGGTGTTCCTT
TCCATCTGGGGACCAAGCAAGTGTGCATAGCATGGTCCAGCTCAAGTTGTCACGATGGAAAAGCATGGCT
GCATGTTTGTATAACGGGGGATGATAAAAATGCAACTGCTAGCTTCATTTACAATGGGAGGCTTGTAGATA
GTGTTGTCTCATGGTCCAATGATATTCTCAGGACCCAGGAATCAGAATGCGTTTGTATCAATGGAACTTGTA
CAGTAGTAATGACTGATGGAAATGCTACAGGAAAAGCTGATACTAAAATACTATTCATTGAGGAGGGGAA
AATCGTTCATACTAGCAAATTGTCAGGAAGTGCTCAGCATGTCGAAGAGTGCTCTTGCTATCCTCGATATCC
TGGTGTCAGATGTGTCTGCAGAGACAACTGGAAAGGATCCAACCGGCCCATCATAGATATAAACATAAAG
GATCATAGCATTGTTTCCAGTTATGTGTGTTCAGGACTTGTTGGAGACACACCCAGAAAAAGCGACAGCT
CCAGCAGTAGCCATTGTTTGAATCCTAACAATGAAGAAGGTGGTCATGGAGTGAAAGGCTGGGCCTTTG
ATGATGGAAATGACGTGTGGATGGGGAGAACAATCAACGAGACGTCACGCTTAGGGTATGAAACCTTCA
AAGTCGTTGAAGGCTGGTCCAACCCTAAGTCCAAATTGCAGATAAATAGGCAAGTCTTAGTTGACAGAGG
TGATAGGTCCGGTTATTCTGGTATTTTCTCTGTTGAAGGCAAAAGCTGCATCAATCGGTGCTTTTATGTGGA
GTTGATTAGGGGAAGAAAAGAGGAAACTGAAGTCTTGTGGACCTCAAACAGTATTGTTGTGTTTTGTGG
CACCTCAGGTACATATGGAACAGGCTCATGGCCTGATGGGGCGGACCTCAATCTCATGCATATATAAGCTT
TCGCAATTTTAGAAAAAACT (SEQ ID NO:25)

>A/Tokyo/UT-GR85/2019NA
ATGAATCCAAATCAAAAGATAATAACGATTGGCTCTGTTTCTCTCACAATTTCCACAATATGCTTCTTCATGC
AAATTGCCATCCTGATAACTACTGTAACATTGCATTTCAAGCAATATGAATTCAACTCCCCCCCAAATAACCA
AGTGATGCTGTGTGAACCAACAATAATAGAAAGAAACATAACAGAGATAGTGTATTTGACCAACACCACC
ATAGAGAAGGAAATATGCCCCAAACCAGCAGAATACAGAAATTGGTCAAAACCGCAATGTGGCATTACAG
GATTTGCACCTTTCTCTAAGGACAATTCGATTAGGCTTTCCGCTGGTGGGGACATCTGGGTGACAAGAGA
ACCTTATGTGTCATGCGATCTTGACAAGTGTTATCAATTTGCCCTTGGACAGGGAACAACACTAAACAACG
TGCATTCAAATAACACAGTACGTGATAGGACCCCTTATCGGACTCTATTGATGAATGAGTTGGGTGTTCCTT
TCCATCTGGGGACCAAGCAAGTGTGCATAGCATGGTCCAGCTCAAGTTGTCACGATGGAAAAGCATGGCT
GCATGTTTGTATAACGGGGGATGATAAAAATGCAACTGCTAGCTTCATTTACAATGGGAGGCTTGTAGATA
GTGTTGTTTCATGGTCCAACGATATTCTCAGGACCCAGGAGTCAGAATGCGTTTGTATCAATGGAACTTGT
ACAGTAGTAATGACTGATGGAAATGCTACAGGAAAGGCTGACACTAAAATACTATTCATTGAGGAGGGGA
AAATCGTACATACTAGCAAATTGTCAGGAAGTGCTCAGCATGTCGAAGAGTGCTCTTGCTATCCTCGATATC
CTGGTGTCAGATGTGTCTGCAGAGACAACTGGAAAGGATCCAACCGGCCCATCATAGATATAAACATAAA
GGATCATAGCATTGTTTCCAGGTATGTGTGTTCAGGACTTGTTGGAGACACACCCAGAAAAAGCGACAGC
TCCAGCAGTAGCCATTGTTTGAACCCTAACAATGAAAAAGGTGGTCATGGAGTGAAAGGCTGGGCCTTT
GATGATGGAAATGACGTGTGGATGGGGAGAACAATCAACGAGACGTCACGCTTAGGGTATGAAACCTTC
AAAGTCGTTGAAGGCTGGTCCAACCCTAAGTCCAAATTGCAGATAAATAGGCAAGTCATAGTTGACAGAG

Figure 8 cont

GTGATAGGTCCGGTTATTCTGGTATTTTCTCTGTTGAAGGCAAAAGCTGCATCAATCGGTGCTTTTATGTRG
AGTTGATTAGGGGAAGAAAAGAGGAAACTGAAGTCTTGTGGACCTCAAACAGTATTGTTGTGTTTTGTG
GCACCTCAGGTACATATGGAACAGGCTCATGGCCTGATGGGGCGGACCTCAATCTCATGCATATATAAGCT
TTCGCAATTTTAGAAAAAACTCCTTGTTTCTACTG (SEQ ID NO:26)

>A/Saint-Petersburg/RII-324S/2019NA
ATGAATCCAAATCAAAAGATAATAACGATTGGCTCTGTTTCTCTCACAATTTCCACAATATGCTTCTTCATGC
AAATTGCCATCCTGATAACTACTGTAACATTGCATTTCAAGCAATATGAATTCAACTCCCCCCCAAATAACCA
AGTGATGCTGTGTGAACCAACAATAATAGAAAGAAACATAACAGAGATAGTGTATTTGACCAACACCACC
ATAGAGAAGGAAATATGCCCCAAACCAGCAGAATACAGAAATTGGTCAAAACCGCAATGTGGCATTACAG
GATTTGCACCTTTCTCTAAGGACAATTCGATTAGGCTTTCCGCTGGTGGGGACATCTGGGTGACAAGAGA
ACCTTATGTGTCATGCGATCTTGACAAGTGTTATCAATTTGCCCTTGGACAGGGGACAACACTAAACAACG
TGCATTCAAATAACACAGTACGTGATAGGACCCCTTACCGGACTCTATTGATGAATGAGTTGGGTGTTCCT
TTCCATCTGGGGACCAAGCAAGTGTGCATAGCATGGTCCAGCTCAAGTTGTCACGATGGAAAAGCATGGC
TGCATGTTTGTATAACGGGGGATGATAAAAATGCAACTGCTAGCTTCATTTACAATGGGAGGCTTGTAGAT
AGTGTTGTTTCATGGTCCAACGATATTCTCAGGACCCAGGAATCAGAATGCGTTTGTATCAATGGAACTTG
TACAGTAGTAATGACTGATGGAAATGCTACAGGAAAAGCTGATACTAAAATACTATTCATCGAGGAGGGG
AAAATCATTCATACTAGCAAATTGTCAGGAAGTGCTCAGCATGTCGAAGAGTGCTCTTGCTATCCTCGATAT
CCTGGTGTCAGATGTGTCTGCAGAGACAACTGGAAAGGATCCAACCGGCCCATCATAGATATAAACATAA
AGGATCATAGCATTGTTTCCAGTTATGTGTGTTCAGGACTTGTTGGAGACACACCCAGAAAAAGCGACAG
CTCCAGCAGTAGCCATTGTTTGAATCCTAACAATGAAGAAGGTGGTCATGGAGTGAAAGGCTGGGCCTTT
GATGATGGAAATGACGTGTGGATGGGGAGAACAATCAACGAGACGTCACGCTTAGGGTATGAAACCTTC
AAAGTCGTTGAAGGCTGGTCCAACCCTAAGTCCAAATTGCAGATAAATAGGCAAGTCATAGTTGACAGAG
GTGATAGGTCCGGTTATTCTGGTATTTTCTCTGTTGAAGGCAAAAGCTGCATCAATCGGTGCTTTTATGTG
GAGTTGATTAGGGGAAGAAAAGAGGAAACTGAAGTCTTGTGGACCTCAAACAGTATTGTTGTGTTTTGT
GGCACCTCAGGTACATATGGAACAGGCTCATGGCCTGATGGGGCGGACCTCAATCTCATGCATATATAAGC
TTTCGCAATTTTAGAAAAAACTCCTTGTTTCTACT (SEQ ID NO:27)

>A/Kanagawa/IC1820/2019NA
ATGAATCCAAATCAAAAGATAATAACGATTGGCTCTGTTTCTCTCACAATTTCCACAATATGCTTCTTCATGC
AAATTGCCATCCTGATAACTACTGTAACATTGCATTTCAAGCAATATGAATTCAACTCCCCCCCAAATAACCA
AGTGATGCTGTGTGAACCAACAATAATAGAAAGAAACATAACAGAGATAGTGTATTTGACCAACACCACC
ATAGAGAAGGAAATATGCCCCAAACCAGCAGAATACAGAAATTGGTCAAAACCGCAATGTGGCATTACAG
GATTTGCACCTTTCTCTAAGGACAATTCGATTAGGCTTTCCGCTGGTGGGGACATCTGGGTGACAAGAGA
ACCTTATGTGTCATGCGATCTTGACAAGTGTTATCAATTTGCCCTTGGACAGGGAACAACACTAAACAACG
TGCATTCAAATAACACAGTACGTGATAGAACCCCTTATCGGACTCTATTGATGAATGAGTTGGGTGTTCCTT

Figure 8 cont.

TCCATCTGGGGACCAAGCAAGTGTGCATAGCATGGTCCAGCTCAAGCTGTCACGATGGAAAAGCATGGC
TGCATGTTTGTATAACGGGGGATGATAAAAATGCAACTGCTAGCTTCATTTACAATGGGAGGCTTGTAGAT
AGTGTTGTTTCATGGTCCAACGATATTCTCAGGACCCAGGAGTCAGAATGCGTTTGTATCAATGGAACTTG
TACAGTAGTAATGACTGATGGAAATGCTACAGGAAAAGCTGATACTAAAATACTATTCATTGAGGAGGGG
AAAATCGTTCATACTAGCAAATTGTCAGGAAGTGCTCAGCATGTCGAAGAGTGCTCTTGCTATCCTCGATAT
CCTGGTGTCAGATGTGTCTGCAGAGACAACTGGAAAGGATCCAACCGGCCCATCATAGATATAAACATAA
AGGATCATAGCATTGTTTCCAGGTATGTGTGTTCAGGACTTGTTGGAGACACACCCAGAAAAAGCGACAG
CTCCAGCAGTAGCCATTGTTTGAACCCTAACAATGAAAAAGGTGATCATGGAGTGAAAGGCTGGGCCTTT
GATGATGGAAATGACGTGTGGATGGGGAGAACAATCAACGAGACGTCGCGCTTAGGGTATGAAACCTTC
AAAGTCGTTGAAGGCTGGTCCAACCCTAAGTCCAAATTGCAGATAAATAGGCAAGTCATAGTTGACAGAG
GTGATAGGTCCGGTTATTCTGGTATTTTCTCTGTTGAAGGCAAAAGCTGCATCAATCGGTGCTTTTATGTG
GAGTTGATTAGGGGAAGAAAAGAGGAAACTGAAGTCTTGTGGACCTCAAACAGTATTGTTGTGTTTTGT
GGCACCTCAGGTACATATGGAACAGGCTCATGGCCTGATGGGGCGGACCTCAATCTCATGCATATATAA
(SEQ ID NO:28)

>A/Kansas/14/2017NA
ATGAATCCAAATCAAAAGATAATAACGATTGGCTCTGTTTCTCTCACCATTTCCACAATATGCTTCTTCATGC
AAATTGCCATCCTGATAACTACTGTAACATTGCATTTCAAGCAATATGAATTCAACTCCCCCCCAAACAACC
AAGTGATGCTGTGTGAACCAACAATAATAGAAAGAAACATAACAGAGATAGTGTATTTGACCAACACCAC
CATAGAGAGGGAAATATGCCCCAAACCAGCAGAATACAGAAATTGGTCAAAACCGCAATGTGGCATTACA
GGATTTGCACCTTTCTCTAAGGACAATTCGATTAGGCTTTCCGCTGGTGGGGACATCTGGGTGACAAGAG
AACCTTATGTGTCATGCGATCCTGACAAGTGTTATCAATTTGCCCTTGGACAGGGAACAACAATAAACAAC
GTGCATTCAAATAACACAGCACGTGATAGGACCCCTCATCGGACTCTATTGATGAATGAGTTGGGTGTTCC
TTTCCATCTGGGGACCAAGCAAGTGTGCATAGCATGGTCCAGCTCAAGTTGTCACGATGGAAAAGCATGG
CTGCATGTTTGTATAACGGGGGATGATAAAAATGCAACTGCTAGTTTCATTTACAATGGGAGGCTTGTAGA
TAGTGTTGTTTCATGGTCCAAAGATATTCTCAGGACCCAGGAGTCAGAATGCGTTTGTATCAATGGAACTT
GTACAGTAGTAATGACTGATGGAAATGCTACAGGAAAAGCTGATACTAAAATATTATTCATTGAGGAGGGG
AAAATCGTTCATACTAGCAAATTGTCAGGAAGTGCTCAGCATGTCGAAGAGTGCTCTTGCTATCCTCGATA
CCCTGGTGTCAGATGTGTCTGCAGAGACAACTGGAAAGGATCCAACCGGCCCATCGTAGATATAAACATA
AAGGATCATAGCATTGTTTCCAGTTATGTGTGTTCAGGACTTGTTGGAGACACACCCAGAAAAACCGACA
GCTCCAGCAGCAGCCATTGCTTGAATCCTAACAATGAAAAGGTGGTCATGGAGTGAAAGGCTGGGCCT
TTGATGATGGAAATGACGTGTGGATGGGGAGAACAATCAACGAGACGTCACGCTTAGGGTATGAAACCT
TCAAAGTCGTTGAAGGCTGGTCCAACCCTAAGTCCAAATTGCAGATAAATAGGCAAGTCATAGTTGACAG
AGGTGATAGGTCCGGTTATTCTGGTATTTTCTCTGTTGAAGGCAAAAGCTGCATCAATCGGTGCTTTTATGT
GGAGTTGATTAGGGGAAGAAAAGAGGAAACTGAAGTCTTGTGGACCTCAAACAGTATTGTTGTGTTTTG

Figure 8 cont.

TGGCACCTCAGGTACATATGGAACAGGCTCATGGCCTGATGGGGCGGACCTCAATCTCATGCATATATAAG
CTTTCGCAATTTTAGAAAAAACT (SEQ ID NO:29)

Figure 9. Exemplary influenza B neuraminidases

AGA18961

```
mlpstiqtlt lfltsggvll slyvsaslsy llysdillkf srteitaptm pldcanasnv 61
qavnrsatkg vtlllpepew myprlscpgs tfqkallisp hrfgetkgns apliirepfi 121
acgpkeckhf althyaaqpg gyyngtredr nklrhlisvk lgkiptvens ifhmaawsgs 181
achdgrewty igvdgpdsna llkikygeay tdtyhsyakn tlrtqesacn ciggdcylmi 241
tdgpasgise crflkiregr iikeifptgr vkhteectcg fasnktieca crdnsytakr 301
pfvklnvetd taeirlmcte tyldtprpnd gsitgpcesn gdkgsggikg gfvhqrmask 361
igrwysrtms ktkrmgmgly vkydgdpwtd sealalsqvm vsmeepgwys fgfeikdkkc 421
dvpcigiemv hdggkttwhs aataiyclmg sgqllwdtvt gvnmtl (SEQ ID NO:30)
```

ACT85963.1

```
mlpstiqtlt lfltsggvll slyvsaslsy llysdillkf spteitaptm pldcanasnv 61
qavnrsatkg vtlllpepew typrlscpgs tfqkallisp hrfgetkgns apliirepfi 121
acgpkeckhf althyaaqpg gyyngtredk nklrhlisvk lgkiptvens ifhmaawsgs 181
achdgrewty igvdgpdsna llkikygeay tdtyhsyann ilrtqesacn ciggdcylmi 241
tdgsasgise crflkiregr iikeifptgr vehteectcg fasnktieca crdnsytakr 301
pfvklnvetd taeirlmcte tyldtprpdd gsitgpcesn gdkgsggikg gfvhqrmask 361
igrwysrtms ktkrmgmgly vkydgdpwtd sdalalsqvm vsmeepgwys fgfeikdkkc 421
dvpcigiemv hdggkktwhs aataiyclmg sgqllwdtvt gvdmal (SEQ ID NO:31)
```

ABL77391.1

```
mlpstiqtlt lfltsggvll slyvsaslsy llysdillkf spteitaptm pldcanasnv 61
qavnrsatkg vtlllpepew typrlscpgs tfqkallisp hrfgetkgns apliirepfi 121
acgpkeckhf althyaaqpg gyyngtrgdr nklrhlisvk lgkiptvens ifhmaawsgs 181
achdgkewty igvdgpdnna llkikygeay tdtyhsyann ilrtqesacn ciggncylmi 241
tdgsasgvse crflkiregr iikeifptgr vkhteectcg fasnktieca crdnsytakr 301
pfvklnvetd taeirlmcte tyldtprpdd gsitgpcesn gdkgsggikg gfvhqrmask 361
igrwysrtms ktkrmgmgly vkydgdpwad sdalalsqvm vsmeepgwys fgfeikdkkc 421
dvpcigiemv hdggketwhs aataiyclmg sgqllwdtvt gvdmal (SEQ ID NO:32)
```

ABF21335.1

```
mlpstiqtlt lfltsggvll slyvsaslsy llysdillkf spkitaptmt ldcanasnvq 61
avnrsatkem tfllpepewt yprlscqgst fqkallisph rfgeargnsa pliirepfia 121
cgpkeckhfa lthyaaqpgg yyngtredrn klrhlisvkl gkiptvensi fhmaawsgsa 181
chdgrewtyi gvdgpdsnal ikikygeayt dtyhsyanni lrtqesacnc iggdcylmit 241
dgsasgiskc rflkiregri ikeifptgrv ehteectcgf asnktiecac rdnnytakrp 301
```

Figure 9 cont.

```
fvklnvetdt aeirlmctet yldtprpddg sitgpcesng dkgrggikgg fvhqrmaski 361
grwysrtmsk termgmelyv kydgdpwtds daldpsgvmv smkepgwysf gfeikdkkcd 421
vpcigiemvh dggkktwhsa ataiyclmgs gqllwdtvtg vdmal (SEQ ID NO:33)
```

AAA43743.1

```
mlpstiqtlt lfltsggvll slyvsaslsy llysdillkf sptkrtaptm sldcanvsnv 61
qavnrsatke mtfllpepew typrlscqgs tfqkallisp hrfgeargns apliirepfi 121
acgpkeckhf althyaaqpg gyyngtrkdr nklrhlisvk lgkiptvens ifhmaawsgs 181
achdgrewty igvdgpdsna likikygeay tdtyhsyann ilrtqesacn ciggdcylmi 241
tdgsasgisk crflkiregr iikeifptgr vehteectcg fasnktieca crdnsytakr 301
pfvklnvetd taeirlmcte tyldtprpdd gsitgpcesn gdkqlggikg qfvhqrmask 361
igrwysrtms ktermgmely vkydgdpwtd sealapsgvm vsmkepgwys fgfeikdkkc 421
dvpcigiemv hdggketwhs aataiyclmg sgqllwdtvt gvdmal (SEQ ID NO:34)
```

AML44612.1 Influenza B virus (B/Victoria/3/2014)

```
mlpstiqtlt lfltsggvll slyvsaslsy llysdillkf srtevtapim pldcanasnv 61
qavnrsatkg vtpllpepew typrlscpgs tfqkallisp hrfqetkgns apliirepfi 121
acgpkeckhf althyaaqpg gyyngtredr nklrhlisvk lgkiptvens ifhmaawsgs 181
achdgrewty igvdgpdsna likikygeay tdtyhsyakn ilrtqesacn ciggdcylmi 241
tdgpasgise crflkiregr iikeifptgr vkhteectcg fasnktieca crdnsytakr 301
pfvklnvetd taeirlmctk tyldtprpnd gsitgpcesd qdegsggikg gfvhqrmask 361
igrwysrtms ktkrmgmgly vkydgdpwtd sealalsgvm vsmeepgwys fgfeikdkkc 421
dvpcigiemv hdggkttwhs aataiyclmg sgqllwdtvt gvnmtl (SEQ ID NO:35)
```

RECOMBINANT INFLUENZA VIRUSES WITH STABILIZED NA

CROSS-REFERENCE TO RELATED APPLICATIONS

This application claims the benefit of the filing date of U.S. application No. 62/965,225, filed on Jan. 24, 2020, the disclosure of which is incorporated by reference 20 to 30 herein.

STATEMENT OF GOVERNMENT FUNDING

This invention was made with government support under HHSN272201400008C awarded by the National Institutes of Health. The government has certain rights in the invention.

BACKGROUND

Influenza is a major respiratory disease in some mammals including horses and is responsible for substantial morbidity and economic losses each year. In addition, influenza virus infections can cause severe systemic disease in some avian species, leading to death. The segmented nature of the influenza virus genome allows for reassortment of segments during virus replication in cells infected with two or more influenza viruses. The reassortment of segments, combined with genetic mutation and drift, can give rise to a myriad of divergent strains of influenza virus over time. The new strains exhibit antigenic variation in their hemagglutinin (HA) and/or neuraminidase (NA) proteins, and in particular the gene coding for the HA protein has a high rate of variability. The predominant current practice for the prevention of flu is vaccination. Most commonly, inactivated virus vaccines are used. As the influenza HA protein is the major target antigen for the protective immune responses of a host to the virus and is highly variable, the isolation of influenza virus and the identification and characterization of the HA antigen in viruses associated with recent outbreaks is important for vaccine production. Based on prevalence and prediction, a vaccine is designed to stimulate a protective immune response against the predominant and expected influenza virus strains.

There are four general types of influenza viruses, Type A, Type B, Type C, and Type D, which are defined by the absence of serological cross reactivity between their internal proteins. Influenza Type A viruses are further classified into subtypes based on antigenic and genetic differences of their glycoproteins, the HA and NA proteins. AN the known HA and NA subtypes (H1 to H18 and N1 to N11) have been isolated from aquatic birds, which are thought to act as a natural reservoir for influenza.

It has been suggested that antibodies against NA play important roles in preventing influenza virus infections. However, the current influenza vaccines, which are made by the inactivation of influenza viruses grown in eggs and purification of the virus antigen, are not able to elicit anti-NA antibodies efficiently.

SUMMARY

One of the causes of the low production of anti-NA antibodies is attributed to the structural instability of the NA protein, which works as a homo-tetramer. The NA tetramer may be disrupted during the antigen purification process. Therefore, the amount of NA contained in current vaccines is insufficient to elicit the production of anti-NA antibodies.

The present disclosure relates to influenza viruses with certain residue(s) or modifications in the NA protein that stabilize its natural homotetramer structure, and methods of making and using that virus, e.g., in a vaccine. In one embodiment, an isolated recombinant influenza virus comprising a neuraminidase (NA) viral segment encoding a NA monomer that forms virions having stabilized NA tetramers is provided. In one embodiment, the recombinant influenza virus has a modified NA stalk relative to a parental NA that results in stabilized tetramers. In one embodiment, the modified NA stalk has a deletion. In one embodiment, the modified NA stalk has an insertion relative to a parental NA. In one embodiment, the modified NA stalk has at least one amino acid substitution relative to a parental NA. In one embodiment, at least one substitution in the modified NA stalk is a cysteine substitution. In one embodiment, the modified NA stalk has at least two substitutions relative to a parental NA. In one embodiment, the NA has a cysteine at position 48 relative to the numbering of N1. In one embodiment, the NA has a cysteine at position 50 relative to the numbering of N1. In one embodiment, the NA has a cysteine at position 48 and position 50 relative to the numbering of N1. In one embodiment, the NA stalk is modified within residues 1 to 10 from the C-terminus of the transmembrane domain relative to a parental NA. In one embodiment, the NA stalk is modified within residues 10 to 20 from the C-terminus of the transmembrane domain. In one embodiment, the NA stalk is modified within residues 20 to 30 from the C-terminus of the transmembrane domain. In one embodiment, the NA stalk is modified within residues 30 to 50 from the C-terminus of the transmembrane domain. In one embodiment, the stalk domain begins at the first residue after the last residue in the transmembrane domain of NA up to the conserved cysteine, or one to two residues before the conserved cysteine, in the head region of NA that forms a disulfide bond (see Blumenkrantz et al., *J. Virol.*, 87:10539 (2013)). In one embodiment, the insertion in the NA stalk is an insertion of 1, 2, 3, 4 or 5, or 5 to 10, or 10 to 20, or more residues. In one embodiment, the deletion in the NA stalk is a deletion of 1, 2, 3, 4 or 5, or 5 to 10, or 10 to 20, or more residues. In one embodiment, a NA that has a cysteine is the stalk region is modified to include a second or third cysteine, e.g., within 1 to 10 or 1 to 5 residues of the other cysteine(s). In one embodiment, a NA has at least two cysteines in the stalk region that are within 1 to 2, 2 to 3, 3 to 4 or 5 up to residues of each other. In one embodiment, a NA has at least two cysteines in the stalk region, one of which is within 5 residues, either N-terminal or C-terminal, of residue 48 in the NA, and the other of which is within 5 residues, either N-terminal or C-terminal, of residue 50 in the NA. In one embodiment, the cysteines are adjacent to each other, e.g., at residues 46 and 47, residues 48, 47 and 48, residues 47 and 48, residues 47, 48 and 49, residues 48 and 49, residues 48, 49, and 50, residues 49 and 50, or residues 49, 50 and 51, and in one embodiment both are in the stalk region. In one embodiment, the cysteines are 2 residues apart and in one embodiment both are in the stalk region. e.g., the cysteines are at residues 46 and 48, 47 and 49, 48 and 50, 49 and 51, 50 and 52, 51 and 53, and the like. In one embodiment, the cysteines are 3 residues apart, e.g., the cysteines are at residues 45 and 48, 46 and 49, 47 and 50, 48 and 51, 49 and 52, 50 and 53, 51 and 54, and the like and in one embodiment both are in the stalk region. In one embodiment, the cysteines are 4 residues apart, e.g., the cysteines are at residues 44 and 48, 45 and 49, 46 and 50, 47 and 51, 48 and 52, 49 and 53, 50 and 54, 51 and 55, and the like and in one embodiment both are in the stalk region. In one embodiment, the stalk region has no more than 10, 9, 8, 7, 6, 5, 4, 3, 2 or 1 cysteine residues. In one embodiment, the cysteine(s) in the stalk region are in the N-terminal 30 residues of the stalk region. In one embodiment, the cysteine(s) in the stalk region are in the N-terminal 20 residues of the stalk region.

As described herein, a highly proliferative recombinant influenza viruses expressing structurally stabilized neuraminidase tetramers was prepared. In one embodiment, recombinant influenza viruses containing either NA-48C or NA-50C or both express stabilized NA tetramers and replicate efficiently. Thus, amino acid mutations in influenza NA that enable the generation of highly proliferative recombinant influenza viruses expressing structurally stabilized NA tetramers can be used to generate influenza vaccine strains that can be used to produce influenza vaccines containing a greater amount of NA antigen. Influenza vaccine strains containing a greater amount of NA antigen that can elicit anti-NA antibodies efficiently.

In one embodiment, a vaccine comprising an effective amount of the recombinant influenza virus or a portion thereof is provided. In one embodiment, the vaccine is a whole virus vaccine. In one embodiment, the vaccine is a split virus vaccine. In one embodiment, the vaccine is a subunit vaccine. In one embodiment, the vaccine further comprises an adjuvant. In one embodiment, the vaccine further comprises a pharmaceutically acceptable carrier. In one embodiment, the carrier is suitable for intranasal or intramuscular administration. In one embodiment, the vaccine further comprises at least one other influenza virus isolate.

In one embodiment, a method of preparing influenza virus having stabilized NA tetramers is provided. The method includes contacting a cell with one or more vectors comprising nucleic acid for an influenza virus NA segment encoding, for example, at least one cysteine in the stalk region, nucleic acid for an influenza virus PA segment, nucleic acid for an influenza virus a PB1 segment, nucleic acid for an influenza virus PB2 segment, nucleic acid for an influenza virus NP segment, nucleic acid for an influenza virus NS segment, nucleic acid for an influenza virus M segment, and nucleic acid for an influenza virus HA segment, in an amount effective to produce influenza virus having stabilized NA tetramers. In one embodiment, the NA is N1, N2, N3 or N5. In one embodiment, the NA is N4, N8, N7, N8 or N9. In one embodiment, the cell is a mammalian cell. In one embodiment, the cell is a Vero cell, 293T cell or MDCK cell.

In one embodiment, a method of making an influenza vaccine is provided. The method includes combining the recombinant virus with an adjuvant or treating the virus with an agent that inactivates the virus. In one embodiment, the method further comprises aliquoting a selected dose of the virus into a receptacle. In one embodiment, the adjuvant comprises immunostimulatory DNA sequences, bacterium-derived components, aluminum salt (alum) or squalene oil-in-water emulsion systems such as MF59 and AS03. In one embodiment, the agent chemically inactivates the virus. In one embodiment, the agent comprises formalin or beta-propiolactone. In one embodiment, the agent comprises a detergent, e.g., a non-ionic detergent, a cationic detergent or an anionic detergent. In one embodiment, the detergent comprises CTAB, Triton, SDS, Neodol 23-8, or sodium desoxycholate. In one embodiment, the method further comprises separating HA and NA from other viral components, e.g., using centrifugation and collection of soluble molecules.

In one embodiment, a method of preparing influenza virus is provided that includes contacting cells with the recombinant virus in an amount effective to yield progeny virus. In one embodiment, the virus is contacted with an avian egg. In one embodiment, the cells are mammalian cells. In one embodiment, the HA of the virus is H1, H3, H5 or H7.

Also provided is a method of preparing stabilized NA tetramers, comprising: contacting a cell with one or more vectors comprising nucleic acid for an influenza virus NA segment encoding at least one cysteine in the stalk region and nucleic acid for an influenza virus HA. In one embodiment, the method further comprises isolating NA and HA from the cell. In one embodiment, the cell is an insect cell.

Further provided is a method of immunizing an avian or a mammal, comprising: administering to the avian or the mammal a composition having an effective amount of the recombinant virus. In one embodiment, the composition comprises at least one other different influenza virus. In one embodiment, the mammal is a human. In one embodiment, the composition is administered intranasally or via injection.

BRIEF DESCRIPTION OF FIGURES

FIG. 2. Amino acid sequence of the NA of A/Yokohama/2017/2003 (SEQ ID NO:1).

FIG. 3. Amino acid sequence for the NA of A/Saitama/103/2014 (SEQ ID NO:2).

FIG. 4. Amino acid sequences for NA of mutant of A/Yokohama/2017/2003 (SEQ ID NO:3).

FIG. 5. Exemplary NA sequences for N3, N4, N, N7, N8, and N9 (SEQ ID Nos. 4-9). The stalk region is indicated by red font, underlining.

FIG. 6. Exemplary viral backbone sequences (SEQ ID Nos.10-14).

FIG. 7. Exemplary NA sequences (SEQ ID Nos. 15-18). The stalk region is indicated by red font, underlining.

FIG. 8. Exemplary NA nucleic acid sequences (SEQ ID Nos 19-29).

FIG. 9. Exemplary influenza B virus NA sequences (SEQ ID Nos. 45-50). In one embodiment, the stalk region in the NA of influenza B virus may be from residue 38 to 86.

DETAILED DESCRIPTION

Definitions

Figure 1:
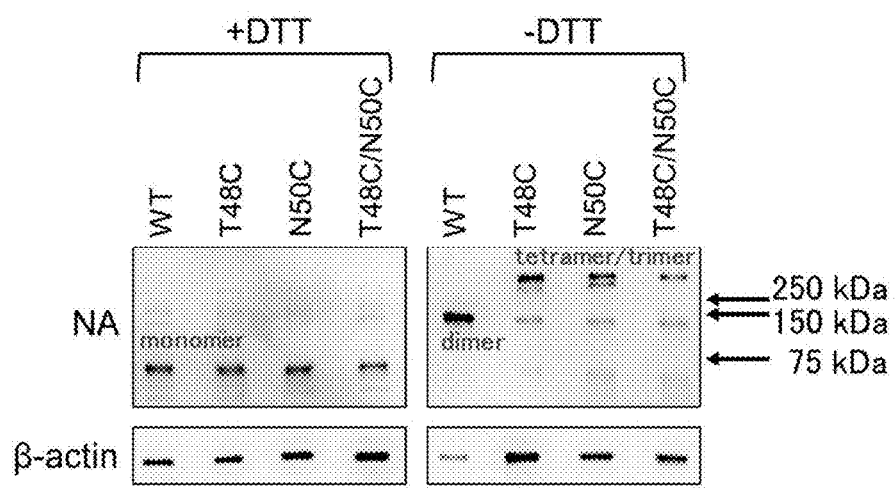
FIG. 1. Western blot to detect NA in hCK cells infected with influenza viruses.
Figure 10:
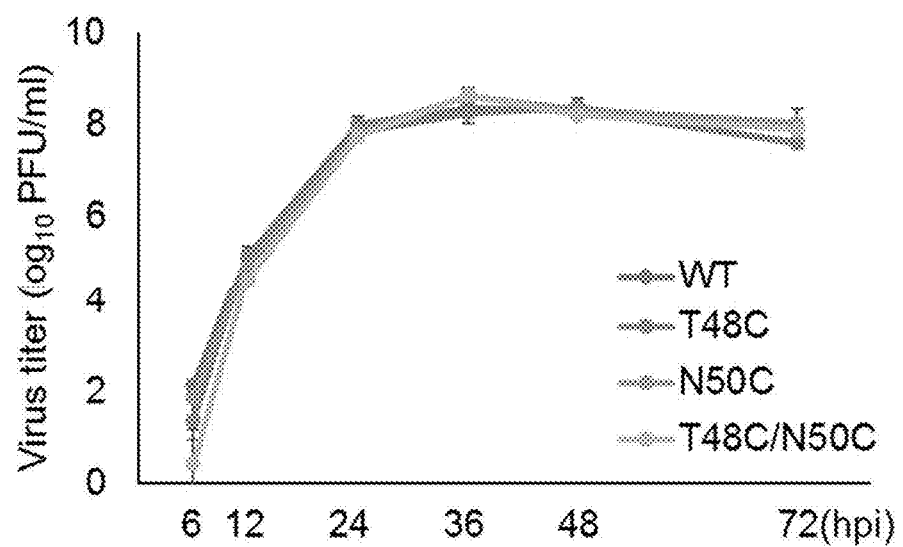
FIG. 10. Virus growth curves. 6+2 reassortant influenza viruses containing the HA and NA viral segments from A/Singapore/GP1908/2015 (H1N1) pdm09 in the backbone of high-yield A/Puerto Rico/8/1934 (H1N1) were prepared using reverse genetics and propagation in hCK cells at 37° C. Mutant viruses with either the NA-T48C or NA-N50C mutation or both mutations were generated. hCK cells were infected with these viruses at a MOI (multiplicity of infection) of 0.001. The supernatants were collected at the indicated times post-infection and virus titers were determined by means of plaque assay in hCK cells.

As used herein, the term "isolated" refers to in vitro preparation and/or isolation of a nucleic acid molecule, e.g., vector or plasmid, peptide or polypeptide (protein), or virus of the invention, so that it is not associated with in vivo substances, or is substantially purified from in vitro substances. An isolated virus preparation is generally obtained by in vitro culture and propagation, and/or via passage in eggs, and is substantially free from other infectious agents.

As used herein, "substantially purified" means the object species is the predominant species, e.g., on a molar basis it is more abundant than any other individual species in a composition, and preferably is at least about 80% of the species present, and optionally 90% or greater, e.g., 95%, 98%, 99% or more, of the species present in the composition.

As used herein, "substantially free" means below the level of detection for a particular infectious agent using standard detection methods for that agent.

A "recombinant" virus is one which has been manipulated in vitro, e.g., using recombinant DNA techniques, to introduce changes to the viral genome. Reassortant viruses can be prepared by recombinant or nonrecombinant techniques.

As used herein, the term "recombinant nucleic acid" or "recombinant DNA sequence or segment" refers to a nucleic acid, e.g., to DNA, that has been derived or isolated from a source, that may be subsequently chemically altered in vitro, so that its sequence is not naturally occurring, or corresponds to naturally occurring sequences that are not positioned as they would be positioned in the native genome. An example of DNA "derived" from a source, would be a DNA sequence that is identified as a useful fragment, and which is then chemically synthesized in essentially pure form. An example of such DNA "isolated" from a source would be a useful DNA sequence that is excised or removed from said source by chemical means. e.g., by the use of restriction endonucleases, so that it can be further manipulated, e.g., amplified, for use in the disclosure, by the methodology of genetic engineering.

As used herein, a "heterologous" influenza virus gene or viral segment is from an influenza virus source that is different than a majority of the other influenza viral genes or viral segments in a recombinant, e.g., reassortant, influenza virus.

The terms "isolated polypeptide", "isolated peptide" or "isolated protein" include a polypeptide, peptide or protein encoded by cDNA or recombinant RNA including one of synthetic origin, or some combination thereof.

The term "recombinant protein" or "recombinant polypeptide" as used herein refers to a protein molecule expressed from a recombinant DNA molecule. In contrast, the term "native protein" is used herein to indicate a protein isolated from a naturally occurring (i.e., a nonrecombinant) source. Molecular biological techniques may be used to produce a recombinant form of a protein with identical properties as compared to the native form of the protein.

Methods of alignment of sequences for comparison are well known in the art. Thus, the determination of percent identity between any two sequences can be accomplished using a mathematical algorithm.

Computer implementations of these mathematical algorithms can be utilized for comparison of sequences to determine sequence identity. Alignments using these programs can be performed using the default parameters. Software for performing BLAST analyses is publicly available through the National Center for Biotechnology Information (http://www.ncbi.nlm.nih.gov). The algorithm may involve first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold. These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when the cumulative alignment score falls off by the quantity X from its maximum achieved value, the cumulative score goes to zero or below due to the accumulation of one or more negative-scoring residue alignments, or the end of either sequence is reached.

In addition to calculating percent sequence identity, the BLAST algorithm may also perform a statistical analysis of the similarity between two sequences. One measure of similarity provided by the BLAST algorithm may be the smallest sum probability (P(N)), which provides an indication of the probability by which a match between two nucleotide or amino acid sequences would occur by chance. For example, a test nucleic acid sequence is considered similar to a reference sequence if the smallest sum probability in a comparison of the test nucleic acid sequence to the reference nucleic acid sequence is less than about 0.1, more preferably less than about 0.01, and most preferably less than about 0.001.

The BLASTN program (for nucleotide sequences) may use as defaults a wordlength (W) of 11, an expectation (E) of 10, a cutoff of 100, M=5, N=−4, and a comparison of both strands. For amino acid sequences, the BLASTP program may use as defaults a wordlength (W) of 3, an expectation (E) of 10, and the BLOSUM62 scoring matrix. See http://www.ncbi.nl m.nih gov. Alignment may also be performed manually by inspection.

For sequence comparison, typically one sequence acts as a reference sequence to which test sequences are compared. When using a sequence comparison algorithm, test and reference sequences are input Into a computer, subsequence coordinates are designated if necessary, and sequence algorithm program parameters are designated. The sequence comparison algorithm then calculates the percent sequence identity for the test sequence(s) relative to the reference sequence, based on the designated program parameters.

Influenza Virus Structure and Propagation

Influenza A viruses possess a genome of eight single-stranded negative-sense viral RNAs (vRNAs) that encode at least ten proteins. The influenza virus life cycle begins with binding of the hemagglutinin (HA) to sialic acid-containing receptors on the surface of the host cell, followed by receptor-mediated endocytosis. The low pH in late endosomes triggers a conformational shift in the HA, thereby exposing the N-terminus of the HA2 subunit (the so-called fusion peptide). The fusion peptide initiates the fusion of the viral and endosomal membrane, and the matrix protein (M1) and RNP complexes are released into the cytoplasm. RNPs consist of the nucleoprotein (NP), which encapsidates vRNA, and the viral polymerase complex, which is formed by the PA, PB1, and PB2 proteins. RNPs are transported into the nucleus, where transcription and replication take place. The RNA polymerase complex catalyzes three different reactions: synthesis of an mRNA with a 5' cap and 3' polyA structure, of a full-length complementary RNA (cRNA), and of genomic vRNA using the cRNA as a template. Newly synthesized vRNAs, NP, and polymerase proteins are then assembled into RNPs, exported from the nucleus, and transported to the plasma membrane, where budding of progeny virus particles occurs. The neuraminidase (NA) protein plays a crucial role late in infection by removing sialic acid from sialyloligosaccharides, thus releasing newly assembled virions from the cell surface and preventing the self aggregation of virus particles. Although virus assembly involves protein-protein and protein-vRNA interactions, the nature of these interactions is largely unknown.

Although influenza B and C viruses are structurally and functionally similar to influenza A virus, there are some differences. For example, influenza B virus does not have a M2 protein with ion channel activity but has BM2 and has a viral segment with both NA and NB sequences. Influenza C virus has only seven viral segments.

Cells that can be Used to Produce Virus

Any cell, e.g., any avian or mammalian cell, such as avian eggs, a human, e.g., 293T or PER.C6® cells, or canine, bovine, equine, feline, swine, ovine, rodent, for instance mink, e.g., MvLu1 cells, or hamster, e.g., CHO cells, or non-human primate, e.g., Vero cells, including mutant cells, which supports efficient replication of influenza virus can be employed to isolate and/or propagate influenza viruses. Isolated viruses can be used to prepare a reassortant virus. In one embodiment, host cells for vaccine production are continuous mammalian or avian cell lines or cell strains. A complete characterization of the cells to be used, may be conducted so that appropriate tests for purity of the final product can be included. Data that can be used for the characterization of a cell includes (a) Information on its origin, derivation, and passage history; (b) information on its growth and morphological characteristics; (c) results of tests of adventitious agents; (d) distinguishing features, such as biochemical. Immunological, and cytogenetic patterns which allow the cells to be clearly recognized among other cell lines; and (e) results of tests for tumorigenicity. In one embodiment, the passage level, or population doubling, of the host cell used is as low as possible.

In one embodiment, the cells are WHO certified, or certifiable, continuous cell lines. The requirements for certifying such cell lines include characterization with respect to at least one of genealogy, growth characteristics, immunological markers, virus susceptibility tumorigenicity and storage conditions, as well as by testing in animals, eggs, and cell culture. Such characterization is used to confirm that the cells are free from detectable adventitious agents. In some countries, karyology may also be required. In addition, tumorigenicity may be tested in cells that are at the same passage level as those used for vaccine production. The virus may be purified by a process that has been shown to give consistent results, before vaccine production (see, e.g., World Health Organization, 1982).

Virus produced by the host cell may be highly purified prior to vaccine or gene therapy formulation. Generally, the purification procedures result in extensive removal of cellular DNA and other cellular components, and adventitious agents. Procedures that extensively degrade or denature DNA may also be used.

Influenza Vaccines

A vaccine includes an isolated recombinant influenza virus of the invention, and optionally one or more other isolated viruses including other isolated influenza viruses, one or more immunogenic proteins or glycoproteins of one or more isolated influenza viruses or one or more other pathogens, e.g., an immunogenic protein from one or more bacteria, non-influenza viruses, yeast or fungi, or isolated nucleic acid encoding one or more viral proteins (e.g., DNA vaccines) including one or more immunogenic proteins of the isolated influenza virus of the invention. In one embodiment, the influenza viruses of the invention may be vaccine vectors for influenza virus or other pathogens.

A complete virion vaccine may be concentrated by ultrafiltration and then purified by zonal centrifugation or by chromatography. Viruses other than the virus of the invention, such as those included in a multivalent vaccine, may be inactivated before or after purification using formalin or beta-propiolactone, for instance.

A subunit vaccine comprises purified glycoproteins. Such a vaccine may be prepared as follows: using viral suspensions fragmented by treatment with detergent, the surface antigens are purified, by ultracentrifugation for example. The subunit vaccines thus contain mainly HA protein, and also NA. The detergent used may be cationic detergent for example, such as hexadecyl trimethyl ammonium bromide (Bachmeyer, 1975), an anionic detergent such as ammonium deoxycholate (Laver & Webster, 1976); or a nonionic detergent such as that commercialized under the name TRITON X100. The hemagglutinin may also be isolated after treatment of the virions with a protease such as bromelin, and then purified. The subunit vaccine may be combined with an attenuated virus of the invention in a multivalent vaccine.

A split vaccine comprises virions which have been subjected to treatment with agents that dissolve lipids. A split vaccine can be prepared as follows: an aqueous suspension of the purified virus obtained as above, inactivated or not, is treated, under stirring, by lipid solvents such as ethyl ether or chloroform, associated with detergents. The dissolution of the viral envelope lipids results in fragmentation of the viral particles. The aqueous phase is recuperated containing the split vaccine, constituted mainly of hemagglutinin and neuraminidase with their original lipid environment removed, and the core or its degradation products. Then the residual infectious particles are inactivated if this has not already been done. The split vaccine may be combined with an attenuated virus of the invention in a multivalent vaccine.

Inactivated Vaccines. Inactivated influenza virus vaccines are provided by inactivating replicated virus using known methods, such as, but not limited to, formalin or β-propiolactone treatment. Inactivated vaccine types that can be used in the invention can include whole-virus (WV) vaccines or subvirion (SV) (split) vaccines. The WV vaccine contains intact, inactivated virus, while the SV vaccine contains purified virus disrupted with detergents that solubilize the lipid-containing viral envelope, followed by chemical inactivation of residual virus.

In addition, vaccines that can be used include those containing the isolated HA and NA surface proteins, which are referred to as surface antigen or subunit vaccines.

Live Attenuated Virus Vaccines. Live, attenuated influenza virus vaccines, such as those including a recombinant virus of the invention can be used for preventing or treating influenza virus infection. Attenuation may be achieved in a single step by transfer of attenuated genes from an attenuated donor virus to a replicated isolate or reassorted virus according to known methods. Since resistance to influenza A virus is mediated primarily by the development of an immune response to the HA and/or NA glycoproteins, the genes coding for these surface antigens come from the reassorted viruses or clinical isolates. The attenuated genes are derived from an attenuated parent. In this approach, genes that confer attenuation generally do not code for the HA and NA glycoproteins.

Viruses (donor influenza viruses) are available that are capable of reproducibly attenuating influenza viruses, e.g., a cold adapted (ca) donor virus can be used for attenuated vaccine production. Live, attenuated reassortant virus vaccines can be generated by mating the ca donor virus with a virulent replicated virus. Reassortant progeny are then selected at 25° C. (restrictive for replication of virulent virus), in the presence of an appropriate antiserum, which inhibits replication of the viruses bearing the surface antigens of the attenuated ca donor virus. Useful reassortants are: (a) infectious, (b) attenuated for seronegative non-adult mammals and immunologically primed adult mammals, (c) immunogenic and (d) genetically stable. The immunogenicity of the ca reassortants parallels their level of replication. Thus, the acquisition of the six transferable genes of the ca donor virus by new wild-type viruses has reproducibly attenuated these viruses for use in vaccinating susceptible mammals both adults and non-adult.

Other attenuating mutations can be introduced into influenza virus genes by site-directed mutagenesis to rescue infectious viruses bearing these mutant genes. Attenuating mutations can be introduced into non-coding regions of the genome, as well as into coding regions. Such attenuating mutations can also be introduced into genes other than the HA or NA, e.g., the PB2 polymerase gene. Thus, new donor viruses can also be generated bearing attenuating mutations introduced by site-directed mutagenesis, and such new donor viruses can be used in the production of live attenuated reassortants vaccine candidates in a manner analogous to that described above for the ca donor virus. Similarly, other known and suitable attenuated donor strains can be reassorted with influenza virus to obtain attenuated vaccines suitable for use in the vaccination of mammals.

In one embodiment, such attenuated viruses maintain the genes from the virus that encode antigenic determinants substantially similar to those of the original clinical isolates. This is because the purpose of the attenuated vaccine is to provide substantially the same antigenicity as the original clinical isolate of the virus, while at the same time lacking pathogenicity to the degree that the vaccine causes minimal chance of inducing a serious disease condition in the vaccinated mammal.

The viruses in a multivalent vaccine can thus be attenuated or inactivated, formulated and administered, according to known methods, as a vaccine to induce an immune response in an animal, e.g., a mammal. Methods are well-known in the art for determining whether such attenuated or inactivated vaccines have maintained similar antigenicity to that of the clinical isolate or high growth strain derived therefrom. Such known methods include the use of antisera or antibodies to eliminate viruses expressing antigenic determinants of the donor virus; chemical selection (e.g., amantadine or rimantadine); HA and NA activity and inhibition; and nucleic acid screening (such as probe hybridization or PCR) to confirm that donor genes encoding the antigenic determinants (e.g., HA or NA genes) are not present in the attenuated viruses.

Pharmaceutical Compositions

Pharmaceutical compositions of the present disclosure, suitable for inoculation, e.g., nasal, parenteral or oral administration, comprise one or more influenza virus isolates, e.g., one or more attenuated or inactivated influenza viruses, a subunit thereof, isolated protein(s) thereof, and/or isolated nucleic acid encoding one or more proteins thereof, optionally further comprising sterile aqueous or non-aqueous solutions, suspensions, and emulsions. The compositions can further comprise auxiliary agents or excipients, as known in the art. The composition of the invention is generally presented in the form of individual doses (unit doses).

Conventional vaccines generally contain about 0.1 to 200 µg, e.g., 30 to 100 µg, 0.1 to 2 µg, 0.5 to 5 µg, 1 to 10 µg 10 µg to 20 µg, 15 µg to 30 µg, or 10 to 30 µg, of HA from each of the strains entering into their composition. The vaccine forming the main constituent of the vaccine composition of the invention may comprise a single influenza virus, or a combination of influenza viruses, for example, at least two or three influenza viruses, including one or more reassortant(s).

Preparations for parenteral administration include sterile aqueous or non-aqueous solutions, suspensions, and/or emulsions, which may contain auxiliary agents or excipients known in the art. Examples of non-aqueous solvents are propylene glycol, polyethylene glycol, vegetable oils such as olive oil, and injectable organic esters such as ethyl oleate. Carriers or occlusive dressings can be used to increase skin permeability and enhance antigen absorption. Liquid dosage forms for oral administration may generally comprise a liposome solution containing the liquid dosage form. Suitable forms for suspending liposomes include emulsions, suspensions, solutions, syrups, and elixirs containing inert diluents commonly used in the art, such as purified water. Besides the inert diluents, such compositions can also include adjuvants, wetting agents, emulsifying and suspending agents, or sweetening, flavoring, or perfuming agents.

When a composition of the present disclosure is used for administration to an individual, it can further comprise salts, buffers, adjuvants, or other substances which are desirable for improving the efficacy of the composition. For vaccines, adjuvants, substances which can augment a specific immune response, can be used. Normally, the adjuvant and the composition are mixed prior to presentation to the immune system, or presented separately, but into the same site of the organism being immunized.

Heterogeneity in a vaccine may be provided by mixing replicated influenza viruses for at least two influenza virus strains, such as 2-20 strains or any range or value therein. Vaccines can be provided for variations in a single strain of an influenza virus, using techniques known in the art.

A pharmaceutical composition according to the present disclosure may further or additionally comprise at least one chemotherapeutic compound, for example, for gene therapy, immunosuppressants, anti-inflammatory agents or immune enhancers, and for vaccines, chemotherapeutics including, but not limited to, gamma globulin, amantadine, guanidine, hydroxybenzimidazole, interferon-$\alpha$, interferon-$\beta$, interferon-$\gamma$, tumor necrosis factor-alpha, thiosemicarbarzones, methisazone, rifampin, ribavirin, a pyrimidine analog, a purine analog, foscarnet, phosphonoacetic acid, acyclovir, dideoxynucleosides, a protease inhibitor, or ganciclovir.

The composition can also contain variable but small quantities of endotoxin-free formaldehyde, and preservatives, which have been found safe and not contributing to undesirable effects in the organism to which the composition is administered.

Pharmaceutical Purposes

The administration of the composition (or the antisera that it elicits) may be for either a "prophylactic" or "therapeutic" purpose. When provided prophylactically, the compositions of the invention which are vaccines are provided before any symptom or clinical sign of a pathogen infection becomes manifest. The prophylactic administration of the composition serves to prevent or attenuate any subsequent infection. When provided prophylactically, the gene therapy compositions of the invention, are provided before any symptom or clinical sign of a disease becomes manifest. The prophylactic administration of the composition serves to prevent or attenuate one or more symptoms or clinical signs associated with the disease.

When provided therapeutically, a viral vaccine is provided upon the detection of a symptom or clinical sign of actual infection. The therapeutic administration of the compound(s) serves to attenuate any actual infection. When provided therapeutically, a gene therapy composition is provided upon the detection of a symptom or clinical sign of the disease. The therapeutic administration of the compound(s) serves to attenuate a symptom or clinical sign of that disease.

Thus, a vaccine composition of the present disclosure may be provided either before the onset of infection (so as to prevent or attenuate an anticipated infection) or after the initiation of an actual infection. Similarly, for gene therapy, the composition may be provided before any symptom or clinical sign of a disorder or disease is manifested or after one or more symptoms are detected.

A composition is said to be "pharmacologically acceptable" if its administration can be tolerated by a recipient mammal. Such an agent is said to be administered in a "therapeutically effective amount" If the amount administered is physiologically significant. A composition of the present invention is physiologically significant if its presence results in a detectable change in the physiology of a recipient patient, e.g., enhances at least one primary or secondary humoral or cellular immune response against at least one strain of an infectious influenza virus.

The "protection" provided need not be absolute, i.e., the influenza Infection need not be totally prevented or eradicated. If there is a statistically significant improvement compared with a control population or set of mammals. Protection may be limited to mitigating the severity or rapidity of onset of symptoms or clinical signs of the influenza virus infection.

Pharmaceutical Administration

A composition of the present disclosure may confer resistance to one or more pathogens, e.g., one or more influenza virus strains, by either passive immunization or active immunization. In active immunization, an attenuated live vaccine composition is administered prophylacticaly to a host (e.g., a mammal), and the host's immune response to the administration protects against infection and/or disease. For passive immunization, the elicited antisera can be recovered and administered to a recipient suspected of having an infection caused by at least one influenza virus strain. A gene therapy composition may yield prophylactic or therapeutic levels of the desired gene product by active immunization.

In one embodiment, the vaccine is provided to a mammalian female (at or prior to pregnancy or parturition), under conditions of time and amount sufficient to cause the production of an immune response which serves to protect both the female and the fetus or newborn (via passive incorporation of the antibodies across the placenta or in the mother's milk).

The present disclosure thus includes methods for preventing or attenuating a disorder or disease, e.g., an infection by at least one strain of pathogen such as an influenza virus. As used herein, a vaccine is said to prevent or attenuate a disease if its administration results either in the total or partial attenuation (i.e., suppression) of a clinical sign or condition of the disease, or in the total or partial immunity of the individual to the disease. As used herein, a gene therapy composition is said to prevent or attenuate a disease if its administration results either in the total or partial attenuation (i.e., suppression) of a clinical sign or condition of the disease, or in the total or partial immunity of the individual to the disease.

A composition having at least one influenza virus of the present disclosure, including one which is attenuated and one or more other isolated viruses, one or more isolated viral proteins thereof, one or more isolated nucleic acid molecules encoding one or more viral proteins thereof, or a combination thereof, may be administered by any means that achieve the intended purposes.

For example, administration of such a composition may be by various parenteral routes such as subcutaneous, intravenous, intradermal, intramuscular, intraperitoneal, intranasal, oral or transdermal routes. Parenteral administration can be accomplished by bolus injection or by gradual perfusion over time.

A typical regimen for preventing, suppressing, or treating an influenza virus related pathology, comprises administration of an effective amount of a vaccine composition as described herein, administered as a single treatment, or repeated as enhancing or booster dosages, over a period up to and including between one week and about 24 months, or any range or value therein.

According to the present disclosure, an "effective amount" of a composition is one that is sufficient to achieve a desired effect. It is understood that the effective dosage may be dependent upon the species, age, sex, health, and weight of the recipient, kind of concurrent treatment, if any, frequency of treatment, and the nature of the effect wanted. The ranges of effective doses provided below are not intended to limit the invention and represent dose ranges.

The dosage of a live, attenuated or killed virus vaccine for an animal such as a mammalian adult organism may be from about $10^2$-$10^{20}$, e.g., $10^3$-$10^{14}$, $10^3$-$10^{12}$, $10^2$-$\mathbf{10^{10}}$, $10^5$-$10^{11}$, $10^6$-$10^{15}$, $10^2$-$10^{10}$, or $10^{15}$-$10^{20}$ plaque forming units (PFU)/kg, about $10^2$-$10^{10}$, $10^3$-$10^{12}$, $10^4$-$10^{10}$, $10^5$-$10^{11}$, $10^6$-$10^{14}$, $10^5$-$10^{12}$, or $10^{14}$-$10^{20}$ plaque forming units (PFU)/kg, or any range or value therein. The dose of one viral isolate vaccine, e.g., in an inactivated vaccine, may range from about 0.1 to 1000, e.g., 0.1 to 10 µg, 1 to 20 µg, 30 to 100 µg, 10 to 50 µg, 50 to 200 µg, or 150 to 300 µg, of HA protein. However, the dosage should be a safe and effective amount as determined by conventional methods, using existing vaccines as a starting point.

The dosage of immunoreactive HA in each dose of replicated virus vaccine may be standardized to contain a suitable amount, e.g., 0.1 µg to 1 µg, 0.5 µg to 5 µg. 1 µg to 10 µg, 10 µg to 20 µg, 15 µg to 30 µg, or 30 µg to 100 µg or any range or value therein, or the amount recommended by government agencies or recognized professional organizations. The quantity of NA can also be standardized.

The dosage of immunoreactive HA in each dose of replicated virus vaccine can be standardized to contain a suitable amount, e.g., 1-50 µg or any range or value therein, or the amount recommended by the U.S. Public Health Service (PHS), which is usually 15 µg, per component for older children >3 years of age, and 7.5 µg per component for children <3 years of age. The quantity of NA can also be standardized, however, this glycoprotein can be labile during the processor purification and storage (Kendal et al., 1980; Kerr et al., 1975). Each 0.5-ml dose of vaccine may contain approximately 0.1 to 0.5 billion viral particles, 0.5 to 2 billion viral particles, 1 to 50 billion virus particles, 1 to 10 billion viral particles, 20 to 40 billion viral particles, 1 to 5 billion viral particles, or 40 to 80 billion viral particles.

Exemplary Viruses and Vaccine Formulations

The present disclosure provides a method that stabilizes the NA tetrameric structure of influenza virus, recombinant viruses having the stabilized NA, and methods of using that virus. For example, NA-48C and/or NA-50C mutations in influenza generate highly proliferative recombinant influenza viruses expressing structurally stabilized NA tetramers that can be used to generate influenza vaccine strains containing a greater amount of NA antigen, e.g., so as to elicit an effective immune response. The influenza vaccines can comprise live attenuated viruses or an inactivated (killed) preparation, e.g., whole virus, subunit or split virus preparation, or exogenously expressed NA and HA. There are three types of inactivated vaccines: whole virus vaccines, split virus vaccines (e.g., disrupted by a detergent), and subunit vaccines (i.e., HA and NA have been further purified by removal of other viral components). In one embodiment, the recombinant virus is grown in eggs and a split inactivated vaccine is prepared therefrom. In one embodiment, the dose in a vaccine contains about 10 to about 20, e.g., 15, μg of HA per strain (for example for a total HA concentration of 45 μg for trivalent and 60 μg for quadrivalent) and is administered as a single dose to those aged >9 years. Younger children (between 6 months and 8 years of age) may need two doses administered 4 weeks apart, if they have not been vaccinated in previous influenza seasons. The standard dose is typically delivered as an intramuscular (i.m.) injection (although intradermal [i.d.] formulations and intranasal formulations are also available).

In one embodiment, whole-virus vaccines are prepared from harvested allantoic fluid, chemically inactivated, e.g., with formalin or β-propiolactone, and subsequently concentrated and purified to remove nonviral protein contaminants. In one embodiment, the split-virus vaccine includes treatment with detergent to dissociate the viral lipid envelope, exposing all viral proteins and subviral elements. In one embodiment, for subunit vaccines, the HA (and NA) protein is further enriched through additional purification steps. Because the split-virus and subunit vaccines had comparable immunogenicity in primed populations but reduced reactogenicity compared to the whole-virus vaccine preparations, most contemporary vaccines since the 1970s have been split-virus or subunit formulations.

Exemplary NA Modifications

The present disclosure thus relates to influenza modification relative to parental NA that stabilize the neuraminidase (NA) tetramer, e.g., of human influenza viruses. Those NA modification(s) may also increase the vaccine virus yield.

Therefore, the disclosure provides isolated recombinant, e.g., reassortant, influenza viruses with selected amino acid residues, insertions, deletions, or any combination thereof, in the stalk region in NA. In one embodiment, the NA is selected to encode a cysteine at residue 48. In one embodiment, the NA is selected to encode a cysteine at position 50. In one embodiment, the NA is selected to encode a cysteine at positions 48 and 50.

In one embodiment, the NA is selected to have a deletion in one or more of residues 1 to 10 after the last residue in the transmembrane domain, which deletion stabilizes the NA tetramer. In one embodiment, the NA is selected to have a deletion in one or more of residues 10 to 20 after the last residue in the transmembrane domain that stabilizes the NA tetramer. In one embodiment, the NA is selected to have a deletion in one or more of residues 20 to 30 after the last residue in the transmembrane domain that stabilizes the NA tetramer. In one embodiment, the NA is selected to have a deletion in one or more of residues 30 to 40 after the last residue in the transmembrane domain that stabilizes the NA tetramer. In one embodiment, the NA is selected to have a deletion in one or more of residues 40 to 50 after the last residue in the transmembrane domain that stabilizes the NA tetramer. In one embodiment, the deletion includes a deletion of 1, 2, 3, 4 or 5 residues in the stalk region. In one embodiment, the deletion includes a deletion of 6, 7, 8, or 9 residues in the stalk region. In one embodiment, the deletion includes a deletion of 10, 11, 12, 13, 14 or 15 residues in the stalk region. In one embodiment, the deletion includes a deletion of 16, 17, 18, or 19 residues in the stalk region. In one embodiment, the deletion includes a deletion of 20, 21, 22, 23, 24 or 25 residues in the stalk region. In one embodiment, the deletion includes a deletion of 26, 27, 28, or 29 residues in the stalk region.

In one embodiment, the NA is selected to have an insertion of one or more amino acid residues in residues 1 to 10 after the last residue in the transmembrane domain, which insertion stabilizes the NA tetramer. In one embodiment, the NA is selected to have an insertion of one or more amino acid residues in residues 10 to 20 after the last residue in the transmembrane domain that stabilizes the NA tetramer. In one embodiment, the NA is selected to have an insertion of one or more amino acid residues 20 to 30 after the last residue in the transmembrane domain that stabilizes the NA tetramer. In one embodiment, the NA is selected to have an insertion of one or more amino acid residues 30 to 40 after the last residue in the transmembrane domain that stabilizes the NA tetramer. In one embodiment, the NA is selected to have an insertion of one or more amino acid residues 40 to 50 after the last residue in the transmembrane domain that stabilizes the NA tetramer. In one embodiment, the insertion includes an insertion of 1, 2, 3, 4 or 5 residues in the stalk region. In one embodiment, the insertion includes an insertion of 6, 7, 8, or 9 residues in the stalk region. In one embodiment, the insertion includes an insertion of 10, 11, 12, 13, 14 or 15 residues in the stalk region. In one embodiment, the insertion includes an insertion of 16, 17, 18, or 19 residues in the stalk region. In one embodiment, the insertion includes an insertion of 20, 21, 22, 23, 24 or 25 residues in the stalk region. In one embodiment, the insertion includes an insertion of 26, 27, 28, or 29 residues in the stalk region.

In one embodiment, the NA is selected to have a substitution of one or more amino acid residues in residues 1 to 10 after the last residue in the transmembrane domain, which substitution stabilizes the NA tetramer. In one embodiment, the NA is selected to have a substitution of one or more amino acid residues in residues 10 to 20 after the last residue in the transmembrane domain that stabilizes the NA tetramer. In one embodiment, the NA is selected to have a substitution of one or more amino acid residues 20 to 30 after the last residue in the transmembrane domain that stabilizes the NA tetramer. In one embodiment, the NA is selected to have a substitution of one or more amino acid residues 30 to 40 after the last residue in the transmembrane domain that stabilizes the NA tetramer. In one embodiment, the NA is selected to have a substitution of one or more amino acid residues 40 to 50 after the last residue in the transmembrane domain that stabilizes the NA tetramer. In one embodiment, the substitution to a cysteine is at a residue that faces towards the stalk region of a NA in another NA molecule, e.g., in a dimer, timer or tetramer.

In one embodiment, the NA is selected to have one or more cysteines at one or more of residues 1 to 10 after the last residue in the transmembrane domain that stabilizes the NA tetramer. In one embodiment, the NA is selected to have one or more cysteines at one or more of residues 10 to 20 after the last residue in the transmembrane domain that stabilizes the NA tetramer. In one embodiment, the NA is selected to have one or more cysteines at one or more of residues 20 to 30 after the last residue in the transmembrane domain that stabilizes the NA tetramer. In one embodiment, the NA is selected to have one or more cysteines at one or more of residues 30 to 40 after the last residue in the transmembrane domain that stabilizes the NA tetramer. In one embodiment, the NA is selected to have one or more cysteines at one or more of residues 40 to 50 after the last residue in the transmembrane domain that stabilizes the NA tetramer. For example, a virus with a NA having a 7 amino acid cytoplasmic tail, a 26 amino acid transmembrane domain and a Cys at residue 48, is a virus that has a cysteine at a residue that is between residues 10 to 20 after the last residue in the transmembrane domain (the numbering for NA is based on N1). In one embodiment, the disclosure provides an isolated recombinant reassortant influenza virus having six "internal" viral segments from a vaccine influenza virus, e.g., PR8UW, a NA viral segment with one or more of the specified modifications, and a HA viral segment, e.g., any of H1-H18, e.g., from a circulating influenza virus. Also provided are compositions comprising the recombinant influenza virus, pharmaceutical compositions such as vaccines.

Thus, for vaccine viruses that are to be grown or passaged in cells, e.g., in eggs, replacement of the residue at any one of residues from 1 to 60 after the last residue in the transmembrane domain, an insertion of one or more residues from 1 to 60 after the last residue in the transmembrane domain or a deletion of one or more residues from 1 to 60 after the last residue in the transmembrane domain, or any combination thereof, in NA, e.g., by mutation, or selection of a NA viral segment for a NA with a particular amino acid, e.g., cysteine, at any one of residues from 1 to 60 after the last residue in the transmembrane domain, an insertion of one or more residues from 1 to 60 after the last residue in the transmembrane domain or a deletion of one or more residues from 1 to 60 after the last residue in the transmembrane domain, or any combination thereof, in NA, wherein the numbering is based on N1, may result in stabilization of NA and/or higher viral titers.

In one embodiment, the disclosure provides an isolated recombinant influenza virus comprising PA, PB1, PB2, NP, NS, M, and HA viral segments and a NA viral segment that encodes an NA selected to encode a particular amino acid, e.g., cysteine, at any one of residues from 1 to 60 after the last residue in the transmembrane domain, an insertion of one or more residues from 1 to 60 after the last residue in the transmembrane domain or a deletion of one or more residues from 1 to 60 after the last residue in the transmembrane domain, wherein the numbering is based on N1, wherein the recombinant influenza virus may have enhanced replication in avian eggs or a NA tetramer with enhanced stability, e.g., during vaccine production.

In one embodiment, the disclosure provides an isolated recombinant influenza virus comprising PA, PB1, PB2, NP, NS, M, and HA viral segments and a NA viral segment that encodes an NA with a replacement (substitution) of a residue at any one of residues from 1 to 60 after the last residue in the transmembrane domain, an insertion of one or more residues from 1 to 60 after the last residue in the transmembrane domain or a deletion of one or more residues from 1 to 60 after the last residue in the transmembrane domain, or any combination thereof, in NA, e.g., by mutation, wherein the numbering is based on N1, wherein the recombinant influenza virus may have enhanced replication in avian eggs or a NA tetramer with enhanced stability, e.g., during vaccine production.

In one embodiment, the isolated recombinant influenza virus is a reassortant. In one embodiment, the NA viral segment encodes a NA that has at least 50%, 55%, 60%, 65%, 70%, 75%, 80%, 85%, 90%. 95%, or 99% amino acid sequence identity to any one of SEQ ID Nos. 1-9, 15-18, 37, or 44-50, or a polypeptide encoded by any one of SEQ ID Nos. 19-29, or having at least 50% 55%, 60% 65%, 70%, 75%, 80%, 85%, 90%, 95%, or 99% amino acid sequence identity to the stalk region in any one of SEQ ID Nos. 1-9, 15-18, 37, or 44-50, or encoded by one of SEQ ID Nos. 19-29. In one embodiment, the NA viral segment encodes a N2, N3, N7, or N9 and the positions in N3, N7, or N9 with the specified modification(s). In one embodiment, the NA viral segment encodes a N1, N4, N5, N5, N8, N10 or N11 with the specified modification(s). In one embodiment, the PA, PB1. PB2. NP, M, and NS viral segments have at least 85% nucleic acid sequence identity to SEQ ID Nos. 30 to 35 or 38 to 43 or encode a polypeptide having at least 80%, 85%, 90%, 95%, or 99 amino acid sequence identity to a polypeptide encoded by SEQ ID Nos. 30-35 or 38 to 43. In one embodiment, the virus is an influenza B virus.

Also provided is a method to prepare influenza virus having a stabilized NA tetramer. The method includes contacting a cell with: a vector for vRNA production comprising a promoter operably inked to an influenza virus PA DNA linked to a transcription termination sequence, a vector for vRNA production comprising a promoter operably inked to an influenza virus PB1 DNA linked to a transcription termination sequence, a vector for vRNA production comprising a promoter operably linked to an influenza virus PB2 DNA linked to a transcription termination sequence, a vector for vRNA production comprising a promoter operably linked to an influenza virus HA DNA linked to a transcription termination sequence, a vector for vRNA production comprising a promoter operably linked to an influenza virus NP DNA linked to a transcription termination sequence, a vector for vRNA production comprising a promoter operably linked to an influenza virus NA DNA linked to a transcription termination sequence, a vector for vRNA production comprising a promoter operably linked to an influenza virus M DNA linked to a transcription termination sequence, and a vector for vRNA production comprising a promoter operably linked to an influenza virus NS DNA linked to a transcription termination sequence, wherein the PB1, PB2, PA, NP, NS, and M DNAs in the vectors for vRNA production are from one or more influenza vaccine virus isolates, wherein the NA DNA in the vector for vRNA production has a modification in the stalk region as described herein, wherein the numbering for NA residues is that for N1; and a vector for mRNA production comprising a promoter operably linked to a DNA segment encoding influenza virus PA, a vector for mRNA production comprising a promoter operably linked to a DNA segment encoding influenza virus PB1, a vector for mRNA production comprising a promoter operably linked to a DNA segment encoding influenza virus PB2, and a vector for mRNA production comprising a promoter operably linked to a DNA segment encoding influenza virus NP, and optionally comprising one or more of: a vector for mRNA production comprising a promoter operably linked to a DNA segment encoding influenza virus HA, a vector for mRNA production comprising a promoter operably linked to a DNA segment encoding influenza virus NA, a vector for mRNA production comprising a promoter operably linked to a DNA segment encoding influenza virus M1, a vector for mRNA production comprising a promoter operably linked to a DNA segment encoding influenza virus M2, a vector for mRNA production comprising a promoter operably linked to a DNA segment encoding influenza virus NS1, or a vector for mRNA production comprising a promoter operably linked to a DNA segment encoding influenza virus NS2; in an amount effective to yield infectious influenza virus. In one embodiment, the NA viral segment encodes a NA that has at least 50%, 55%, 60%, 65%, 70%, 75%, 80%, 85%, 90%, 95%, or 99% amino acid sequence identity to any one of SEQ ID Nos. 1-9, 15-18, 37, or 44-50, or having at least 50%, 55%, 60%, 65%, 70%, 75%, 80%, 85%, 90%, 95%, or 99% amino acid sequence identity to the stalk region in any one of SEQ ID Nos. 1-9, 15-18, 37, or 44-50. In one embodiment, the NA is N1, N4, N5, N6, N8, N10 or N11.

In one embodiment, the HA is H1, H3, H5, H7, or H9. In one embodiment, the virus is an influenza A virus. In one embodiment, PA, PB1, PB2, NP, M, and NS viral segments have at least 85%, 85%, 90%, 95%, or 99% nucleic acid sequence identity to SEQ ID Nos. 30 to 35 or 38 to 43 or encode a polypeptide having at least 80%, 85%, 90%, 95%, or 99% amino acid sequence identity to a polypeptide encoded by SEQ ID Nos. 30-35 or 38 to 43. In one embodiment, HA is H2, H4, H5, H6, H8, or any of H10-H18.

In one embodiment, the virus is an influenza B virus.

Further provided is a method of immunizing an avian or a mammal with a composition having an effective amount of the virus described herein. In one embodiment, the composition comprises at least one other different influenza virus. In one embodiment, the mammal is a human. In one embodiment, the composition is administered intranasally or via injection.

In one embodiment, the disclosure provides isolated influenza type A virus with a characteristic residue(s), insertion and/or deletion, or a combination thereof, in NA described herein. In one embodiment, the isolated influenza type A virus with a characteristic residue(s), insertion and/or deletion, or a combination thereof, has a NA with at least 50%, 55%, 60%, 65%, 70%, 75%, 80%, 85%, 90%, 95%, or 99% amino acid sequence identity to any one of SEQ ID Nos. 1-9, 15-18, 37, or 44-50, or a polypeptide encoded by any one of SEQ ID Nos. 19-29, or having at least 50%, 55%, 60%, 65%, 70%, 75%, 80%, 85%, 90%, 95%, or 99% amino acid sequence identity to the stalk region in any one of SEQ ID Nos. 1-9, 15-18, 37, or 44-50 or encoded by one of SEQ ID Nos. 19-29.

In one embodiment, the isolated influenza type A virus of the invention with a characteristic residue(s) and/or deletion, or a combination thereof, has an HA from anyone of subtypes 1-18 of HA. In one embodiment the characteristic residue is a conservative substitution. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine: a group of amino acids having amide-containing side chains is asparagine and glutamine; a group of amino acids having aromatic side chains is phenylalanine, tyrosine and tryptophan; a group of amino acids having basic side chains is lysine, arginine and histidine; and a group of amino acids having sulfur-containing side chain is cysteine and methionine. In one embodiment, conservative amino acid substitution groups are: threonine-valine-leucine-isoleucine-alanine; phenylalanine-tyrosine; lysine-arginine; alanine-valine; glutamic-aspartic; and asparagine-glutamine. In one embodiment, the characteristic residue is a non-conservative substitution.

In one embodiment, a mutation is introduced into a NA viral segment of an influenza virus isolate, e.g., via recombinant DNA techniques including site-specific mutagenesis, or replacing a portion of the NA coding sequence with a portion that includes the characteristic residue(s), insertion or deletion. In one embodiment, a NA viral segment with a characteristic residue, insertion and/or deletion described herein is combined with a HA segment, and internal viral segments of an influenza vaccine virus.

The disclosure provides a plurality of influenza virus vectors of the invention, e.g., those useful to prepare reassortant viruses including 6:1:1 reassortants, 6:2 reassortants and 7:1 reassortants. A 6:1:1 reassortant is an influenza virus with 6 internal viral segments from a vaccine virus, a HA viral segment that is from a different (second) viral isolate than the vaccine virus, and a NA viral segment with a characteristic residue(s), insertion, and/or deletion, or a combination thereof, as described herein, which is from a different viral source than the HA segment and the vaccine virus; a 6:2 reassortant is an influenza virus with 6 internal viral segments from a vaccine virus, and a NA viral segment having a characteristic residue(s), insertion and/or deletion, or a combination thereof, which segment is from the same source as the HA segment, and a HA viral segment from a different viral isolate than the vaccine virus; and a 7:1 reassortant, in one embodiment, is an influenza virus with 6 Internal viral segments and a HA segment from a vaccine virus, and a NA segment that is modified to include the characteristic residue(s) and/or deletion, or a combination thereof, which NA segment is from a different viral source than the vaccine virus.

In one embodiment of the invention, the plurality includes vectors for vRNA production selected from a vector comprising a promoter operably linked to an influenza virus PA DNA linked to a transcription termination sequence, a vector comprising a promoter operably linked to an influenza virus PB1 DNA linked to a transcription termination sequence, a vector comprising a promoter operably linked to an influenza virus PB2 DNA linked to a transcription termination sequence, a vector comprising a promoter operably linked to an influenza virus HA DNA linked to a transcription termination sequence, a vector comprising a promoter operably linked to an influenza virus NP DNA linked to a transcription termination sequence, a vector comprising a promoter operably linked to an influenza virus NA DNA linked to a transcription termination sequence, a vector comprising a promoter operably linked to an influenza virus M DNA linked to a transcription termination sequence, and a vector comprising a operably linked to an influenza virus NS DNA linked to a transcription termination sequence. In one embodiment, the DNAs for vRNA production of PB1, PB2, PA, NP, M, and NS, have sequences from an influenza virus that replicates to high titers in cultured mammalian cells such as MDCK cells, Vero cells or PER.C6® cells or embryonated eggs, and/or from a vaccine virus, e.g., one that does not cause significant disease in humans. The DNA for vRNA production of NA may be from any NA, e.g., any of N1-N11, and the DNA for vRNA production of HA may be from any HA, e.g., H1-H18. In one embodiment, the DNAs for vRNA production may be for an influenza B or C virus. For example, the DNAs for vRNA production include influenza B virus PA, PB1, PB2, NP. NS, and M or influenza B virus PA, PB1, PB2, NP, NS, M, and NA, wherein the vRNA for NA has a NA with a characteristic residue, insertion and/or deletion as described herein. The DNAs for vRNA production of NA and HA may be from different strains or isolates (6:1:1 reassortants) or from the same strain or isolate (6:2 reassortants), or the NA or HA may be from the same strain or isolate as that for the internal genes (7:1 reassortant). The plurality also includes vectors for mRNA production selected from a vector encoding influenza virus PA, a vector encoding influenza virus PB1, a vector encoding influenza virus PB2, and a vector encoding influenza virus NP, and optionally one or more vectors encoding NP, NS, M, e.g., M1 and M2, HA or NA. The vectors encoding viral proteins may further include a transcription termination sequence.

Viruses that may provide the internal genes for reassortants within the scope of the invention include viruses that have high titers, e.g., titers of at least about $10^5$ PFU/mL, e.g., at least $10^6$ PFU/mL, $10^7$ PFU/mL or $10^8$ PFU/mL; high titers in embryonated eggs, e.g., titers of at least about $10^7$ $EID_{50}$/mL, e.g., at least $10^8$ $EID_{50}$/mL, $10^9$ $EID_{50}$/mL or $10^{10}$ $EID_{50}$/mL; high titers in MDCK cells, e.g., titers of at least about $10^7$ PFU/mL, e.g., at least $10^8$ PFU/mL, or high titers in two of more of those host cells.

Other reassortants with internal genes from other PR8 isolates or vaccine viruses may be employed in recombinant reassortant viruses.

In one embodiment, the DNAs for the internal genes for PB1, PB2, PA, NP, M, and NS encode proteins with substantially the same activity as a corresponding polypeptide encoded by one of SEQ ID NOs:30-35 or 38-43. As used herein, "substantially the same activity" includes an activity that is about 0.1%, 1%, 10%, 30%, 50%, 90%, e.g., up to 100% or more, or detectable protein level that is about 80%, 90% or more, the activity or protein level, respectively, of the corresponding full-length polypeptide. In one embodiment, the nucleic acid a sequence encoding a polypeptide which is substantially the same as, e.g., having at least 80%, e.g., 90%, 92%, 95%, 97% or 99%, including any integer between 80 and 99, contiguous amino acid sequence identity to, a polypeptide encoded by one of SEQ ID NOs:30-35 or 38-43. In one embodiment, the isolated and/or purified nucleic acid molecule comprises a nucleotide sequence which is substantially the same as, e.g., having at least 50%, e.g., 60%, 70%, 80% or 90%, including any integer between 50 and 100, or more contiguous nucleic acid sequence identity to one of SEQ ID NOs:30-35 or 38-43 and, in one embodiment, also encodes a polypeptide having at least 80%, e.g., 90%, 92%, 95%, 97% or 99%, including any integer between 80 and 99, contiguous amino acid sequence identity to a polypeptide encoded by one of SEQ ID NOs: 30-35 or 38-43. In one embodiment, the influenza virus polypeptide has one or more, for instance, 2, 5, 10, 15, 20 or more, conservative amino acids substitutions, e.g., conservative substitutions of up to 10% or 20% of the residues, relative to a polypeptide encoded by one of SEQ ID NOs: 30-35 or 38-43. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine: a group of amino acids having amide-containing side chains is asparagine and glutamine; a group of amino acids having aromatic side chains is phenylalanine, tyrosine and tryptophan; a group of amino acids having basic side chains is lysine, arginine and histidine; and a group of amino acids having sulfur-containing side chain is cysteine and methionine.

In one embodiment, conservative amino acid substitution groups are: valine-leucine-isoleucine; phenylalanine-tyrosine; lysine-arginine; alanine-valine; glutamic-aspartic; and asparagine-glutamine. In one embodiment, the influenza virus polypeptide has one or more, for instance, 2, 3 or 4, nonconservative amino acid substitutions, relative to a polypeptide encoded by one of SEQ ID NOs:30-35.

In one embodiment, the nucleic acid is a sequence encoding a NA polypeptide which is substantially the same as, e.g., having at least 50%, 55% 60%, 65%, 70%, 75%, 80%, e.g., 90%, 92%, 95%, 97% or 99%, including any integer between 80 and 99, contiguous amino acid sequence identity to, one of Accession Nos. ACP41107.1 (N1), AIK26357.1 (N7), ALH21372.1 (N9), or BAK86313.1 (N2), the sequences of which are incorporated by reference herein, or at least the stalk region thereof. In one embodiment, the isolated and/or purified nucleic acid molecule encodes a polypeptide having at least 50%, 55%, 60%, 65%, 70%, 75%, 80%. e.g., 90%, 92%, 95%, 97% or 99%, including any integer between 80 and 99, contiguous amino acid sequence identity to any one of Accession Nos. ACP41107.1 (N1), AIK26357.1 (N7), ALH21372.1 (N9), or BAK86313.1 (N2), the sequences of which are incorporated by reference herein, or at least the stalk region thereof. In one embodiment, the influenza virus polypeptide has one or more, for instance, 2, 5, 10, 15, 20 or more, conservative amino acids substitutions, e.g., conservative substitutions of up to 10% or 20% of the residues, relative to SEQ ID NOs:1-18, or one of Accession Nos. ACP41107.1 (N1) AIK26357.1 (N7), ALH21372.1 (N9), or BAK86313.1 (N2), or at least the stalk region thereof. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine and tryptophan; a group of amino acids having basic side chains is lysine, arginine and histidine; and a group of amino acids having sulfur-containing side chain is cysteine and methionine. In one embodiment, conservative amino acid substitution groups are: valine-leucine-isoleucine; phenylalanine-tyrosine; lysine-arginine; alanine-valine; glutamic-aspartic; and asparagine-glutamine. In one embodiment, the influenza virus polypeptide has one or more, for instance, 2, 3 or 4, nonconservative amino acid substitutions, relative to a polypeptide having one of SEQ ID NOs:1-18, 3, or one of Accession Nos. ACP41107.1 (N1) AIK26357.1 (N7), ALH21372.1 (N9), or BAK8313.1 (N2), or at least the stalk region thereof.

The invention thus includes the use of isolated and purified vectors or plasmids, which express or encode influenza virus proteins, or express or encode influenza vRNA, both native and recombinant vRNA. The vectors comprise influenza cDNA, e.g., influenza A (e.g., any influenza A gene including any of the 18 HA or 11 NA subtypes), B or C DNA (see Fields *Virology* (Fields et al. (eds.), Lippincott, Williams and wickens (2013), which is specifically incorporated by reference herein). Any suitable promoter or transcription termination sequence may be employed to express a protein or peptide, e.g., a viral protein or peptide, a protein or peptide of a nonviral pathogen, or a therapeutic protein or peptide.

A composition or plurality of vectors of the invention may also comprise a heterologous gene or open reading frame of interest, e.g., a foreign gene encoding an immunogenic peptide or protein useful as a vaccine or in gene replacement, for instance may encode an epitope useful in a cancer therapy or vaccine, or a peptide or polypeptide useful in gene therapy. When preparing virus, the vector or plasmid comprising the gene or cDNA of interest may substitute for a vector or plasmid for an influenza viral gene or may be in addition to vectors or plasmids for all influenza viral genes. Thus, another embodiment of the invention comprises a composition or plurality of vectors as described above in which one of the vectors is replaced with, or further comprises, 5' influenza virus sequences optionally including 5' influenza virus coding sequences or a portion thereof, linked to a desired nucleic acid sequence, e.g., a desired cDNA, linked to 3' influenza virus sequences optionally including 3' influenza virus coding sequences or a portion thereof. In one embodiment, the desired nucleic acid sequence such as a cDNA is in an antisense (antigenic) orientation. The introduction of such a vector in conjunction with the other vectors described above to a host cell permissive for influenza virus replication results in recombinant virus comprising vRNA corresponding to the heterologous sequences of the vector.

The promoter in a vector for vRNA production may be a RNA polymerase I promoter, a RNA polymerase II promoter, a RNA polymerase III promoter, a T7 promoter, or a T3 promoter, and optionally the vector comprises a transcription termination sequence such as a RNA polymerase I transcription termination sequence, a RNA polymerase II transcription termination sequence, a RNA polymerase III transcription termination sequence, or a ribozyme. Ribozymes within the scope of the invention include, but are not limited to, tetrahymena ribozymes, RNase P, hammerhead ribozymes, hairpin ribozymes, hepatitis ribozyme, as well as synthetic ribozymes. In one embodiment, the RNA polymerase I promoter is a human RNA polymerase I promoter.

The promoter or transcription termination sequence in a vRNA or virus protein expression vector may be the same or different relative to the promoter or any other vector. In one embodiment, the vector or plasmid which expresses influenza vRNA comprises a promoter suitable for expression in at least one particular host cell, e.g., avian or mammalian host cells such as canine, feline, equine, bovine, ovine, or primate cells including human cells, or for expression in more than one host.

In one embodiment, at least one vector for vRNA comprises a RNA polymerase II promoter linked to a ribozyme sequence linked to viral coding sequences linked to another ribozyme sequences, optionally linked to a RNA polymerase I transcription termination sequence. In one embodiment, at least 2, e.g., 3, 4, 5, 6, 7 or 8, vectors for vRNA production comprise a RNA polymerase II promoter, a first ribozyme sequence, which is 5' to a sequence corresponding to viral sequences including viral coding sequences, which is 5' to a second ribozyme sequence, which is 5' to a transcription termination sequence. Each RNA polymerase II promoter in each vRNA vector may be the same or different as the RNA polymerase II promoter in any other vRNA vector. Similarly, each ribozyme sequence in each vRNA vector may be the same or different as the ribozyme sequences in any other vRNA vector. In one embodiment, the ribozyme sequences in a single vector are not the same.

In one embodiment, at least one vector comprises sequences corresponding to those encoding PB1, PB2, PA, NP, M, or NS, or a portion thereof, having substantially the same activity as a corresponding polypeptide encoded by one of SEQ ID NOs:30-35, e.g., a sequence encoding a polypeptide with at least 80%, e.g., 85%, 90%, 92%, 95%, 98%, 99% or 100%, including any integer between 80 and 100, amino acid identity to a polypeptide encoded by one of SEQ ID NOs:30-35. Optionally, two vectors may be employed in place of the vector comprising a promoter operably linked to an influenza virus M cDNA linked to a transcription termination sequence, e.g., a vector comprising a promoter operably linked to an influenza virus M1 cDNA linked to a transcription termination sequence and a vector comprising a promoter operably linked to an influenza virus M2 cDNA linked to a transcription termination sequence.

A plurality of the vectors of the invention may be physically linked or each vector may be present on an individual plasmid or other, e.g., linear, nucleic acid delivery vehicle. In one embodiment, each vRNA production vector is on a separate plasmid. In one embodiment, each mRNA production vector is on a separate plasmid.

The invention also provides a method to prepare influenza virus. The method comprises contacting a cell with a plurality of the vectors of the invention, e.g., sequentially or simultaneously, in an amount effective to yield infectious influenza virus. The invention also includes isolating virus from a cell contacted with the plurality of vectors. Thus, the invention further provides isolated virus, as well as a host cell contacted with the plurality of vectors or virus of the invention. In another embodiment, the invention includes contacting the cell with one or more vectors, either vRNA or protein production vectors, prior to other vectors, either vRNA or protein production vectors. In one embodiment, the promoter for VRNA vectors employed in the method is a RNA polymerase I promoter, a RNA polymerase II promoter, a RNA polymerase II promoter, a T3 promoter or a T7 promoter. In one embodiment, the RNA polymerase I promoter is a human RNA polymerase I promoter. In one embodiment, each vRNA vector employed in the method is on a separate plasmid. In one embodiment, the vRNA vectors employed in the method are on one plasmid or on two or three different plasmids. In one embodiment, each mRNA vector employed in the method is on a separate plasmid. In one embodiment, the mRNA vectors for PA, PB1, PB2 and NP employed in the method are on one plasmid or on two or three different plasmids.

The methods of producing virus described herein, which do not require helper virus infection, are useful in viral mutagenesis studies, and in the production of vaccines (e.g., for AIDS, influenza, hepatitis B, hepatitis C, rhinovirus, filoviruses, malaria, herpes, and foot and mouth disease) and gene therapy vectors (e.g., for cancer, AIDS, adenosine deaminase, muscular dystrophy, omithine transcarbamylase deficiency and central nervous system tumors). Thus, a virus for use in medical therapy (e.g., for a vaccine or gene therapy) Is provided.

The Invention also provides isolated viral polypeptides, and methods of preparing and using recombinant virus of the invention. The methods include administering to a host organism. e.g., a mammal, an effective amount of the influenza virus of the invention, e.g., an inactivated virus preparation, optionally in combination with an adjuvant and/or a carrier, e.g., in an amount effective to prevent or ameliorate infection of an animal such as a mammal by that virus or an antigenically closely related virus. In one embodiment, the virus is administered intramuscularly while in another embodiment, the virus is administered intranasally. In some dosing protocols, all doses may be administered intramuscularly or intranasally, while in others a combination of intramuscular and intranasal administration is employed. The vaccine may further contain other isolates of influenza virus including recombinant influenza virus, other pathogen(s), additional biological agents or microbial components, e.g., to form a multivalent vaccine. In one embodiment, intranasal vaccination, for instance containing with inactivated influenza virus, and a mucosal adjuvant may induce virus-specific IgA and neutralizing antibody in the nasopharynx as well as serum IgG.

The influenza virus of the invention may employed with other anti-virials, e.g., amantadine, rimantadine, and/or neuraminidase inhibitors, e.g., may be administered separately in conjunction with those anti-virials, for instance, administered before, during and/or after.

One example of an influenza A virus (A/Yokohama/2013/2003(H3N2)) neuraminidase protein sequence and its stalk region is provided below (stalk region is underlined).

MNPNQKIITI GSVSLTISTI CFFMQIAILI TTVTLHFKQY EFNSPPNNQV MLCEPTIIER NITEIVYLTN TTIEKEICPK LAEYRNWSKP QCNITGFAPF SKDNSIRLSA GGDRANTREP YVSCDPDKCY QFALGQGTTL NNVHSNDIVH DRTPYRTLLM NELGVPFHLG TKQVCIAVVSS SSCHDGKAVVL HVCVTGDDEN ATASFIYNGR LADSIVSWSK KILRTQESEC VCINGTCTVV MTDGSASGKA DTKILFIEEG KIVHTSTLSG SAQHVEECSC YPRYPGVRCV CRDNWKGSNR PIVDINIKDY SIVSSYVCSG LVGDTPRKND SSSSSHCLDP NNEEGGHGVK GVVAFDDGNDV WMGRTISEKL RSGYETFKVI EGWSNPNSKL QINRQVIVDR GNRSGYSGIF SVEGKSCINR CFYVELIRGR KQETEVLWIS NSIVVFCGTS GTYGTGSWPD GADINLMPI (SEQ ID NO:1)

Another example of an influenza A virus (A/Yokohama/47/2002(H1N2)) neuraminidase sequence and its stalk region is shown below (stalk region is underlined).

MNPNQKIITI GSVSLTIATI CFLMQIAILV TTVTLHFKQY ECNSPPNNQV MLCEPTIIER NITEIVYLTN TTIEKEICPK LAEYRNWSKP QCNITGFAPF SKDNSIRLSA GGDIWVTREP YVSCDPDKCY QFALGQGTTL NNGHSNDTVH DRTPYRTLLM NELGVPFHLG TKQVCIAWSS SSCHDGKAWL HVCVTGDDGN ATASFIYNGR LVDSIGSWSK KILRTQESEC VCINGTCTVV MTDGSASGKA DTKILFIEEG KIVHTSLLSG SAQHVEECSC YPRYPGVRCV CRDNWKGSNR PIVDINVKDY SIVSSYVCSG LVGDTPRKND SSSSSHCLDP NNEEGGHGVK GWAFDDGNDV VVMGRTISEKL RSGYETFKVI EGV'VSKPNSKL QINRQVIVDR GNRSGYSGIF SVEGKSCINR CFYVELIRGR NQETEVLWTS NSIVVFCGTS GTYGTGSWPD GADINLMPI (SEQ ID NO:3)

The amino acid sequence for Singapore0019 NA and its stalk region is as follows (stalk region is underlined):

MNPNQKIITIGSVSLTISTICFFMQIAILITTVTLHFKQYEENSPPNNQVMLC EPTIIERNITEIVYLTNTTIEKEICPKPAEYRNWSKPQCGITGFAPFSKDNSI RLSAGGDIWVTREPYVSCDPDKCYQFALGQGTTLNNVHSNNTVRDRTPY RTLLMNELGVPFHLGTKQVCIAWSSSSCHDGKAWLHVCITGDDKNATASF IYNGRLIDSVVSWSKDILRTQESECVCINGTCTVVMTDGNATGKADTKILFI EEGKIVHTSKLSGSAQHVEECSCYPRYPGVRCVCRDNWKGSNRPIVDINI KDHSIVSSYVCSGLVGDTPRKNDSSSSSHCLNPNNEEGGHGVKGWAFDD GNDVWMGRTINETSRLGYETFKVVEGWSNPKSKLQINRQVIVDIRGDIRSG YSGIFSVEGKSCINRCFYVELIRGIRKEETEVLINTSNSIVVFCGTSGTYGTG SWPDGADLNLMHI (SEQ ID NO:2).

The NA for A/Alaska/232/2015 has the following sequence (stalk region is underlined):

mnpngkiiti gsysltisti cffEngiaili ttvtlhfkdy efrispnnnqv mIcentiier nitelvylln ttiekeicpk paeyrnwskp gcgitglapf skdnsirlsa ggdiwvtrep yvscdpdkcy gfaigggill nnvhsnntvr drtpyrtllm nelgvpfhlg tkqvciawss sschdgkawl hvcitgddkn atasfiyngr lvdsvvswsk dilrtgesec vcingtctvv mtdgnatgka dtkilfieeg kivhtsklsg saghveecsc ypiypgvrcv crdnwkgsnr pivdinikdh sivssyvcsglvgdtprknd ssssshclnp nneegghgvk gwafddgndv wmgrtinets rigyelfkvv egwsnpkskl ginrqvivdr gdrsgysgif svegkscinr cfyvelirgr keetevlwts nsivvfcgts gtygtgswpd gadlnlmhi (SEQ ID NO:44).

NA nucleotide sequence for A/SingaporeIGP1908/2015 (H1N1) pdm09 agntaaaatgaatccaaaccaaaagataataaccattggtcgatcagtatgacaattggaatggctaacttaatattacaaattggaaacataa tctcaatatgggttagccactcaattcaaattggaaatcaaagccagattgaaacatgcaatcaaagcgtcattacttatgaaaacaacacttgg gtaaatcagacatatgttaacatcaacaacaccaactttactgetggacaatcagtggtttccgtaaaanageggacaancctctetctgccc tgttagtggatgggctatatacagtaaagacaacagtgtaagaatcggttccaagggggatgtgtttgtcataagggaaccattcatatcatgc tctccengaaatgcagaacctIcttettgactcaaagggccttgetaaataacaaacattccaatggaaccattaaagacaggagcccatatc gaaccetaatgagclgtcctattggigaagttecctctccatacaactcaagatttgagtcagtcgcttggtcagcaagtgctigtcatgatggc atcaanggctaacaattggaatactggcccagacagtggggcagtggctatgitaaagtacaatggcataataacagacactatcaagagn ggaggaacaatatatigagaacacaagagtctgaatgtgcatglgtaaatggitctigcataccataatgaccgatggaccaagtgatggaca ggcctcatacaaaatcttcagaataaaaaagggaaaaataatcaaatcagtcgaaataaaagcccctaattatcactatgaggaatgctcctg tlaccctgattctagigaaatcacatgtglgtgcagggataactggcatggctcgaatcgaccgtgggigtetttcaaccagaatctggaatatc agatgggatacatatgcagIggggttttcggagacaatccacgccctaatgataaaacaggcagttatggtccagtatcgtctaataaagca aalggagtaaaaggattacattcaaatacggcaatggigtliggatagggagaactaaaagcattagticaagaaaaggitttgagatgatag ggatccgaatggatggactgggactgacataaattctcaataaagcaagatatcgtaggaataaatgagtggtcagggtatagcgggagtt ttgacagcalccagaactaacagggctggattgtataagaccitgatctgggagaactaataagagggcgacccgaagagaacacaatct ggactagcgggagcagcatatcctittgtggtgtaaacagtgacactgtgggttggtettggccagacggtgctgagtigccatitaccattga caagtaatagttcaaaaaact (SEQ ID NO:36)

Amino acid sequence for NA of A'Sinapore/GP1908/2015 (H1N) pdm09 (stalk is underlined)

MNPNQKIITIGSISMTIGMANLILQIGNIISIWVSHSIQIGNQSQIETCNOSVITYENNTWVN QTYVNISNTN-

FAAGQSVVSVKLAGNSSLCPVSGWAIYSKDNS-
VRIGSKGDVFVIREPHSC
SPLECRTFFLTQGALLNDKHSNGTICKDR-
SPYRTLMSCPIGEVPSPYNSRFESVAWSASACH
DGINWLTIGISGPDSGAVAVIKYNGHTDITKSWRN-
NIERTQESECACVNGSGETIMIDGP SDGQASYKI-
FRIEKGKIIKSVEMKAPNYHYEECSCYPDS-
SEITCVCRDNWHGSNRPWVSF
NQNLEYQMGYICSGVFGDNPRPNDKTCB-
SCGPVSSNCIANGVKGFSFKYGNGVWIGRTKS
ISSRKGEEMTWDPNGWTGTDNKFSIKQDIVGIN-
EWSGYSGSFVQHPELTGLDCIRPCFWV ELIR-
GRPEENTIWTSGSSISFCGVNSDTVGWSWPD-
GAELPFTIDK (SEQ ID NO:37)

In some cases, in one or more modifications can also be introduced into HA, PA, PB1, PB2, NP, M1, M2, NS2, PB1-F2, PA-X, and/or NS1 proteins (and nucleic acids encoding such proteins).

Besides enhanced stability during vaccine production, enhanced growth of the virus when passaged through embryonated chicken eggs or cultured cells may be observed when the modified NA proteins are expressed and such expression may result in significantly higher viral titers. Thus, the invention provides a method for making influenza viruses with enhanced replication in cell culture or embryonated eggs. The method includes providing cels suitable for influenza vaccine production; Infecting the cells with viruses having modified neuraminidase; and isolating virus strains with enhanced growth relative to the one or more unmodified viral isolates. In some cases, a method for making influenza viruses with enhanced replication in cell culture can involve, serially culturing one or more influenza virus isolates in embryonated chicken eggs; and isolating serially cultured virus with enhanced growth relative to the one or more isolates prior to serial culture. In some cases, the viruses can be grown or passaged within cells in culture, e.g., MDCK or Vero cells.

As discussed herein, the modified neuraminidases can be expressed in a variety of influenza strains. For example, A/Puerto Rico/8/34 (H1N1), "PR8," virus often serves as the genetic backbone for generation of inactivated influenza vaccines.

In one embodiment, vectors for vRNA production can include a vector comprising a promoter operably linked to a modified NA DNA linked to a transcription termination sequence, a vector comprising a promoter operably linked to an influenza virus PB1 DNA linked to a transcription termination sequence, a vector comprising a promoter operably linked to an influenza virus PB2 DNA linked to a transcription termination sequence, a vector comprising a promoter operably linked to an influenza virus HA DNA linked to a transcription termination sequence, a vector comprising a promoter operably linked to an influenza virus NP DNA linked to a transcription termination sequence, a vector comprising a promoter operably linked to an influenza virus NA DNA linked to a transcription termination sequence, a vector comprising a promoter operably linked to an influenza virus M DNA linked to a transcription termination sequence, and a vector comprising a operably linked to an influenza virus NS DNA linked to a transcription termination sequence. In one embodiment, the DNAs for vRNA production of PB1, PB2, PA, NP, M, and NS, have sequences from an influenza virus that replicates to high titers in cultured mammalian cells such as MDCK cells, Vero cells or PER.C6@ cells or embryonated eggs, and/or from a vaccine virus, e.g., one that does not cause significant disease in humans. The DNA for vRNA production of NA may be from any NA, e.g., any of N1-N11, and the DNA for vRNA production of HA may be from any HA, e.g., H1-H18. In one embodiment, the DNAs for vRNA production may be for an influenza B or C virus. The DNAs for vRNA production of NA and HA may be from different strains or isolates (6:1:1 reassortants) or from the same strain or isolate (6:2 reassortants), or the NA may be from the same strain or isolate as that for the internal genes (7:1 reassortant). Vectors for mRNA production can include a vector encoding a modified NA, a vector encoding influenza virus PA, a vector encoding influenza virus PB1, a vector encoding influenza virus PB2, and a vector encoding influenza virus NP, and optionally one or more vectors encoding NP, NS, M, e.g., M1 and M2, HA or NA. The vectors encoding viral proteins may further include a transcription termination sequence.

Other reassortants with internal genes from other PR8 isolates or vaccine viruses may be employed in recombinant reassortant viruses of the invention. In particular, 5:1:2 reassortants having UW-PR8 PB1. PB2. PA, NP, and M ("5") and PR8(Cam) NS ("1"); 6:1:1 reassortants having UW-PR8 (modified) NA, PB1, PB2, PA, NP, and M ("6") and PR8(Cam) NS ("1"); and 7:1 reassortants having UW-PR8 PB1, PB2, PA, NP. M, (modified) NA, and NS ("7") may be employed.

The neuraminidases that can be modified can have any sequence including but not limited to the sequences described herein. However, in some cases, the modified neuraminidases can have substantially the same activity as a corresponding polypeptide described by sequence herein. As used herein, "substantially the same activity" includes an activity that is about 0.1%, 1%, 10%, 30%, 50%, 90%, e.g., up to 100% or more activity, or a detectable protein level that is about 80%, 90% or more protein level, of the corresponding protein described herein. In one embodiment, the nucleic acid encodes a polypeptide which is substantially the same as, e.g., having at least 80%, e.g., 90%, 92%, 95%, 97%, 98%, or 99%, including any integer between 80 and 99, contiguous amino acid sequence identity to a polypeptide encoded by one of sequences described herein. In one embodiment, the isolated and/or purified nucleic acid molecule comprises a nucleotide sequence which is substantially the same as, e.g., having at least 50%, e.g., 60%, 70%, 80% or 90%, including any integer between 50 and 100, or more contiguous nucleic acid sequence identity to one of the nucleic acid sequences described herein. In one embodiment, a nucleic acid also encodes a polypeptide having at least 80%, e.g., 90%, 92%, 95%, 97%, 98%, or 99%, including any integer between 80 and 99, contiguous amino acid sequence identity to a polypeptide described herein.

Exemplary viral sequences for a master vaccine strain (PR8UW) are as follows:
PA
AGCGAAAGCA GGTACTGATC CAAAATGGAA GAT-
TTTGTGC GACAATGCTT CAATCCGATG
ATTGTCGAGC TTGCGGAAAA AACAATGAAA
GAGTATGGGG AGGACCTGAA AATCGAAACA
AACAAATTTG CAGCAATATG CACTCACTTG
GAAGTATGCT TCATGTATTC AGATTTTCAC
TTCATCAATG AGCAAGGCGA GTCAATAATC
GTAGAACTTG GTGATCCAAA TGCACTTTTG
AAGCACAGAT TTGAAATAAT CGAGGGAAGA
GATCGCACAA TGGCCTGGAC AGTAGTAAAC
AGTATTTGCA ACACTACAGG GGCTGAGAAA
CCAAAGTTTC TACCAGATTT GTATGATTAC
AAGGAGAATA GATTCATCGA AATTGGAGTA
ACAAGGAGAG AAGTTCACAT ATACTATCTG GAAAAGGCCA ATAAAATTAA ATCTGAGAAA ACACACATCC ACATTTTCTC GTTCACTGGG GAAGAAATGG CCACAAAGGC AGACTACACT CTCGATGAAG AAAGCAGGGC TAGGATCAAA ACCAGACTAT TCACCATAAG ACAAGAAATG GCCAGCAGAG GCCTCTGGGA TTCCTTTCGT CAGTCCGAGA GAGGAGAAGA GACAATTGAA GAAAGGTTTG AAATCACAGG AACAATGCGC AAGCTTGCCG ACCAAAGTCT CCCGCCGAAC TTCTCCAGCC TTGAAAATTT TAGAGCCTAT GTGGATGGAT TCGAACCGAA CGGCTACATT GAGGGCAAGC TGTCTCAAAT GTCCAAAGAA GTAAATGCTA GAATTGAACC TTTTTTGAAA ACAACACCAC GACCACTTAG ACTTCCGAAT GGGCCTCCCT GTTCTCAGCG GTCCAAATTC CTGCTGATGG ATGCCTTAAA ATTAAGCATT GAGGACCCAA GTCATGAAGG AGAGGGAATA CCGCTATATG ATGCAATCAA ATGCATGAGA ACATTCTTTG GATGGAAGGA ACCCAATGTT GTTAAACCAC ACGAAAGGG AATAAATCCA AATTATCTTC TGTCATGGAA GCAAGTACTG GCAGAACTGC AGGACATTGA GAATGAGGAG AAAATTCCAA AGACTAAAAA TATGAAGAAA ACAAGTCAGC TAAAGTGGGC ACTTGGTGAG AACATGGCAC CAGAAAAGGT AGACTTTGAC GACTGTAAAG ATGTAGGTGA TTTGAAGCAA TATGATAGTG ATGAACCAGA ATTGAGGTCG CTTGCAAGTT GGATTCAGAA TGAGTTTAAC AAGGCATGCG AACTGACAGA TTCAAGCTGG ATAGAGCTCG ATGAGATTGG AGAAGATGTG GCTCCAATTG AACACATTGC AAGCATGAGA AGGAATTATT TCACATCAGA GGTGTCTCAC TGCAGAGCCA CAGAATACAT AATGAAGGGA GTGTACATCA ATACTGCCTT GCTTAATGCA TCTTGTGCAG CAATGGATGA TTTCCAATTA ATTCCAATGA TAAGCAAGTG TAGAACTAAG GAGGGAAGGC GAAAGACCAA CTTGTATGGT TTCATCATAA AAGGAAGATC CCACTTAAGG AATGACACCG ACGTGGTAAA CTTTGTGAGC ATGGAGTTTT CTCTCACTGA CCCAAGACTT GAACCACATA AATGGGAGAA GTACTGTGTT CTTGAGATAG GAGATATGCT TATAAGAAGT GCCATAGGCC AGGTTTCAAG GCCCATGTTC TTGTATGTGA GAACAAATGG AACCTCAAAA ATTAAAATGA AATGGGGAAT GGAGATGAGG CGTTGCCTCC TCCAGTCACT TCAACAAATT GAGAGTATGA TTGAAGCTGA GTCCTCTGTC AAAGAGAAAG ACATGACCAA AGAGTTCTTT GAGAACAAAT CAGAAACATG GCCCATTGGA GAGTCCCCCA AAGGAGTGGA GGAAAGTTCC ATTGGGAAGG TCTGCAGGAC TTTATTAGCA AAGTCGGTAT TCAACAGCTT GTATGCATCT CCACAACTAG AAGGATTTTC AGCTGAATCA AGAAAACTGC TTCTTATCGT TCAGGCTCTT AGGGACAACC TGGAACCTGG GACCTTTGAT CTTGGGGGGC TATATGAAGC AATTGAGGAG TGCCTGATTA ATGATCCCTG GGTTTTGCTT AATGCTTCTT GGTTCAACTC CTTCCTTACA CATGCATTGA GTTAGTTGTG GCAGTGCTAC TATTTGCTAT CCATACTGTC CAAAAAGTA CCTTGTTTCT ACT (SEQ ID NO:30)

PB1
AGCGAAAGCAGGCAAACCATTTGAATGGATGT-CAATCCGACCTTACTTTTCT-TAAAAGTGCCAGCACA AAATGC-TATAAGCACAACTTTCCCTTATACTGGAGACCC-TCCTTACAGCCATGGGACAGGAACAGGA TACAC-CATGGATACTGTCAACAGGACA-CATCAGTACTCAGAAAAGGGAA-GATGGACAACAAACACCG AAACTGGAGCACCGCAACTCAACCCGATT-GATGGGCC-ACTGCCAGAAGACAATGAACCAAGTGGTTA TGCCCAAACAGATTGTGTATTGGAGGC-GATGGCTTTCCTTGAGGAATCCCATCCTGGTAT-TTTTGAAA ACTCGTGTATTGAAACGATG-GAGGTTGTTCAGCAAACACGAGTAGACAAGC-TGACACAAGGCCGACA GACC-TATGACTGGACTCTAAATAGAAAC-CAACCTGCTGCAACAGCATTGGC-CAACACAATAGAAGTG TTCAGATCAAATGGCCTCACGGCCAAT-GAGTCTGGAAGGCTCATAGACTTCCT-TAAGGATGTAATGG AGTCAAT-GAACAAAGAAGAAATGGGGATCACAACTCATT-TTCAGAGAAAGAGACGGGTGAGAGACAA TATGACTAAGAAAATGA-TAACACAGAGAACAATGGGTAAAAGAAGCA-GAGATTGAACAAAGGAGTT ATCTAATTAGAG-CATTGACCCTGAACACAATGACCAAAGATGCT-GAG-AGAGGGAAGCTAAAACGGAG AGCAAT-TGCAACCCCAGG-GATGCAAATAAGGGGGTTTGTATACTTTGTTGA-GACACTGGCAAGGAGT ATATGTGAGAAACTT-GAACAATCAGGGTTGCCAGTTGGAGGCAAT-GAGAAGAAAGCAAAGTTGGCAA ATGTTGTAAGGAAGATGATGACCAAT-TCTCAGGACACCGAACTTTCTTTCACCATCACTG-GAGATAAC ACCAAATG-GAACGAAAATCAGAATCCTCGGATGTTTTGG-CCATGATCACATATATGACCAGAAATCA GCCCGAATGGTTCAGAAATGTTCTAAGTAT-TGCTCCAATAATGTTCTCAAACAAAATGGCGA-GACTGG GAAAAGGGTATATGTTT-GAGAGCAAGAGTATGAAACTTAGAACTCAAAT-ACCTGCAGAAATGCTAGCA AGCATCGATTT-GAAATATTTCAATGATTCAACAAGAAAGAAGATT-GAAAAAATCCGACCGCTCTTAATA GAGGGGACTGCATCATTGAGCCCTGGAATGAT-GATGGGCATGTTCAATATGTTAAGCACTGTATTAG GCGTCTCCATCCTGAATCTTGGACAAAAGAGA-TACACCAAGACTACTTACTGGTGG-GATGGTCTTCA ATCCTCTGACGATTTTGCTCT-GATTGTGAATGCACCCAATCATGAAGGGATTC-AAGCCGGAGTCGAC AGGTTT-TATCGAACCTGTAAGCTACTTGGAATCAATAT-GAGCAAGAAAAGTGTTACATAAACAGAAC AGGTACATTTGAATTCACAAGTTTTTTCTATCGT-TATGGGTTTGTGCCAATTTCAGCATG-GAGCTTCC CAGTTTTGGGGTGTCTGGAT-CAACGAGTCAGCGGACATGAGTATTGGAGTTA-CTGTCATCAAAAAC AATATGATAAACAAT-GATCTTGGTCCAGCAACAGCT-CAAATGGCCCTTCAGTTGTTCATCAAGATTA CAGGTACACGTACCGATGC-CATATAGGTGACACACAAATACAAACCCGAA-GATCATTTGAAATAAAGA AACTGTGG-GAGCAAACCCGTTCCAAAGCTGGACTGCTGG-TCTCCGACGGAGGCCCAAATTTATACAA CATT-AGAAATCTCCACATTCCT-GAAGTCTGCCTAAAATGGGAATTGATGGATGAG-GATTACCAGGGG

CGTTTATGCAACCCACTGAACCCATTTGTCAGC- CATAAAGAAATTGAATCAATGAACAATGCAGT- GAT GATGCCAGCACATGGTCCAGCCAAAAA- CATGGAGTATGATGCTGTTGCAACAACAC- ACTCCTGGATC CCCAAAAGAAATCGATC- CATCTTGAATACAAGTCAAAGAGGAGTACTT- GAGGATGAACAAATGTACCA AAGGTGCTGCAAT- TTATTTGAAAAATTCTTCCCCAGCAGTTCATACA- GAAGACCAGTCGGGATATCCA GTATGGTG- GAGGCTATGGTTTCCAGAGCCCGAATT- GATGCACGGATTGATTTCGAATCTGGAAGGAT AAAGAAAGAAGAGTTCACTGAGATCATGAA- GATCTGTTCCACCATTGAAGAGCTCA- GACGGCAAAAA TAGTGAATTTAGCTTGTCCTT- CATGAAAAAATGCCTTGTTTCTACT (SEQ ID NO:31)

PB2

AGCGAAAGCA GGTCAATTAT ATTCAATATG GAAAGAATAA AAGAACTACG AAATCTAATG TCGCAGTCTC GCACCCGCGA GATACTCACA AAAACCACCG TGGACCATAT GGCCATAATC AAGAAGTACA CATCAGGAAG ACAGGAGAAG AACCCAGCAC TTAGGATGAA ATGGATGATG GCAATGAAAT ATCCAATTAC AGCAGACAAG AGGATAACGG AAATGATTCC TGAGAGAAAT GAGCAAGGAC AAACTTTATG GAGTAAAATG AATGATGCCG GATCAGACCG AGTGATGGTA TCACCTCTGG CTGTGACATG GTGGAATAGG AATGGACCAA TAACAAATAC AGTTCATTAT CCAAAAATCT ACAAAACTTA TTTTGAAAGA GTCGAAAGGC TAAAGCATGG AACCTTTGGC CCTGTCCATT TTAGAAACCA AGTCAAAATA CGTCGGAGAG TTGACATAAA TCCTGGTCAT GCAGATCTCA GTGCCAAGGA GGCACAGGAT GTAATCATGG AAGTTGTTTT CCCTAACGAA GTGGGAGCCA GGATACTAAC ATCGGAATCG CAACTAACGA TAACCAAAGA GAAGAAAGAA GAACTCCAGG ATTGCAAAAT TTCTCCTTTG ATGGTTGCAT ACATGTTGGA GAGAGAACTG GTCCGCAAAA CGAGATTCCT CCCAGTGGCT GGTGGAACAA GCAGTGTGTA CATTGAAGTG TTGCATTTGA CTCAAGGAAC ATGCTGGGAA CAGATGTATA CTCCAGGAGG GGAAGTGAGG AATGATGATG TTGATCAAAG CTTGATTATT GCTGCTAGGA ACATAGTGAG AAGAGCTGCA GTATCAGCAG ATCCACTAGC ATCTTTATTG GAGATGTGCC ACAGCACACA GATTGGTGGA ATT- AGGATGG TAGACATCCT TAGGCAGAAC CCAACAGAAG AGCAAGCCGT GGATATATGC AAGGCTGCAA TGGGACTGAG AATTAGCTCA TCCTTCAGTT TTGGTGGATT CACATTTAAG AGAACAAGCG GATCATCAGT CAAGAGAGAG GAAGAGGTGC TTACGGGCAA TCTTCAAACA TTGAAGATAA GAGTGCATGA GGGATATGAA GAGTTCACAA TGGTTGGGAG AAGAGCAACA GCCATACTCA GAAAAGCAAC CAGGAGATTG ATTCAGCTGA TAGTGAGTGG GAGAGACGAA CAGTCGATTG CCGAAGCAAT AATTGTGGCC ATGGTATTTT CACAAGAGGA TTGTATGATA AAAGCAGTCA GAGGTGATCT GAATTTCGTC AATAGGGCGA ATCAACGATT GAATCCTATG CAT- CAACTTT TAAGACATTT TCAGAAGGAT GCGAAAGTGC TTTTTCAAAA TTGGGGAGTT GAACCTATCG ACAATGTGAT GGGAATGATT GGGATATTGC CCGACATGAC TCCAAGCATC GAGATGTCAA TGAGAGGAGT GAGAATCAGC AAAATGGGTG TAGATGAGTA CTCCAGCACG

GAGAGGGTAG TGGTGAGCAT TGACCGTTTT TTGAGAATCC GGGACCAACG AGGAAATGTA CTACTGTCTC CCGAGGAGGT CAGTGAAACA CAGGGAACAG AGAAACTGAC AATAACTTAC TCATCGTCAA TGATGTGGGA GATTAATGGT CCT- GAATCAG TGTTGGTCAA TACCTATCAA TGGAT- CATCA GAAACTGGGA AACTGTTAAA ATTCAGTGGT CCCAGAACCC TACAATGCTA TACAATAAAA TGGAATTTGA ACCATTTCAG TCTTTAGTAC CTAAGGCCAT TAGAGGCCAA TACAGTGGGT TTGTAAGAAC TCTGTTCCAA CAAATGAGGG ATGTGCTTGG GACATTTGAT ACCGCACAGA TAATAAAACT TCTTCCCTTC GCAGCCGCTC CACCAAAGCA AAGTAGAATG CAGTTCTCCT CATTTACTGT GAATGTGAGG GGATCAGGAA TGAGAATACT TGTAAGGGGC AATTCTCCTG TATTCAACTA TAACAAGGCC ACGAAGAGAC TCACAGTTCT CGGAAAGGAT GCTGGCACTT TAACTGAAGA CCCAGATGAA GGCACAGCTG GAGTGGAGTC CGCTGTTCTG AGGGGATTCC TCATTCTGGG CAAAGAAGAC AAGAGATATG GGCCAGCACT AAGCATCAAT GAACTGAGCA ACCTTGCGAA AGGAGAGAAG GCTAATGTGC TAATTGGCCA AGGAGACGTG GTGTTGGTAA TGAAACGGAA ACGGGACTCT AGCATACTTA CTGACAGCCA GACAGCGACC AAAAGAATTC GGATGGCCAT CAATTAGTGT CGAATAGTTT AAAAACGACC TTGTTTCTAC T (SEQ ID NO:32)

NP

AGCAAAAGCA GGGTAGATAA TCACTCACTG AGTGACATCA AAATCATGGC GTCTCAAGGC ACCAAACGAT CTTACGAACA GATGGAGACT GATGGAGAAC GCCAGAATGC CACTGAAATC AGAGCATCCG TCGGAAAAAT GATTGGTGGA ATGGCAGCAT TCTACATCCA AATGTGCACC GAACTCAAAC TCAGTGATTA TGAGGGACGG TTGATCCAAA ACAGCTTAAC AATAGAGAGA ATGGTGCTCT CTGCTTTTGA CGAAAGGAGA AATAAATACC TTGAAGAACA TCCCAGTGCG GGGAAAGATC CTAAGAAAAC TGGAGGACCT ATATACAGGA GAGTAAACGG AAAGTGGATG AGAGAACTCA TCCTTTATGA CAAAGAAGAA ATAAGGCGAA TCTGGCGCCA AGCTAATAAT GGTGACGATG CAACGGCTGG TCTGACTCAC ATGATGATCT GGCATTCCAA TTTGAATGAT GCAACTTATC AGAGGACAAG AGCTCTTGTT CGCACCGGAA TGGATCCCAG GATGTGCTCT CTGATGCAAG GTTCAACTCT CCCTAGGAGG TCTGGAGCCG CAGGTGCTGC AGTCAAAGGA GTTGGAACAA TGGTGATGGA ATTGGTCAGA ATGATCAAAC GTTGGAACAA TGATCGGAAC TTCTGGAGGG GTGAGAATGG ACGAAAAACA AGAATTGCTT ATGAAAGAAT GTGCAACATT CTCAAAGGGA AATTTCAAAC TGCTGCACAA AAAGCAATGA TGGATCAAGT GAGAGAGAGC CGGAACCCAG GAATGCTGA GTTCGAAGAT CTCACTTTTC TAGCACGGTC TGCACTCATA TTGAGAGGGT CGGTTGCTCA CAAGTCCTGC CTGCCTGCCT GTGTGTATGG ACCTGCCGTA GCCAGTGGGT ACGACTTTGA AAGGGAGGGA TACTCTCTAG TCGGAATAGA CCCTTTCAGA CTGCTTCAAA ACAGCCAAGT GTACAGCCTA ATCAGACCAA ATGAGAATCC AGCACACAAG AGTCAACTGG TGTGGATGGC ATGCCATTCT GC CGCATTTG AAGATCTAAG AGTATTAAGC TTCAT- CAAAG GGACGAAGGT GCTCCCAAGA

GGGAAGCTTT CCACTAGAGG AGTTCAAATT GCTTCCAATG AAAATATGGA GACTATGGAA TCAAGTACAC TTGAACTGGA AAGCAGGTAC TGGGCCATAA GGACCAGAAG TGGAGGAAAC ACCAATCAAC AGAGGGCATC TGCGGGCCAA ATCAGCATAC AACCTACGTT CTCAGTACAG AGAAATCTCC CTTTTGACAG AACAACCATT ATGGCAGCAT TCAATGGGAA TACAGAGGGG AGAACATCTG ACATGAGGAC CGAAATCATA AGGATGATGG AAAGTGCAAG ACCAGAAGAT GTGTCTTTCC AGGGGCGGGG AGTCTTCGAG CTCTCGGACG AAAAGGCAGC GAGCCCGATC GTGCCTTCCT TTGACATGAG TAATGAAGGA TCTTATTTCT TCGGAGACAA TGCAGAGGAG TACGACAATT AAAGAAAAAT ACCCTTGTTT CTACT (SEQ ID NO:33)

M
AGCAAAAGCA GGTAGATATT GAAAGATGAG TCTTCTAACC GAGGTCGAAA CGTACGTACT CTCTATCATC CCGTCAGGCC CCCTCAAAGC CGAGATCGCA CAGAGACTTG AAGATGTCTT TGCAGGGAAG AACACCGATC TTGAGGTTCT CATGGAATGG CTAAAGACAA GACCAATCCT GTCACCTCTG ACTAAGGGGA TTTTAGGATT TGTGTTCACG CTCACCGTGC CCAGTGAGCG AGGACTGCAG CGTAGACGCT TTGTCCAAAA TGCCCTTAAT GGGAACGGGG ATCCAAATAA CATGGACAAA GCAGTTAAAC TGTATAGGAA GCTCAAGAGG GAGATAACAT TCCATGGGGC CAAAGAAATC TCACTCAGTT ATTCTGCTGG TGCACTTGCC AGTTGTATGG GCCTCATATA CAACAGGATG GGGGCTGTGA CCACTGAAGT GGCATTTGGC CTGGTATGTG CAACCTGTGA ACAGATTGCT GACTCCAGC ATCGGTCTOA TAGGCAAATG GTGACAACAA CCAATCCACT AATCAGACAT GAGAACAGAA TGGTTTTAGC CAGCACTACA GCTAAGGCTA TGGAGCAAAT GGCTGGATCG AGTGAGCAAG CAGCAGAGGC CATGGAGGTT GCTAGTCAGG CTAGACAAAT GGTGCAAGCG ATGAGAACCA TTGGGACTCA TCCTAGCTCC AGTGCTGGTC TGAAAAATGA TCTTCTTGAA AATTTGCAGG CCTATCAGAA ACGAATGGGG GTGCAGATGC AACGGTTCAA GTGATCCTCT CACTATTGCC GCAAATATCA TTGGGATCTT GCACTTGACA TTGTGGATTC TTGATCGTCT TTTTTTCAAA TGCATTTACC GTCGCTTTAA ATACGGACTG AAAGGAGGGC CTTCTACGGA AGGAGTGCCA AAGTCTATGA GGGAAGAATA TCGAAAGGAA CAGCAGAGTG CTGTGGATGC TGACGATGGT CATTTTGTCA GCATAGAGCT GGAGTAAAAA ACTACCTTGT TTCTACT (SEQ ID NO:34)

NS
AGCAAAAGCA GGGTGACAAA AACATAATGG ATCCAAACAC TGTGTCAAGC TTTCAGGTAG ATTGCTTTCT TTGGCATGTC CGCAAACGAG TTGCAGACCA AGAACTAGGC GATGCCCCAT TCCTTGATCG GCTTCGCCGA GATCAGAAAT CCCTAAGAGG AAGGGGCAGT ACTCTCGGTC TGGACATCAA GACAGCCACA CGTGCTGGAA AGCAGATAGT GGAGCGGATT CTGAAAGAAG AATCCGATGA GGCACTTAAA ATGACCATGG CCTCTGTACC TGCGTCGCGT TACCTAACTG ACATGACTCT TGAGGAAATG TCAAGGGACT GGTCCATGCT CATACCCAAG CAGAAAGTGG CAGGCCCTCT TTGTATCAGA ATGGACCAGG CGATCATGGA TAAGAACATC ATACTGAAAG CGAACTTCAG TGTGATTTTT GACCGGCTGG AGACTCTAAT ATTGCTAAGG GCTTTCACCG AAGAGGGAGC AATTGTTGGC GAAATTTCAC CATTGCCTTC TCTTCCAGGA CATACTGCTG AGGATGTCAA AAATGCAGTT GGAGTCCTCA TCGGAGGACT TGAATGGAAT GATAACACAG TTCGAGTCTC TGAAACTCTA CAGAGATTCG CTTGGAGAAG CAGTAATGAG AATGGGAGAC CTCCACTCAC TCCAAAACAG AAACGAGAAA TGGCGGGAAC AATTAGGTCA GAAGTTTGAA GAAATAAGAT GGTTGATTGA AGAAGTGAGA CACAAACTGA AGATAACAGA GAATAGTTTT GAGCAAATAA CATTTATGCA AGCCTTACAT CTATGCTTG AAGTGGAGCA AGAGATAAGA ACTTTCTCGT TTCAGCTTAT TTAGTACTAA AAAACACCCT TGTTTCTACT (SEQ 10 NO:35).

Sequences for the internal segments of another master train (Cambridge) are shown below:

agcgaaagca ggtcaattat attcaatatg gaaagaataa agaactaag aaatctaatg tcgcagtctc gcacccgcga gatactcaca aaaaccaccg tggaccatat ggccataatc aagaagtaca catcaggaag acaggagaag aacccagcac ttaggatgaa atggatgatg gcaatgaaat atccaattac agcagacaag aggataacgg aaatgattcc tgagagaaat gagcaaggac aaactttatg gagtaaaatg aatgatgccg gatcagaccg agtgatggta tcacctctgg ctgtgacatg gtggaatagg aatggaccaa tgacaaatac agttcattat ccaaaaatct acaaaactta Itttgaaaga gtcgaaaggc taaagcatgg aacctttggc cctgtccatt ttagaaacca agtcaaaata cgtcggagag ttgacataaa tcctggtcat gcagatctca gtgccaagga ggcacaggat gtaatcatgg aagttgtttt ccctaacgaa gtgggagcca ggatactaac atcggaatcg caactaacga taaccaaaga gaagaaagaa gaactccagg attgcaaaat ttctcctttg atggttgcat acatgttgga gagagaactg gtccgcaaaa cgagattcct cccagtggct ggtggaacaa gcagtgtgta cattgaagtg ttgcatttga ctcaaggaac atgctgggaa cagatgtata ctccaggagg ggaagtgaag aatgatgatg ttgatcaaag cttgattatt gctgctagga acatagtgag aagagctgca gtatcagcag acccactagc atctttattg gagatgtgcc acagcacaca gattggtgga attaggatgg tagacatcct taagcagaac ccaacagaag agcaagccgt ggatatatgc aaggctgcaa tgggactgag aattagctca tccttc gtt ttggtggatt cacatttaag agaacaagcg gatcatcagt caagagagag gaagaggtgc ttacgggcaa tcttcaaaca ttgaagataa gagtgcatga gggatctgaa gagttcacaa tgg1tgggact aagagcaaca gccatactca gaaaagcaac caggagattg attcagctga tagtgagtgg gagagacgaa cagtcgattg ccgaagcaat aattgtggcc atggtatttt cacaagagga ttgtatgata aaagcagtta gaagtgatct gaatttcgtc aatagggcga atcagcgact gaatcctatg catcaacttt taagacattt tcagaaggat gcgaaagtgc tttttcaaaa ttggggagtt gaacctatcg acaatgtgat gggaatgatt gggatattgc ccgacatgac tccaagcatc gagatgtcaa tgagaggagt gagaatcagc aaaatgggtg tagatgagta ctccagcacg gagagggtag tggtgagcat tgaccggttc ttgagagtca gggaccaacg aggaaatgta ctactgtctc ccgaggaggt cagtgaaaca cagggaacag agaaactgac aataacttac tcatcgtcaa tgataggga gattaatggt cct-gaatcag tgttggtcaa tacctatcaa tggatcatca gaaactggga aactgttaaa attcagtggt cccagaaccc tacaatgcta tacaataaaa tggaatttga accatttcag IcIttaatac ctaaggccat tagaggccaa tacagtgggt ttgtaaaaac tctgttccaa caaatgaggg atgtgcttgg gacatttqat accgcacaga taataaaact tcttcccttc gcagccgctc caccaaagca aagtagaatg cagttctcct catttactgt gaatgtgagg ggatcaggaa tgagaatact tgtaaggggc aattctcctg tattcaacta caacaaggcc acgaagagac tcacagttct cggaaaggat actggcactt taaccgaaga cccagatgaa ggcacagctg gagtggagtc cgctgttctg aggggattcc tcattctggg caaagaagac aggagatatg ggccagcatt aagcatcaat gaactgagca accttgcgaa aggagagaag gctaatgtgc taattgggca aggagacgtg gtgttggtaa tgaaacgaaa acgggactct agcatactta ctgacagcca gacagcgacc aaaagaattc ggatggccat caattagtgt cgaatagttt aaaaacgacc ttgtttctac t (SEQ ID NO:38)

agcgaaagca ggcaaaccat ttgaatggat gtcaatccga ccttactttt cttaaaagtg ccagcacaaa atgctataag cacaactttc ccttataccg gactaccctcc ttacagccat gggacaggaa caggatacac catggatact gtcaacagga cacatcagta ctcagaaaag ggaagatgga caacaaacac cgaaactgga gcaccgcaaclcaacccgat tgatgggcca ctgccagaag acaatgaacc aagtggttat gcccaaacag attgtgtatt ggaagcaatg gotttccttg aggaatccca tcctggtatt tttgaaaact cgtgtattga aacgatggag gttgttcagc aaacacgagt actacaagclq acacaaggcc gacagaccla tgactggact ttaaatagaa accagcctgc tgcaacagca ttggccaaca caatagaagt gttcagatca aatggcctca cggccaatga gtcaggaagg ctcatagact tccttaagga tgtaatggag tcaatgaaaa aaaagaaat ggggatcaca actcattttc agagaaagag acgggtgaga gacaatatga ctaagaaaat gataacacag agaacaatag gtaaaggaa acagagattg aacaaaaggg gttatctaat tagagcatta accctgaaca caatgaccaa agatgctgag agagggaagc taaaacggag agcaattgca accccaggga tgcaaataag ggggtttgta tactttgttg agacactggc aaggagtata tgtgagaaac ttgaacaatc agggttgcca gttggaggca atgagaagaa agcaaagttg gcaaalgttg taaggaagat gatgaccaat tclcaggaca ccgaactttc tttcaccatc actggagata acaccaaatg gaacgaaaat cagaatcctc ggatgttttt ggccatgatc acatatatga ccagaaatca gcccgaatgg ttcagaaatg ttctaagtat tgctccaata algtt tcaa acaaaatggc gagactggga aaagggtata tgtttgagag caagagtatg aaacttagaa ctcaaatacc tgcagaaatg ctagcaagca ltgattlgaa atatttcaat gattcaacaa gaaagaagat tgaaaaaatc caaccgctct taataqaggg gactgcatca ttgagccctg gaatgatgat gggcatgttc aaatatgtta gcactgtatt aggcgtctcc atcctgaatc ttggacaaaa gagatacacc aagactactt actggtggga tgglcttcaa tcctctgacg atttgtctct gattgtgaat gcacccaatc atgaaggat tcaagccgga gtcgacaggt ttatcgaac ctgtaagcta cttggaatca atatgagcaa gaaaaagtct tacataaaca gaacaggtac atttgaattc acaagtttt tctatcgtta tgggtttgtt gccaatttca gcatggagct tcccagtttt ggggtgtctg ggatcaacga gtcagcggac atgagtattg gagttactgt catcaaaaac aatatgataa acaatgatct tggtccagca acagctcaaa tggccttca gttgttcatc aaagattaca ggtacacgta ccgatgccat agaggtgaca cacaaataca aacccgaaga tcatttgaaa taaagaaact gtgggagcaa acccgttcca aagctggact gctggtctcc gacggaggcc caaatttata caacattaga aatctccaca ttcctgaagt ctgcctaaaa tgggaattga tggatgagga ttaccagggg cgtttatgca acccactgaa cccatttgtc agccataaag aaattgaatc aatgaacaat gcagtgatga tgccagcaca tggtccagcc aaaaacatgg agtatgatgc tgttgcaaca acacactcct ggatcsccaa aagaaatcga tccatcttga atacaagtca agaggagta cttgaagalg aacaaatgta ccaaaggtgc tgcaattta ttgaaaaatt cttccccagc agttcataca gaagaccagt cggatatcc agtatggtga aggctatggt ttccagagcc cgaattgatg cacgattga tttcgaatct ggaaggataa agaagaaga gttcactgag atcatgaaga lctgltccac cattgaagag ctcagacggc aaaaatagtg aatttagctt gtccttcatg aaaaaatgcc ttgtttctac t (SEQ ID NO:39)

agcgaaagca ggtactgatt caaaatggaa gallttglqc gacaatgctt caatccgatg allgtcgagc ltgcggaaaa aacaatgaaa gagtatgggg aggacctgaa aatcgaaaca aacaaatttg cagcaatatg cactcacttg claagtatgct lcatgtattc agatttccac ttcatcaatg agcaaggcga gtcaataatc gtagaacttg gtgatccctaa tgcartttg aagcacagat ttgaaataat cgaggaagaa gatcgcacaa tggcctggac agtagtaaac agtatttgca acactacagg ggctgagaaa ccaaagtttc taccagattt gtatgattac aaggaaaata gattcatcga aattggaata acaaggagag aaattcacat atactatcta gaaaaggcca ataaaattaa atctgagaaa acacacatcc acattttctc gttcactggg gaagaaatgg ccacaaggc cgactacact ctcgatgaag aaagcagggc taggatcaaa accaggctat tcaccataag acaagaaatg gccagcagag gcctctggga ttccttcgt cagtccgaga gaggagaaga claccattaaa gaaaggtttg aaalcacaag aacaatgcgc aagcttgccg accaaagtct cccgccgaac ttctccagcc ttgaaaattt tagagcctat gtggatggat tcgaaccgaa cggctacatt gagggcaagc lgtctcaaat gtccaaagaa gtaaatgcta gaattgaacc ttttttgaaa acaacaccac gaccacttag acttccgaat gggccttcct gttctcagcg gtccaaattc ctgctgatgg atgccttaaa attaagcatt ctaggaccaa gtcatgaagg agaggclaata ccgctatatg atgcaatcaa algcatclaga acattctttg gatggaagga acccaatgtt gttaaaccac acgaaaaggg aataaatcca aattatcttc tgtcatggaa gcaagtactg gcagaactgc aggacattga gaatgaggag aaaattccaa agactaaaaa tatgaaaaaa acaagtcagc taaagtgggc acttggtgag aacatggcac cagaaaaggt agactttgac gactgtaaag atgtaggtga tttgaagcaa tatgatagtg atgaaccaga attgaggtcg cttgcaagtt ggattcagaa tgagttcaac aaggcatgcg aactgacaga ttcaagctgc atagagcttg atgagattgg agaagtgtgt gctccaattg aacacattgc aagcatgaga aggaattatt tcacatcaga ggtgtctcac tgcagagcca cagaatacat aatgaagggg gtgtacatca atactgcctt acttaatgca tcttgtgcag caatggatga tttccaatta attccaatga taagcaagtg tagaactaag gaggggaagg c gaaagaccaa cttgtatggt ttcatcataa aaggaagatc ccacttaagg aatgacaccg acgtggtaaa ctttgtgagc atggagtttt ctctcactga cccaagactt gaaccacaca atgggagaa gtactgtgtt cttgagatag gagatatgct lctaagaactt gccataggcc aggtttcaag gcccatgttc ttgtatgtga ggacaaatgg aacctcaaaa attaaaatga aatgggggaat ggagatgagg cgttgtctcc tccagtcact tcaacaaatt gagaglatga ttgaagctga gtcctctgtc aaagagaaag acatgaccaa agagttctft clagaacaaat cagaaacatg gcccattgga gagtctccca aaggagtgga ggaaagttcc attgggaagg tctgcaggac lttattagca aagtcggtat taacagctt gtatgcatct ccacaactag aaggattttc agctgaatca agaaactgc ttcctatcgt tcaggctctt agggacaatc tggaacctgg gaccttgat cttgggggc tatatgaagc aattgaggag tgcctaatta atgatccctg ggttttgctt aatgcttctt ggttcaactc cttccttaca catgcattga gttagttgtg gcagtgctac tatttgctat ccatactgtc caaaaaagta ccttgttct act (SEQ ID NO:40)

agcaaaagca gggtagataa tcactcactg agtgacatca aaatcatggc gtcccaaggc accaaacggt cttacgaaca gatggagact gatggagaac gccagaatgc cactgaaatc agagcatccg tcggaaaaat gattggtgaa attggacgat tctacatcca aatgtgcaca ctaacttaaac lcagtqatta tgagggacgg ttgatccaaa acactcttaac aatagagaga atggtgctct ctgctttga cgaaaggaga aataaatacc tggaagaaca tcccagtgcg gggaaagatc ctaagaaaac tggaggacct atatacgaaa gagtaaacgg aaagtggatg agagaactca tcctttatga caaagaagaa ataaggcgaa tctgcgccca agctaataat ggtgacgatg caacggctgg tctgactcac atgatgtct ggcattccaa tttgaatgat gcaacttatc agaggacaag ggctcttgtt cgcaccggaa tggatcccag gatgtgtctc tgatgcaag gttcaactct cccctaggagg tctggagccg caggtgctgc agtcaaagga gttggaacaa tggtgatgga attggtcagg atgatcaaac gtgggalcaa tgatcggaac ttctggaggg gtgagaatgg acgaaaaaca agaattgctt atgaaagaat gtgcaacatt ctcaagggaa atttcaaac tgctgcacaa aaagcaatga tggatcaagt gagagagagc cggaacccag ggaatgctga gttcgaagat ctcacttttc tagcacggtc tgcactcata ttgagagggt cggttgctca caagtcctgc ctgcctgcct gtgtgtatgg acctgccgta gccagtgggt acgactttga aagagaggga tactctctag tcggaataga ccctttcaga ctgcttcaaa acagccaagt gtacagccta atcagaccaa atgaaaatcc agcacacaag agtcaactgc tgtgatgcc atgccattct gccgcatttt aagatctaag agtattgagc ttcatcaaag ggacgaaggt ggtcccaaga gggaagcttt ccactagagg agttcaaatt gcttccaatg aaaatatgga gactatggaa tcaagtacac ttgaactgag aagcaggtac tgggccataa ggaccagaag tggaggaaac accaatcaac agagggcatc tacgagccaa atcagcatac aacctacgtt ctcagtacag agaaatctcc cttttgacag aacaaccgtt atggcagcat tcactgggaa tacagagggg agaacatctg acatgaggac cgaaatcata aggatgatgg aaagtgcaag accagaagat gtgtcttcc aggggcgggg agtcttcgag ctctcggacg aaaaggcagc gagcccgatc gtgcctcct tgacalgag taatgaagga tcttatttct tcggagacaa tgcagaggag tacgacaatt aaagaaaaat accttgttt ctact (SEQ ID NO:41)

agcaaaagca ggtagatatt gaaagatgag tcttctaacc gaggtcgaaa cgtacgttct ctctatcatc ccgtcaggcc ccctcaaagc cgagatcgca cagagacttg aagatgtctt tgcagggaag aacaccgatc ttgaggttct catggaatgg ctaaagacaa gaccaatcct glcacctctg actaagggga ttttaggatt tglgttcacq ctcaccgtgc ccagtgagcg aggactgcag cgtagacgct ttgtccaaaa tgcccttaat gggaacgggg atccaaataa catggacaaa gcagttaaac tgtataggaa gctcaagagg gagataacat tccatggggc caaagaaatc tcactcagtt attctgctgg tgcacttgcc agttgtatgg gcctcatata caacaggatg gggcctgtga ccactgaagt ggcatttggc ctgqtatatg caacctgtga acagattgct gactcccagc
atcqglctca taggcaaatg gtgacaacaa ccaacccact aatcagacat
gagaacagaa tggttttagc cagcactaca gctaaggcta tggagcaaat
ggctggatcg agtgagcaag cagcagaggc catggaggtt gctagtcgg
ctaggcaaat ggtgcaagcg atgagaacca ttgggactca tcctagctcc
agtgctggtc tgaaaaatga tcttcttgaa aatttgcagg cclatcactaa
acgaatgggg gtgcagatgc aacggttcaa gtgatcctct cgctattgcc
gcaaatatca ttgggatctt gcacttgata ttgtggattc ttgatcgtct tttttt-
caaa tgcatttacc gtcgctttaa atacggactg aaaggagggc cttc-
tacgga aggagtgcca aagtctatga gggaagaata tcgaaaggaa
cagcagagtg ctgtggatqc tgacgatggt cattttgtca ctcatagagct
ggagtaaaaa actaccttgt ttctact (SEQ 10 NO:42)
agcaaaagca gggtgacaaa gacatatgg atccaaacac tgtgtcaagc
tttcggtag attgctttct ttggcatgtc cgcaaacgag ttgcagacca
agaactaggt gatgccccat tccttctatcg gcttcgccga gatcagaaat
ccctaagaga aaggggcagc actcttggtc tggacatcga gacagccaca
cgtgctggaa agcagatagt ggagcggatt ctgaaagaag aatccgatga
ggcacttaaa atgaccatgg cctctgtacc tgcgtcgcgt tacctaaccg
acatgactct tgaggaaatg tcaagggaat ggtccatgct catacccaag
cagaaagtgg caggccctct ttgtatcaga atggaccagg caalcatgga
taaaaacatc atactgaaag cgaacttcag tgtgatttt gaccggctgg
agactctaat attgctaagg gctttcaccg aagagggagc aattgltggc
gaaatttcac cattgccttc tcttccagga catactgctg aggatgtcaa
aaatgcagtt ggagtcctca tcggaggact tgaatggaat gataacacag
ttcgaglctc tgaaactcta cagagattcg cttggagaag cagtaatgag
aatgggagac ctccactcac tccaaaacag aaacgagaaa tggcgggaac
aattaggtca gaaglttgaa gaaataagat ggttgattga agaagtgaga
cacaaactga aggtaacaga gaatagtttt gagcaaataa catttatgca
agccttacat ctattgcttg aagtggagca agagataaga actttctcat
ttcagcttat ttaataataa aaaacaccct tgtttctact (SEQ ID NO:43)

Exemplary Embodiments

In one embodiment, an isolated recombinant influenza virus comprising a neuraminidase (NA) viral segment encoding a NA monomer that forms virions having stabilized NA tetramers is provided. In one embodiment, the recombinant influenza virus has a modified NA stalk that results in stabilized tetramers relative to an influenza virus having a NA with an unmodified NA stalk. In one embodiment, the modified NA stalk has a deletion. In one embodiment, the modified NA stalk has an insertion. In one embodiment, the modified NA stalk has at least one amino acid substitution relative to the unmodified stalk. In one embodiment, the modified stalk has two or more of: a deletion, an insertion, or at least one amino acid substitution. In one embodiment, the at least one substitution in the modified NA stalk is a cysteine substitution. In one embodiment, the modified NA stalk has at least two substitutions. In one embodiment, the NA has a cysteine at position 48 relative to the numbering of N1. In one embodiment, the NA has a cysteine at position 50 relative to the numbering of N1. In one embodiment, the NA has a cysteine at position 48 and position 50 relative to the numbering of N1. In one embodiment, the NA stalk is modified within residues 1 to 10 from the C-terminus of the transmembrane domain. In one embodiment, the NA stalk is modified within residues 10 to 20 from the C-terminus of the transmembrane domain. In one embodiment, the NA stalk is modified within residues 20 to 30 from the C-terminus of the transmembrane domain. In one embodiment, the NA stalk is modified within residues 30 to 50 from the C-terminus of the transmembrane domain.

For example, the recombinant influenza virus may have a N1 NA, and that N2 may have one or two cysteines in the stalk region, e.g., spaced apart with at least one residue in between, e.g., the stalk may have the following sequence:

SIQIGNQSQIETCNQSVIrrENNTWVNQT TVNISNTN-
  FAAGQSVVSVKLAGNSS (SEQ ID NO:51),
which could be modified to, for example,
IQIGNQSQIECCNQSVITYENNTWVNQTYVNISNTN-
  FAAGQSVVSVKLAGNSS (SEQ ID NO:52),
IQIGNQSQIECCNQSVITYENNTWVNQTYVNISNTN-
  FAAGQSVVSVKLAGNSS (SEQ ID NO:53),
IQIGNQSQIECCCQSVITYENNTWVNQTYVNISNTN-
  FAAGQSVVSVKLAGNSS(SEQ ID NO. 54),
IIQIGNQSQICTCNQSVITYENNTWVNQTYVNISNTN-
  FAAGQSVVSVKLAGNSS (SEQ ID NO:55), or
IQICiNQSQIETCNCSVITYENNTWVNQTYVNISNTN-
  FAAGQSVVSVKLAGNSS (SEQ ID NO:56), In one embodiment, a vaccine comprising an effective amount of the recombinant influenza virus or a portion thereof is provided. In one embodiment, the vaccine is a whole virus vaccine. In one embodiment, the vaccine is a split virus vaccine. In one embodiment, the vaccine is a subunit vaccine. In one embodiment, the vaccine further comprises an adjuvant. In one embodiment, the vaccine further comprises a pharmaceutically acceptable carrier. In one embodiment, the carrier is suitable for intranasal or intramuscular administration. In one embodiment, the vaccine further comprises at least one other influenza virus isolate. In one embodiment, the vaccine further comprises at least one other microbe or microbial antigen, e.g., a non-influenza virus, a bacterial or fungal antigen.

In one embodiment, a method of preparing influenza virus having stabilized NA tetramers is provided. The method includes contacting a cell with one or more vectors comprising nucleic acid for an influenza virus NA segment encoding a NA monomer that forms virions having stabilized NA tetramers, nucleic acid for an influenza virus PA segment, nucleic acid for an influenza virus a PB1 segment, nucleic acid for an influenza virus PB2 segment, nucleic acid for an influenza virus NP segment, nucleic acid for an influenza virus NS segment, nucleic acid for an influenza virus M segment, and nucleic acid for an influenza virus HA segment, in an amount effective to produce influenza virus having stabilized NA tetramers. In one embodiment, the NA is N1, N2, N3 or N5. In one embodiment, the cell is a mammalian cell. In one embodiment, the cell is a 293T, PER.C6), MDCK, MvLu1, CHO or Vero cell, or a cell in an avian egg.

In one embodiment, a method of making an influenza vaccine is provided comprising: providing the recombinant virus; and combining the virus with an adjuvant or treating the virus with an agent that inactivates the virus. In one embodiment, the method includes aliquoting a dose of the virus into a receptacle. In one embodiment, the adjuvant comprises immunostimulatory DNA sequences, bacterium-derived components, aluminum salt (alum) or squalene oil-in-water emulsion systems such as MF59 and AS03. In one embodiment, wherein the agent chemically inactivates the virus. In one embodiment, the agent comprises formalin or beta-propiolactone. In one embodiment, the agent comprises a detergent. In one embodiment, the detergent is a non-ionic detergent. In one embodiment, the detergent is a cationic detergent. In one embodiment, the detergent is an anionic detergent. In one embodiment, the detergent comprises CTAB, ammonium deoxycholate, Triton, SDS, Neodol 23-6, or sodium desoxycholate. In one embodiment, the agent comprises ether. In one embodiment, the method further comprises separating HA and NA from other viral components.

In one embodiment, a method of preparing influenza virus is provided comprising: contacting cells with the recombinant virus in an amount effective to yield progeny virus. In one embodiment, the virus is contacted with an avian egg. In one embodiment, the cells are mammalian cells. In one embodiment, the HA of the virus is H1, H3, H5 or H7.

Further provided is a method of preparing stabilized NA tetramers. The method includes contacting a cell with one or more vectors comprising nucleic acid for an influenza virus NA segment encoding a NA monomer that forms virions having stabilized NA tetramers and nucleic acid for an influenza virus HA. In one embodiment, the method further comprises isolating NA and HA from the cell. In one embodiment, the cell is an insect cell. In one embodiment, the cell is a CHO, MDCK, Vero, or EB68 cell.

Also provided is isolated virus prepared by the above-described methods.

In one embodiment, a method of immunizing an avian or a mammal is provided comprising: administering to the avian or the mammal a composition having an effective amount of the above-described virus. In one embodiment, the composition comprises at least one other different influenza virus. In one embodiment, the mammal is a human. In one embodiment, the composition is administered intranasally or via injection.

Further provided is a method comprising passaging the virus in eggs.

The invention will be described by the following non-limiting examples.

Example 1

Neuraminidase (NA) is one of the major transmembrane glycoproteins of influenza viruses. It has been suggested that antibodies against NA play important roles in preventing influenza virus infection. However, the current influenza vaccines, which are made by inactivating egg-grown influenza viruses and purifying virus antigen, do not efficiently elicit the production of anti-NA antibodies. One possible reason for the low production of anti-NA antibodies is the structural instability of the NA protein, which functions as a homo-tetramer; the NA tetramer is apparently disrupted during the antigen purification process. Therefore, the amount of NA contained in vaccines is insufficient to elicit the production of anti-NA antibodies.

The establishment of a method that stabilizes the NA tetrameric structure may solve this problem. The amino acids 48C and 50C in NA have previously been introduced to NA in vitro (Silva et al., 2013); however, the effect of these amino acids on influenza virus replication or replication efficiency was unknown. As described herein, recombinant influenza viruses containing either the NA-48C or NA-50C mutation or both mutations expressed a stabilized NA tetramer and replicated efficiently.

Methods

A 6+2 reassortant influenza viruses containing the HA and NA gene segments from A/Singapore/GP1908/2015 (H1N1) pdm09 in the backbone of high-yield A/Puerto Rico/811934 (H1N1) was prepared using reverse genetics and propagation in hCK cells at 37° C. Mutant viruses with either the NA-T48C or NA-N50C mutation or both mutations were generated. hCK cells were infected with these viruses at a MOI (multiplicity of infection) of 1. Cells were lysed at 9 hours post-infection with or without DTT, and NA was detected by western blotting.

Results

In the presence of DTT, only the band representing the NA monomer was detected. In the absence of DTT, the band representing the WT-NA dimer was detected. For the mutant viruses, bands representing tetrameric NA-T48C, NA-N50C, and NA-T48C/N50C were detected. This result demonstrates that the ratio of tetrameric NA was increased by NA-T48C, NA-N50C, or both. Stabilization may be detected by any method, e.g., sialidase activity.

CONCLUSION

The NA-48C and NA-50C mutations, either singly or in combination, can stabilize the NA tetrameric structure. These amino acid mutations are thus helpful to establish a new vaccine strain that can elicit greater amounts of NA antibodies compared with those elicited by current vaccine strains.

REFERENCES

Avery's Drug Treatment: Principles and Practice of Clinical Pharmacology and TheraDeutics, 3rd edition, ADIS Press, Ltd., Williams and Wilkins, Baltimore, Md. (1987).

Aymard-Henry et al., Virology: A Practical Approach, Oxford IRL Press, Oxford. 119-150 (1985).

Bachmeyer. Intervitrology 5:260 (1975).

Berkow et al., eds., The Merck Manual, 16th edition, Merck & Co., Rahway, N.J. (1992).

Bachmayer et al., Postgrad. Med., 2:380 (1976).

Brady et al., J. Hyg., 77:173 (1976).

Brady et al., J. Hyg., 7:161 (1976).

Chen et al., Cell, 173:417 (2018).

Da Silva et al., J. Biol. Chem., 28:644 (2013).

Duxbury et al., J. Immunol., 101:62 (1968).

Hatta et al., Science, 293:1840 (2001).

Horimoto et al., J Virol., 68:3120 (1994).

Horimoto et al., Vaccine, 24:3669 (2006).

Keitel et al., in Textbook of Influenza, eds. Nickolson, K. G., Webster, R. G., and Hay, A. (Blackwell, Oxford), pp. 373-390 (1998).

Kuwahara et al., Jpn. J. Infect. Dis. 71:234 (2018).

Laver & Webster, Virology, 69:511 (1976).

Neumann et al., Adv. Virus Res., 53:265 (1999).

Neumann et al., J. Gen. Virol., 2:2635 (2002).

Neumann et al., J Virol., 71:9690 (1997).

Neumann et al., Proc. Natl. Acad. Sci. USA, 96:9345 (1999).

Neumann et al., Virology, 287:243 (2001).

Osol (ed.), Remington's Pharmaceutical Sciences, Mack Publishing Co., Easton, Pa. 1324-1341 (1980).

Sugawara et al., Biologicals, 30:303 (2002).

Webby & Webster et al., Science 302:1519 (2003).

Wood & Robertson, Nat. Rev. Microbiol., 2:842 (2004).

World Health Organization TSR No. 673 (1982).

World Health Organization. Confirmed human cases of avian influenza A (H5N1). http://www.who.int/csr/disease/avian_influenza/country/en/index.html All publications, patents and patent applications are incorporated herein by reference. While in the foregoing specification this invention has been described in relation to certain preferred embodiments thereof, and many details have been set forth for purposes of illustration, it will be apparent to those skilled in the art that the invention is susceptible to additional embodiments and that certain of the details described herein may be varied considerably without departing from the basic principles of the invention.

What is claimed is:

1. An isolated recombinant influenza virus comprising stabilized NA tetramers and a neuraminidase (NA) viral segment encoding a modified NA monomer that forms virions having the stabilized NA tetramers relative to a corresponding influenza virus having a parental NA viral segment encoding an unmodified NA monomer, wherein the modified NA monomer comprises a modified NA stalk that results in the stabilized NA tetramers, wherein the modified NA has a cysteine at position 48 or position 50 or both positions of 48 and 50 relative to the numbering of NA1 of SEQ ID NO:37.

2. The recombinant influenza virus of claim 1 wherein the modified NA stalk further comprises a deletion, an insertion, at least one other amino acid substitution, or any combination thereof.

3. The recombinant influenza virus of claim 1 wherein the at least one substitution in the modified NA stalk is a cysteine substitution.

4. The recombinant influenza virus of claim 1 wherein the NA stalk is modified within residues 1 to 10 or residues 10 to 20 from the C-terminus of the transmembrane domain.

5. A vaccine comprising an effective amount of an isolated recombinant influenza virus comprising a neuraminidase (NA) viral segment encoding a modified NA monomer that forms virions having the stabilized NA tetramers relative to a corresponding influenza virus having a NA viral segment encoding an unmodified NA monomer, wherein the modified NA monomer comprises a modified NA stalk having a cysteine at position 48 or at position 50 or at both positions 48 and 50, relative to the parental NA, that results in the stabilized NA tetramers and optionally comprising an adjuvant or carrier, wherein the modified NA has a cysteine at position 48 or position 50 or both positions of 48 and 50 relative to the numbering of NA1 of SEQ ID NO:37 and wherein the vaccine is an inactivated whole virus vaccine or a split virus vaccine of influenza virus.

6. The vaccine of claim 5 which comprises an adjuvant or a carrier.

7. A method of making an influenza vaccine, comprising: providing the recombinant virus of claim 1; and combining the virus with an adjuvant or treating the virus with an agent that inactivates the virus.

8. The method of claim 7 wherein the adjuvant comprises immunostimulatory DNA sequences, bacterium-derived components, aluminum salt (alum) or a squalene oil-in-water emulsion.

9. The method of claim 7 wherein the agent chemically inactivates the virus.

10. The method of claim 7 wherein the agent comprises a detergent.

11. The method of claim 7 further comprising separating HA and NA from other viral components.

12. The method of claim 8 wherein the squalene oil-in-water emulsion system comprises MF59 or AS03.

* * * * *

SEQUENCE LISTING

<160> NUMBER OF SEQ ID NOS: 56

<210> SEQ ID NO 1
<211> LENGTH: 469
<212> TYPE: PRT
<213> ORGANISM: Influenza A

<400> SEQUENCE: 1

```
Met Asn Pro Asn Gln Lys Ile Ile Thr Ile Gly Ser Val Ser Leu Thr
1               5                   10                  15

Ile Ser Thr Ile Cys Phe Phe Met Gln Ile Ala Ile Leu Ile Thr Thr
            20                  25                  30

Val Thr Leu His Phe Lys Gln Tyr Glu Phe Asn Ser Pro Pro Asn Asn
        35                  40                  45

Gln Val Met Leu Cys Glu Pro Thr Ile Ile Glu Arg Asn Ile Thr Glu
    50                  55                  60

Ile Val Tyr Leu Thr Asn Thr Thr Ile Glu Lys Glu Ile Cys Pro Lys
65                  70                  75                  80

Leu Ala Glu Tyr Arg Asn Trp Ser Lys Pro Gln Cys Asn Ile Thr Gly
                85                  90                  95

Phe Ala Pro Phe Ser Lys Asp Asn Ser Ile Arg Leu Ser Ala Gly Gly
            100                 105                 110

Asp Ile Trp Val Thr Arg Glu Pro Tyr Val Ser Cys Asp Pro Asp Lys
        115                 120                 125

Cys Tyr Gln Phe Ala Leu Gly Gln Gly Thr Thr Leu Asn Asn Val His
    130                 135                 140

Ser Asn Asp Ile Val His Asp Arg Thr Pro Tyr Arg Thr Leu Leu Met
145                 150                 155                 160

Asn Glu Leu Gly Val Pro Phe His Leu Gly Thr Lys Gln Val Cys Ile
                165                 170                 175

Ala Trp Ser Ser Ser Ser Cys His Asp Gly Lys Ala Trp Leu His Val
            180                 185                 190

Cys Val Thr Gly Asp Asp Glu Asn Ala Thr Ala Ser Phe Ile Tyr Asn
        195                 200                 205

Gly Arg Leu Ala Asp Ser Ile Val Ser Trp Ser Lys Lys Ile Leu Arg
    210                 215                 220

Thr Gln Glu Ser Glu Cys Val Cys Ile Asn Gly Thr Cys Thr Val Val
225                 230                 235                 240

Met Thr Asp Gly Ser Ala Ser Gly Lys Ala Asp Thr Lys Ile Leu Phe
                245                 250                 255

Ile Glu Glu Gly Lys Ile Val His Thr Ser Thr Leu Ser Gly Ser Ala
            260                 265                 270

Gln His Val Glu Glu Cys Ser Cys Tyr Pro Arg Tyr Pro Gly Val Arg
        275                 280                 285

Cys Val Cys Arg Asp Asn Trp Lys Gly Ser Asn Arg Pro Ile Val Asp
    290                 295                 300

Ile Asn Ile Lys Asp Tyr Ser Ile Val Ser Ser Tyr Val Cys Ser Gly
305                 310                 315                 320

Leu Val Gly Asp Thr Pro Arg Lys Asn Asp Ser Ser Ser Ser His
                325                 330                 335

Cys Leu Asp Pro Asn Asn Glu Glu Gly Gly His Gly Val Lys Gly Trp
            340                 345                 350

Ala Phe Asp Asp Gly Asn Asp Val Trp Met Gly Arg Thr Ile Ser Glu
        355                 360                 365
```

```
Lys Leu Arg Ser Gly Tyr Glu Thr Phe Lys Val Ile Glu Gly Trp Ser
    370                 375                 380

Asn Pro Asn Ser Lys Leu Gln Ile Asn Arg Gln Val Ile Val Asp Arg
385                 390                 395                 400

Gly Asn Arg Ser Gly Tyr Ser Gly Ile Phe Ser Val Glu Gly Lys Ser
                405                 410                 415

Cys Ile Asn Arg Cys Phe Tyr Val Glu Leu Ile Arg Gly Arg Lys Gln
                420                 425                 430

Glu Thr Glu Val Leu Trp Thr Ser Asn Ser Ile Val Val Phe Cys Gly
            435                 440                 445

Thr Ser Gly Thr Tyr Gly Thr Gly Ser Trp Pro Asp Gly Ala Asp Ile
    450                 455                 460

Asn Leu Met Pro Ile
465

<210> SEQ ID NO 2
<211> LENGTH: 469
<212> TYPE: PRT
<213> ORGANISM: Influenza A

<400> SEQUENCE: 2

Met Asn Pro Asn Gln Lys Ile Ile Thr Ile Gly Ser Val Ser Leu Thr
1               5                   10                  15

Ile Ser Thr Ile Cys Phe Phe Met Gln Ile Ala Ile Leu Ile Thr Thr
                20                  25                  30

Val Thr Leu His Phe Lys Gln Tyr Glu Phe Asn Ser Pro Pro Asn Asn
            35                  40                  45

Gln Val Met Leu Cys Glu Pro Thr Ile Ile Glu Arg Asn Ile Thr Glu
        50                  55                  60

Ile Val Tyr Leu Thr Asn Thr Thr Ile Glu Lys Glu Ile Cys Pro Lys
65                  70                  75                  80

Pro Ala Glu Tyr Arg Asn Trp Ser Lys Pro Gln Cys Gly Ile Thr Gly
                85                  90                  95

Phe Ala Pro Phe Ser Lys Asp Asn Ser Ile Arg Leu Ser Ala Gly Gly
                100                 105                 110

Asp Ile Trp Val Thr Arg Glu Pro Tyr Val Ser Cys Asp Pro Asp Lys
            115                 120                 125

Cys Tyr Gln Phe Ala Leu Gly Gln Gly Thr Thr Leu Asn Asn Val His
        130                 135                 140

Ser Asn Asn Thr Val Arg Asp Arg Thr Pro Tyr Arg Thr Leu Leu Met
145                 150                 155                 160

Asn Glu Leu Gly Val Pro Phe His Leu Gly Thr Lys Gln Val Cys Ile
                165                 170                 175

Ala Trp Ser Ser Ser Cys His Asp Gly Lys Ala Trp Leu His Val
                180                 185                 190

Cys Ile Thr Gly Asp Asp Lys Asn Ala Thr Ala Ser Phe Ile Tyr Asn
            195                 200                 205

Gly Arg Leu Ile Asp Ser Val Val Ser Trp Ser Lys Asp Ile Leu Arg
        210                 215                 220

Thr Gln Glu Ser Glu Cys Val Cys Ile Asn Gly Thr Cys Thr Val Val
225                 230                 235                 240

Met Thr Asp Gly Asn Ala Thr Gly Lys Ala Asp Thr Lys Ile Leu Phe
                245                 250                 255

Ile Glu Glu Gly Lys Ile Val His Thr Ser Lys Leu Ser Gly Ser Ala
                260                 265                 270
```

```
Gln His Val Glu Glu Cys Ser Cys Tyr Pro Arg Tyr Pro Gly Val Arg
        275                 280                 285

Cys Val Cys Arg Asp Asn Trp Lys Gly Ser Asn Arg Pro Ile Val Asp
290                 295                 300

Ile Asn Ile Lys Asp His Ser Ile Val Ser Ser Tyr Val Cys Ser Gly
305                 310                 315                 320

Leu Val Gly Asp Thr Pro Arg Lys Asn Asp Ser Ser Ser Ser His
                325                 330                 335

Cys Leu Asn Pro Asn Asn Glu Glu Gly Gly His Gly Val Lys Gly Trp
            340                 345                 350

Ala Phe Asp Asp Gly Asn Asp Val Trp Met Gly Arg Thr Ile Asn Glu
            355                 360                 365

Thr Ser Arg Leu Gly Tyr Glu Thr Phe Lys Val Val Glu Gly Trp Ser
        370                 375                 380

Asn Pro Lys Ser Lys Leu Gln Ile Asn Arg Gln Val Ile Val Asp Arg
385                 390                 395                 400

Gly Asp Arg Ser Gly Tyr Ser Gly Ile Phe Ser Val Glu Gly Lys Ser
                405                 410                 415

Cys Ile Asn Arg Cys Phe Tyr Val Glu Leu Ile Arg Gly Arg Lys Glu
            420                 425                 430

Glu Thr Glu Val Leu Trp Thr Ser Asn Ser Ile Val Val Phe Cys Gly
        435                 440                 445

Thr Ser Gly Thr Tyr Gly Thr Gly Ser Trp Pro Asp Gly Ala Asp Leu
    450                 455                 460

Asn Leu Met His Ile
465

<210> SEQ ID NO 3
<211> LENGTH: 469
<212> TYPE: PRT
<213> ORGANISM: Influenza A

<400> SEQUENCE: 3

Met Asn Pro Asn Gln Lys Ile Ile Thr Ile Gly Ser Val Ser Leu Thr
1               5                   10                  15

Ile Ala Thr Ile Cys Phe Leu Met Gln Ile Ala Ile Leu Val Thr Thr
            20                  25                  30

Val Thr Leu His Phe Lys Gln Tyr Glu Cys Asn Ser Pro Asn Asn
        35                  40                  45

Gln Val Met Leu Cys Glu Pro Thr Ile Ile Glu Arg Asn Ile Thr Glu
    50                  55                  60

Ile Val Tyr Leu Thr Asn Thr Thr Ile Glu Lys Glu Ile Cys Pro Lys
65                  70                  75                  80

Leu Ala Glu Tyr Arg Asn Trp Ser Lys Pro Gln Cys Asn Ile Thr Gly
                85                  90                  95

Phe Ala Pro Phe Ser Lys Asp Asn Ser Ile Arg Leu Ser Ala Gly Gly
            100                 105                 110

Asp Ile Trp Val Thr Arg Glu Pro Tyr Val Ser Cys Asp Pro Asp Lys
        115                 120                 125

Cys Tyr Gln Phe Ala Leu Gly Gln Gly Thr Thr Leu Asn Asn Gly His
    130                 135                 140

Ser Asn Asp Thr Val His Asp Arg Thr Pro Tyr Arg Thr Leu Leu Met
145                 150                 155                 160

Asn Glu Leu Gly Val Pro Phe His Leu Gly Thr Lys Gln Val Cys Ile
```

```
                165                 170                 175
Ala Trp Ser Ser Ser Cys His Asp Gly Lys Ala Trp Leu His Val
            180                 185                 190

Cys Val Thr Gly Asp Asp Gly Asn Ala Thr Ala Ser Phe Ile Tyr Asn
            195                 200                 205

Gly Arg Leu Val Asp Ser Ile Gly Ser Trp Ser Lys Lys Ile Leu Arg
            210                 215                 220

Thr Gln Glu Ser Glu Cys Val Cys Ile Asn Gly Thr Cys Thr Val Val
225                 230                 235                 240

Met Thr Asp Gly Ser Ala Ser Gly Lys Ala Asp Thr Lys Ile Leu Phe
                245                 250                 255

Ile Glu Glu Gly Lys Ile Val His Thr Ser Leu Leu Ser Gly Ser Ala
                260                 265                 270

Gln His Val Glu Glu Cys Ser Cys Tyr Pro Arg Tyr Pro Gly Val Arg
                275                 280                 285

Cys Val Cys Arg Asp Asn Trp Lys Gly Ser Asn Arg Pro Ile Val Asp
            290                 295                 300

Ile Asn Val Lys Asp Tyr Ser Ile Val Ser Ser Tyr Val Cys Ser Gly
305                 310                 315                 320

Leu Val Gly Asp Thr Pro Arg Lys Asn Asp Ser Ser Ser Ser Ser His
                325                 330                 335

Cys Leu Asp Pro Asn Asn Glu Glu Gly Gly His Gly Val Lys Gly Trp
            340                 345                 350

Ala Phe Asp Asp Gly Asn Asp Val Trp Met Gly Arg Thr Ile Ser Glu
                355                 360                 365

Lys Leu Arg Ser Gly Tyr Glu Thr Phe Lys Val Ile Glu Gly Trp Ser
            370                 375                 380

Lys Pro Asn Ser Lys Leu Gln Ile Asn Arg Gln Val Ile Val Asp Arg
385                 390                 395                 400

Gly Asn Arg Ser Gly Tyr Ser Gly Ile Phe Ser Val Glu Gly Lys Ser
                405                 410                 415

Cys Ile Asn Arg Cys Phe Tyr Val Glu Leu Ile Arg Gly Arg Asn Gln
            420                 425                 430

Glu Thr Glu Val Leu Trp Thr Ser Asn Ser Ile Val Val Phe Cys Gly
                435                 440                 445

Thr Ser Gly Thr Tyr Gly Thr Gly Ser Trp Pro Asp Gly Ala Asp Ile
            450                 455                 460

Asn Leu Met Pro Ile
465

<210> SEQ ID NO 4
<211> LENGTH: 468
<212> TYPE: PRT
<213> ORGANISM: Influenza A

<400> SEQUENCE: 4

Met Asn Pro Asn Gln Lys Ile Ile Thr Ile Gly Val Val Asn Thr Thr
1               5                   10                  15

Leu Ser Thr Ile Ala Leu Leu Ile Gly Val Gly Asn Leu Ile Phe Asn
                20                  25                  30

Thr Val Ile His Glu Lys Ile Gly Asp His Gln Thr Val Ile His Pro
            35                  40                  45

Thr Thr Thr Thr Pro Ala Ile Pro Asn Cys Ser Asp Thr Ile Ile Thr
        50                  55                  60
```

-continued

```
Tyr Asn Asn Thr Val Ile Asn Asn Ile Thr Thr Ile Ile Thr Glu Ala
 65                  70                  75                  80

Glu Arg Leu Phe Lys Pro Pro Leu Pro Leu Cys Pro Phe Arg Gly Phe
             85                  90                  95

Phe Pro Phe His Lys Asp Asn Ala Ile Arg Leu Gly Glu Asn Lys Asp
            100                 105                 110

Val Ile Val Thr Arg Glu Pro Tyr Val Ser Cys Asp Asn Asp Asn Cys
            115                 120                 125

Trp Ser Phe Ala Leu Ala Gln Gly Ala Leu Leu Gly Thr Lys His Ser
130                 135                 140

Asn Gly Thr Ile Lys Asp Arg Thr Pro Tyr Arg Ser Leu Ile Gln Phe
145                 150                 155                 160

Pro Ile Gly Thr Ala Pro Val Leu Gly Asn Tyr Lys Glu Ile Cys Ile
                165                 170                 175

Ala Trp Ser Ser Ser Ser Cys Phe Asp Gly Lys Glu Trp Met His Val
                180                 185                 190

Cys Met Thr Gly Asn Asp Asn Asp Ala Ser Ala Gln Ile Ile Tyr Ala
                195                 200                 205

Gly Arg Met Thr Asp Ser Ile Lys Ser Trp Lys Arg Asp Ile Leu Arg
210                 215                 220

Thr Gln Glu Ser Glu Cys Gln Cys Ile Asp Gly Thr Cys Val Val Ala
225                 230                 235                 240

Val Thr Asp Gly Pro Ala Ala Asn Ser Ala Asp His Arg Val Tyr Trp
                245                 250                 255

Ile Arg Glu Gly Arg Ile Val Lys Tyr Glu Asn Val Pro Lys Thr Lys
                260                 265                 270

Ile Gln His Leu Glu Glu Cys Ser Cys Tyr Val Asp Ile Asp Val Tyr
                275                 280                 285

Cys Ile Cys Arg Asp Asn Trp Lys Gly Ser Asn Arg Pro Trp Met Arg
                290                 295                 300

Ile Asn Asn Glu Thr Ile Leu Glu Thr Gly Tyr Val Cys Ser Lys Phe
305                 310                 315                 320

His Ser Asp Thr Pro Arg Pro Ala Asp Pro Ser Thr Val Ser Cys Asp
                325                 330                 335

Ser Pro Ser Asn Val Asn Gly Gly Pro Gly Val Lys Gly Phe Gly Phe
                340                 345                 350

Lys Val Gly Asn Asp Val Trp Leu Gly Arg Thr Met Ser Thr Ser Gly
                355                 360                 365

Arg Ser Gly Phe Glu Ile Ile Lys Val Ala Glu Gly Trp Ile Asn Ser
370                 375                 380

Pro Asn His Ala Lys Ser Val Thr Gln Thr Leu Val Ser Asn Asn Asp
385                 390                 395                 400

Trp Ser Gly Tyr Ser Gly Ser Phe Ile Val Lys Thr Lys Ala Cys Phe
                405                 410                 415

Gln Pro Cys Phe Tyr Val Glu Leu Ile Arg Gly Arg Pro Asn Lys Asn
                420                 425                 430

Asp Asp Val Ser Trp Thr Ser Asn Ser Ile Val Thr Phe Cys Gly Leu
                435                 440                 445

Asp Asn Glu Pro Gly Ser Gly Asn Trp Pro Asp Gly Ser Asn Ile Gly
                450                 455                 460

Phe Met Pro Lys
465
```

<210> SEQ ID NO 5
<211> LENGTH: 470
<212> TYPE: PRT
<213> ORGANISM: Influenza A

<400> SEQUENCE: 5

Met Asn Pro Asn Gln Lys Ile Ile Thr Ile Gly Ser Val Ser Ile Ile
1               5                   10                  15

Leu Thr Thr Ile Gly Leu Leu Leu Gln Ile Thr Ser Leu Cys Ser Ile
            20                  25                  30

Trp Phe Ser His Tyr Asn Gln Val Thr Gln Thr His Glu Gln Pro Cys
        35                  40                  45

Ser Asn Asn Thr Thr Asn Tyr Tyr Asn Glu Thr Phe Val Asn Val Thr
    50                  55                  60

Asn Val Gln Asn Asn Tyr Thr Thr Val Ile Glu Pro Ser Ala Pro Asp
65                  70                  75                  80

Val Val His Tyr Ser Ser Gly Arg Asp Leu Cys Pro Ile Arg Gly Trp
                85                  90                  95

Ala Pro Leu Ser Lys Asp Asn Gly Ile Arg Ile Gly Ser Arg Gly Glu
            100                 105                 110

Val Phe Val Ile Arg Glu Pro Phe Ile Ser Cys Ser Ile Ser Glu Cys
        115                 120                 125

Arg Thr Phe Phe Leu Thr Gln Gly Ala Leu Leu Asn Asp Lys His Ser
130                 135                 140

Asn Gly Thr Val Lys Asp Arg Ser Pro Phe Arg Thr Leu Met Ser Cys
145                 150                 155                 160

Pro Ile Gly Val Ala Pro Ser Pro Ser Asn Ser Arg Phe Glu Ser Val
                165                 170                 175

Ala Trp Ser Ala Thr Ala Cys Ser Asp Gly Pro Gly Trp Leu Thr Leu
            180                 185                 190

Gly Ile Thr Gly Pro Asp Ala Thr Ala Val Ala Val Leu Lys Tyr Asn
        195                 200                 205

Gly Ile Ile Thr Asp Thr Leu Lys Ser Trp Lys Gly Asn Ile Met Arg
210                 215                 220

Thr Gln Glu Ser Glu Cys Val Cys Gln Asp Glu Phe Cys Tyr Thr Leu
225                 230                 235                 240

Ile Thr Asp Gly Pro Ser Asp Ala Gln Ala Phe Tyr Lys Ile Leu Lys
                245                 250                 255

Ile Arg Lys Gly Lys Ile Val Ser Met Lys Asp Val Asp Ala Thr Gly
            260                 265                 270

Phe His Phe Glu Glu Cys Ser Cys Tyr Pro Ser Gly Thr Asp Ile Glu
        275                 280                 285

Cys Val Cys Arg Asp Asn Trp Arg Gly Ser Asn Arg Pro Trp Ile Arg
290                 295                 300

Phe Asn Ser Asp Leu Asp Tyr Gln Ile Gly Tyr Val Cys Ser Gly Ile
305                 310                 315                 320

Phe Gly Asp Asn Pro Arg Pro Val Asp Gly Thr Gly Ser Cys Asn Ser
                325                 330                 335

Pro Val Asn Asn Gly Lys Gly Arg Tyr Gly Val Lys Gly Phe Ser Phe
            340                 345                 350

Arg Tyr Gly Asp Gly Val Trp Ile Gly Arg Thr Lys Ser Leu Glu Ser
        355                 360                 365

Arg Ser Gly Phe Glu Met Val Trp Asp Ala Asn Gly Trp Val Ser Thr
370                 375                 380

```
Asp Lys Asp Ser Asn Gly Val Gln Asp Ile Ile Asp Asn Asp Asn Trp
385                 390                 395                 400

Ser Gly Tyr Ser Gly Ser Phe Ser Ile Arg Gly Glu Thr Thr Gly Arg
            405                 410                 415

Asn Cys Thr Val Pro Cys Phe Trp Val Glu Met Ile Arg Gly Gln Pro
            420                 425                 430

Lys Glu Lys Thr Ile Trp Thr Ser Gly Ser Ser Ile Ala Phe Cys Gly
            435                 440                 445

Val Asn Ser Asp Thr Thr Gly Trp Ser Trp Pro Asp Gly Ala Leu Leu
            450                 455                 460

Pro Phe Asp Ile Asp Lys
465                 470

<210> SEQ ID NO 6
<211> LENGTH: 470
<212> TYPE: PRT
<213> ORGANISM: Influenza A

<400> SEQUENCE: 6

Met Asn Pro Asn Gln Lys Ile Ile Cys Ile Ser Ala Thr Gly Met Thr
1               5                   10                  15

Leu Ser Val Val Ser Leu Leu Ile Gly Ile Ala Asn Leu Gly Leu Asn
                20                  25                  30

Ile Gly Leu His Tyr Lys Met Gly Asp Thr Pro Asp Val Asn Ile Pro
            35                  40                  45

Asn Met Asn Glu Thr Asn Ser Thr Thr Thr Ile Ile Asn Asn His Thr
        50                  55                  60

Gln Asn Asn Phe Thr Asn Ile Thr Asn Ile Ile Val Asn Lys Asn Glu
65                  70                  75                  80

Glu Gly Thr Phe Leu Asn Leu Thr Lys Pro Leu Cys Glu Val Asn Ser
                85                  90                  95

Trp His Ile Leu Ser Lys Asp Asn Ala Ile Arg Ile Gly Glu Asp Ala
            100                 105                 110

His Ile Leu Val Thr Arg Glu Pro Tyr Leu Ser Cys Asp Pro Gln Gly
        115                 120                 125

Cys Arg Met Phe Ala Leu Ser Gln Gly Thr Thr Leu Arg Gly Arg His
130                 135                 140

Ala Asn Gly Thr Ile His Asp Arg Ser Pro Phe Arg Ala Leu Ile Ser
145                 150                 155                 160

Trp Glu Met Gly Gln Ala Pro Ser Pro Tyr Asn Val Arg Val Glu Cys
                165                 170                 175

Ile Gly Trp Ser Ser Thr Ser Cys His Asp Gly Ile Ser Arg Met Ser
            180                 185                 190

Ile Cys Met Ser Gly Ala Asn Asn Asn Ala Ser Ala Val Val Trp Tyr
        195                 200                 205

Gly Gly Arg Pro Val Thr Glu Ile Pro Ser Trp Ala Gly Asn Ile Leu
210                 215                 220

Arg Thr Gln Glu Ser Glu Cys Val Cys His Lys Gly Ile Cys Pro Val
225                 230                 235                 240

Val Met Thr Asp Gly Pro Ala Asn Asn Arg Ala Ala Thr Lys Ile Ile
                245                 250                 255

Tyr Phe Lys Glu Gly Lys Ile Gln Lys Ile Glu Glu Leu Ala Gly Asn
            260                 265                 270

Thr Gln His Ile Glu Glu Cys Ser Cys Tyr Gly Ala Val Gly Val Ile
        275                 280                 285
```

```
Lys Cys Ile Cys Arg Asp Asn Trp Lys Gly Ala Asn Arg Pro Val Ile
            290                 295                 300

Thr Ile Asp Pro Glu Met Met Thr His Thr Ser Lys Tyr Leu Cys Ser
305                 310                 315                 320

Lys Ile Leu Thr Asp Thr Ser Arg Pro Asn Asp Pro Thr Asn Gly Asn
                325                 330                 335

Cys Asp Ala Pro Ile Thr Gly Gly Ser Pro Asp Pro Gly Val Lys Gly
                340                 345                 350

Phe Ala Phe Leu Asp Arg Glu Asn Ser Trp Leu Gly Arg Thr Ile Ser
            355                 360                 365

Lys Asp Ser Arg Ser Gly Tyr Glu Met Leu Lys Val Pro Asn Ala Glu
    370                 375                 380

Thr Asp Thr Gln Ser Gly Pro Ile Ser His Gln Val Ile Val Asn Asn
385                 390                 395                 400

Gln Asn Trp Ser Gly Tyr Ser Gly Ala Phe Ile Asp Tyr Trp Ala Asn
                405                 410                 415

Lys Glu Cys Phe Asn Pro Cys Phe Tyr Val Glu Leu Ile Arg Gly Arg
            420                 425                 430

Pro Lys Glu Ser Ser Val Leu Trp Thr Ser Asn Ser Ile Val Ala Leu
                435                 440                 445

Cys Gly Ser Lys Glu Arg Leu Gly Ser Trp Ser Trp His Asp Gly Ala
    450                 455                 460

Glu Ile Ile Tyr Phe Lys
465                 470

<210> SEQ ID NO 7
<211> LENGTH: 470
<212> TYPE: PRT
<213> ORGANISM: Influenza A

<400> SEQUENCE: 7

Met Asn Pro Asn Gln Lys Leu Phe Ala Leu Ser Gly Val Ala Ile Ala
1               5                   10                  15

Leu Ser Ile Leu Asn Leu Leu Ile Gly Ile Ser Asn Val Gly Leu Asn
            20                  25                  30

Val Ser Leu His Leu Lys Gly Ser Ser Asp Gln Asp Lys Asn Trp Thr
        35                  40                  45

Cys Thr Ser Val Thr Gln Asn Asn Thr Thr Leu Ile Glu Asn Thr Tyr
    50                  55                  60

Val Asn Asn Thr Thr Val Ile Asp Lys Glu Thr Gly Thr Ala Lys Pro
65                  70                  75                  80

Asn Tyr Leu Met Leu Asn Lys Ser Leu Cys Lys Val Glu Gly Trp Val
                85                  90                  95

Val Val Ala Lys Asp Asn Ala Ile Arg Phe Gly Glu Ser Glu Gln Ile
            100                 105                 110

Ile Val Thr Arg Glu Pro Tyr Val Ser Cys Asp Pro Leu Gly Cys Lys
        115                 120                 125

Met Tyr Ala Leu His Gln Gly Thr Thr Ile Arg Asn Lys His Ser Asn
    130                 135                 140

Gly Thr Ile His Asp Arg Thr Ala Phe Arg Gly Leu Ile Ser Thr Pro
145                 150                 155                 160

Leu Gly Ser Pro Pro Val Val Ser Asn Ser Asp Phe Leu Cys Val Gly
                165                 170                 175

Trp Ser Ser Thr Ser Cys His Asp Gly Ile Gly Arg Met Thr Ile Cys
```

```
            180                 185                 190
Val Gln Gly Asn Asn Asp Asn Ala Thr Ala Thr Val Tyr Tyr Asp Arg
        195                 200                 205

Arg Leu Thr Thr Thr Ile Lys Thr Trp Ala Gly Asn Ile Leu Arg Thr
    210                 215                 220

Gln Glu Ser Glu Cys Val Cys His Asn Gly Thr Cys Val Val Ile Met
225                 230                 235                 240

Thr Asp Gly Ser Ala Ser Ser Gln Ala Tyr Thr Lys Val Leu Tyr Phe
                245                 250                 255

His Lys Gly Leu Val Ile Lys Glu Glu Ala Leu Lys Gly Ser Ala Arg
            260                 265                 270

His Ile Glu Glu Cys Ser Cys Tyr Gly His Asn Ser Lys Val Thr Cys
        275                 280                 285

Val Cys Arg Asp Asn Trp Gln Gly Ala Asn Arg Pro Val Ile Glu Ile
    290                 295                 300

Asp Met Asn Ala Met Glu His Thr Ser Gln Tyr Leu Cys Thr Gly Val
305                 310                 315                 320

Leu Thr Asp Thr Ser Arg Pro Ser Asp Lys Ser Met Gly Asp Cys Asn
                325                 330                 335

Asn Pro Ile Thr Gly Ser Pro Gly Ala Pro Gly Val Lys Gly Phe Gly
            340                 345                 350

Phe Leu Asp Ser Ser Asn Thr Trp Leu Gly Arg Thr Ile Ser Pro Arg
        355                 360                 365

Ser Arg Ser Gly Phe Glu Met Leu Lys Ile Pro Asn Ala Glu Thr Asp
    370                 375                 380

Pro Asn Ser Lys Ile Thr Glu Arg Gln Glu Ile Val Asp Asn Asn Asn
385                 390                 395                 400

Trp Ser Gly Tyr Ser Gly Ser Phe Ile Asp Tyr Trp Asp Glu Ser Ser
                405                 410                 415

Glu Cys Tyr Asn Pro Cys Phe Tyr Val Glu Leu Ile Arg Gly Arg Pro
            420                 425                 430

Glu Glu Ala Lys Tyr Val Gly Trp Thr Ser Asn Ser Leu Ile Ala Leu
        435                 440                 445

Cys Gly Ser Pro Ile Ser Val Gly Ser Gly Ser Phe Pro Asp Gly Ala
    450                 455                 460

Gln Ile Gln Tyr Phe Ser
465                 470

<210> SEQ ID NO 8
<211> LENGTH: 470
<212> TYPE: PRT
<213> ORGANISM: Influenza A

<400> SEQUENCE: 8

Met Asn Pro Asn Gln Lys Ile Ile Thr Val Gly Ser Val Ser Leu Gly
1               5                   10                  15

Leu Val Val Leu Asn Ile Leu Leu His Ile Val Ser Ile Thr Val Thr
            20                  25                  30

Val Leu Val Leu Pro Gly Asn Gly Asn Asn Lys Asn Cys Asn Glu Thr
        35                  40                  45

Val Ile Arg Glu Tyr Asn Glu Thr Val Arg Ile Glu Lys Val Thr Gln
    50                  55                  60

Trp His Asn Thr Asn Val Ile Glu Tyr Ile Glu Lys Pro Glu Ser Gly
65                  70                  75                  80
```

His Phe Met Asn Asn Thr Glu Ala Leu Cys Asp Ala Lys Gly Phe Ala
            85                  90                  95

Pro Phe Ser Lys Asp Asn Gly Ile Arg Ile Gly Ser Arg Gly His Val
        100                 105                 110

Phe Val Ile Arg Glu Pro Phe Val Ser Cys Ser Pro Thr Glu Cys Arg
    115                 120                 125

Thr Phe Phe Leu Thr Gln Gly Ser Leu Leu Asn Asp Lys His Ser Asn
130                 135                 140

Gly Thr Val Lys Asp Arg Ser Pro Tyr Arg Thr Leu Met Ser Val Glu
145                 150                 155                 160

Ile Gly Gln Ser Pro Asn Val Tyr Gln Ala Arg Phe Glu Ala Val Ala
                165                 170                 175

Trp Ser Ala Thr Ala Cys His Asp Gly Lys Lys Trp Met Thr Ile Gly
            180                 185                 190

Val Thr Gly Pro Asp Ala Lys Ala Val Ala Val Val His Tyr Gly Gly
        195                 200                 205

Ile Pro Thr Asp Val Ile Asn Ser Trp Ala Gly Asp Ile Leu Arg Thr
    210                 215                 220

Gln Glu Ser Ser Cys Thr Cys Ile Gln Gly Glu Cys Tyr Trp Val Met
225                 230                 235                 240

Thr Asp Gly Pro Ala Asn Arg Gln Ala Gln Tyr Arg Ala Phe Lys Ala
                245                 250                 255

Lys Gln Gly Lys Ile Val Gly Gln Thr Glu Ile Ser Phe Asn Gly Ser
            260                 265                 270

His Ile Glu Glu Cys Ser Cys Tyr Pro Asn Glu Gly Lys Val Glu Cys
        275                 280                 285

Val Cys Arg Asp Asn Trp Thr Gly Thr Asn Arg Pro Val Leu Val Ile
    290                 295                 300

Ser Pro Asp Leu Ser Tyr Arg Ala Gly Tyr Leu Cys Ala Gly Leu Pro
305                 310                 315                 320

Ser Asp Thr Pro Arg Gly Glu Asp Ser Gln Phe Thr Gly Ser Cys Thr
                325                 330                 335

Ser Pro Val Gly Asn Gln Gly Tyr Gly Val Lys Gly Phe Gly Phe Arg
            340                 345                 350

Gln Gly Asn Asp Val Trp Met Gly Arg Thr Ile Ser Arg Thr Ser Arg
        355                 360                 365

Ser Gly Phe Glu Ile Leu Lys Val Arg Asn Gly Trp Val Gln Asn Ser
    370                 375                 380

Lys Glu Gln Ile Lys Arg Gln Val Val Val Asp Asn Leu Lys Trp Ser
385                 390                 395                 400

Gly Tyr Ser Gly Ser Phe Thr Leu Pro Val Glu Leu Thr Lys Arg Asn
                405                 410                 415

Cys Leu Val Pro Cys Phe Trp Val Glu Met Ile Arg Gly Lys Pro Glu
            420                 425                 430

Glu Lys Thr Ile Trp Thr Ser Ser Ser Ile Val Met Cys Gly Val
        435                 440                 445

Asp His Glu Ile Ala Asp Trp Ser Trp His Asp Gly Ala Ile Leu Pro
450                 455                 460

Phe Asp Ile Asp Lys Met
465                 470

<210> SEQ ID NO 9
<211> LENGTH: 465
<212> TYPE: PRT

<213> ORGANISM: Influenza A

<400> SEQUENCE: 9

Met Asn Pro Asn Gln Lys Ile Leu Cys Thr Ser Ala Thr Ala Ile Ile
1 5 10 15

Ile Gly Ala Ile Ala Val Leu Ile Gly Ile Ala Asn Leu Gly Leu Asn
20 25 30

Ile Gly Leu His Leu Lys Pro Gly Cys Asn Cys Ser His Ser Gln Pro
35 40 45

Glu Thr Thr Asn Thr Ser Gln Thr Ile Ile Asn Asn Tyr Tyr Asn Glu
50 55 60

Thr Asn Ile Thr Asn Ile Gln Met Glu Glu Arg Thr Ser Arg Asn Phe
65 70 75 80

Asn Asn Leu Thr Lys Gly Leu Cys Thr Ile Asn Ser Trp His Ile Tyr
85 90 95

Gly Lys Asp Asn Ala Val Arg Ile Gly Glu Ser Ser Asp Val Leu Val
100 105 110

Thr Arg Glu Pro Tyr Val Ser Cys Asp Pro Asp Glu Cys Arg Phe Tyr
115 120 125

Ala Leu Ser Gln Gly Thr Thr Ile Arg Gly Lys His Ser Asn Gly Thr
130 135 140

Ile His Asp Arg Ser Gln Tyr Arg Ala Leu Ile Ser Trp Pro Leu Ser
145 150 155 160

Ser Pro Pro Thr Val Tyr Asn Ser Arg Val Glu Cys Ile Gly Trp Ser
165 170 175

Ser Thr Ser Cys His Asp Gly Lys Ser Arg Met Ser Ile Cys Ile Ser
180 185 190

Gly Pro Asn Asn Asn Ala Ser Ala Val Val Trp Tyr Asn Arg Arg Pro
195 200 205

Val Thr Glu Ile Asn Thr Trp Ala Arg Asn Ile Leu Arg Thr Gln Glu
210 215 220

Ser Glu Cys Val Cys His Asn Gly Val Cys Pro Val Val Phe Thr Asp
225 230 235 240

Gly Ser Ala Thr Gly Pro Ala Asp Thr Arg Ile Tyr Tyr Phe Lys Glu
245 250 255

Gly Lys Ile Leu Lys Trp Glu Ser Leu Thr Gly Thr Ala Lys His Ile
260 265 270

Glu Glu Cys Ser Cys Tyr Gly Glu Arg Thr Gly Ile Thr Cys Thr Cys
275 280 285

Arg Asp Asn Trp Gln Gly Ser Asn Arg Pro Val Ile Gln Ile Asp Pro
290 295 300

Val Ala Met Thr His Thr Ser Gln Tyr Ile Cys Ser Pro Val Leu Thr
305 310 315 320

Asp Asn Pro Arg Pro Asn Asp Pro Asn Ile Gly Lys Cys Asn Asp Pro
325 330 335

Tyr Pro Gly Asn Asn Asn Asn Gly Val Lys Gly Phe Ser Tyr Leu Asp
340 345 350

Gly Ala Asn Thr Trp Leu Gly Arg Thr Ile Ser Thr Ala Ser Arg Ser
355 360 365

Gly Tyr Glu Met Leu Lys Val Pro Asn Ala Leu Thr Asp Asp Arg Ser
370 375 380

Lys Pro Ile Gln Gly Gln Thr Ile Val Leu Asn Ala Asp Trp Ser Gly
385 390 395 400

```
Tyr Ser Gly Ser Phe Met Asp Tyr Trp Ala Glu Gly Asp Cys Tyr Arg
                405                 410                 415

Ala Cys Phe Tyr Val Glu Leu Ile Arg Gly Arg Pro Lys Glu Asp Lys
            420                 425                 430

Val Trp Trp Thr Ser Asn Ser Ile Val Ser Met Cys Ser Ser Thr Glu
        435                 440                 445

Phe Leu Gly Gln Trp Asn Trp Pro Asp Gly Ala Lys Ile Glu Tyr Phe
    450                 455                 460

Leu
465

<210> SEQ ID NO 10
<211> LENGTH: 759
<212> TYPE: PRT
<213> ORGANISM: Influenza A

<400> SEQUENCE: 10

Met Glu Arg Ile Lys Glu Leu Arg Asn Leu Met Ser Gln Ser Arg Thr
1               5                   10                  15

Arg Glu Ile Leu Thr Lys Thr Thr Val Asp His Met Ala Ile Ile Lys
            20                  25                  30

Lys Tyr Thr Ser Gly Arg Gln Glu Lys Asn Pro Ala Leu Arg Met Lys
        35                  40                  45

Trp Met Met Ala Met Lys Tyr Pro Ile Thr Ala Asp Lys Arg Ile Thr
    50                  55                  60

Glu Met Ile Pro Glu Arg Asn Glu Gln Gly Gln Thr Leu Trp Ser Lys
65                  70                  75                  80

Met Asn Asp Ala Gly Ser Asp Arg Val Met Val Ser Pro Leu Ala Val
                85                  90                  95

Thr Trp Trp Asn Arg Asn Gly Pro Met Thr Asn Thr Val His Tyr Pro
            100                 105                 110

Lys Ile Tyr Lys Thr Tyr Phe Glu Arg Val Glu Arg Leu Lys His Gly
        115                 120                 125

Thr Phe Gly Pro Val His Phe Arg Asn Gln Val Lys Ile Arg Arg Arg
    130                 135                 140

Val Asp Ile Asn Pro Gly His Ala Asp Leu Ser Ala Lys Glu Ala Gln
145                 150                 155                 160

Asp Val Ile Met Glu Val Val Phe Pro Asn Glu Val Gly Ala Arg Ile
                165                 170                 175

Leu Thr Ser Glu Ser Gln Leu Thr Ile Thr Lys Glu Lys Lys Glu Glu
            180                 185                 190

Leu Gln Asp Cys Lys Ile Ser Pro Leu Met Val Ala Tyr Met Leu Glu
        195                 200                 205

Arg Glu Leu Val Arg Lys Thr Arg Phe Leu Pro Val Ala Gly Gly Thr
    210                 215                 220

Ser Ser Val Tyr Ile Glu Val Leu His Leu Thr Gln Gly Thr Cys Trp
225                 230                 235                 240

Glu Gln Met Tyr Thr Pro Gly Gly Glu Val Lys Asn Asp Asp Val Asp
                245                 250                 255

Gln Ser Leu Ile Ile Ala Ala Arg Asn Ile Val Arg Arg Ala Ala Val
            260                 265                 270

Ser Ala Asp Pro Leu Ala Ser Leu Leu Glu Met Cys His Ser Thr Gln
        275                 280                 285

Ile Gly Gly Ile Arg Met Val Asp Ile Leu Lys Gln Asn Pro Thr Glu
    290                 295                 300
```

-continued

Glu Gln Ala Val Asp Ile Cys Lys Ala Ala Met Gly Leu Arg Ile Ser
305                 310                 315                 320

Ser Ser Phe Ser Phe Gly Gly Phe Thr Phe Lys Arg Thr Ser Gly Ser
            325                 330                 335

Ser Val Lys Arg Glu Glu Val Leu Thr Gly Asn Leu Gln Thr Leu
        340                 345                 350

Lys Ile Arg Val His Glu Gly Ser Glu Glu Phe Thr Met Val Gly Arg
            355                 360                 365

Arg Ala Thr Ala Ile Leu Arg Lys Ala Thr Arg Leu Ile Gln Leu
        370                 375                 380

Ile Val Ser Gly Arg Asp Glu Gln Ser Ile Ala Glu Ala Ile Ile Val
385                 390                 395                 400

Ala Met Val Phe Ser Gln Glu Asp Cys Met Ile Lys Ala Val Arg Gly
            405                 410                 415

Asp Leu Asn Phe Val Asn Arg Ala Asn Gln Arg Leu Asn Pro Met His
            420                 425                 430

Gln Leu Leu Arg His Phe Gln Lys Asp Ala Lys Val Leu Phe Gln Asn
        435                 440                 445

Trp Gly Val Glu Pro Ile Asp Asn Val Met Gly Met Ile Gly Ile Leu
450                 455                 460

Pro Asp Met Thr Pro Ser Ile Glu Met Ser Met Arg Gly Val Arg Ile
465                 470                 475                 480

Ser Lys Met Gly Val Asp Glu Tyr Ser Ser Thr Glu Arg Val Val
            485                 490                 495

Ser Ile Asp Arg Phe Leu Arg Val Arg Asp Gln Arg Gly Asn Val Leu
            500                 505                 510

Leu Ser Pro Glu Glu Val Ser Glu Thr Gln Gly Thr Glu Lys Leu Thr
        515                 520                 525

Ile Thr Tyr Ser Ser Ser Met Met Trp Glu Ile Asn Gly Pro Glu Ser
        530                 535                 540

Val Leu Val Asn Thr Tyr Gln Trp Ile Ile Arg Asn Trp Glu Thr Val
545                 550                 555                 560

Lys Ile Gln Trp Ser Gln Asn Pro Thr Met Leu Tyr Asn Lys Met Glu
            565                 570                 575

Phe Glu Pro Phe Gln Ser Leu Val Pro Lys Ala Ile Arg Gly Gln Tyr
            580                 585                 590

Ser Gly Phe Val Arg Thr Leu Phe Gln Gln Met Arg Asp Val Leu Gly
        595                 600                 605

Thr Phe Asp Thr Ala Gln Ile Ile Lys Leu Leu Pro Phe Ala Ala Ala
        610                 615                 620

Pro Pro Lys Gln Ser Arg Met Gln Phe Ser Ser Phe Thr Val Asn Val
625                 630                 635                 640

Arg Gly Ser Gly Met Arg Ile Leu Val Arg Gly Asn Ser Pro Val Phe
            645                 650                 655

Asn Tyr Asn Lys Ala Thr Lys Arg Leu Thr Val Leu Gly Lys Asp Ala
            660                 665                 670

Gly Thr Leu Thr Glu Asp Pro Asp Glu Gly Thr Ala Gly Val Glu Ser
        675                 680                 685

Ala Val Leu Arg Gly Phe Leu Ile Leu Gly Lys Glu Asp Arg Arg Tyr
        690                 695                 700

Gly Pro Ala Leu Ser Ile Asn Glu Leu Ser Asn Leu Ala Lys Gly Glu
705                 710                 715                 720

```
Lys Ala Asn Val Leu Ile Gly Gln Gly Asp Val Val Leu Val Met Lys
                    725                 730                 735

Arg Lys Arg Asp Ser Ser Ile Leu Thr Asp Ser Gln Thr Ala Thr Lys
            740                 745                 750

Arg Ile Arg Met Ala Ile Asn
        755

<210> SEQ ID NO 11
<211> LENGTH: 757
<212> TYPE: PRT
<213> ORGANISM: Influenza A

<400> SEQUENCE: 11

Met Asp Val Asn Pro Thr Leu Leu Phe Leu Lys Val Pro Ala Gln Asn
1               5                   10                  15

Ala Ile Ser Thr Thr Phe Pro Tyr Thr Gly Asp Pro Pro Tyr Ser His
                20                  25                  30

Gly Thr Gly Thr Gly Tyr Thr Met Asp Thr Val Asn Arg Thr His Gln
            35                  40                  45

Tyr Ser Glu Lys Gly Arg Trp Thr Thr Asn Thr Glu Thr Gly Ala Pro
50                  55                  60

Gln Leu Asn Pro Ile Asp Gly Pro Leu Pro Glu Asp Asn Glu Pro Ser
65                  70                  75                  80

Gly Tyr Ala Gln Thr Asp Cys Val Leu Glu Ala Met Ala Phe Leu Glu
                85                  90                  95

Glu Ser His Pro Gly Ile Phe Glu Asn Ser Cys Ile Glu Thr Met Glu
            100                 105                 110

Val Val Gln Gln Thr Arg Val Asp Lys Leu Thr Gln Gly Arg Gln Thr
        115                 120                 125

Tyr Asp Trp Thr Leu Asn Arg Asn Gln Pro Ala Ala Thr Ala Leu Ala
    130                 135                 140

Asn Thr Ile Glu Val Phe Arg Ser Asn Gly Leu Thr Ala Asn Glu Ser
145                 150                 155                 160

Gly Arg Leu Ile Asp Phe Leu Lys Asp Val Met Glu Ser Met Lys Lys
                165                 170                 175

Glu Glu Met Gly Ile Thr Thr His Phe Gln Arg Lys Arg Arg Val Arg
            180                 185                 190

Asp Asn Met Thr Lys Lys Met Ile Thr Gln Arg Thr Ile Gly Lys Arg
        195                 200                 205

Lys Gln Arg Leu Asn Lys Arg Gly Tyr Leu Ile Arg Ala Leu Thr Leu
    210                 215                 220

Asn Thr Met Thr Lys Asp Ala Glu Arg Gly Lys Leu Lys Arg Arg Ala
225                 230                 235                 240

Ile Ala Thr Pro Gly Met Gln Ile Arg Gly Phe Val Tyr Phe Val Glu
                245                 250                 255

Thr Leu Ala Arg Ser Ile Cys Glu Lys Leu Glu Gln Ser Gly Leu Pro
            260                 265                 270

Val Gly Gly Asn Glu Lys Lys Ala Lys Leu Ala Asn Val Val Arg Lys
        275                 280                 285

Met Met Thr Asn Ser Gln Asp Thr Glu Leu Ser Phe Thr Ile Thr Gly
    290                 295                 300

Asp Asn Thr Lys Trp Asn Glu Asn Gln Asn Pro Arg Met Phe Leu Ala
305                 310                 315                 320

Met Ile Thr Tyr Met Thr Arg Asn Gln Pro Glu Trp Phe Arg Asn Val
                325                 330                 335
```

```
Leu Ser Ile Ala Pro Ile Met Phe Ser Asn Lys Met Ala Arg Leu Gly
            340                 345                 350

Lys Gly Tyr Met Phe Glu Ser Lys Ser Met Lys Leu Arg Thr Gln Ile
            355                 360                 365

Pro Ala Glu Met Leu Ala Ser Ile Asp Leu Lys Tyr Phe Asn Asp Ser
            370                 375                 380

Thr Arg Lys Lys Ile Glu Lys Ile Arg Pro Leu Leu Ile Glu Gly Thr
385                 390                 395                 400

Ala Ser Leu Ser Pro Gly Met Met Gly Met Phe Asn Met Leu Ser
            405                 410                 415

Thr Val Leu Gly Val Ser Ile Leu Asn Leu Gly Gln Lys Arg Tyr Thr
            420                 425                 430

Lys Thr Thr Tyr Trp Trp Asp Gly Leu Gln Ser Ser Asp Asp Phe Ala
            435                 440                 445

Leu Ile Val Asn Ala Pro Asn His Glu Gly Ile Gln Ala Gly Val Asp
            450                 455                 460

Arg Phe Tyr Arg Thr Cys Lys Leu Leu Gly Ile Asn Met Ser Lys Lys
465                 470                 475                 480

Lys Ser Tyr Ile Asn Arg Thr Gly Thr Phe Glu Phe Thr Ser Phe Phe
            485                 490                 495

Tyr Arg Tyr Gly Phe Val Ala Asn Phe Ser Met Glu Leu Pro Ser Phe
            500                 505                 510

Gly Val Ser Gly Ile Asn Glu Ser Ala Asp Met Ser Ile Gly Val Thr
            515                 520                 525

Val Ile Lys Asn Asn Met Ile Asn Asn Asp Leu Gly Pro Ala Thr Ala
            530                 535                 540

Gln Met Ala Leu Gln Leu Phe Ile Lys Asp Tyr Arg Tyr Thr Tyr Arg
545                 550                 555                 560

Cys His Arg Gly Asp Thr Gln Ile Gln Thr Arg Arg Ser Phe Glu Ile
            565                 570                 575

Lys Lys Leu Trp Glu Gln Thr Arg Ser Lys Ala Gly Leu Leu Val Ser
            580                 585                 590

Asp Gly Gly Pro Asn Leu Tyr Asn Ile Arg Asn Leu His Ile Pro Glu
            595                 600                 605

Val Cys Leu Lys Trp Glu Leu Met Asp Glu Asp Tyr Gln Gly Arg Leu
            610                 615                 620

Cys Asn Pro Leu Asn Pro Phe Val Ser His Lys Glu Ile Glu Ser Met
625                 630                 635                 640

Asn Asn Ala Val Met Met Pro Ala His Gly Pro Ala Lys Asn Met Glu
            645                 650                 655

Tyr Asp Ala Val Ala Thr Thr His Ser Trp Ile Pro Lys Arg Asn Arg
            660                 665                 670

Ser Ile Leu Asn Thr Ser Gln Arg Gly Val Leu Glu Asp Glu Gln Met
            675                 680                 685

Tyr Gln Arg Cys Cys Asn Leu Phe Glu Lys Phe Phe Pro Ser Ser Ser
            690                 695                 700

Tyr Arg Arg Pro Val Gly Ile Ser Ser Met Val Glu Ala Met Val Ser
705                 710                 715                 720

Arg Ala Arg Ile Asp Ala Arg Ile Asp Phe Glu Ser Gly Arg Ile Lys
            725                 730                 735

Lys Glu Glu Phe Thr Glu Ile Met Lys Ile Cys Ser Thr Ile Glu Glu
            740                 745                 750
```

Leu Arg Arg Gln Lys
        755

<210> SEQ ID NO 12
<211> LENGTH: 716
<212> TYPE: PRT
<213> ORGANISM: Influenza A

<400> SEQUENCE: 12

Met Glu Asp Phe Val Arg Gln Cys Phe Asn Pro Met Ile Val Glu Leu
1               5                   10                  15

Ala Glu Lys Thr Met Lys Glu Tyr Gly Glu Asp Leu Lys Ile Glu Thr
            20                  25                  30

Asn Lys Phe Ala Ala Ile Cys Thr His Leu Glu Val Cys Phe Met Tyr
        35                  40                  45

Ser Asp Phe His Phe Ile Asn Glu Gln Gly Glu Ser Ile Ile Val Glu
    50                  55                  60

Leu Gly Asp Pro Asn Ala Leu Leu Lys His Arg Phe Glu Ile Ile Glu
65                  70                  75                  80

Gly Arg Asp Arg Thr Met Ala Trp Thr Val Val Asn Ser Ile Cys Asn
                85                  90                  95

Thr Thr Gly Ala Glu Lys Pro Lys Phe Leu Pro Asp Leu Tyr Asp Tyr
            100                 105                 110

Lys Glu Asn Arg Phe Ile Glu Ile Gly Val Thr Arg Arg Glu Val His
        115                 120                 125

Ile Tyr Tyr Leu Glu Lys Ala Asn Lys Ile Lys Ser Glu Lys Thr His
    130                 135                 140

Ile His Ile Phe Ser Phe Thr Gly Glu Glu Met Ala Thr Arg Ala Asp
145                 150                 155                 160

Tyr Thr Leu Asp Glu Glu Ser Arg Ala Arg Ile Lys Thr Arg Leu Phe
                165                 170                 175

Thr Ile Arg Gln Glu Met Ala Ser Arg Gly Leu Trp Asp Ser Phe Arg
            180                 185                 190

Gln Ser Glu Arg Gly Glu Glu Thr Ile Glu Glu Arg Phe Glu Ile Thr
        195                 200                 205

Gly Thr Met Arg Lys Leu Ala Asp Gln Ser Leu Pro Pro Asn Phe Ser
    210                 215                 220

Ser Leu Glu Asn Phe Arg Ala Tyr Val Asp Gly Phe Glu Pro Asn Gly
225                 230                 235                 240

Tyr Ile Glu Gly Lys Leu Ser Gln Met Ser Lys Glu Val Asn Ala Arg
                245                 250                 255

Ile Glu Pro Phe Leu Lys Thr Thr Pro Arg Pro Leu Arg Leu Pro Asn
            260                 265                 270

Gly Pro Pro Cys Ser Gln Arg Ser Lys Phe Leu Leu Met Asp Ala Leu
        275                 280                 285

Lys Leu Ser Ile Glu Asp Pro Ser His Glu Gly Glu Gly Ile Pro Leu
    290                 295                 300

Tyr Asp Ala Ile Lys Cys Met Arg Thr Phe Phe Gly Trp Lys Glu Pro
305                 310                 315                 320

Asn Val Val Lys Pro His Glu Lys Gly Ile Asn Pro Asn Tyr Leu Leu
                325                 330                 335

Ser Trp Lys Gln Val Leu Ala Glu Leu Gln Asp Ile Glu Asn Glu Glu
            340                 345                 350

Lys Ile Pro Lys Thr Lys Asn Met Lys Lys Thr Ser Gln Leu Lys Trp
        355                 360                 365

```
Ala Leu Gly Glu Asn Met Ala Pro Glu Lys Val Asp Phe Asp Asp Cys
        370                 375                 380

Lys Asp Val Gly Asp Leu Lys Gln Tyr Asp Ser Asp Glu Pro Glu Leu
385                 390                 395                 400

Arg Ser Leu Ala Ser Trp Ile Gln Asn Glu Phe Asn Lys Ala Cys Glu
                405                 410                 415

Leu Thr Asp Ser Ser Trp Ile Glu Leu Asp Glu Ile Gly Glu Asp Val
            420                 425                 430

Ala Pro Ile Glu His Ile Ala Ser Met Arg Arg Asn Tyr Phe Thr Ser
        435                 440                 445

Glu Val Ser His Cys Arg Ala Thr Glu Tyr Ile Met Lys Gly Val Tyr
    450                 455                 460

Ile Asn Thr Ala Leu Leu Asn Ala Ser Cys Ala Ala Met Asp Asp Phe
465                 470                 475                 480

Gln Leu Ile Pro Met Ile Ser Lys Cys Arg Thr Lys Glu Gly Arg Arg
                485                 490                 495

Lys Thr Asn Leu Tyr Gly Phe Ile Ile Lys Gly Arg Ser His Leu Arg
            500                 505                 510

Asn Asp Thr Asp Val Val Asn Phe Val Ser Met Glu Phe Ser Leu Thr
        515                 520                 525

Asp Pro Arg Leu Glu Pro His Lys Trp Glu Lys Tyr Cys Val Leu Glu
    530                 535                 540

Ile Gly Asp Met Leu Leu Arg Ser Ala Ile Gly Gln Val Ser Arg Pro
545                 550                 555                 560

Met Phe Leu Tyr Val Arg Thr Asn Gly Thr Ser Lys Ile Lys Met Lys
                565                 570                 575

Trp Gly Met Glu Met Arg Arg Cys Leu Leu Gln Ser Leu Gln Gln Ile
            580                 585                 590

Glu Ser Met Ile Glu Ala Glu Ser Ser Val Lys Glu Lys Asp Met Thr
        595                 600                 605

Lys Glu Phe Phe Glu Asn Lys Ser Glu Thr Trp Pro Ile Gly Glu Ser
    610                 615                 620

Pro Lys Gly Val Glu Glu Ser Ser Ile Gly Lys Val Cys Arg Thr Leu
625                 630                 635                 640

Leu Ala Lys Ser Val Phe Asn Ser Leu Tyr Ala Ser Pro Gln Leu Glu
                645                 650                 655

Gly Phe Ser Ala Glu Ser Arg Lys Leu Leu Leu Ile Val Gln Ala Leu
            660                 665                 670

Arg Asp Asn Leu Glu Pro Gly Thr Phe Asp Leu Gly Gly Leu Tyr Glu
        675                 680                 685

Ala Ile Glu Glu Cys Leu Ile Asn Asp Pro Trp Val Leu Leu Asn Ala
    690                 695                 700

Ser Trp Phe Asn Ser Phe Leu Thr His Ala Leu Ser
705                 710                 715

<210> SEQ ID NO 13
<211> LENGTH: 498
<212> TYPE: PRT
<213> ORGANISM: Influenza A

<400> SEQUENCE: 13

Met Ala Ser Gln Gly Thr Lys Arg Ser Tyr Glu Gln Met Glu Thr Asp
1               5                   10                  15

Gly Glu Arg Gln Asn Ala Thr Glu Ile Arg Ala Ser Val Gly Lys Met
```

-continued

```
                20                  25                  30
Ile Gly Gly Ile Gly Arg Phe Tyr Ile Gln Met Cys Thr Glu Leu Lys
            35                  40                  45

Leu Ser Asp Tyr Glu Gly Arg Leu Ile Gln Asn Ser Leu Thr Ile Glu
 50                  55                  60

Arg Met Val Leu Ser Ala Phe Asp Glu Arg Asn Lys Tyr Leu Glu
 65              70                  75                  80

Glu His Pro Ser Ala Gly Lys Asp Pro Lys Thr Gly Gly Pro Ile
                85                  90                  95

Tyr Arg Arg Val Asn Gly Lys Trp Met Arg Glu Leu Ile Leu Tyr Asp
                100                 105                 110

Lys Glu Glu Ile Arg Arg Ile Trp Arg Gln Ala Asn Gly Asp Asp
                115                 120                 125

Ala Thr Ala Gly Leu Thr His Met Met Ile Trp His Ser Asn Leu Asn
            130                 135                 140

Asp Ala Thr Tyr Gln Arg Thr Arg Ala Leu Val Arg Thr Gly Met Asp
145                 150                 155                 160

Pro Arg Met Cys Ser Leu Met Gln Gly Ser Thr Leu Pro Arg Arg Ser
                165                 170                 175

Gly Ala Ala Gly Ala Ala Val Lys Gly Val Gly Thr Met Val Met Glu
                180                 185                 190

Leu Val Arg Met Ile Lys Arg Gly Ile Asn Asp Arg Asn Phe Trp Arg
                195                 200                 205

Gly Glu Asn Gly Arg Lys Thr Arg Ile Ala Tyr Glu Arg Met Cys Asn
                210                 215                 220

Ile Leu Lys Gly Lys Phe Gln Thr Ala Ala Gln Lys Ala Met Met Asp
225                 230                 235                 240

Gln Val Arg Glu Ser Arg Asn Pro Gly Asn Ala Glu Phe Glu Asp Leu
                245                 250                 255

Thr Phe Leu Ala Arg Ser Ala Leu Ile Leu Arg Gly Ser Val Ala His
                260                 265                 270

Lys Ser Cys Leu Pro Ala Cys Val Tyr Gly Pro Ala Val Ala Ser Gly
                275                 280                 285

Tyr Asp Phe Glu Arg Glu Gly Tyr Ser Leu Val Gly Ile Asp Pro Phe
                290                 295                 300

Arg Leu Leu Gln Asn Ser Gln Val Tyr Ser Leu Ile Arg Pro Asn Glu
305                 310                 315                 320

Asn Pro Ala His Lys Ser Gln Leu Val Trp Met Ala Cys His Ser Ala
                325                 330                 335

Ala Phe Glu Asp Leu Arg Val Leu Ser Phe Ile Lys Gly Thr Lys Val
                340                 345                 350

Val Pro Arg Gly Lys Leu Ser Thr Arg Gly Val Gln Ile Ala Ser Asn
                355                 360                 365

Glu Asn Met Glu Thr Met Glu Ser Ser Thr Leu Glu Leu Arg Ser Arg
                370                 375                 380

Tyr Trp Ala Ile Arg Thr Arg Ser Gly Gly Asn Thr Asn Gln Gln Arg
385                 390                 395                 400

Ala Ser Ala Gly Gln Ile Ser Ile Gln Pro Thr Phe Ser Val Gln Arg
                405                 410                 415

Asn Leu Pro Phe Asp Arg Thr Thr Val Met Ala Ala Phe Thr Gly Asn
                420                 425                 430

Thr Glu Gly Arg Thr Ser Asp Met Arg Thr Glu Ile Ile Arg Met Met
                435                 440                 445
```

Glu Ser Ala Arg Pro Glu Asp Val Ser Phe Gln Gly Arg Gly Val Phe
       450                 455                 460

Glu Leu Ser Asp Glu Lys Ala Ala Ser Pro Ile Val Pro Ser Phe Asp
465                 470                 475                 480

Met Ser Asn Glu Gly Ser Tyr Phe Phe Gly Asp Asn Ala Glu Glu Tyr
                485                 490                 495

Asp Asn

<210> SEQ ID NO 14
<211> LENGTH: 252
<212> TYPE: PRT
<213> ORGANISM: Influenza A

<400> SEQUENCE: 14

Met Ser Leu Leu Thr Glu Val Glu Thr Tyr Val Leu Ser Ile Ile Pro
1               5                   10                  15

Ser Gly Pro Leu Lys Ala Glu Ile Ala Gln Arg Leu Glu Asp Val Phe
                20                  25                  30

Ala Gly Lys Asn Thr Asp Leu Glu Val Leu Met Glu Trp Leu Lys Thr
            35                  40                  45

Arg Pro Ile Leu Ser Pro Leu Thr Lys Gly Ile Leu Gly Phe Val Phe
    50                  55                  60

Thr Leu Thr Val Pro Ser Glu Arg Gly Leu Gln Arg Arg Arg Phe Val
65                  70                  75                  80

Gln Asn Ala Leu Asn Gly Asn Gly Asp Pro Asn Asn Met Asp Lys Ala
                85                  90                  95

Val Lys Leu Tyr Arg Lys Leu Lys Arg Glu Ile Thr Phe His Gly Ala
            100                 105                 110

Lys Glu Ile Ser Leu Ser Tyr Ser Ala Gly Ala Leu Ala Ser Cys Met
        115                 120                 125

Gly Leu Ile Tyr Asn Arg Met Gly Ala Val Thr Thr Glu Val Ala Phe
    130                 135                 140

Gly Leu Val Cys Ala Thr Cys Glu Gln Ile Ala Asp Ser Gln His Arg
145                 150                 155                 160

Ser His Arg Gln Met Val Thr Thr Thr Asn Pro Leu Ile Arg His Glu
                165                 170                 175

Asn Arg Met Val Leu Ala Ser Thr Thr Ala Lys Ala Met Glu Gln Met
            180                 185                 190

Ala Gly Ser Ser Glu Gln Ala Ala Glu Ala Met Glu Val Ala Ser Gln
        195                 200                 205

Ala Arg Gln Met Val Gln Ala Met Arg Thr Ile Gly Thr His Pro Ser
    210                 215                 220

Ser Ser Ala Gly Leu Lys Asn Asp Leu Leu Glu Asn Leu Gln Ala Tyr
225                 230                 235                 240

Gln Lys Arg Met Gly Val Gln Met Gln Arg Phe Lys
                245                 250

<210> SEQ ID NO 15
<211> LENGTH: 469
<212> TYPE: PRT
<213> ORGANISM: Influenza A

<400> SEQUENCE: 15

Met Asn Pro Asn Gln Lys Ile Ile Thr Ile Gly Ser Val Cys Met Thr
1               5                   10                  15

-continued

```
Ile Gly Met Ala Asn Leu Ile Leu Gln Ile Gly Asn Ile Ile Ser Ile
            20                  25                  30
Trp Ile Ser His Ser Ile Gln Leu Gly Asn Gln Asn Gln Ile Glu Thr
        35                  40                  45
Cys Asn Gln Ser Val Ile Thr Tyr Glu Asn Asn Thr Trp Val Asn Gln
50                  55                  60
Thr Tyr Val Asn Ile Ser Asn Thr Asn Phe Ala Ala Gly Gln Ser Val
65                  70                  75                  80
Val Ser Val Lys Leu Ala Gly Asn Ser Ser Leu Cys Pro Val Ser Gly
                85                  90                  95
Trp Ala Ile Tyr Ser Lys Asp Asn Ser Val Arg Ile Gly Ser Lys Gly
            100                 105                 110
Asp Val Phe Val Ile Arg Glu Pro Phe Ile Ser Cys Ser Pro Leu Glu
        115                 120                 125
Cys Arg Thr Phe Phe Leu Thr Gln Gly Ala Leu Leu Asn Asp Lys His
130                 135                 140
Ser Asn Gly Thr Ile Lys Asp Arg Ser Pro Tyr Arg Thr Leu Met Ser
145                 150                 155                 160
Cys Pro Ile Gly Glu Val Pro Ser Pro Tyr Asn Ser Arg Phe Glu Ser
                165                 170                 175
Val Ala Trp Ser Ala Ser Ala Cys His Asp Gly Ile Asn Trp Leu Thr
            180                 185                 190
Ile Gly Ile Ser Gly Pro Asp Asn Gly Ala Val Ala Val Leu Lys Tyr
        195                 200                 205
Asn Gly Ile Ile Thr Asp Thr Ile Lys Ser Trp Arg Asn Asn Ile Leu
210                 215                 220
Arg Thr Gln Glu Ser Glu Cys Ala Cys Val Asn Gly Ser Cys Phe Thr
225                 230                 235                 240
Val Met Thr Asp Gly Pro Ser Asn Gly Gln Ala Ser Tyr Lys Ile Phe
                245                 250                 255
Arg Ile Glu Lys Gly Lys Ile Val Lys Ser Val Glu Met Asn Ala Pro
            260                 265                 270
Asn Tyr His Tyr Glu Glu Cys Ser Cys Tyr Pro Asp Ser Ser Glu Ile
        275                 280                 285
Thr Cys Val Cys Arg Asp Asn Trp His Gly Ser Asn Arg Pro Trp Val
290                 295                 300
Ser Phe Asn Gln Asn Leu Glu Tyr Gln Ile Gly Tyr Ile Cys Ser Gly
305                 310                 315                 320
Ile Phe Gly Asp Asn Pro Arg Pro Asn Asp Lys Thr Gly Ser Cys Gly
                325                 330                 335
Pro Val Ser Ser Asn Gly Ala Asn Gly Val Lys Gly Phe Ser Phe Lys
            340                 345                 350
Tyr Gly Asn Gly Val Trp Ile Gly Arg Thr Lys Ser Ile Ser Ser Arg
        355                 360                 365
Asn Gly Phe Glu Met Ile Trp Asp Pro Asn Gly Trp Thr Gly Thr Asp
370                 375                 380
Asn Asn Phe Ser Ile Lys Gln Asp Ile Val Gly Ile Asn Glu Trp Ser
385                 390                 395                 400
Gly Tyr Ser Gly Ser Phe Val Gln His Pro Glu Leu Thr Gly Leu Asp
                405                 410                 415
Cys Ile Arg Pro Cys Phe Trp Val Glu Leu Ile Arg Gly Arg Pro Lys
            420                 425                 430
Glu Asn Thr Ile Trp Thr Ser Gly Ser Ser Ile Ser Phe Cys Gly Val
```

```
              435                 440                 445
Asn Ser Asp Thr Val Gly Trp Ser Trp Pro Asp Gly Ala Glu Leu Pro
    450                 455                 460

Phe Thr Ile Asp Lys
465

<210> SEQ ID NO 16
<211> LENGTH: 470
<212> TYPE: PRT
<213> ORGANISM: Influenza A

<400> SEQUENCE: 16

Met Asn Pro Asn Gln Lys Leu Phe Ala Leu Ser Gly Val Ala Ile Ala
1               5                   10                  15

Leu Ser Ile Leu Asn Leu Leu Ile Gly Ile Ser Asn Val Gly Leu Asn
            20                  25                  30

Val Ser Leu His Leu Lys Gly Ser Ser Asp Gln Asp Lys Asn Trp Thr
        35                  40                  45

Cys Thr Ser Val Thr Gln Asn Asn Thr Thr Leu Ile Glu Asn Thr Tyr
    50                  55                  60

Val Asn Asn Thr Thr Val Ile Asp Lys Glu Thr Gly Thr Ala Lys Pro
65                  70                  75                  80

Asn Tyr Leu Met Leu Asn Lys Ser Leu Cys Lys Val Glu Gly Trp Val
                85                  90                  95

Val Val Ala Lys Asp Asn Ala Ile Arg Phe Gly Glu Ser Glu Gln Ile
            100                 105                 110

Ile Val Thr Arg Glu Pro Tyr Val Ser Cys Asp Pro Leu Gly Cys Lys
        115                 120                 125

Met Tyr Ala Leu His Gln Gly Thr Thr Ile Arg Asn Lys His Ser Asn
    130                 135                 140

Gly Thr Ile His Asp Arg Thr Ala Phe Arg Gly Leu Ile Ser Thr Pro
145                 150                 155                 160

Leu Gly Ser Pro Pro Val Val Ser Asn Ser Asp Phe Leu Cys Val Gly
                165                 170                 175

Trp Ser Ser Thr Ser Cys His Asp Gly Ile Gly Arg Met Thr Ile Cys
            180                 185                 190

Val Gln Gly Asn Asn Asp Asn Ala Thr Ala Thr Val Tyr Tyr Asp Arg
        195                 200                 205

Arg Leu Thr Thr Thr Ile Lys Thr Trp Ala Gly Asn Ile Leu Arg Thr
    210                 215                 220

Gln Glu Ser Glu Cys Val Cys His Asn Gly Thr Cys Val Val Ile Met
225                 230                 235                 240

Thr Asp Gly Ser Ala Ser Ser Gln Ala Tyr Thr Lys Val Leu Tyr Phe
                245                 250                 255

His Lys Gly Leu Val Ile Lys Glu Glu Ala Leu Lys Gly Ser Ala Arg
            260                 265                 270

His Ile Glu Glu Cys Ser Cys Tyr Gly His Asn Ser Lys Val Thr Cys
        275                 280                 285

Val Cys Arg Asp Asn Trp Gln Gly Ala Asn Arg Pro Val Ile Glu Ile
    290                 295                 300

Asp Met Asn Ala Met Glu His Thr Ser Gln Tyr Leu Cys Thr Gly Val
305                 310                 315                 320

Leu Thr Asp Thr Ser Arg Pro Ser Asp Lys Ser Met Gly Asp Cys Asn
                325                 330                 335
```

```
Asn Pro Ile Thr Gly Ser Pro Gly Ala Pro Gly Val Lys Gly Phe Gly
                    340                 345                 350

Phe Leu Asp Ser Ser Asn Thr Trp Leu Gly Arg Thr Ile Ser Pro Arg
            355                 360                 365

Ser Arg Ser Gly Phe Glu Met Leu Lys Ile Pro Asn Ala Glu Thr Asp
        370                 375                 380

Pro Asn Ser Lys Ile Thr Glu Arg Gln Glu Ile Val Asp Asn Asn Asn
385                 390                 395                 400

Trp Ser Gly Tyr Ser Gly Ser Phe Ile Asp Tyr Trp Asp Glu Ser Ser
                405                 410                 415

Glu Cys Tyr Asn Pro Cys Phe Tyr Val Glu Leu Ile Arg Gly Arg Pro
            420                 425                 430

Glu Glu Ala Lys Tyr Val Gly Trp Thr Ser Asn Ser Leu Ile Ala Leu
        435                 440                 445

Cys Gly Ser Pro Ile Ser Val Gly Ser Gly Ser Phe Pro Asp Gly Ala
    450                 455                 460

Gln Ile Gln Tyr Phe Ser
465                 470

<210> SEQ ID NO 17
<211> LENGTH: 465
<212> TYPE: PRT
<213> ORGANISM: Influenza A

<400> SEQUENCE: 17

Met Asn Pro Asn Gln Lys Ile Leu Cys Thr Ser Ala Thr Ala Ile Ile
1               5                   10                  15

Ile Gly Ala Ile Ala Val Leu Ile Gly Ile Ala Asn Leu Gly Leu Asn
            20                  25                  30

Ile Gly Leu His Leu Lys Pro Gly Cys Asn Cys Ser His Ser Gln Pro
        35                  40                  45

Glu Thr Thr Asn Thr Ser Gln Thr Ile Ile Asn Asn Tyr Tyr Asn Glu
    50                  55                  60

Thr Asn Ile Thr Asn Ile Gln Met Glu Glu Arg Thr Ser Arg Asn Phe
65                  70                  75                  80

Asn Asn Leu Thr Lys Gly Leu Cys Thr Ile Asn Ser Trp His Ile Tyr
                85                  90                  95

Gly Lys Asp Asn Ala Val Arg Ile Gly Glu Ser Ser Asp Val Leu Val
            100                 105                 110

Thr Arg Glu Pro Tyr Val Ser Cys Asp Pro Asp Glu Cys Arg Phe Tyr
        115                 120                 125

Ala Leu Ser Gln Gly Thr Thr Ile Arg Gly Lys His Ser Asn Gly Thr
    130                 135                 140

Ile His Asp Arg Ser Gln Tyr Arg Ala Leu Ile Ser Trp Pro Leu Ser
145                 150                 155                 160

Ser Pro Pro Thr Val Tyr Asn Ser Arg Val Glu Cys Ile Gly Trp Ser
                165                 170                 175

Ser Thr Ser Cys His Asp Gly Lys Ser Arg Met Ser Ile Cys Ile Ser
            180                 185                 190

Gly Pro Asn Asn Asn Ala Ser Ala Val Val Trp Tyr Asn Arg Arg Pro
        195                 200                 205

Val Ala Glu Ile Asn Thr Trp Ala Arg Asn Ile Leu Arg Thr Gln Glu
    210                 215                 220

Ser Glu Cys Val Cys His Asn Gly Val Cys Pro Val Val Phe Thr Asp
225                 230                 235                 240
```

```
Gly Ser Ala Thr Gly Pro Ala Asp Thr Arg Ile Tyr Tyr Phe Lys Glu
            245                 250                 255

Gly Lys Ile Leu Lys Trp Glu Ser Leu Thr Gly Thr Ala Lys His Ile
            260                 265                 270

Glu Glu Cys Ser Cys Tyr Gly Glu Arg Thr Gly Ile Thr Cys Thr Cys
            275                 280                 285

Arg Asp Asn Trp Gln Gly Ser Asn Arg Pro Val Ile Gln Ile Asp Pro
            290                 295                 300

Val Ala Met Thr His Thr Ser Gln Tyr Ile Cys Ser Pro Val Leu Thr
305                 310                 315                 320

Asp Asn Pro Arg Pro Asn Asp Pro Asn Ile Gly Lys Cys Asn Asp Pro
            325                 330                 335

Tyr Pro Gly Asn Asn Asn Asn Gly Val Lys Gly Phe Ser Tyr Leu Asp
            340                 345                 350

Gly Ala Asn Thr Trp Leu Gly Arg Thr Ile Ser Thr Ala Ser Arg Ser
            355                 360                 365

Gly Tyr Glu Met Leu Lys Val Pro Asn Ala Leu Thr Asp Asp Arg Ser
            370                 375                 380

Lys Pro Ile Gln Gly Gln Thr Ile Val Leu Asn Ala Asp Trp Ser Gly
385                 390                 395                 400

Tyr Ser Gly Ser Phe Met Asp Tyr Trp Ala Glu Gly Asp Cys Tyr Arg
            405                 410                 415

Ala Cys Phe Tyr Val Glu Leu Ile Arg Gly Arg Pro Lys Glu Asp Lys
            420                 425                 430

Val Trp Trp Thr Ser Asn Ser Ile Val Ser Met Cys Ser Ser Thr Glu
            435                 440                 445

Phe Leu Gly Gln Trp Asn Trp Pro Asp Gly Ala Lys Ile Glu Tyr Phe
            450                 455                 460

Leu
465

<210> SEQ ID NO 18
<211> LENGTH: 469
<212> TYPE: PRT
<213> ORGANISM: Influenza A

<400> SEQUENCE: 18

Met Asn Pro Asn Gln Lys Ile Ile Thr Ile Gly Ser Val Ser Leu Thr
1               5                   10                  15

Ile Ser Thr Ile Cys Phe Phe Met Gln Ile Ala Ile Leu Ile Thr Thr
            20                  25                  30

Val Thr Leu His Phe Lys Gln Tyr Glu Phe Asn Ser Pro Pro Asn Asn
            35                  40                  45

Gln Val Met Leu Cys Glu Pro Thr Ile Ile Glu Arg Asn Ile Thr Glu
50                  55                  60

Ile Val Tyr Leu Thr Asn Thr Thr Ile Glu Lys Glu Ile Cys Pro Lys
65                  70                  75                  80

Leu Ala Glu Tyr Arg Asn Trp Ser Lys Pro Gln Cys Asn Ile Thr Gly
            85                  90                  95

Phe Ala Pro Phe Ser Lys Asp Asn Ser Ile Arg Leu Ser Ala Gly Gly
            100                 105                 110

Asp Ile Trp Val Thr Arg Glu Pro Tyr Val Ser Cys Asp Pro Asp Lys
            115                 120                 125

Cys Tyr Gln Phe Ala Leu Gly Gln Gly Thr Thr Leu Asn Asn Val His
```

```
                130                 135                 140
Ser Asn Asp Ile Val His Asp Arg Thr Pro Tyr Arg Thr Leu Leu Met
145                 150                 155                 160

Asn Glu Leu Gly Val Pro Phe His Leu Gly Thr Lys Gln Val Cys Ile
                165                 170                 175

Ala Trp Ser Ser Ser Cys His Asp Gly Lys Ala Trp Leu His Val
                180                 185                 190

Cys Val Thr Gly Asp Asp Glu Asn Ala Thr Ala Ser Phe Ile Tyr Asn
                195                 200                 205

Gly Arg Leu Ala Asp Ser Ile Val Ser Trp Ser Lys Lys Ile Leu Arg
            210                 215                 220

Thr Gln Glu Ser Glu Cys Val Cys Ile Asn Gly Thr Cys Thr Val Val
225                 230                 235                 240

Met Thr Asp Gly Ser Ala Ser Gly Lys Ala Asp Thr Lys Ile Leu Phe
                245                 250                 255

Ile Glu Glu Gly Lys Ile Val His Thr Ser Thr Leu Ser Gly Ser Ala
                260                 265                 270

Gln His Val Glu Glu Cys Ser Cys Tyr Pro Arg Tyr Pro Gly Val Arg
                275                 280                 285

Cys Val Cys Arg Asp Asn Trp Lys Gly Ser Asn Arg Pro Ile Val Asp
            290                 295                 300

Ile Asn Ile Lys Asp Tyr Ser Ile Val Ser Ser Tyr Val Cys Ser Gly
305                 310                 315                 320

Leu Val Gly Asp Thr Pro Arg Lys Asn Asp Ser Ser Ser Ser His
                325                 330                 335

Cys Leu Asp Pro Asn Asn Glu Glu Gly Gly His Gly Val Lys Gly Trp
                340                 345                 350

Ala Phe Asp Asp Gly Asn Asp Val Trp Met Gly Arg Thr Ile Ser Glu
                355                 360                 365

Lys Leu Arg Ser Gly Tyr Glu Thr Phe Lys Val Ile Glu Gly Trp Ser
            370                 375                 380

Asn Pro Asn Ser Lys Leu Gln Ile Asn Arg Gln Val Ile Val Asp Arg
385                 390                 395                 400

Gly Asn Arg Ser Gly Tyr Ser Gly Ile Phe Ser Val Glu Gly Lys Ser
                405                 410                 415

Cys Ile Asn Arg Cys Phe Tyr Val Glu Leu Ile Arg Gly Arg Lys Gln
                420                 425                 430

Glu Thr Glu Val Leu Trp Thr Ser Asn Ser Ile Val Val Phe Cys Gly
                435                 440                 445

Thr Ser Gly Thr Tyr Gly Thr Gly Ser Trp Pro Asp Gly Ala Asp Ile
            450                 455                 460

Asn Leu Met Pro Ile
465

<210> SEQ ID NO 19
<211> LENGTH: 1434
<212> TYPE: DNA
<213> ORGANISM: Influenza A

<400> SEQUENCE: 19
atgaatccaa atcaaaagat aataacgatt ggctctgttt ctctcaccat ttccacaata    60 tgcttttttca tgcaaattgc cattttgata actactgtaa cattgcattt caagcaatat   120
gaattcaact cccccccaaa caaccaagtg atgctgtgtg aaccaacaat aatagaaaga   180
```

-continued

```
aacataacag agatagtgta tttaaccaac accaccatag agaaggaaat atgccccaaa      240
ccagcagaat acagaaattg gtcaaaaccg caatgtggca ttacaggatt tgcacctttc      300
tctaaggaca attcgatcag gctttccgct ggtggggaca tctgggtgac aagagaacct      360
tatgtgtcat gcgatcctga caagtgttat caatttgccc ttggacaggg aacaacacta      420
aacaacgtgc attcaaataa caaagtacgt gataggaccc cttatcggac tctattgatg      480
aatgagttgg gtgttccttt ccatctgggg accaagcaag tgtgcatagc atggtccagc      540
tcaagttgtc acgatggaaa agcatggctg catgtttgta taacggggga tgataaaaat      600
gcaactgcta gcttcattta caatggggagg cttgtagata tgttgtttc atggtccaaa      660 gatattctca ggacccagga gtcagaatgc atttgtatca atggaacttg tacagtagta      720
atgactgatg gaagtgcttc aggaaaaagct gatactaaaa tactattcat tgaggagggg      780
aaaatcgttc atactagcac attgtcagga agtgctcagc atgtcgaaga gtgctcttgc      840
tatcctcgat atcctggtgt cagatgtgtc tgcagagaca actggaaggg ctccaatcgg      900
cccatcgtag atataaacat aaaggatcat agcattgttt ccagttatgt gtgttcagga      960
cttgttggag acacacccag aaaaaacgac agctccagca gtagccattg tttggatcct     1020
aacaatgaag aaggtggtca tggagtgaaa ggctgggcct tgatgatgg aaatgacgtg     1080 tggatgggaa gaacaatcaa cgagacgtca cgcttagggt atgaaacctt caaagtcatt     1140
gaaggctggt ccaaccctaa gtccaaattg cagacaaata gcaagtcat agttgacaga     1200 ggtgataggt ccggttattc tggtatttc tctgttgaag gcaaaagctg cataaatcgg     1260
tgcttttatg tggagttgat taggggaaga aaagaggaaa ctgaagtctt gtggacctca     1320
aacagtattg ttgtgttttg tggcacctca ggtacatatg aacaggctc atggcctgat     1380 ggggcggacc tcaatctcat gcctatataa gctttcgcaa ttttagaaaa aact          1434
```

<210> SEQ ID NO 20
<211> LENGTH: 1434
<212> TYPE: DNA
<213> ORGANISM: Influenza A

<400> SEQUENCE: 20

```
atgaatccaa atcaaaagat aataacgatt ggctctgttt ctctcaccat ttccacaata      60 tgcttttca tgcaaattgc cattttgata actactgtaa cattgcattt caagcaatat     120
gaattcaact ccccccccaaa caaccaagtg atgctgtgtg aaccaacaat aatagaaaga     180
aacataacag agatagtgta tttaaccaac accaccatag agaaggaaat atgccccaaa     240
ccagcagaat acagaaattg gtcaaaaccg caatgtggca ttacaggatt tgcacctttc     300
tctaaggaca attcgatcag gctttccgct ggtggggaca tctgggtgac aagagaacct     360
tatgtgtcat gcgatcctga caagtgttat caatttgccc ttggacaggg aacaacacta     420
aacaacgtgc attcaaataa caaagtacgt gaaaggaccc cttatcggac tctattgatg     480
aatgagttgg gtgttccttt ccatctgggg accaagcaag tgtgcatagc atggtccagc     540
tcaagttgtc acgatggaaa agcatggctg catgtttgta taacggggga tgataaaaat     600
gcaactgcta gcttcattta caatggggagg cttgtagata tgttgtttc atggtccaaa     660 gatattctca ggacccagga gtcagaatgc atttgtatca atggaacttg tacagtagta     720
atgactgatg gaagtgcttc aggaaaaagct gatactaaaa tactattcat tgaggagggg     780
aaaatcgttc atactagcac attgtcagga agtgctcagc atgtcgaaga gtgctcttgc     840
tatcctcgat atcctggtgt cagatgtgtc tgcagagaca actggaaggg ctccaatcgg     900
```

```
cccatcgtag atataaacat aaaggatcat agcattgttt ccagttatgt gtgttcagga    960
cttgttggag acacacccag aaaaaacgac agctccagca gtagccattg tttggatcct   1020
aacaatgaag aaggtggtgg cggagtgaaa ggctgggcct ttgatgatgg aaatgacgtg   1080
tggatgggaa gaacaatcaa cgagaagtca cgcttagggt atgaaacctt caaagtcatt   1140
gaaggctggt ccaaccctaa gtccaaattg cagacaaata ggcaagtcat agttgacaga   1200
ggtgataggt ccggttattc tggtattttc tctgttgaag gcaaaagctg cataaatcgg   1260
tgcttttatg tggagttgat taggggaaga aaagaggaaa ctgaagtctt gtggacctca   1320
aacagtattg ttgtgttttg tggcacctca ggtacatatg gaacaggctc atggcctgat   1380
ggggcggacc tcaatctcat gcctatataa gctttcgcaa ttttagaaaa aact         1434
```

<210> SEQ ID NO 21
<211> LENGTH: 1410
<212> TYPE: DNA
<213> ORGANISM: Influenza A

<400> SEQUENCE: 21

```
atgaatccaa atcaaaagat aataacgatt ggctctgttt ctctcaccat ttccacaata     60
tgcttcttca tgcaaattgc catcctgata actactgtaa cattgcattt caagcaatat    120
gaattcaact cccccccaaa caaccaagtg atgctgtgtg aaccaacaat aatagaaaga    180
aacataacag agatagtgta tttgaccaac accaccatag agaaggaaat atgccccaaa    240
ccagcagaat acagaaattg gtcaaaaccg caatgtggca ttacaggatt tgcacctttc    300
tctaaggaca attcgattag ctttccgct ggtgggggaca tctgggtgac aagagaacct    360
tatgtgtcat gcgatcctga caagtgttat caatttgccc ttggacaggg aacaacacta    420
aacaacgtgc attcaaataa cacagtacgt gataggaccc cttatcggac tctattgatg    480
aatgagttgg gtgttccttt ccatctgggg accaagcaag tgtgcatagc atggtccagc    540
tcaagttgtc acgatggaaa agcatggctg catgtttgta taacggggga tgataaaaat    600
gcaactgcta gcttcattta caatgggagg cttgtagata gtgttgtttc atggtccaaa    660
gatattctca ggacccagga gtcagaatgc gtttgtatca atggaacttg tacagtagta    720
atgactgatg gaaatgctac aggaaaagct gatactaaaa tactattcat tgaggagggg    780
aaaatcgttc atactagcaa attgtcagga agtgctcagc atgtcgaaga gtgctcttgc    840
tatcctcgat atcctggtgt cagatgtgtc tgcagagaca actggaaagg atccaaccgg    900
cccatcgtag atataaacat aaaggatcat agcattgttt ccagttatgt gtgttcagga    960
cttgttggag acacacccag aaaaaacgac agctccagca gtagccattg tttgaatcct   1020
aacaatgaag aaggtggtca tggagtgaaa ggctgggcct ttgatgatgg aaatgacgtg   1080
tggatgggga gaacaatcaa cgagacgtca cgcttagggt atgaaacctt caaagtcgtt   1140
gaaggctggt ccaaccctaa gtccaaattg cagataaata ggcaagtcat agttgacaga   1200
ggtgataggt ccggttattc tggtattttc tctgttgaag gcaaaagctg catcaatcgg   1260
tgcttttatg tggagttgat taggggaaga aaagaggaaa ctgaagtctt gtggacctca   1320
aacagtattg ttgtgttttg tggcacctca ggtacatatg gaacaggctc atggcctgat   1380
ggggcggacc tcaatctcat gcatatataa                                     1410
```

<210> SEQ ID NO 22
<211> LENGTH: 1410
<212> TYPE: DNA

<213> ORGANISM: Influenza A

<400> SEQUENCE: 22

```
atgaatccaa atcaaaagat aataacgatt ggctctgttt ctctcaccat ttccacaata    60
tgcttcttca tgcaaattgc catcctgata actactgtaa cattgcattt caagcaatat   120
gaattcaact cccccccaaa caaccaagtg atgctgtgtg aaccaacaat aatagaaaga   180
aacataacag atagtgta tttgaccaac accaccatag agaaggaaat atgccccaaa    240
ccagcagaat acagaaattg gtcaaaaccg caatgtggca ttacaggatt tgcacctttc   300
tctaaggaca attcgattag cttttccgct ggtggggaca tctgggtgac aagagaacct   360
tatgtgtcat gcgatcctga caagtgttat caatttgccc ttggacaggg aacaacacta   420
aacaacgtgc attcaaataa caaagtacgt gagggaccc cttatcggac tctattgatg    480
aatgagttgg gtgttccttt ccatctgggg accaagcaag tgtgcatagc atggtccagc   540
tcaagttgtc acgatggaaa agcatggctg catgtttgta acgggggga tgataaaaat   600
gcaactgcta gcttcattta caatgggagg cttgtagata gtgttgtttc atggtccaaa   660
gatattctca ggacccagga gtcagaatgc gtttgtatca atggaacttg tacagtagta   720
atgactgatg gaagtgctac aggaaaagct gatactaaaa tactattcat tgaggagggg   780
aaaatcgttc atactagcaa attgtcagga agtgctcagc atgtcgaaga gtgctcttgc   840
tatcctcgat atcctggtgt cagatgtgtc tgcagagaca actggaaagg atccaaccgg   900
cccatcgtag atataaacat aaaggatcat agcattgttt ccagttatgt gtgttcagga   960
cttgttggag acacacccag aaaaaacgac agctccagca gtagccattg tttgaatcct  1020
aacaatgaag aaggtgttca tggagtgaaa ggctgggcct ttgatgatgg aaatgacgtg  1080
tggatgggga gaacaatcaa cgagaagtca cgcttagggt atgaaacctt caaagtcgtt  1140
gaaggctggt ccaaccctaa gtccaaattg cagataaata ggcaagtcat agttgacaga  1200
ggtgataggt ccggttattc tggtattttc tctgttgaag caaaagctg catcaatcgg   1260
tgcttttatg tggagttgat taggggaaga aaagaggaaa ctgaagtctt gtggacctca  1320
aacagtattg ttgtgttttg tggcacctca ggtacatatg aacaggctc atggcctgat  1380
ggggcggacc tcaatctcat gcatatataa                                   1410
```

<210> SEQ ID NO 23
<211> LENGTH: 1411
<212> TYPE: DNA
<213> ORGANISM: Influenza A

<400> SEQUENCE: 23

```
atgaatccaa atcaaaagat aataacgatt ggctctgttt ctctcacaat ttccacaata    60
tgcttcttca tgcaaattgc catcctgata actactgtaa cattgcattt caagcaatat   120
gaattcaact cccccccaaa taaccaagtg atgctgtgtg aaccaacaat aatagaaaga   180
aacataacag atagtgta tttgaccaac accaccatag agaaggaaat atgccccaaa    240
ccagcagaat acagaaattg gtcaaaaccg caatgtggca ttacaggatt tgcacctttc   300
tctaaagaca attcgattag cttttccgct ggtggggaca tctgggtgac aagagaacct   360
tatgtgtcat gcgatcttga caagtgttat caatttgccc ttggacaggg aacaacacta   420
aacaacgtgc attcaaataa cacagtacgt gataggaccc cttatcggac tctattgatg   480
aatgagttgg gtgttccttt ccatctgggg accaagcaag tgtgcatagc atggtccagc   540
tcaagttgtc acgatggaaa agcatggctg catgtttgta acgggggga tgataaaaat   600
```

```
gcaactgcta gcttcattta cawatgggag gcttgtagat agtgttgttt catggtcc

| | |
|---|---|
| tgcttttatg tggagttgat taggggaaga aaagaggaaa ctgaagtctt gtggacctca | 1320 |
| aacagtattg ttgtgttttg tggcacctca ggtacatatg aacaggctc atggcctgat | 1380 |
| ggggcggacc tcaatctcat gcatatataa | 1410 |

<210> SEQ ID NO 25
<211> LENGTH: 1434
<212> TYPE: DNA
<213> ORGANISM: Influenza A

<400> SEQUENCE: 25

| | |
|---|---|
| atgaatccaa atcaaaagat aataacgatt ggctctgttt ctctcacaat ttccacaata | 60 |
| tgcttcttca tgcaaattgc catcctgata actactgtaa cattgcattt caagcaatat | 120 |
| gaattcaact ccccccccaaa taccaagtg atgctgtgtg aaccaacaat aatagaaaga | 180 |
| aacataacag agatagtgta tttgaccaac accaccatag agaaggaaat atgccccaaa | 240 |
| ccagcagaat acagaaattg gtcaaaaccg caatgtggca ttacaggatt tgcacctttc | 300 |
| tctaaggaca attcgattag ctttccgct ggtggggaca tctgggtgac aagagaacct | 360 |
| tatgtgtcat gcgatcttga caagtgttat caatttgccc ttggacaggg aacaacacta | 420 |
| aacaacgtgc attcaaataa cacagtacgt gataggaccc cttatcggac tctattgatg | 480 |
| aatgagttgg gtgttccttt ccatctgggg accaagcaag tgtgcatagc atggtccagc | 540 |
| tcaagttgtc acgatggaaa agcatggctg catgtttgta taacggggga tgataaaaat | 600 |
| gcaactgcta gcttcattta caatgggagg cttgtagata gtgttgtctc atggtccaat | 660 |
| gatattctca ggacccagga atcagaatgc gtttgtatca atggaacttg tacagtagta | 720 |
| atgactgatg gaaatgctac aggaaaagct gatactaaaa tactattcat tgaggagggg | 780 |
| aaaatcgttc atactagcaa attgtcagga agtgctcagc atgtcgaaga gtgctcttgc | 840 |
| tatcctcgat atcctggtgt cagatgtgtc tgcagagaca ctggaaagg atccaaccgg | 900 |
| cccatcatag atataaacat aaaggatcat agcattgttt ccagttatgt gtgttcagga | 960 |
| cttgttggag acacacccag aaaaagcgac agctccagca gtagccattg tttgaatcct | 1020 |
| aacaatgaag aaggtggtca tggagtgaaa ggctgggcct tgatgatgg aaatgacgtg | 1080 |
| tggatgggga gaacaatcaa cgagacgtca cgcttagggt atgaaacctt caaagtcgtt | 1140 |
| gaaggctggt ccaaccctaa gtccaaattg cagataaata gcaagtctt agttgacaga | 1200 |
| ggtgataggt ccggttattc tggtattttc tctgttgaag gcaaaagctg catcaatcgg | 1260 |
| tgcttttatg tggagttgat taggggaaga aaagaggaaa ctgaagtctt gtggacctca | 1320 |
| aacagtattg ttgtgttttg tggcacctca ggtacatatg aacaggctc atggcctgat | 1380 |
| ggggcggacc tcaatctcat gcatatataa gctttcgcaa ttttagaaaa aact | 1434 |

<210> SEQ ID NO 26
<211> LENGTH: 1448
<212> TYPE: DNA
<213> ORGANISM: Influenza A

<400> SEQUENCE: 26
atgaatccaa atcaaaagat aataacgatt ggctctgttt ctctcacaat ttccacaata 60
tgcttcttca tgcaaattgc catcctgata actactgtaa cattgcattt caagcaatat 120
gaattcaact cccccccaaa taaccaagtg atgctgtgtg aaccaacaat aatagaaaga 180
aacataacag agatagtgta tttgaccaac accaccatag agaaggaaat atgccccaaa 240
ccagcagaat acagaaattg gtcaaaaccg caatgtggca ttacaggatt tgcacctttc 300

```
tctaaggaca attcgattag ctttccgct ggtggggaca tctgggtgac aagagaacct      360
tatgtgtcat gcgatcttga caagtgttat caatttgccc ttggacaggg aacaacacta      420
aacaacgtgc attcaaataa cacagtacgt gataggaccc cttatcggac tctattgatg      480
aatgagttgg gtgttccttt ccatctgggg accaagcaag tgtgcatagc atggtccagc      540
tcaagttgtc acgatggaaa agcatggctg catgtttgta taacggggga tgataaaaat      600
gcaactgcta gcttcattta caatgggagg cttgtagata tgttgtttc atggtccaac      660 gatattctca ggacccagga gtcagaatgc gtttgtatca atggaacttg tacagtagta      720
atgactgatg gaaatgctac aggaaaggct gacactaaaa tactattcat tgaggagggg      780
aaaatcgtac atactagcaa attgtcagga agtgctcagc atgtcgaaga gtgctcttgc      840
tatcctcgat atcctggtgt cagatgtgtc tgcagagaca actggaaagg atccaaccgg      900
cccatcatag atataaacat aaaggatcat agcattgttt ccaggtatgt gtgttcagga      960
cttgttggag acacacccag aaaaagcgac agctccagca gtagccattg tttgaaccct     1020
aacaatgaaa aaggtggtca tggagtgaaa ggctgggcct ttgatgatgg aaatgacgtg     1080
tggatgggga gaacaatcaa cgagacgtca cgcttagggt atgaaacctt caaagtcgtt     1140
gaaggctggt ccaaccctaa gtccaaattg cagataaata ggcaagtcat agttgacaga     1200
ggtgataggt ccggttattc tggtattttc tctgttgaag gcaaaagctg catcaatcgg     1260
tgcttttatg trgagttgat taggggaaga aaagaggaaa ctgaagtctt gtggacctca     1320
aacagtattg ttgtgttttg tggcacctca ggtacatatg aacaggctc atggcctgat     1380 ggggcggacc tcaatctcat gcatatataa gctttcgcaa ttttagaaaa aactccttgt     1440
ttctactg                                                              1448

<210> SEQ ID NO 27
<211> LENGTH: 1448
<212> TYPE: DNA
<213> ORGANISM: Influenza A

<400> SEQUENCE: 27
atgaatccaa atcaaaagat aataacgatt ggctctgttt ctctcacaat ttccacaata      60
tgcttcttca tgcaaattgc catcctgata actactgtaa cattgcattt caagcaatat      120
gaattcaact cccccccaaa taaccaagtg atgctgtgtg aaccaacaat aatagaaaga      180
aacataacag agatagtgta tttgaccaac accaccatag agaaggaaat atgccccaaa      240
ccagcagaat acagaaattg gtcaaaaccg caatgtggca ttacaggatt tgcacctttc      300
tctaaggaca attcgattag ctttccgct ggtggggaca tctgggtgac aagagaacct      360
tatgtgtcat gcgatcttga caagtgttat caatttgccc ttggacaggg gacaacacta      420
aacaacgtgc attcaaataa cacagtacgt gataggaccc cttaccggac tctattgatg      480
aatgagttgg gtgttccttt ccatctgggg accaagcaag tgtgcatagc atggtccagc      540
tcaagttgtc acgatggaaa agcatggctg catgtttgta taacggggga tgataaaaat      600
gcaactgcta gcttcattta caatgggagg cttgtagata tgttgtttc atggtccaac      660 gatattctca ggacccagga atcagaatgc gtttgtatca atggaacttg tacagtagta      720
atgactgatg gaaatgctac aggaaaagct gatactaaaa tactattcat cgaggagggg      780
aaaatcattc atactagcaa attgtcagga agtgctcagc atgtcgaaga gtgctcttgc      840
tatcctcgat atcctggtgt cagatgtgtc tgcagagaca actggaaagg atccaaccgg      900
```

```
cccatcatag atataaacat aaaggatcat agcattgttt ccagttatgt gtgttcagga      960
cttgttggag acacacccag aaaaagcgac agctccagca gtagccattg tttgaatcct     1020
aacaatgaag aaggtggtca tggagtgaaa ggctgggcct ttgatgatgg aaatgacgtg     1080
tggatgggga gaacaatcaa cgagacgtca cgcttagggt atgaaacctt caaagtcgtt     1140
gaaggctggt ccaaccctaa gtccaaattg cagataaata ggcaagtcat agttgacaga     1200
ggtgataggt ccggttattc tggtattttc tctgttgaag gcaaaagctg catcaatcgg     1260
tgcttttatg tggagttgat taggggaaga aaagaggaaa ctgaagtctt gtggacctca     1320
aacagtattg ttgtgttttg tggcacctca ggtacatatg aacaggctc atggcctgat      1380 ggggcggacc tcaatctcat gcatatataa gctttcgcaa ttttagaaaa aaactccttg     1440
tttctact                                                             1448

<210> SEQ ID NO 28
<211> LENGTH: 1410
<212> TYPE: DNA
<213> ORGANISM: Influenza A

<400> SEQUENCE: 28
atgaatccaa atcaaaagat aataacgatt ggctctgttt ctctcacaat ttccacaata      60
tgcttcttca tgcaaattgc catcctgata actactgtaa cattgcattt caagcaatat     120
gaattcaact ccccccccaaa taccaagtg atgctgtgtg aaccaacaat aatagaaaga     180
aacataacag agatagtgta tttgaccaac accaccatag agaaggaaat atgccccaaa     240
ccagcagaat acagaaattg gtcaaaaccg caatgtggca ttacaggatt tgcaccttc      300 tctaaggaca attcgattag ctttccgct ggtgggaca tctgggtgac aagagaacct      360
tatgtgtcat gcgatcttga caagtgttat caatttgccc ttggacaggg aacaacacta     420
aacaacgtgc attcaaataa cacagtacgt gatagaaccc cttatcggac tctattgatg     480
aatgagttgg gtgttccttt ccatctgggg accaagcaag tgtgcatagc atggtccagc     540
tcaagctgtc acgatggaaa agcatggctg catgtttgta taacgggga tgataaaaat     600 gcaactgcta gcttcattta caatgggagg cttgtagata gtgttgtttc atggtccaac     660
gatattctca ggacccagga gtcagaatgc gtttgtatca atggaacttg tacagtagta     720
atgactgatg gaaatgctac aggaaaagct gatactaaaa tactattcat tgaggagggg     780
aaaatcgttc atactagcaa attgtcagga agtgctcagc atgtcgaaga gtgctcttgc     840
tatcctcgat atcctggtgt cagatgtgtc tgcagagaca actggaaagg atccaaccgg     900
cccatcatag atataaacat aaaggatcat agcattgttt ccaggtatgt gtgttcagga     960
cttgttggag acacacccag aaaaagcgac agctccagca gtagccattg tttgaaccct     1020
aacaatgaaa aaggtgatca tggagtgaaa ggctgggcct ttgatgatgg aaatgacgtg     1080
tggatgggga gaacaatcaa cgagacgtcg cgcttagggt atgaaacctt caaagtcgtt     1140
gaaggctggt ccaaccctaa gtccaaattg cagataaata ggcaagtcat agttgacaga     1200
ggtgataggt ccggttattc tggtattttc tctgttgaag gcaaaagctg catcaatcgg     1260
tgcttttatg tggagttgat taggggaaga aaagaggaaa ctgaagtctt gtggacctca     1320
aacagtattg ttgtgttttg tggcacctca ggtacatatg aacaggctc atggcctgat      1380 ggggcggacc tcaatctcat gcatatataa                                     1410

<210> SEQ ID NO 29
<211> LENGTH: 1434
```

<212> TYPE: DNA
<213> ORGANISM: Influenza A

<400> SEQUENCE: 29

```
atgaatccaa atcaaaagat aataacgatt ggctctgttt ctctcaccat ttccacaata     60
tgcttcttca tgcaaattgc catcctgata actactgtaa cattgcattt caagcaatat    120
gaattcaact cccccccaaa caaccaagtg atgctgtgtg aaccaacaat aatagaaaga    180
aacataacag agatagtgta tttgaccaac accaccatag agagggaaat atgccccaaa    240
ccagcagaat acagaaattg gtcaaaaccg caatgtggca ttacaggatt tgcacctttc    300
tctaaggaca attcgattag gctttccgct ggtggggaca tctgggtgac aagagaacct    360
tatgtgtcat gcgatcctga caagtgttat caatttgccc ttggacaggg aacaacaata    420
aacaacgtgc attcaaataa cacagcacgt gataggaccc ctcatcggac tctattgatg    480
aatgagttgg gtgttccttt ccatctgggg accaagcaag tgtgcatagc atggtccagc    540
tcaagttgtc acgatggaaa agcatggctg catgtttgta taacgggggga tgataaaaat    600
gcaactgcta gtttcattta caatgggagg cttgtagata gtgttgtttc atggtccaaa    660
gatattctca ggacccagga gtcagaatgc gtttgtatca atggaacttg tacagtagta    720
atgactgatg gaaatgctac aggaaaagct gatactaaaa tattattcat tgaggagggg    780
aaaatcgttc atactagcaa attgtcagga agtgctcagc atgtcgaaga gtgctcttgc    840
tatcctcgat accctggtgt cagatgtgtc tgcagagaca actggaaagg atccaaccgg    900
cccatcgtag atataaacat aaaggatcat agcattgttt ccagttatgt gtgttcagga    960
cttgttggag acacacccag aaaaaccgac agctccagca gcagccattg cttgaatcct   1020
aacaatgaaa aaggtggtca tggagtgaaa ggctgggcct ttgatgatgg aaatgacgtg   1080
tggatgggga gaacaatcaa cgagacgtca cgcttagggt atgaaacctt caaagtcgtt   1140
gaaggctggt ccaaccctaa gtccaaattg cagataaata ggcaagtcat agttgacaga   1200
ggtgataggt ccggttattc tggtattttc tctgttgaag gcaaaagctg catcaatcgg   1260
tgcttttatg tggagttgat taggggaaga aaagaggaaa ctgaagtctt gtggacctca   1320
aacagtattg ttgtgttttg tggcacctca ggtacatatg gaacaggctc atggcctgat   1380
ggggcggacc tcaatctcat gcatatataa gctttcgcaa ttttagaaaa aact         1434
```

<210> SEQ ID NO 30
<211> LENGTH: 2233
<212> TYPE: DNA
<213> ORGANISM: Influenza A

<400> SEQUENCE: 30

```
agcgaaagca ggtactgatc caaaatggaa gattttgtgc gacaatgctt caatccgatg     60
attgtcgagc ttgcggaaaa aacaatgaaa gagtatgggg aggacctgaa aatcgaaaca    120
aacaaatttg cagcaatatg cactcacttg gaagtatgct tcatgtattc agattttcac    180
ttcatcaatg agcaaggcga gtcaataatc gtagaacttg gtgatccaaa tgcacttttg    240
aagcacagat ttgaaataat cgagggaaga gatcgcacaa tggcctggac agtagtaaac    300
agtatttgca acactacagg ggctgagaaa ccaaagtttc taccagattt gtatgattac    360
aaggagaata gattcatcga aattggagta acaaggagag aagttcacat atactatctg    420
gaaaaggcca ataaaattaa atctgagaaa acacacatcc acattttctc gttcactggg    480
gaagaaatgg ccacaaaggc agactacact ctcgatgaag aaagcagggc taggatcaaa    540
```

```
accagactat tcaccataag acaagaaatg ccagcagag gcctctggga ttcctttcgt      600
cagtccgaga gaggagaaga gacaattgaa gaaaggtttg aaatcacagg aacaatgcgc      660
aagcttgccg accaaagtct cccgccgaac ttctccagcc ttgaaaattt tagagcctat      720
gtggatggat tcgaaccgaa cggctacatt gagggcaagc tgtctcaaat gtccaaagaa      780
gtaaatgcta gaattgaacc ttttttgaaa acaacaccac gaccacttag acttccgaat      840
gggcctccct gttctcagcg gtccaaattc ctgctgatgg atgccttaaa attaagcatt      900
gaggacccaa gtcatgaagg agagggaata ccgctatatg atgcaatcaa atgcatgaga      960
acattctttg gatggaagga acccaatgtt gttaaaccac acgaaaaggg aataaatcca     1020
aattatcttc tgtcatggaa gcaagtactg gcagaactgc aggacattga gaatgaggag     1080
aaaattccaa agactaaaaa tatgaagaaa acaagtcagc taaagtgggc acttggtgag     1140
aacatggcac cagaaaaggt agactttgac gactgtaaag atgtaggtga tttgaagcaa     1200
tatgatagtg atgaaccaga attgaggtcg cttgcaagtt ggattcagaa tgagtttaac     1260
aaggcatgcg aactgacaga ttcaagctgg atagagctcg atgagattgg agaagatgtg     1320
gctccaattg aacacattgc aagcatgaga aggaattatt tcacatcaga ggtgtctcac     1380
tgcagagcca cagaatacat aatgaaggga gtgtacatca atactgcctt gcttaatgca     1440
tcttgtgcag caatggatga tttccaatta attccaatga taagcaagtg tagaactaag     1500
gagggaaggc gaaagaccaa cttgtatggt ttcatcataa aaggaagatc ccacttaagg     1560
aatgacaccg acgtggtaaa ctttgtgagc atggagtttt ctctcactga cccaagactt     1620
gaaccacata aatgggagaa gtactgtgtt cttgagatag agatatgct tataagaagt     1680 gccataggcc aggtttcaag gcccatgttc ttgtatgtga aacaaatgg aacctcaaaa     1740 attaaaatga atggggaat ggagatgagg cgttgcctcc tccagtcact tcaacaaatt     1800
gagagtatga ttgaagctga gtcctctgtc aaagagaaag acatgaccaa agagttcttt     1860
gagaacaaat cagaaacatg gccattgga gagtccccca aaggagtgga ggaaagttcc     1920
attgggaagg tctgcaggac tttattagca aagtcggtat caacagctt gtatgcatct     1980 ccacaactag aaggatttc agctgaatca agaaaactgc ttcttatcgt tcaggctctt     2040
agggacaacc tggaacctgg gacctttgat cttggggggc tatatgaagc aattgaggag     2100
tgcctgatta atgatccctg ggttttgctt aatgcttctt ggttcaactc cttccttaca     2160
catgcattga gttagttgtg gcagtgctac tatttgctat ccatactgtc caaaaaagta     2220
ccttgtttct act                                                       2233
```

<210> SEQ ID NO 31
<211> LENGTH: 2341
<212> TYPE: DNA
<213> ORGANISM: Influenza A

<400> SEQUENCE: 31

```
agcgaaagca ggcaaaccat ttgaatggat gtcaatccga ccttactttt cttaaaagtg       60
ccagcacaaa atgctataag cacaactttc ccttatactg gagaccctcc ttacagccat      120
gggacaggaa caggatacac catggatact gtcaacagga cacatcagta ctcagaaaag      180
ggaagatgga caacaaacac cgaaactgga gcaccgcaac tcaacccgat tgatgggcca      240
ctgccagaag acaatgaacc aagtggttat gcccaaacag attgtgtatt ggaggcgatg      300
gctttccttg aggaatccca tcctggtatt tttgaaaact cgtgtattga acgatggag      360 gttgttcagc aaacacgagt agacaagctg acacaaggcc gacagaccta tgactggact      420
```

-continued

```
ctaaatagaa accaacctgc tgcaacagca ttggccaaca caatagaagt gttcagatca    480
aatggcctca cggccaatga gtctggaagg ctcatagact tccttaagga tgtaatggag    540
tcaatgaaca agaagaaat ggggatcaca actcattttc agagaaagag acgggtgaga     600
gacaatatga ctaagaaaat gataacacag agaacaatgg gtaaaagaa gcagagattg     660
aacaaaagga gttatctaat tagagcattg accctgaaca caatgaccaa agatgctgag    720
agagggaagc taaacggag agcaattgca accccaggga tgcaaataag ggggtttgta     780
tactttgttg agacactggc aaggagtata tgtgagaaac ttgaacaatc agggttgcca    840
gttggaggca atgagaagaa agcaaagttg gcaaatgttg taaggaagat gatgaccaat    900
tctcaggaca ccgaactttc tttcaccatc actggagata caccaaatg gaacgaaaat     960
cagaatcctc ggatgttttt ggccatgatc acatatatga ccagaaatca gcccgaatgg    1020
ttcagaaatg ttctaagtat tgctccaata atgttctcaa acaaaatggc gagactggga    1080
aaagggtata tgtttgagag caagagtatg aaacttagaa ctcaaatacc tgcagaaatg    1140
ctagcaagca tcgatttgaa atatttcaat gattcaacaa gaagaagat tgaaaaaatc    1200
cgaccgctct aatagaggg gactgcatca ttgagccctg aatgatgat gggcatgttc      1260
aatatgttaa gcactgtatt aggcgtctcc atcctgaatc ttggacaaaa gagatacacc    1320
aagactactt actggtggga tggtcttcaa tcctctgacg attttgctct gattgtgaat    1380
gcacccaatc atgaagggat tcaagccgga gtcgacaggt tttatcgaac ctgtaagcta    1440
cttggaatca atatgagcaa gaaaagtct tacataaaca gaacaggtac atttgaattc    1500
acaagttttt tctatcgtta tgggtttgtt gccaatttca gcatggagct tcccagtttt    1560
ggggtgtctg ggatcaacga gtcagcggac atgagtattg gagttactgt catcaaaaac    1620
aatatgataa acaatgatct tggtccagca acagctcaaa tggcccttca gttgttcatc    1680
aaagattaca ggtacacgta ccgatgccat ataggtgaca cacaaataca aacccgaaga    1740
tcatttgaaa taagaaact gtgggagcaa acccgttcca aagctggact gctggtctcc    1800
gacggaggcc caaatttata caacattaga atctccaca ttcctgaagt ctgcctaaaa     1860
tgggaattga tggatgagga ttaccagggg cgtttatgca acccactgaa ccatttgtc    1920
agccataaag aaattgaatc aatgaacaat gcagtgatga tgccagcaca tggtccagcc    1980
aaaaacatgg agtatgatgc tgttgcaaca acacactcct ggatcccaa agaaatcga     2040
tccatcttga atacaagtca aagaggagta cttgaggatg aacaaatgta ccaaaggtgc    2100
tgcaatttat ttgaaaaatt cttccccagc agttcataca aagaccagt cgggatatcc    2160
agtatggtgg aggctatggt ttccagagcc cgaattgatg cacggattga tttcgaatct    2220
ggaaggataa agaagaaga gttcactgag atcatgaaga tctgttccac cattgaagag    2280
ctcagacggc aaaaatagtg aatttagctt gtccttcatg aaaaatgcc ttgtttctac     2340
t                                                                    2341
```

<210> SEQ ID NO 32
<211> LENGTH: 2341
<212> TYPE: DNA
<213> ORGANISM: Influenza A

<400> SEQUENCE: 32

```
agcgaaagca ggtcaattat attcaatatg gaaagaataa agaactacg aaatctaatg     60
tcgcagtctc gcacccgcga gatactcaca aaaaccaccg tggaccatat ggccataatc    120
```

| | | | | |
|---|---|---|---|---|
| aagaagtaca | catcaggaag | acaggagaag | aacccagcac | ttaggatgaa atggatgatg | 180 |
| gcaatgaaat | atccaattac | agcagacaag | aggataacgg | aaatgattcc tgagagaaat | 240 |
| gagcaaggac | aaactttatg | gagtaaaatg | aatgatgccg | gatcagaccg agtgatggta | 300 |
| tcacctctgg | ctgtgacatg | gtggaatagg | aatggaccaa | taacaaatac agttcattat | 360 |
| ccaaaaatct | acaaaactta | ttttgaaaga | gtcgaaaggc | taaagcatgg aacctttggc | 420 |
| cctgtccatt | ttagaaacca | agtcaaaata | cgtcggagag | ttgacataaa tcctggtcat | 480 |
| gcagatctca | gtgccaagga | ggcacaggat | gtaatcatgg | aagttgtttt ccctaacgaa | 540 |
| gtgggagcca | ggatactaac | atcggaatcg | caactaacga | taaccaaaga gaagaaagaa | 600 |
| gaactccagg | attgcaaaat | ttctcctttg | atggttgcat | acatgttgga gagagaactg | 660 |
| gtccgcaaaa | cgagattcct | cccagtggct | ggtggaacaa | gcagtgtgta cattgaagtg | 720 |
| ttgcatttga | ctcaaggaac | atgctgggaa | cagatgtata | ctccaggagg ggaagtgagg | 780 |
| aatgatgatg | ttgatcaaag | cttgattatt | gctgctagga | acatagtgag aagagctgca | 840 |
| gtatcagcag | atccactagc | atctttattg | gagatgtgcc | acagcacaca gattggtgga | 900 |
| attaggatgg | tagacatcct | taggcagaac | ccaacagaag | agcaagccgt ggatatatgc | 960 |
| aaggctgcaa | tgggactgag | aattagctca | tccttcagtt | ttggtggatt cacatttaag | 1020 |
| agaacaagcg | gatcatcagt | caagagagag | gaagaggtgc | ttacgggcaa tcttcaaaca | 1080 |
| ttgaagataa | gagtgcatga | gggatatgaa | gagttcacaa | tggttgggag aagagcaaca | 1140 |
| gccatactca | gaaaagcaac | caggagattg | attcagctga | tagtgagtgg gagagacgaa | 1200 |
| cagtcgattg | ccgaagcaat | aattgtggcc | atggtatttt | cacaagagga ttgtatgata | 1260 |
| aaagcagtca | gaggtgatct | gaatttcgtc | aatagggcga | atcaacgatt gaatcctatg | 1320 |
| catcaacttt | taagacattt | tcagaaggat | gcgaaagtgc | tttttcaaaa ttggggagtt | 1380 |
| gaacctatcg | acaatgtgat | gggaatgatt | gggatattgc | ccgacatgac tccaagcatc | 1440 |
| gagatgtcaa | tgagaggagt | gagaatcagc | aaaatgggtg | tagatgagta ctccagcacg | 1500 |
| gagagggtag | tggtgagcat | tgaccgtttt | ttgagaatcc | gggaccaacg aggaaatgta | 1560 |
| ctactgtctc | ccgaggaggt | cagtgaaaca | cagggaacag | agaaactgac aataacttac | 1620 |
| tcatcgtcaa | tgatgtggga | gattaatggt | cctgaatcag | tgttggtcaa tacctatcaa | 1680 |
| tggatcatca | gaaactggga | aactgttaaa | attcagtggt | cccagaaccc tacaatgcta | 1740 |
| tacaataaaa | tggaatttga | accatttcag | tctttagtac | ctaaggccat tagaggccaa | 1800 |
| tacagtgggt | ttgtaagaac | tctgttccaa | caaatgaggg | atgtgcttgg gacatttgat | 1860 |
| accgcacaga | taataaaact | tcttcccttc | gcagccgctc | caccaaagca agtagaatg | 1920 |
| cagttctcct | catttactgt | gaatgtgagg | ggatcaggaa | tgagaatact tgtaaggggc | 1980 |
| aattctcctg | tattcaacta | taacaaggcc | acgaagagac | tcacagttct cggaaaggat | 2040 |
| gctggcactt | taactgaaga | cccagatgaa | ggcacagctg | gagtggagtc cgctgttctg | 2100 |
| aggggattcc | tcattctggg | caagaagac | aagagatatg | gccagcact aagcatcaat | 2160 |
| gaactgagca | accttgcgaa | aggagagaag | gctaatgtgc | taattgggca aggagacgtg | 2220 |
| gtgttggtaa | tgaaacggaa | acgggactct | agcatactta | ctgacagcca gacagcgacc | 2280 |
| aaaagaattc | ggatggccat | caattagtgt | cgaatagttt | aaaaacgacc ttgtttctac | 2340 |
| t | | | | | 2341 |

<210> SEQ ID NO 33
<211> LENGTH: 1565

```
<212> TYPE: DNA
<213> ORGANISM: Influenza A

<400> SEQUENCE: 33
agcaaaagca gggtagataa tcactcactg agtgacatca aaatcatggc gtctcaaggc 60
accaaacgat cttacgaaca gatggagact gatggagaac gccagaatgc cactgaaatc 120
agagcatccg tcggaaaaat gattggtgga attggacgat tctacatcca aatgtgcacc 180
gaactcaaac tcagtgatta tgagggacgg ttgatccaaa acagcttaac aatagagaga 240
atggtgctct ctgcttttga cgaaaggaga aataaatacc ttgaagaaca tcccagtgcg 300
gggaaagatc ctaagaaaac tggaggacct atatacagga gagtaaacgg aaagtggatg 360
agagaactca tcctttatga caaagaagaa ataaggcgaa tctggcgcca agctaataat 420
ggtgacgatg caacggctgg tctgactcac atgatgatct ggcattccaa tttgaatgat 480
gcaacttatc agaggacaag agctcttgtt cgcaccggaa tggatcccag gatgtgctct 540
ctgatgcaag gttcaactct ccctaggagg tctggagccg caggtgctgc agtcaaagga 600
gttggaacaa tggtgatgga attggtcaga atgatcaaac gtgggatcaa tgatcggaac 660
ttctggaggg gtgagaatgg acgaaaaaca agaattgctt atgaaagaat gtgcaacatt 720
ctcaaaggga aatttcaaac tgctgcacaa aaagcaatga tggatcaagt gagagagagc 780
cggaacccag ggaatgctga gttcgaagat ctcacttttc tagcacggtc tgcactcata 840
ttgagagggt cggttgctca caagtcctgc ctgcctgcct gtgtgtatgg acctgccgta 900
gccagtgggt acgactttga aagggaggga tactctctag tcggaataga ccctttcaga 960
ctgcttcaaa acagccaagt gtacagccta atcagaccaa atgagaatcc agcacacaag 1020
agtcaactgg tgtggatggc atgccattct gccgcatttg aagatctaag agtattaagc 1080
ttcatcaaag ggacgaaggt gctcccaaga gggaagcttt ccactagagg agttcaaatt 1140
gcttccaatg aaaatatgga gactatggaa tcaagtacac ttgaactgag aagcaggtac 1200
tgggccataa ggaccagaag tggaggaaac accaatcaac agagggcatc tgcgggccaa 1260
atcagcatac aacctacgtt ctcagtacag agaaatctcc cttttgacag aacaaccatt 1320
atggcagcat tcaatgggaa tacagagggg agaacatctg acatgaggac cgaaatcata 1380
aggatgatgg aaagtgcaag accagaagat gtgtctttcc aggggcgggg agtcttcgag 1440
ctctcggacg aaaaggcagc gagcccgatc gtgccttcct ttgacatgag taatgaagga 1500
tcttatttct tcggagacaa tgcagaggag tacgacaatt aaagaaaaat acccttgttt 1560
ctact 1565

<210> SEQ ID NO 34
<211> LENGTH: 1027
<212> TYPE: DNA
<213> ORGANISM: Influenza A
<400> SEQUENCE: 34
agcaaaagca ggtagatatt gaaagatgag tcttctaacc gaggtcgaaa cgtacgtact 60
ctctatcatc ccgtcaggcc ccctcaaagc cgagatcgca cagagacttg aagatgtctt 120
tgcagggaag aacaccgatc ttgaggttct catggaatgg ctaaagacaa gaccaatcct 180
gtcacctctg actaagggga ttttaggatt tgtgttcacg ctcaccgtgc ccagtgagcg 240
aggactgcag cgtagacgct ttgtccaaaa tgcccttaat gggaacgggg atccaaataa 300
catggacaaa gcagttaaac tgtataggaa gctcaagagg gagataacat tccatggggc 360
```

| | |
|---|---|
| caaagaaatc tcactcagtt attctgctgg tgcacttgcc agttgtatgg gcctcatata | 420 |
| caacaggatg ggggctgtga ccactgaagt ggcatttggc ctggtatgtg caacctgtga | 480 |
| acagattgct gactcccagc atcggtctca taggcaaatg gtgacaacaa ccaatccact | 540 |
| aatcagacat gagaacagaa tggttttagc cagcactaca gctaaggcta tggagcaaat | 600 |
| ggctggatcg agtgagcaag cagcagaggc catggaggtt gctagtcagg ctagacaaat | 660 |
| ggtgcaagcg atgagaacca tgggactca tcctagctcc agtgctggtc tgaaaaatga | 720 |
| tcttcttgaa aatttgcagg cctatcagaa acgaatgggg gtgcagatgc aacggttcaa | 780 |
| gtgatcctct cactattgcc gcaaatatca ttgggatctt gcacttgaca ttgtggattc | 840 |
| ttgatcgtct ttttttcaaa tgcatttacc gtcgctttaa atacggactg aaaggagggc | 900 |
| cttctacgga aggagtgcca aagtctatga gggaagaata tcgaaaggaa cagcagagtg | 960 |
| ctgtggatgc tgacgatggt cattttgtca gcatagagct ggagtaaaaa actaccttgt | 1020 |
| ttctact | 1027 |

<210> SEQ ID NO 35
<211> LENGTH: 890
<212> TYPE: DNA
<213> ORGANISM: Influenza A

<400> SEQUENCE: 35

| | |
|---|---|
| agcaaaagca gggtgacaaa acataatgg atccaaacac tgtgtcaagc tttcaggtag | 60 |
| attgctttct ttggcatgtc cgcaaacgag ttgcagacca agaactaggc gatgccccat | 120 |
| tccttgatcg gcttcgccga gatcagaaat ccctaagagg aaggggcagt actctcggtc | 180 |
| tggacatcaa gacagccaca cgtgctggaa agcagatagt ggagcggatt ctgaaagaag | 240 |
| aatccgatga ggcacttaaa atgaccatgg cctctgtacc tgcgtcgcgt tacctaactg | 300 |
| acatgactct tgaggaaatg tcaagggact ggtccatgct catacccaag cagaaagtgg | 360 |
| caggccctct ttgtatcaga atggaccagg cgatcatgga taagaacatc atactgaaag | 420 |
| cgaacttcag tgtgattttt gaccggctgg agactctaat attgctaagg ctttcaccg | 480 |
| aagagggagc aattgttggc gaaatttcac cattgccttc tcttccagga catactgctg | 540 |
| aggatgtcaa aaatgcagtt ggagtcctca tcggaggact tgaatggaat gataacacag | 600 |
| ttcgagtctc tgaaactcta cagagattcg cttggagaag cagtaatgag aatgggagac | 660 |
| ctccactcac tccaaaacag aaacgagaaa tggcgggaac aattaggtca gaagtttgaa | 720 |
| gaaataagat ggttgattga agaagtgaga cacaaactga agataacaga gaatagtttt | 780 |
| gagcaaataa catttatgca agccttacat ctattgcttg aagtggagca agagataaga | 840 |
| actttctcgt tcagcttat ttagtactaa aaacaccct tgtttctact | 890 |

<210> SEQ ID NO 36
<211> LENGTH: 1433
<212> TYPE: DNA
<213> ORGANISM: Influenza A

<400> SEQUENCE: 36

| | |
|---|---|
| agtttaaaat gaatccaaac caaaagataa taaccattgg ttcgatcagt atgacaattg | 60 |
| gaatggctaa cttaatatta caaattggaa acataatctc aatatgggtt agccactcaa | 120 |
| ttcaaattgg aaatcaaagc cagattgaaa catgcaatca aagcgtcatt acttatgaaa | 180 |
| acaacacttg ggtaaatcag acatatgtta acatcagcaa caccaacttt gctgctggac | 240 |
| agtcagtggt ttccgtgaaa ttagcgggca attcctctct ctgccctgtt agtggatggg | 300 |

```
ctatatacag taaagacaac agtgtaagaa tcggttccaa gggggatgtg tttgtcataa      360
gggaaccatt catatcatgc tctcccttgg aatgcagaac cttcttcttg actcaagggg      420
ccttgctaaa tgacaaacat tccaatggaa ccattaaaga caggagccca tatcgaaccc      480
taatgagctg tcctattggt gaagttccct ctccatacaa ctcaagattt gagtcagtcg      540
cttggtcagc aagtgcttgt catgatggca tcaattggct aacaattgga atttctggcc      600
cagacagtgg ggcagtggct gtgttaaagt acaatggcat aataacagac actatcaaga      660
gttggaggaa caatatattg agaacacaag agtctgaatg tgcatgtgta aatggttctt      720
gctttaccat aatgaccgat ggaccaagtg atggacaggc tcatacaaa atcttcagaa       780 tagaaaaggg aaagataatc aaatcagtcg aaatgaaagc ccctaattat cactatgagg      840
aatgctcctg ttaccctgat tctagtgaaa tcacatgtgt gtgcagggat aactggcatg      900
gctcgaatcg accgtgggtg tctttcaacc agaatctgga atatcagatg ggatacatat      960
gcagtggggt tttcggagac aatccacgcc taatgataa acaggcagt tgtggtccag       1020 tatcgtctaa tggagcaaat ggagtaaaag gattttcatt caaatacggc aatggtgttt      1080 ggataggag aactaaaagc attagttcaa gaaaaggttt tgagatgatt tgggatccga      1140
atggatggac tgggactgac aataaattct caataaagca agatatcgta ggaataaatg      1200
agtggtcagg gtatagcggg agttttgttc agcatccaga actaacaggg ctggattgta      1260
taagaccttg cttctgggtt gaactaataa gagggcgacc cgaagagaac acaatctgga      1320
ctagcgggag cagcatatcc ttttgtggtg taaacagtga cactgtgggt tggtcttggc      1380
cagacggtgc tgagttgcca tttaccattg acaagtaatt tgttcaaaaa act             1433

<210> SEQ ID NO 37
<211> LENGTH: 469
<212> TYPE: PRT
<213> ORGANISM: Influenza A

<400> SEQUENCE: 37

Met Asn Pro Asn Gln Lys Ile Ile Thr Ile Gly Ser Ile Ser Met Thr
1               5                   10                  15

Ile Gly Met Ala Asn Leu Ile Leu Gln Ile Gly Asn Ile Ile Ser Ile
            20                  25                  30

Trp Val Ser His Ser Ile Gln Ile Gly Asn Gln Ser Gln Ile Glu Thr
        35                  40                  45

Cys Asn Gln Ser Val Ile Thr Tyr Glu Asn Asn Thr Trp Val Asn Gln
    50                  55                  60

Thr Tyr Val Asn Ile Ser Asn Thr Asn Phe Ala Ala Gly Gln Ser Val
65                  70                  75                  80

Val Ser Val Lys Leu Ala Gly Asn Ser Ser Leu Cys Pro Val Ser Gly
                85                  90                  95

Trp Ala Ile Tyr Ser Lys Asp Asn Ser Val Arg Ile Gly Ser Lys Gly
            100                 105                 110

Asp Val Phe Val Ile Arg Glu Pro Phe Ile Ser Cys Ser Pro Leu Glu
        115                 120                 125

Cys Arg Thr Phe Phe Leu Thr Gln Gly Ala Leu Leu Asn Asp Lys His
    130                 135                 140

Ser Asn Gly Thr Ile Lys Asp Arg Ser Pro Tyr Arg Thr Leu Met Ser
145                 150                 155                 160

Cys Pro Ile Gly Glu Val Pro Ser Pro Tyr Asn Ser Arg Phe Glu Ser
                165                 170                 175
```

Val Ala Trp Ser Ala Ser Ala Cys His Asp Gly Ile Asn Trp Leu Thr
            180                 185                 190

Ile Gly Ile Ser Gly Pro Asp Ser Gly Ala Val Ala Val Leu Lys Tyr
            195                 200                 205

Asn Gly Ile Ile Thr Asp Thr Ile Lys Ser Trp Arg Asn Asn Ile Leu
210                 215                 220

Arg Thr Gln Glu Ser Glu Cys Ala Cys Val Asn Gly Ser Cys Phe Thr
225                 230                 235                 240

Ile Met Thr Asp Gly Pro Ser Asp Gly Gln Ala Ser Tyr Lys Ile Phe
            245                 250                 255

Arg Ile Glu Lys Gly Lys Ile Ile Lys Ser Val Glu Met Lys Ala Pro
            260                 265                 270

Asn Tyr His Tyr Glu Glu Cys Ser Cys Tyr Pro Asp Ser Ser Glu Ile
            275                 280                 285

Thr Cys Val Cys Arg Asp Asn Trp His Gly Ser Asn Arg Pro Trp Val
            290                 295                 300

Ser Phe Asn Gln Asn Leu Glu Tyr Gln Met Gly Tyr Ile Cys Ser Gly
305                 310                 315                 320

Val Phe Gly Asp Asn Pro Arg Pro Asn Asp Lys Thr Gly Ser Cys Gly
            325                 330                 335

Pro Val Ser Ser Asn Gly Ala Asn Gly Val Lys Gly Phe Ser Phe Lys
            340                 345                 350

Tyr Gly Asn Gly Val Trp Ile Gly Arg Thr Lys Ser Ile Ser Ser Arg
            355                 360                 365

Lys Gly Phe Glu Met Ile Trp Asp Pro Asn Gly Trp Thr Gly Thr Asp
            370                 375                 380

Asn Lys Phe Ser Ile Lys Gln Asp Ile Val Gly Ile Asn Glu Trp Ser
385                 390                 395                 400

Gly Tyr Ser Gly Ser Phe Val Gln His Pro Glu Leu Thr Gly Leu Asp
            405                 410                 415

Cys Ile Arg Pro Cys Phe Trp Val Glu Leu Ile Arg Gly Arg Pro Glu
            420                 425                 430

Glu Asn Thr Ile Trp Thr Ser Gly Ser Ser Ile Ser Phe Cys Gly Val
            435                 440                 445

Asn Ser Asp Thr Val Gly Trp Ser Trp Pro Asp Gly Ala Glu Leu Pro
450                 455                 460

Phe Thr Ile Asp Lys
465

<210> SEQ ID NO 38
<211> LENGTH: 2341
<212> TYPE: DNA
<213> ORGANISM: Influenza A

<400> SEQUENCE: 38
agcgaaagca ggtcaattat attcaatatg gaaagaataa agaactaag aaatctaatg       60 tcgcagtctc gcacccgcga gatactcaca aaaaccaccg tggaccatat ggccataatc     120
aagaagtaca catcaggaag acaggagaag aacccagcac ttaggatgaa atggatgatg     180
gcaatgaaat atccaattac agcagacaag aggataacgg aaatgattcc tgagagaaat     240
gagcaaggac aaactttatg gagtaaaatg aatgatgccg gatcagaccg agtgatggta     300
tcacctctgg ctgtgacatg gtggaatagg aatggaccaa tgacaaatac agttcattat     360
ccaaaaatct acaaaactta ttttgaaaga gtcgaaaggc taaagcatgg aacctttggc     420

```
cctgtccatt ttagaaacca agtcaaaata cgtcggagag ttgacataaa tcctggtcat      480
gcagatctca gtgccaagga ggcacaggat gtaatcatgg aagttgtttt ccctaacgaa      540
gtgggagcca ggatactaac atcggaatcg caactaacga taaccaaaga gaagaaagaa      600
gaactccagg attgcaaaat ttctcctttg atggttgcat acatgttgga gagagaactg      660
gtccgcaaaa cgagattcct cccagtggct ggtggaacaa gcagtgtgta cattgaagtg      720
ttgcatttga ctcaaggaac atgctgggaa cagatgtata ctccaggagg ggaagtgaag      780
aatgatgatg ttgatcaaag cttgattatt gctgctagga acatagtgag aagagctgca      840
gtatcagcag acccactagc atctttattg gagatgtgcc acagcacaca gattggtgga      900
attaggatgg tagacatcct taagcagaac ccaacagaag agcaagccgt ggatatatgc      960
aaggctgcaa tgggactgag aattagctca tccttcagtt ttggtggatt cacatttaag     1020
agaacaagcg gatcatcagt caagagagag gaagaggtgc ttacgggcaa tcttcaaaca     1080
ttgaagataa gagtgcatga gggatctgaa gagttcacaa tggttgggag aagagcaaca     1140
gccatactca gaaaagcaac caggagattg attcagctga tagtgagtgg gagagacgaa     1200
cagtcgattg ccgaagcaat aattgtggcc atggtatttt cacaagagga ttgtatgata     1260
aaagcagtta gaggtgatct gaatttcgtc aatagggcga atcagcgact gaatcctatg     1320
catcaacttt taagacattt tcagaaggat gcgaaagtgc tttttcaaaa ttggggagtt     1380
gaacctatcg acaatgtgat gggaatgatt gggatattgc ccgacatgac tccaagcatc     1440
gagatgtcaa tgagaggagt gagaatcagc aaaatgggtg tagatgagta ctccagcacg     1500
gagagggtag tggtgagcat tgaccggttc ttgagagtca gggaccaacg aggaaatgta     1560
ctactgtctc ccgaggaggt cagtgaaaca cagggaacag agaaactgac aataacttac     1620
tcatcgtcaa tgatgtggga gattaatggt cctgaatcag tgttggtcaa tacctatcaa     1680
tggatcatca gaaactggga aactgttaaa attcagtggt cccagaaccc tacaatgcta     1740
tacaataaaa tggaatttga accatttcag tctttagtac ctaaggccat tagaggccaa     1800
tacagtgggt ttgtaagaac tctgttccaa caaatgaggg atgtgcttgg gacatttgat     1860
accgcacaga taataaaact tcttcccttc gcagccgctc caccaaagca aagtagaatg     1920
cagttctcct catttactgt gaatgtgagg ggatcaggaa tgagaatact tgtaaggggc     1980
aattctcctg tattcaacta caacaaggcc acgaagagac tcacagttct cggaaaggat     2040
gctggcactt taaccgaaga cccagatgaa ggcacagctg gagtggagtc cgctgttctg     2100
aggggattcc tcattctggg caagaagac aggagatatg gccagcatt aagcatcaat     2160
gaactgagca accttgcgaa aggagagaag gctaatgtgc taattgggca aggagacgtg     2220
gtgttggtaa tgaaacgaaa acgggactct agcatactta ctgacagcca gacagcgacc     2280
aaaagaattc ggatggccat caattagtgt cgaatagttt aaaaacgacc ttgtttctac     2340
t                                                                    2341

<210> SEQ ID NO 39
<211> LENGTH: 2341
<212> TYPE: DNA
<213> ORGANISM: Influenza A

<400> SEQUENCE: 39
agcgaaagca ggcaaaccat ttgaatggat gtcaatccga ccttactttt cttaaaagtg       60
ccagcacaaa atgctataag cacaactttc ccttataccg gagaccctcc ttacagccat      120
```

| | |
|---|---|
| gggacaggaa caggatacac catggatact gtcaacagga cacatcagta ctcagaaaag | 180 |
| ggaagatgga caacaaacac cgaaactgga gcaccgcaac tcaacccgat tgatgggcca | 240 |
| ctgccagaag acaatgaacc aagtggttat gcccaaacag attgtgtatt ggaagcaatg | 300 |
| gctttccttg aggaatccca tcctggtatt tttgaaaact cgtgtattga acgatggag | 360 |
| gttgttcagc aaacacgagt agacaagctg acacaaggcc gacagaccta tgactggact | 420 |
| ttaaatagaa accagcctgc tgcaacagca ttggccaaca caatagaagt gttcagatca | 480 |
| aatggcctca cggccaatga gtcaggaagg ctcatagact tccttaagga tgtaatggag | 540 |
| tcaatgaaaa aagaagaaat ggggatcaca actcattttc agagaaagag acgggtgaga | 600 |
| gacaatatga ctaagaaaat gataacacag agaacaatag gtaaaggaa acagagattg | 660 |
| aacaaagggg gttatctaat tagagcattg accctgaaca caatgaccaa agatgctgag | 720 |
| agagggaagc taaaacggag agcaattgca accccaggga tgcaaataag ggggtttgta | 780 |
| tactttgttg agacactggc aaggagtata tgtgagaaac ttgaacaatc agggttgcca | 840 |
| gttggaggca atgagaagaa agcaaagttg gcaaatgttg taaggaagat gatgaccaat | 900 |
| tctcaggaca ccgaactttc tttcaccatc actggagata acaccaaatg gaacgaaaat | 960 |
| cagaatcctc ggatgttttt ggccatgatc acatatatga ccagaaatca gcccgaatgg | 1020 |
| ttcagaaatg ttctaagtat tgctccaata atgttctcaa acaaaatggc gagactggga | 1080 |
| aaagggtata tgtttgagag caagagtatg aaacttagaa ctcaaatacc tgcagaaatg | 1140 |
| ctagcaagca ttgatttgaa atatttcaat gattcaacaa gaagaagat tgaaaaaatc | 1200 |
| cgaccgctct taatagaggg gactgcatca ttgagccctg aatgatgat gggcatgttc | 1260 |
| aatatgttaa gcactgtatt aggcgtctcc atcctgaatc ttggacaaaa gagatacacc | 1320 |
| aagactactt actggtggga tggtcttcaa tcctctgacg atttgctct gattgtgaat | 1380 |
| gcacccaatc atgaagggat tcaagccgga gtcgacaggt tttatcgaac ctgtaagcta | 1440 |
| cttggaatca atatgagcaa gaaaaagtct tacataaaca gaacaggtac atttgaattc | 1500 |
| acaagttttt tctatcgtta tgggtttgtt gccaatttca gcatggagct tcccagtttt | 1560 |
| ggggtgtctg ggatcaacga gtcagcggac atgagtattg gagttactgt catcaaaaac | 1620 |
| aatatgataa acaatgatct tggtccagca acagctcaaa tggccccttca gttgttcatc | 1680 |
| aaagattaca ggtacacgta ccgatgccat agaggtgaca cacaaataca aacccgaaga | 1740 |
| tcatttgaaa taagaaact gtgggagcaa acccgttcca aagctggact gctggtctcc | 1800 |
| gacgaggcc caaatttata caacattaga aatctccaca ttcctgaagt ctgcctaaaa | 1860 |
| tgggaattga tggatgagga ttaccagggg cgtttatgca acccactgaa cccatttgtc | 1920 |
| agccataaag aaattgaatc aatgaacaat gcagtgatga tgccagcaca tggtccagcc | 1980 |
| aaaaacatgg agtatgatgc tgttgcaaca acacactcct ggatcccaa agaaatcga | 2040 |
| tccatcttga atacaagtca aagaggagta cttgaagatg aacaaatgta ccaaggtgc | 2100 |
| tgcaatttat ttgaaaaatt cttccccagc agttcataca aagaccagt cgggatatcc | 2160 |
| agtatggtgg aggctatggt ttccagagcc cgaattgatg cacggattga tttcgaatct | 2220 |
| ggaaggataa agaagaaga gttcactgag atcatgaaga tctgttccac cattgaagag | 2280 |
| ctcagacggc aaaaatagtg aatttagctt gtccttcatg aaaaaatgcc ttgtttctac | 2340 |
| t | 2341 |

<210> SEQ ID NO 40
<211> LENGTH: 2233

-continued

<212> TYPE: DNA
<213> ORGANISM: Influenza A

<400> SEQUENCE: 40

```
agcgaaagca ggtactgatt caaaatggaa gattttgtgc gacaatgctt caatccgatg 60
attgtcgagc ttgcggaaaa aacaatgaaa gagtatgggg aggacctgaa aatcgaaaca 120
aacaaatttg cagcaatatg cactcacttg gaagtatgct tcatgtattc agatttccac 180
ttcatcaatg agcaaggcga gtcaataatc gtagaacttg gtgatcctaa tgcacttttg 240
aagcacagat ttgaaataat cgagggaaga gatcgcacaa tggcctggac agtagtaaac 300
agtatttgca acactacagg ggctgagaaa ccaaagtttc taccagattt gtatgattac 360
aaggaaaata gattcatcga aattggagta acaaggagag aagttcacat atactatctg 420
gaaaaggcca ataaaattaa atctgagaaa acacacatcc acatttttctc gttcactggg 480
gaagaaatgg ccacaagggc cgactacact ctcgatgaag aaagcagggc taggatcaaa 540
accaggctat tcaccataag acaagaaatg gccagcagag gcctctggga ttcctttcgt 600
cagtccgaga gaggagaaga gacaattgaa gaaaggtttg aaatcacagg aacaatgcgc 660
aagcttgccg accaaagtct cccgccgaac ttctccagcc ttgaaaattt tagagcctat 720
gtggatggat tcgaaccgaa cggctacatt gagggcaagc tgtctcaaat gtccaaagaa 780
gtaaatgcta gaattgaacc tttttttgaaa acaacaccac gaccacttag acttccgaat 840
gggcctccct gttctcagcg gtccaaattc ctgctgatgg atgccttaaa attaagcatt 900
gaggacccaa gtcatgaagg agagggaata ccgctatatg atgcaatcaa atgcatgaga 960
acattctttg gatggaagga acccaatgtt gttaaaccac acgaaaaggg aataaatcca 1020
aattatcttc tgtcatggaa gcaagtactg gcagaactgc aggacattga gaatgaggag 1080
aaaattccaa agactaaaaa tatgaaaaaa acaagtcagc taaagtgggc acttggtgag 1140
aacatggcac cagaaaaggt agactttgac gactgtaaag atgtaggtga tttgaagcaa 1200
tatgatagtg atgaaccaga attgaggtcg cttgcaagtt ggattcagaa tgagttcaac 1260
aaggcatgcg aactgacaga ttcaagctgg atagagcttg atgagattgg agaagatgtg 1320
gctccaattg aacacattgc aagcatgaga aggaattatt tcacatcaga ggtgtctcac 1380
tgcagagcca cagaatacat aatgaagggg gtgtacatca atactgcctt acttaatgca 1440
tcttgtgcag caatggatga tttccaatta attccaatga taagcaagtg tagaactaag 1500
gagggaaggc gaaagaccaa cttgtatggt ttcatcataa aaggaagatc ccacttaagg 1560
aatgacaccg acgtggtaaa ctttgtgagc atggagtttt ctctcactga cccaagactt 1620
gaaccacaca aatgggagaa gtactgtgtt cttgagatag gagatatgct tctaagaagt 1680
gccataggcc aggtttcaag gcccatgttc ttgtatgtga ggacaaatgg aacctcaaaa 1740
attaaaatga aatggggaat ggagatgagg cgttgtctcc tccagtcact tcaacaaatt 1800
gagagtatga ttgaagctga gtcctctgtc aaagagaaag acatgaccaa agagttcttt 1860
gagaacaaat cagaaacatg gcccattgga gagtctccca aaggagtgga ggaaagttcc 1920
attgggaagg tctgcaggac tttattagca aagtcggtat ttaacagctt gtatgcatct 1980
ccacaactag aaggattttc agctgaatca agaaaactgc ttcttatcgt tcaggctctt 2040
agggacaatc tggaacctgg gacctttgat cttgggggc tatatgaagc aattgaggag 2100
tgcctaatta atgatccctg ggttttgctt aatgcttctt ggttcaactc cttccttaca 2160
catgcattga gttagttgtg gcagtgctac tatttgctat ccatactgtc caaaaaagta 2220
```
ccttgtttct act                                                          2233

<210> SEQ ID NO 41
<211> LENGTH: 1565
<212> TYPE: DNA
<213> ORGANISM: Influenza A

<400> SEQUENCE: 41
agcaaaagca gggtagataa tcactcactg agtgacatca aaatcatggc gtcccaaggc    60
accaaacggt cttacgaaca gatggagact gatggagaac gccagaatgc cactgaaatc   120
agagcatccg tcggaaaaat gattggtgga attggacgat tctacatcca aatgtgcaca   180
gaacttaaac tcagtgatta tgaggacgg ttgatccaaa acagcttaac aatagagaga   240
atggtgctct ctgcttttga cgaaaggaga aataaatacc tggaagaaca tcccagtgcg   300
gggaaagatc ctaagaaaac tggaggacct atatacagaa gagtaaacgg aaagtggatg   360
agagaactca tcctttatga caaagaagaa ataaggcgaa tctggcgcca agctaataat   420
ggtgacgatg caacggctgg tctgactcac atgatgatct ggcattccaa tttgaatgat   480
gcaacttatc agaggacaag ggctcttgtt cgcaccggaa tggatccag gatgtgctct   540
ctgatgcaag gttcaactct ccctaggagg tctggagccg caggtgctgc agtcaaagga   600
gttggaacaa tggtgatgga attggtcagg atgatcaaac gtgggatcaa tgatcggaac   660
ttctggaggg gtgagaatgg acgaaaaaca agaattgctt atgaaagaat gtgcaacatt   720
ctcaaaggga aatttcaaac tgctgcacaa aaagcaatga tggatcaagt gagagagagc   780
cggaacccag gaatgctga gttcgaagat ctcacttttc tagcacggtc tgcactcata   840
ttgagagggt cggttgctca caagtcctgc ctgcctgcct gtgtgtatgg acctgccgta   900
gccagtgggt acgactttga agagaggga tactctctag tcggaataga ccctttcaga   960
ctgcttcaaa acagccaagt gtacagccta atcagaccaa atgagaatcc agcacacaag  1020
agtcaactgg tgtggatggc atgccattct gccgcatttg aagatctaag agtattgagc  1080
ttcatcaaag ggacgaaggt ggtcccaaga gggaagcttt ccactagagg agttcaaatt  1140
gcttccaatg aaaatatgga gactatgaa tcaagtacac ttgaactgag aagcaggtac  1200
tgggccataa ggaccagaag tggaggaaac accaatcaac agagggcatc tgcgggccaa  1260
atcagcatac aacctacgtt ctcagtacag agaaatctcc cttttgacag aacaaccgtt  1320
atggcagcat tcactgggaa tacagagggg agaacatctg acatgaggac cgaaatcata  1380
aggatgatgg aaagtgcaag accagaagat gtgtcttttcc agggcgggg agtcttcgag  1440
ctctcggacg aaaaggcagc gagcccgatc gtgccttcct ttgacatgag taatgaagga  1500
tcttatttct cggagacaa tgcagaggag tacgacaatt aaagaaaaat acccttgttt  1560
ctact                                                                1565

<210> SEQ ID NO 42
<211> LENGTH: 1027
<212> TYPE: DNA
<213> ORGANISM: Influenza A

<400> SEQUENCE: 42
agcaaaagca ggtagatatt gaaagatgag tcttctaacc gaggtcgaaa cgtacgttct    60
ctctatcatc ccgtcaggcc ccctcaaagc cgagatcgca cagagacttg aagatgtctt   120
tgcagggaag aacaccgatc ttgaggttct catggaatgg ctaaagacaa gaccaatcct   180
gtcacctctg actaagggga ttttaggatt tgtgttcacg ctcaccgtgc ccagtgagcg   240

```
aggactgcag cgtagacgct ttgtccaaaa tgcccttaat gggaacgggg atccaaataa      300
catggacaaa gcagttaaac tgtataggaa gctcaagagg gagataacat ccatggggc      360 caaagaaatc tcactcagtt attctgctgg tgcacttgcc agttgtatgg gcctcatata      420
caacaggatg ggggctgtga ccactgaagt ggcatttggc ctggtatgtg caacctgtga      480
acagattgct gactcccagc atcggtctca taggcaaatg gtgacaacaa ccaacccact      540
aatcagacat gagaacagaa tggttttagc cagcactaca gctaaggcta tggagcaaat      600
ggctggatcg agtgagcaag cagcagaggc catggaggtt gctagtcagg ctaggcaaat      660
ggtgcaagcg atgagaacca tgggactcaa tcctagctcc agtgctggtc tgaaaaatga      720
tcttcttgaa aatttgcagg cctatcagaa acgaatgggg gtgcagatgc aacggttcaa      780
gtgatcctct cgctattgcc gcaaatatca ttgggatctt gcacttgata ttgtggattc      840
ttgatcgtct tttttcaaa tgcatttacc gtcgctttaa atacggactg aaaggagggc       900
cttctacgga aggagtgcca aagtctatga gggaagaata tcgaaaggaa cagcagagtg      960
ctgtggatgc tgacgatggt cattttgtca gcatagagct ggagtaaaaa actaccttgt     1020
ttctact                                                               1027

<210> SEQ ID NO 43
<211> LENGTH: 890
<212> TYPE: DNA
<213> ORGANISM: Influenza A

<400> SEQUENCE: 43
agcaaaagca gggtgacaaa gacataatgg atccaaacac tgtgtcaagc tttcaggtag       60
attgctttct ttggcatgtc cgcaaacgag ttgcagacca agaactaggt gatgccccat      120
tccttgatcg gcttcgccga gatcagaaat ccctaagagg aaggggcagc actcttggtc      180
tggacatcga gacagccaca cgtgctggaa agcagatagt ggagcggatt ctgaaagaag      240
aatccgatga ggcacttaaa atgaccatgg cctctgtacc tgcgtcgcgt tacctaaccg      300
acatgactct tgaggaaatg tcaagggaat ggtccatgct catacccaag cagaaagtgg      360
caggccctct ttgtatcaga atggaccagg cgatcatgga taaaaacatc atactgaaag      420
cgaacttcag tgtgattttt gaccggctgg agactctaat attgctaagg ctttcaccg       480 aagagggagc aattgttggc gaaatttcac cattgccttc tcttccagga catactgctg      540
aggatgtcaa aaatgcagtt ggagtcctca tcggaggact tgaatggaat gataacacag      600
ttcgagtctc tgaaactcta cagagattcg cttggagaag cagtaatgag aatgggagac      660
ctccactcac tccaaaacag aaacgagaaa tggcgggaac aattaggtca gaagtttgaa      720 gaataagat ggttgattga agaagtgaga cacaaactga aggtaacaga aatagtttt      780 gagcaaataa catttatgca agccttacat ctattgcttg aagtggagca agagataaga      840
actttctcat ttcagcttat ttaataataa aaaacaccct tgtttctact                890
```

<210> SEQ ID NO 44
<211> LENGTH: 469
<212> TYPE: PRT
<213> ORGANISM: Influenza A

<400> SEQUENCE: 44

Met Asn Pro Asn Gln Lys Ile Ile Thr Ile Gly Ser Val Ser Leu Thr
1               5                   10                  15

Ile Ser Thr Ile Cys Phe Phe Met Gln Ile Ala Ile Leu Ile Thr Thr

```
            20                  25                  30
Val Thr Leu His Phe Lys Gln Tyr Glu Phe Asn Ser Pro Pro Asn Asn
            35                  40                  45
Gln Val Met Leu Cys Glu Pro Thr Ile Ile Glu Arg Asn Ile Thr Glu
            50                  55                  60
Ile Val Tyr Leu Thr Asn Thr Thr Ile Glu Lys Glu Ile Cys Pro Lys
 65                  70                  75                  80
Pro Ala Glu Tyr Arg Asn Trp Ser Lys Pro Gln Cys Gly Ile Thr Gly
                    85                  90                  95
Phe Ala Pro Phe Ser Lys Asp Asn Ser Ile Arg Leu Ser Ala Gly Gly
                100                 105                 110
Asp Ile Trp Val Thr Arg Glu Pro Tyr Val Ser Cys Asp Pro Asp Lys
                115                 120                 125
Cys Tyr Gln Phe Ala Leu Gly Gln Gly Thr Thr Leu Asn Asn Val His
                130                 135                 140
Ser Asn Asn Thr Val Arg Asp Arg Thr Pro Tyr Arg Thr Leu Leu Met
145                 150                 155                 160
Asn Glu Leu Gly Val Pro Phe His Leu Gly Thr Lys Gln Val Cys Ile
                165                 170                 175
Ala Trp Ser Ser Ser Cys His Asp Gly Lys Ala Trp Leu His Val
                180                 185                 190
Cys Ile Thr Gly Asp Asp Lys Asn Ala Thr Ala Ser Phe Ile Tyr Asn
                195                 200                 205
Gly Arg Leu Val Asp Ser Val Val Ser Trp Ser Lys Asp Ile Leu Arg
                210                 215                 220
Thr Gln Glu Ser Glu Cys Val Cys Ile Asn Gly Thr Cys Thr Val Val
225                 230                 235                 240
Met Thr Asp Gly Asn Ala Thr Gly Lys Ala Asp Thr Lys Ile Leu Phe
                245                 250                 255
Ile Glu Glu Gly Lys Ile Val His Thr Ser Lys Leu Ser Gly Ser Ala
                260                 265                 270
Gln His Val Glu Glu Cys Ser Cys Tyr Pro Arg Tyr Pro Gly Val Arg
                275                 280                 285
Cys Val Cys Arg Asp Asn Trp Lys Gly Ser Asn Arg Pro Ile Val Asp
                290                 295                 300
Ile Asn Ile Lys Asp His Ser Ile Val Ser Ser Tyr Val Cys Ser Gly
305                 310                 315                 320
Leu Val Gly Asp Thr Pro Arg Lys Asn Asp Ser Ser Ser Ser His
                325                 330                 335
Cys Leu Asn Pro Asn Asn Glu Glu Gly Gly His Gly Val Lys Gly Trp
                340                 345                 350
Ala Phe Asp Asp Gly Asn Asp Val Trp Met Gly Arg Thr Ile Asn Glu
                355                 360                 365
Thr Ser Arg Leu Gly Tyr Glu Thr Phe Lys Val Val Glu Gly Trp Ser
                370                 375                 380
Asn Pro Lys Ser Lys Leu Gln Ile Asn Arg Gln Val Ile Val Asp Arg
385                 390                 395                 400
Gly Asp Arg Ser Gly Tyr Ser Gly Ile Phe Ser Val Glu Gly Lys Ser
                405                 410                 415
Cys Ile Asn Arg Cys Phe Tyr Val Glu Leu Ile Arg Gly Arg Lys Glu
                420                 425                 430
Glu Thr Glu Val Leu Trp Thr Ser Asn Ser Ile Val Val Phe Cys Gly
                435                 440                 445
```

```
Thr Ser Gly Thr Tyr Gly Thr Gly Ser Trp Pro Asp Gly Ala Asp Leu
    450                 455                 460

Asn Leu Met His Ile
465

<210> SEQ ID NO 45
<211> LENGTH: 466
<212> TYPE: PRT
<213> ORGANISM: Influenza B

<400> SEQUENCE: 45

Met Leu Pro Ser Thr Ile Gln Thr Leu Thr Leu Phe Leu Thr Ser Gly
1               5                   10                  15

Gly Val Leu Leu Ser Leu Tyr Val Ser Ala Ser Leu Ser Tyr Leu Leu
            20                  25                  30

Tyr Ser Asp Ile Leu Leu Lys Phe Ser Arg Thr Glu Ile Thr Ala Pro
        35                  40                  45

Ile Met Pro Leu Asp Cys Ala Asn Ala Ser Asn Val Gln Ala Val Asn
    50                  55                  60

Arg Ser Ala Thr Lys Gly Val Thr Leu Leu Leu Pro Glu Pro Glu Trp
65                  70                  75                  80

Met Tyr Pro Arg Leu Ser Cys Pro Gly Ser Thr Phe Gln Lys Ala Leu
                85                  90                  95

Leu Ile Ser Pro His Arg Phe Gly Glu Thr Lys Gly Asn Ser Ala Pro
            100                 105                 110

Leu Ile Ile Arg Glu Pro Phe Ile Ala Cys Gly Pro Lys Glu Cys Lys
        115                 120                 125

His Phe Ala Leu Thr His Tyr Ala Ala Gln Pro Gly Gly Tyr Tyr Asn
    130                 135                 140

Gly Thr Arg Glu Asp Arg Asn Lys Leu Arg His Leu Ile Ser Val Lys
145                 150                 155                 160

Leu Gly Lys Ile Pro Thr Val Glu Asn Ser Ile Phe His Met Ala Ala
                165                 170                 175

Trp Ser Gly Ser Ala Cys His Asp Gly Arg Glu Trp Thr Tyr Ile Gly
            180                 185                 190

Val Asp Gly Pro Asp Ser Asn Ala Leu Leu Lys Ile Lys Tyr Gly Glu
        195                 200                 205

Ala Tyr Thr Asp Thr Tyr His Ser Tyr Ala Lys Asn Thr Leu Arg Thr
    210                 215                 220

Gln Glu Ser Ala Cys Asn Cys Ile Gly Gly Asp Cys Tyr Leu Met Ile
225                 230                 235                 240

Thr Asp Gly Pro Ala Ser Gly Ile Ser Glu Cys Arg Phe Leu Lys Ile
                245                 250                 255

Arg Glu Gly Arg Ile Ile Lys Glu Ile Phe Pro Thr Gly Arg Val Lys
            260                 265                 270

His Thr Glu Glu Cys Thr Cys Gly Phe Ala Ser Asn Lys Thr Ile Glu
        275                 280                 285

Cys Ala Cys Arg Asp Asn Ser Tyr Thr Ala Lys Arg Pro Phe Val Lys
    290                 295                 300

Leu Asn Val Glu Thr Asp Thr Ala Glu Ile Arg Leu Met Cys Thr Glu
305                 310                 315                 320

Thr Tyr Leu Asp Thr Pro Arg Pro Asn Asp Gly Ser Ile Thr Gly Pro
                325                 330                 335

Cys Glu Ser Asn Gly Asp Lys Gly Ser Gly Gly Ile Lys Gly Gly Phe
```

```
                 340                 345                 350
Val His Gln Arg Met Ala Ser Lys Ile Gly Arg Trp Tyr Ser Arg Thr
             355                 360                 365

Met Ser Lys Thr Lys Arg Met Gly Met Gly Leu Tyr Val Lys Tyr Asp
         370                 375                 380

Gly Asp Pro Trp Thr Asp Ser Glu Ala Leu Ala Leu Ser Gly Val Met
385                 390                 395                 400

Val Ser Met Glu Glu Pro Gly Trp Tyr Ser Phe Gly Phe Glu Ile Lys
                 405                 410                 415

Asp Lys Lys Cys Asp Val Pro Cys Ile Gly Ile Glu Met Val His Asp
             420                 425                 430

Gly Gly Lys Thr Thr Trp His Ser Ala Ala Thr Ala Ile Tyr Cys Leu
         435                 440                 445

Met Gly Ser Gly Gln Leu Leu Trp Asp Thr Val Thr Gly Val Asn Met
     450                 455                 460

Thr Leu
465

<210> SEQ ID NO 46
<211> LENGTH: 466
<212> TYPE: PRT
<213> ORGANISM: Influenza B

<400> SEQUENCE: 46

Met Leu Pro Ser Thr Ile Gln Thr Leu Thr Leu Phe Leu Thr Ser Gly
1               5                   10                  15

Gly Val Leu Leu Ser Leu Tyr Val Ser Ala Ser Leu Ser Tyr Leu Leu
             20                  25                  30

Tyr Ser Asp Ile Leu Leu Lys Phe Ser Pro Thr Glu Ile Thr Ala Pro
         35                  40                  45

Thr Met Pro Leu Asp Cys Ala Asn Ala Ser Asn Val Gln Ala Val Asn
     50                  55                  60

Arg Ser Ala Thr Lys Gly Val Thr Leu Leu Leu Pro Glu Pro Glu Trp
65                  70                  75                  80

Thr Tyr Pro Arg Leu Ser Cys Pro Gly Ser Thr Phe Gln Lys Ala Leu
                 85                  90                  95

Leu Ile Ser Pro His Arg Phe Gly Glu Thr Lys Gly Asn Ser Ala Pro
             100                 105                 110

Leu Ile Ile Arg Glu Pro Phe Ile Ala Cys Gly Pro Lys Glu Cys Lys
         115                 120                 125

His Phe Ala Leu Thr His Tyr Ala Ala Gln Pro Gly Gly Tyr Tyr Asn
     130                 135                 140

Gly Thr Arg Glu Asp Lys Asn Lys Leu Arg His Leu Ile Ser Val Lys
145                 150                 155                 160

Leu Gly Lys Ile Pro Thr Val Glu Asn Ser Ile Phe His Met Ala Ala
                 165                 170                 175

Trp Ser Gly Ser Ala Cys His Asp Gly Arg Glu Trp Thr Tyr Ile Gly
             180                 185                 190

Val Asp Gly Pro Asp Ser Asn Ala Leu Leu Lys Ile Lys Tyr Gly Glu
         195                 200                 205

Ala Tyr Thr Asp Thr Tyr His Ser Tyr Ala Asn Asn Ile Leu Arg Thr
     210                 215                 220

Gln Glu Ser Ala Cys Asn Cys Ile Gly Gly Asp Cys Tyr Leu Met Ile
225                 230                 235                 240
```

-continued

```
Thr Asp Gly Ser Ala Ser Gly Ile Ser Glu Cys Arg Phe Leu Lys Ile
                245                 250                 255
Arg Glu Gly Arg Ile Ile Lys Glu Ile Phe Pro Thr Gly Arg Val Glu
            260                 265                 270
His Thr Glu Glu Cys Thr Cys Gly Phe Ala Ser Asn Lys Thr Ile Glu
        275                 280                 285
Cys Ala Cys Arg Asp Asn Ser Tyr Thr Ala Lys Arg Pro Phe Val Lys
    290                 295                 300
Leu Asn Val Glu Thr Asp Thr Ala Glu Ile Arg Leu Met Cys Thr Glu
305                 310                 315                 320
Thr Tyr Leu Asp Thr Pro Arg Pro Asp Asp Gly Ser Ile Thr Gly Pro
                325                 330                 335
Cys Glu Ser Asn Gly Asp Lys Gly Ser Gly Gly Ile Lys Gly Gly Phe
            340                 345                 350
Val His Gln Arg Met Ala Ser Lys Ile Gly Arg Trp Tyr Ser Arg Thr
        355                 360                 365
Met Ser Lys Thr Lys Arg Met Gly Met Gly Leu Tyr Val Lys Tyr Asp
    370                 375                 380
Gly Asp Pro Trp Thr Asp Ser Asp Ala Leu Ala Leu Ser Gly Val Met
385                 390                 395                 400
Val Ser Met Glu Glu Pro Gly Trp Tyr Ser Phe Gly Phe Glu Ile Lys
                405                 410                 415
Asp Lys Lys Cys Asp Val Pro Cys Ile Gly Ile Glu Met Val His Asp
            420                 425                 430
Gly Gly Lys Lys Thr Trp His Ser Ala Ala Thr Ala Ile Tyr Cys Leu
        435                 440                 445
Met Gly Ser Gly Gln Leu Leu Trp Asp Thr Val Thr Gly Val Asp Met
    450                 455                 460
Ala Leu
465

<210> SEQ ID NO 47
<211> LENGTH: 466
<212> TYPE: PRT
<213> ORGANISM: Influenza B

<400> SEQUENCE: 47

Met Leu Pro Ser Thr Ile Gln Thr Leu Thr Leu Phe Leu Thr Ser Gly
1               5                   10                  15
Gly Val Leu Leu Ser Leu Tyr Val Ser Ala Ser Leu Ser Tyr Leu Leu
            20                  25                  30
Tyr Ser Asp Ile Leu Leu Lys Phe Ser Pro Thr Glu Ile Thr Ala Pro
        35                  40                  45
Thr Met Pro Leu Asp Cys Ala Asn Ala Ser Asn Val Gln Ala Val Asn
    50                  55                  60
Arg Ser Ala Thr Lys Gly Val Thr Leu Leu Pro Glu Pro Glu Trp
65                  70                  75                  80
Thr Tyr Pro Arg Leu Ser Cys Pro Gly Ser Thr Phe Gln Lys Ala Leu
                85                  90                  95
Leu Ile Ser Pro His Arg Phe Gly Glu Thr Lys Gly Asn Ser Ala Pro
            100                 105                 110
Leu Ile Ile Arg Glu Pro Phe Ile Ala Cys Gly Pro Lys Glu Cys Lys
        115                 120                 125
His Phe Ala Leu Thr His Tyr Ala Ala Gln Pro Gly Gly Tyr Tyr Asn
    130                 135                 140
```

Gly Thr Arg Gly Asp Arg Asn Lys Leu Arg His Leu Ile Ser Val Lys
145                 150                 155                 160

Leu Gly Lys Ile Pro Thr Val Glu Asn Ser Ile Phe His Met Ala Ala
                165                 170                 175

Trp Ser Gly Ser Ala Cys His Asp Gly Lys Glu Trp Thr Tyr Ile Gly
            180                 185                 190

Val Asp Gly Pro Asp Asn Asn Ala Leu Leu Lys Ile Lys Tyr Gly Glu
            195                 200                 205

Ala Tyr Thr Asp Thr Tyr His Ser Tyr Ala Asn Asn Ile Leu Arg Thr
        210                 215                 220

Gln Glu Ser Ala Cys Asn Cys Ile Gly Gly Asn Cys Tyr Leu Met Ile
225                 230                 235                 240

Thr Asp Gly Ser Ala Ser Gly Val Ser Glu Cys Arg Phe Leu Lys Ile
                245                 250                 255

Arg Glu Gly Arg Ile Ile Lys Glu Ile Phe Pro Thr Gly Arg Val Lys
            260                 265                 270

His Thr Glu Glu Cys Thr Cys Gly Phe Ala Ser Asn Lys Thr Ile Glu
        275                 280                 285

Cys Ala Cys Arg Asp Asn Ser Tyr Thr Ala Lys Arg Pro Phe Val Lys
290                 295                 300

Leu Asn Val Glu Thr Asp Thr Ala Glu Ile Arg Leu Met Cys Thr Glu
305                 310                 315                 320

Thr Tyr Leu Asp Thr Pro Arg Pro Asp Asp Gly Ser Ile Thr Gly Pro
                325                 330                 335

Cys Glu Ser Asn Gly Asp Lys Gly Ser Gly Gly Ile Lys Gly Gly Phe
            340                 345                 350

Val His Gln Arg Met Ala Ser Lys Ile Gly Arg Trp Tyr Ser Arg Thr
        355                 360                 365

Met Ser Lys Thr Lys Arg Met Gly Met Gly Leu Tyr Val Lys Tyr Asp
370                 375                 380

Gly Asp Pro Trp Ala Asp Ser Asp Ala Leu Ala Leu Ser Gly Val Met
385                 390                 395                 400

Val Ser Met Glu Glu Pro Gly Trp Tyr Ser Phe Gly Phe Glu Ile Lys
                405                 410                 415

Asp Lys Lys Cys Asp Val Pro Cys Ile Gly Ile Glu Met Val His Asp
            420                 425                 430

Gly Gly Lys Glu Thr Trp His Ser Ala Ala Thr Ala Ile Tyr Cys Leu
        435                 440                 445

Met Gly Ser Gly Gln Leu Leu Trp Asp Thr Val Thr Gly Val Asp Met
450                 455                 460

Ala Leu
465

<210> SEQ ID NO 48
<211> LENGTH: 465
<212> TYPE: PRT
<213> ORGANISM: Influenza B

<400> SEQUENCE: 48

Met Leu Pro Ser Thr Ile Gln Thr Leu Thr Leu Phe Leu Thr Ser Gly
1               5                   10                  15

Gly Val Leu Leu Ser Leu Tyr Val Ser Ala Ser Leu Ser Tyr Leu Leu
            20                  25                  30

Tyr Ser Asp Ile Leu Leu Lys Phe Ser Pro Lys Ile Thr Ala Pro Thr

```
            35                  40                  45
Met Thr Leu Asp Cys Ala Asn Ala Ser Asn Val Gln Ala Val Asn Arg
 50                  55                  60

Ser Ala Thr Lys Glu Met Thr Phe Leu Leu Pro Glu Pro Glu Trp Thr
 65                  70                  75                  80

Tyr Pro Arg Leu Ser Cys Gln Gly Ser Thr Phe Gln Lys Ala Leu Leu
                 85                  90                  95

Ile Ser Pro His Arg Phe Gly Glu Ala Arg Gly Asn Ser Ala Pro Leu
            100                 105                 110

Ile Ile Arg Glu Pro Phe Ile Ala Cys Gly Pro Lys Glu Cys Lys His
        115                 120                 125

Phe Ala Leu Thr His Tyr Ala Ala Gln Pro Gly Gly Tyr Tyr Asn Gly
    130                 135                 140

Thr Arg Glu Asp Arg Asn Lys Leu Arg His Leu Ile Ser Val Lys Leu
145                 150                 155                 160

Gly Lys Ile Pro Thr Val Glu Asn Ser Ile Phe His Met Ala Ala Trp
                165                 170                 175

Ser Gly Ser Ala Cys His Asp Gly Arg Glu Trp Thr Tyr Ile Gly Val
            180                 185                 190

Asp Gly Pro Asp Ser Asn Ala Leu Ile Lys Ile Lys Tyr Gly Glu Ala
        195                 200                 205

Tyr Thr Asp Thr Tyr His Ser Tyr Ala Asn Asn Ile Leu Arg Thr Gln
    210                 215                 220

Glu Ser Ala Cys Asn Cys Ile Gly Gly Asp Cys Tyr Leu Met Ile Thr
225                 230                 235                 240

Asp Gly Ser Ala Ser Gly Ile Ser Lys Cys Arg Phe Leu Lys Ile Arg
                245                 250                 255

Glu Gly Arg Ile Ile Lys Glu Ile Phe Pro Thr Gly Arg Val Glu His
            260                 265                 270

Thr Glu Glu Cys Thr Cys Gly Phe Ala Ser Asn Lys Thr Ile Glu Cys
        275                 280                 285

Ala Cys Arg Asp Asn Asn Tyr Thr Ala Lys Arg Pro Phe Val Lys Leu
    290                 295                 300

Asn Val Glu Thr Asp Thr Ala Glu Ile Arg Leu Met Cys Thr Glu Thr
305                 310                 315                 320

Tyr Leu Asp Thr Pro Arg Pro Asp Asp Gly Ser Ile Thr Gly Pro Cys
                325                 330                 335

Glu Ser Asn Gly Asp Lys Gly Arg Gly Gly Ile Lys Gly Gly Phe Val
            340                 345                 350

His Gln Arg Met Ala Ser Lys Ile Gly Arg Trp Tyr Ser Arg Thr Met
        355                 360                 365

Ser Lys Thr Glu Arg Met Gly Met Glu Leu Tyr Val Lys Tyr Asp Gly
    370                 375                 380

Asp Pro Trp Thr Asp Ser Asp Ala Leu Asp Pro Ser Gly Val Met Val
385                 390                 395                 400

Ser Met Lys Glu Pro Gly Trp Tyr Ser Phe Gly Phe Glu Ile Lys Asp
                405                 410                 415

Lys Lys Cys Asp Val Pro Cys Ile Gly Ile Glu Met Val His Asp Gly
            420                 425                 430

Gly Lys Lys Thr Trp His Ser Ala Ala Thr Ala Ile Tyr Cys Leu Met
        435                 440                 445

Gly Ser Gly Gln Leu Leu Trp Asp Thr Val Thr Gly Val Asp Met Ala
    450                 455                 460
```

Leu
465

<210> SEQ ID NO 49
<211> LENGTH: 466
<212> TYPE: PRT
<213> ORGANISM: Influenza B

<400> SEQUENCE: 49

Met Leu Pro Ser Thr Ile Gln Thr Leu Thr Leu Phe Leu Thr Ser Gly
1               5                   10                  15

Gly Val Leu Leu Ser Leu Tyr Val Ser Ala Ser Leu Ser Tyr Leu Leu
            20                  25                  30

Tyr Ser Asp Ile Leu Leu Lys Phe Ser Pro Thr Lys Arg Thr Ala Pro
        35                  40                  45

Thr Met Ser Leu Asp Cys Ala Asn Val Ser Asn Val Gln Ala Val Asn
    50                  55                  60

Arg Ser Ala Thr Lys Glu Met Thr Phe Leu Leu Pro Glu Pro Glu Trp
65                  70                  75                  80

Thr Tyr Pro Arg Leu Ser Cys Gln Gly Ser Thr Phe Gln Lys Ala Leu
                85                  90                  95

Leu Ile Ser Pro His Arg Phe Gly Glu Ala Arg Gly Asn Ser Ala Pro
            100                 105                 110

Leu Ile Ile Arg Glu Pro Phe Ile Ala Cys Gly Pro Lys Glu Cys Lys
        115                 120                 125

His Phe Ala Leu Thr His Tyr Ala Ala Gln Pro Gly Gly Tyr Tyr Asn
    130                 135                 140

Gly Thr Arg Lys Asp Arg Asn Lys Leu Arg His Leu Ile Ser Val Lys
145                 150                 155                 160

Leu Gly Lys Ile Pro Thr Val Glu Asn Ser Ile Phe His Met Ala Ala
                165                 170                 175

Trp Ser Gly Ser Ala Cys His Asp Gly Arg Glu Trp Thr Tyr Ile Gly
            180                 185                 190

Val Asp Gly Pro Asp Ser Asn Ala Leu Ile Lys Ile Lys Tyr Gly Glu
        195                 200                 205

Ala Tyr Thr Asp Thr Tyr His Ser Tyr Ala Asn Asn Ile Leu Arg Thr
    210                 215                 220

Gln Glu Ser Ala Cys Asn Cys Ile Gly Gly Asp Cys Tyr Leu Met Ile
225                 230                 235                 240

Thr Asp Gly Ser Ala Ser Gly Ile Ser Lys Cys Arg Phe Leu Lys Ile
                245                 250                 255

Arg Glu Gly Arg Ile Ile Lys Glu Ile Phe Pro Thr Gly Arg Val Glu
            260                 265                 270

His Thr Glu Glu Cys Thr Cys Gly Phe Ala Ser Asn Lys Thr Ile Glu
        275                 280                 285

Cys Ala Cys Arg Asp Asn Ser Tyr Thr Ala Lys Arg Pro Phe Val Lys
    290                 295                 300

Leu Asn Val Glu Thr Asp Thr Ala Glu Ile Arg Leu Met Cys Thr Glu
305                 310                 315                 320

Thr Tyr Leu Asp Thr Pro Arg Pro Asp Asp Gly Ser Ile Thr Gly Pro
                325                 330                 335

Cys Glu Ser Asn Gly Asp Lys Gly Leu Gly Gly Ile Lys Gly Gly Phe
            340                 345                 350

Val His Gln Arg Met Ala Ser Lys Ile Gly Arg Trp Tyr Ser Arg Thr

```
                355                 360                 365
Met Ser Lys Thr Glu Arg Met Gly Met Glu Leu Tyr Val Lys Tyr Asp
            370                 375                 380

Gly Asp Pro Trp Thr Asp Ser Glu Ala Leu Ala Pro Ser Gly Val Met
385                 390                 395                 400

Val Ser Met Lys Glu Pro Gly Trp Tyr Ser Phe Gly Phe Glu Ile Lys
                405                 410                 415

Asp Lys Lys Cys Asp Val Pro Cys Ile Gly Ile Glu Met Val His Asp
            420                 425                 430

Gly Gly Lys Glu Thr Trp His Ser Ala Ala Thr Ala Ile Tyr Cys Leu
        435                 440                 445

Met Gly Ser Gly Gln Leu Leu Trp Asp Thr Val Thr Gly Val Asp Met
    450                 455                 460

Ala Leu
465

<210> SEQ ID NO 50
<211> LENGTH: 466
<212> TYPE: PRT
<213> ORGANISM: Influenza B

<400> SEQUENCE: 50

Met Leu Pro Ser Thr Ile Gln Thr Leu Thr Leu Phe Leu Thr Ser Gly
1               5                   10                  15

Gly Val Leu Leu Ser Leu Tyr Val Ser Ala Ser Leu Ser Tyr Leu Leu
            20                  25                  30

Tyr Ser Asp Ile Leu Leu Lys Phe Ser Arg Thr Glu Val Thr Ala Pro
        35                  40                  45

Ile Met Pro Leu Asp Cys Ala Asn Ala Ser Asn Val Gln Ala Val Asn
    50                  55                  60

Arg Ser Ala Thr Lys Gly Val Thr Pro Leu Leu Pro Glu Pro Glu Trp
65                  70                  75                  80

Thr Tyr Pro Arg Leu Ser Cys Pro Gly Ser Thr Phe Gln Lys Ala Leu
                85                  90                  95

Leu Ile Ser Pro His Arg Phe Gly Glu Thr Lys Gly Asn Ser Ala Pro
            100                 105                 110

Leu Ile Ile Arg Glu Pro Phe Ile Ala Cys Gly Pro Lys Glu Cys Lys
        115                 120                 125

His Phe Ala Leu Thr His Tyr Ala Ala Gln Pro Gly Gly Tyr Tyr Asn
    130                 135                 140

Gly Thr Arg Glu Asp Arg Asn Lys Leu Arg His Leu Ile Ser Val Lys
145                 150                 155                 160

Leu Gly Lys Ile Pro Thr Val Glu Asn Ser Ile Phe His Met Ala Ala
                165                 170                 175

Trp Ser Gly Ser Ala Cys His Asp Gly Arg Glu Trp Thr Tyr Ile Gly
            180                 185                 190

Val Asp Gly Pro Asp Ser Asn Ala Leu Leu Lys Ile Lys Tyr Gly Glu
        195                 200                 205

Ala Tyr Thr Asp Thr Tyr His Ser Tyr Ala Lys Asn Ile Leu Arg Thr
    210                 215                 220

Gln Glu Ser Ala Cys Asn Cys Ile Gly Gly Asp Cys Tyr Leu Met Ile
225                 230                 235                 240

Thr Asp Gly Pro Ala Ser Gly Ile Ser Glu Cys Arg Phe Leu Lys Ile
                245                 250                 255
```

```
Arg Glu Gly Arg Ile Ile Lys Glu Ile Phe Pro Thr Gly Arg Val Lys
                260                 265                 270

His Thr Glu Glu Cys Thr Cys Gly Phe Ala Ser Asn Lys Thr Ile Glu
            275                 280                 285

Cys Ala Cys Arg Asp Asn Ser Tyr Thr Ala Lys Arg Pro Phe Val Lys
        290                 295                 300

Leu Asn Val Glu Thr Asp Thr Ala Glu Ile Arg Leu Met Cys Thr Lys
305                 310                 315                 320

Thr Tyr Leu Asp Thr Pro Arg Pro Asn Asp Gly Ser Ile Thr Gly Pro
                325                 330                 335

Cys Glu Ser Asp Gly Asp Glu Gly Ser Gly Gly Ile Lys Gly Gly Phe
            340                 345                 350

Val His Gln Arg Met Ala Ser Lys Ile Gly Arg Trp Tyr Ser Arg Thr
        355                 360                 365

Met Ser Lys Thr Lys Arg Met Gly Met Gly Leu Tyr Val Lys Tyr Asp
370                 375                 380

Gly Asp Pro Trp Thr Asp Ser Glu Ala Leu Ala Leu Ser Gly Val Met
385                 390                 395                 400

Val Ser Met Glu Glu Pro Gly Trp Tyr Ser Phe Gly Phe Glu Ile Lys
                405                 410                 415

Asp Lys Lys Cys Asp Val Pro Cys Ile Gly Ile Glu Met Val His Asp
            420                 425                 430

Gly Gly Lys Thr Thr Trp His Ser Ala Ala Thr Ala Ile Tyr Cys Leu
        435                 440                 445

Met Gly Ser Gly Gln Leu Leu Trp Asp Thr Val Thr Gly Val Asn Met
450                 455                 460

Thr Leu
465

<210> SEQ ID NO 51
<211> LENGTH: 54
<212> TYPE: PRT
<213> ORGANISM: Influenza A

<400> SEQUENCE: 51

Ser Ile Gln Ile Gly Asn Gln Ser Gln Ile Glu Thr Cys Asn Gln Ser
1               5                   10                  15

Val Ile Thr Tyr Glu Asn Asn Thr Trp Val Asn Gln Thr Tyr Val Asn
            20                  25                  30

Ile Ser Asn Thr Asn Phe Ala Ala Gly Gln Ser Val Val Ser Val Lys
        35                  40                  45

Leu Ala Gly Asn Ser Ser
    50

<210> SEQ ID NO 52
<211> LENGTH: 53
<212> TYPE: PRT
<213> ORGANISM: Artificial Sequence
<220> FEATURE:
<223> OTHER INFORMATION: A synthetic sequence

<400> SEQUENCE: 52

Ile Gln Ile Gly Asn Gln Ser Gln Ile Glu Cys Cys Asn Gln Ser Val
1               5                   10                  15

Ile Thr Tyr Glu Asn Asn Thr Trp Val Asn Gln Thr Tyr Val Asn Ile
            20                  25                  30

Ser Asn Thr Asn Phe Ala Ala Gly Gln Ser Val Val Ser Val Lys Leu
```

Ala Gly Asn Ser Ser
    50

<210> SEQ ID NO 53
<211> LENGTH: 53
<212> TYPE: PRT
<213> ORGANISM: Artificial Sequence
<220> FEATURE:
<223> OTHER INFORMATION: A synthetic sequence

<400> SEQUENCE: 53

Ile Gln Ile Gly Asn Gln Ser Gln Ile Glu Thr Cys Cys Gln Ser Val
1               5                   10                  15

Ile Thr Tyr Glu Asn Asn Thr Trp Val Asn Gln Thr Tyr Val Asn Ile
            20                  25                  30

Ser Asn Thr Asn Phe Ala Ala Gly Gln Ser Val Val Ser Val Lys Leu
        35                  40                  45

Ala Gly Asn Ser Ser
    50

<210> SEQ ID NO 54
<211> LENGTH: 53
<212> TYPE: PRT
<213> ORGANISM: Artificial Sequence
<220> FEATURE:
<223> OTHER INFORMATION: A synthetic sequence

<400> SEQUENCE: 54

Ile Gln Ile Gly Asn Gln Ser Gln Ile Glu Cys Cys Cys Gln Ser Val
1               5                   10                  15

Ile Thr Tyr Glu Asn Asn Thr Trp Val Asn Gln Thr Tyr Val Asn Ile
            20                  25                  30

Ser Asn Thr Asn Phe Ala Ala Gly Gln Ser Val Val Ser Val Lys Leu
        35                  40                  45

Ala Gly Asn Ser Ser
    50

<210> SEQ ID NO 55
<211> LENGTH: 53
<212> TYPE: PRT
<213> ORGANISM: Artificial Sequence
<220> FEATURE:
<223> OTHER INFORMATION: A synthetic sequence

<400> SEQUENCE: 55

Ile Gln Ile Gly Asn Gln Ser Gln Ile Cys Thr Cys Asn Gln Ser Val
1               5                   10                  15

Ile Thr Tyr Glu Asn Asn Thr Trp Val Asn Gln Thr Tyr Val Asn Ile
            20                  25                  30

Ser Asn Thr Asn Phe Ala Ala Gly Gln Ser Val Val Ser Val Lys Leu
        35                  40                  45

Ala Gly Asn Ser Ser
    50

<210> SEQ ID NO 56
<211> LENGTH: 53
<212> TYPE: PRT
<213> ORGANISM: Artificial Sequence
<220> FEATURE:
<223> OTHER INFORMATION: A synthetic sequence

```
<400> SEQUENCE: 56

Ile Gln Ile Gly Asn Gln Ser Gln Ile Glu Thr Cys Asn Cys Ser Val
1               5                   10                  15

Ile Thr Tyr Glu Asn Asn Thr Trp Val Asn Gln Thr Tyr Val Asn Ile
                20                  25                  30

Ser Asn Thr Asn Phe Ala Ala Gly Gln Ser Val Val Ser Val Lys Leu
            35                  40                  45

Ala Gly Asn Ser Ser
        50
```